United States Patent
Dales et al.

(10) Patent No.: US 8,293,768 B2
(45) Date of Patent: *Oct. 23, 2012

(54) ORGANIC COMPOUNDS

(75) Inventors: Natalie Dales, Arlington, MA (US); Julia Fonarev, Richmond (CA); Jianmin Fu, Coquitlam (CA); Rajender Kamboj, Burnaby (CA); Vishnumurthy Kodumuru, Burnaby (CA); Shifeng Liu, Port Coquitlam (CA); Natalia Pokrovskaia, New Westminster (CA); Vandna Raina, Burnaby (CA); Shaoyi Sun, Coquitlam (CA); Zaihui Zhang, Vancouver (CA)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/231,075

(22) Filed: Sep. 13, 2011

(65) Prior Publication Data

US 2012/0004164 A1   Jan. 5, 2012

Related U.S. Application Data

(63) Continuation of application No. 12/377,499, filed as application No. PCT/US2007/075802 on Aug. 13, 2007, now Pat. No. 8,063,084.

(60) Provisional application No. 60/822,459, filed on Aug. 15, 2006.

(51) Int. Cl.
  *A61K 31/425* (2006.01)
  *A61K 31/433* (2006.01)
  *A61K 31/4196* (2006.01)
  *C07D 203/02* (2006.01)
  *C07D 249/08* (2006.01)
  *C07D 285/10* (2006.01)

(52) U.S. Cl. ..... 514/336; 514/385; 514/438; 546/268.1; 548/300.1; 549/79

(58) Field of Classification Search .................. 514/336, 514/385, 438; 546/268.1; 548/300.1; 549/79
See application file for complete search history.

(56) References Cited

U.S. PATENT DOCUMENTS

| | | | |
|---|---|---|---|
| 3,298,914 A | 1/1967 | Schmidt et al. | |
| 3,998,952 A | 12/1976 | Ilvespaa | |
| 4,058,617 A | 11/1977 | Ilvespaa | |
| 4,086,240 A | 4/1978 | Wu et al. | |
| 4,116,969 A | 9/1978 | Wu et al. | |
| 4,886,817 A | 12/1989 | Takeda et al. | |
| 5,451,592 A | 9/1995 | Reitz et al. | |
| 6,022,875 A | 2/2000 | Zimmer et al. | |
| 8,049,016 B2* | 11/2011 | Chowdhury et al. | 548/196 |
| 8,063,084 B2* | 11/2011 | Dales et al. | 514/385 |
| 2003/0087936 A1 | 5/2003 | Shia et al. | |
| 2004/0053973 A1 | 3/2004 | Ohkawa et al. | |
| 2009/0156615 A1 | 6/2009 | Dales et al. | |
| 2009/0264444 A1 | 10/2009 | Chowdhury et al. | |
| 2010/0029718 A1 | 2/2010 | Dales et al. | |
| 2010/0029722 A1 | 2/2010 | Dales et al. | |
| 2010/0239520 A1 | 9/2010 | Dales et al. | |

FOREIGN PATENT DOCUMENTS

| | | |
|---|---|---|
| CH | 455806 | 5/1968 |
| CH | 463517 | 10/1968 |
| DE | 2 348 284 A1 | 4/1974 |
| EP | 1 621 539 A1 | 2/2006 |
| GB | 986562 | 3/1965 |
| IL | 44282 A | 1/1979 |
| NL | 6511486 | 3/1966 |
| WO | 96-36616 A1 | 11/1996 |
| WO | 9921555 A2 | 5/1999 |
| WO | 0110865 A1 | 2/2001 |
| WO | 0162954 A2 | 8/2001 |
| WO | 0174811 A2 | 10/2001 |
| WO | 02051442 A1 | 7/2002 |
| WO | 02-085838 A1 | 10/2002 |
| WO | 02100433 A1 | 12/2002 |
| WO | 2004-009558 A2 | 1/2004 |
| WO | 2004-096781 A1 | 11/2004 |
| WO | 2005077937 A1 | 8/2005 |
| WO | 2006034440 A2 | 3/2006 |
| WO | 2008127349 A2 | 10/2008 |
| WO | 2009103739 A1 | 8/2009 |
| WO | 2009156484 A2 | 12/2009 |

OTHER PUBLICATIONS

Patani et al., Chem. Rev., 1996, vol. 98(8), pp. 3147-3176, esp. p. 3149.*
Robert et al.; "Synthesis and antileishmanial activity of new imidazolidin-2-one derivatives"; European Journal of Medicinal Chemistry; 38(7-8):711-718 (2003).
Alvarez et al.; "Inhibition of Parasite Protein Kinase C by New Antileishmanial Imidazolidin-2-one Compounds"; Journal of Enzyme Inhibition and Medicinal Chemistry; 17(6):443-447 (2002).
Kosary et al.; "Synthesis of thiazole derivatives with positive inotropic effect"; Pharmazie; 42(6):373-375 (1987).
Patini et al.; "Bioisosterism: A Rational Approach in Drug Design"; Chem. Rev.; 96(8):3147-3176 (1996).
Anjaneyulu et al.; "Nitroimidazoles: Part XXII—Synthesis of potential metabolites of satranidazole by non-nitroreductive and nitroreductive routes"; Indian Journal of Chemistry; 30B:399-406 (1991).
Beyer et al.; "Die Synthese von 1-[Thiazolyl-(2)]-imidazolonen-(2)"; Uber Thiazole (XLIV); pp. 2118-2122 (1966) [English Version and original].
ISLIP et al.; "Substituted Thiazolylureas"; Journal of Medicinal Chemistry; 15(1):101-103 (1972).
Kosary et al.; "Synthesis of pyridylthiazoles as antisecretory agents."; Pharmazie; 44(3):191-193 (1989)[Abstract only] Article in German.
Nagarajan et al.; "Nitroimidazoles: Part IV—1-Sulphonyl (carbamoyl/thiocarbamoyl)-3-(1-methyl-5-nitroimidazol-2-yl)-2-imidazolidinones"; Indian Journal of Chemistry; 21B:928-940 (1982).

(Continued)

*Primary Examiner* — Susannah Chung
(74) *Attorney, Agent, or Firm* — Joshua Roth

(57) ABSTRACT

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

2 Claims, No Drawings

OTHER PUBLICATIONS

Sasaki et al.; "Studies on Heteroaromaticity. XIV. Ring-opening Reaction of N-[beta-(5-Nitro-2-furyl)vinyl]- and N-(2-Furyl)-N'-ethyleneurea"; Bulletin of the Chemical Society of Japan; 41(5):1258-1260 (1968).

Schmidt et al.; "A New Group of Antischistosomal Compounds"; Angewandte Chemie—International Edition; 5 (10):857-908 (1966).

Sugiyama et al.; "Condensed Thienopyrimidines. I. Synthesis and Gastric Antisecretory Activity of 2,3-Dihydro-5H-oxazolothienopyrimidin-5-one Derivatives"; Chem. Pharm Bull.; 37(8):2091-2102 (1989).

* cited by examiner

ORGANIC COMPOUNDS

RELATED APPLICATIONS

This application is a continuation of U.S. application Ser. No. 12/377,499, which was the National Stage of International Application No. PCT/US2007/075802, filed on Aug. 13, 2007, which claims benefit under 35 U.S.C. §119(e) of U.S. Provisional Application No. 60/822,459, filed Aug. 15, 2006, the contents of which are incorporated herein by reference in their entirety.

The present invention relates generally to the field of inhibitors of stearoyl-CoA desaturase, such as heterocyclic derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome, dermatological disorders and the like.

BACKGROUND OF THE INVENTION

Acyl desaturase enzymes catalyze the formation of a double bond in fatty acids derived from either dietary sources or de novo synthesis in the liver. In mammals, at least three fatty acid desaturases exists, each with differing specificity: delta-9, delta-6, and delta-5, which introduce a double bond at the 9-10, 6-7, and 5-6 positions respectively.

Stearoyl-CoA desaturases (SCDs) act with cofactors (other agents) such as NADPH, cytochrome b5, cytochrome b5 reductase, Fe, and molecular $O_2$ to introduce a double bond into the C9-C10 position (delta 9) of saturated fatty acids, when conjugated to Coenzyme A (CoA). The preferred substrates are palmitoyl-CoA (16:0) and stearoyl-CoA (18:0), which are converted to palmitoleoyl-CoA (16:1) and oleyl-CoA (18:1), respectively. The resulting mono-unsaturated fatty acids are substrates for further metabolism by fatty acid elongases or incorporation into phospholipids, triglycerides, and cholesterol esters. A number of mammalian SCD genes have been cloned. For example, two genes have been identified in humans (hSCD1 and hSCD5) and four SCD genes have been isolated from mouse (SCD1, SCD2, SCD3, and SCD4). While the basic biochemical role of SCD has been known in rats and mice since the 1970s (Jeffcoat, R. et al., *Eur. J. Biochem.* (1979), Vol. 101, No. 2, pp. 439-445; de Antueno, R. et al., *Lipids* (1993), Vol. 28, No. 4, pp. 285-290), it has only recently been directly implicated in human disease processes.

The two human SCD genes have been previously described: hSCD1 by Brownlie et. al., PCT published patent application, WO 01/62954, the disclosure of which is hereby incorporated by reference in its entirety, and hSCD2 by Brownlie, PCT published patent application, WO 02/26944, incorporated herein by reference in its entirety.

To date, the only small-molecule, drug-like compounds known that specifically inhibit or modulate SCD activity are found in the following PCT Published Patent Applications: WO 06/034338, WO 06/034446, WO 06/034441, WO 06/034440, WO 06/034341, WO 06/034315, WO 06/034312, WO 06/034279, WO 06/014168, WO 05/011657, WO 05/011656, WO 05/011655, WO 05/011654, WO 05/011653, WO 06/130986, WO 07/009,236, WO 06/086447, WO 06/101521, WO 06/125178, WO 06/125179, WO 06/125180, WO 06/125181, WO 06/125194, WO 07/044,085, WO 07/046,867, WO 07/046,868, WO 07/050124, and WO 07/056,846. SCD inhibitors have also been described in the following publications: Zhao et al. "Discovery of 1-(4-phenoxypiperidin-1-yl)-2-arylaminoethanone stearoyl CoA desaturase 1 inhibitors", *Biorg. Med. Chem. Lett.*, (2007) Vol. 17, No. 12, 3388-3391 and Liu et al. "Discovery of potent, orally bioavailable stearoyl-CoA desaturase 1 inhibitors", *J. Med. Chem.*, E-publication May 27, 2007. Before the discovery of the above compounds, only certain long-chain hydrocarbons, analogs of the substrate stearic acid, had been used to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA, while cis-9, trans-11 conjugated linoleic acid does not. Cyclopropenoid fatty acids, such as those found in stercula and cotton seeds, are also known to inhibit SCD activity. For example, sterculic acid (8-(2 octylcyclopropenyl)octanoic acid) and malvalic acid (7-(2-oclylcyclopropenyl)heptanoic acid) are C18 and C16 derivatives of sterculoyl and malvaloyl fatty acids, respectively, having cyclopropene rings at their C9-C10 position. These agents must be coupled to CoA to act as inhibitors, and are believed to inhibit SCD enzymatic activity by direct interaction with the enzyme complex, thus inhibiting delta-9 desaturation. Other agents that may inhibit SCD activity include thia-fatty acids, such as 9-thiastearic acid (also called 8-nonylthiooctanoic acid) and other fatty acids.

There is a major unmet need for small molecule inhibitors of SCD enzyme activity because compelling evidence now exists that SCD activity is directly implicated in common human disease processes: See e.g., Attie, A. D. et al., "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al., "Role for stearoyl-CoA desaturase-1 in leptin mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. U.S.A.* (2002), Vol. 99, No. 7, pp. 11482-6.

The present invention solves this problem by presenting new drug-like classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

SUMMARY OF THE INVENTION

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of Formula (I):

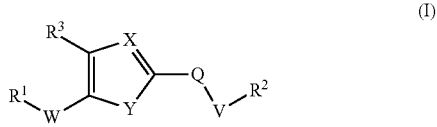

wherein:
X is N or CH;
Y is NH, O, S or N—$CH_3$;

Q is

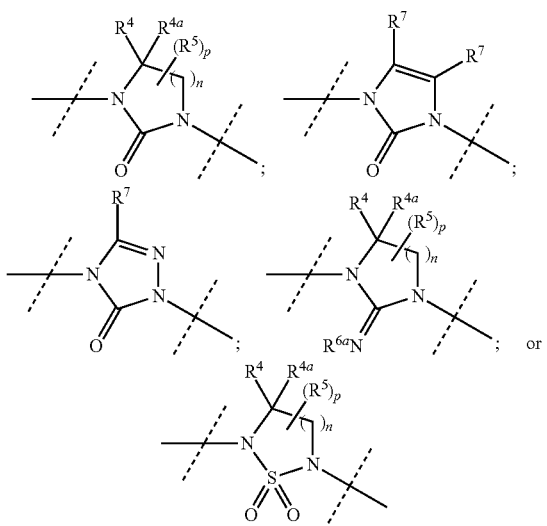

W is selected from —N(R$^6$)C(O)—, —C(O)N(R$^6$)—, —OC(O)N(R$^6$)—, —N(R$^6$)C(O)O—, —N(R$^6$)C(O)N(R$^6$)—, —O—, —S—, —N(R$^6$)—, —S(O)$_t$—, —N(R$^6$)S(O)$_t$—, —S(O)$_t$N(R$^6$)—, —OS(O)$_t$N(R$^6$)—, —C(O)—, —OC(O)—, —C(O)O—, —N(R$^6$)C(=N(R$^{6a}$))N(R$^6$)—, —N(R$^6$)((R$^{6a}$)N=)C—, —C(=N(R$^{6a}$))N(R$^6$)—, or a direct bond;

V is selected from —R$^8$—C(O)N(R$^6$)—, —R$^8$—OC(O)N(R$^6$)—, —S(O)$_t$—, —S(O)$_2$N(R$^6$)—, —R$^8$—C(O)—, —R$^8$—C(O)O—, —C(=N(R$^{6a}$))N(R$^6$)—, or a direct bond;

n is 1, 2, or 3;

p is 0, 1, 2, to 2n;

t is 1 or 2;

R$^1$ is selected from the group consisting of halo, hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl, or heteroarylalkyl;

or R$^1$ is a multi-ring structure having 2 to 4 rings wherein the rings are independently selected from the group consisting of cycloalkyl, heterocyclyl, aryl and heteroaryl and where some or all of the rings may be fused to each other;

R$^2$ is selected from the group consisting of hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of hydrogen, alkyl, alkenyl, alkynyl, alkoxy, hydroxyalkyl, alkoxyalkyl, cycloalkyl, cycloalkylalkyl, heterocyclyl, aryl, aralkyl, heteroaryl, halo, haloalkyl, haloalkoxy, cyano, or —N(R$^6$)$_2$;

each of R$^4$ and R$^{4a}$ are independently selected from the group consisting of hydrogen, alkyl, haloalkyl, hydroxyl, hydroxyalkyl, alkoxy, cycloalkylalkyl or aralkyl;

or R$^4$ and R$^{4a}$ are together to form an oxo (=O) group or a cycloaklyl;

R$^5$ is selected from the group consisting of alkyl, aryl, cycloalkyl, heteroaryl, heterocyclyl, hydroxyalkyl, alkoxy, cycloalkylalkyl, aralkyl, —N(R$^6$)C(O)R$^2$, —C(O)N(R$^6$)R$^2$, —OC(O)N(R$^6$)R$^2$, —N(R$^6$)C(O)OR$^2$, —N(R$^6$)C(O)N(R$^6$)R$^2$, —OR$^2$, —SR$^2$, —N(R$^6$)R$^2$, —S(O)$_t$R$^2$, —N(R$^6$)S(O)$_2$R$^2$, —S(O)$_2$N(R$^6$)R$^2$, —OS(O)$_2$N(R$^6$)R$^2$, —C(O)R$^2$, —OC(O)R$^2$, —C(O)OR$^2$, —N(R$^6$)C(=N(R$^{6a}$))N(R$^6$)R$^2$, —N(R$^6$)C(=S)N(R$^6$)R$^2$, —N(R$^6$)((R$^{6a}$)N=)CR$^2$, or —C(=N(R$^{6a}$))N(R$^6$)R$^2$;

each R$^6$ is independently selected from the group consisting of hydrogen, alkyl, hydroxyalkyl, cycloalkylalkyl, aryl, heteroaryl, heterocyclyl or aralkyl;

each R$^{6a}$ is independently selected from the group consisting of hydrogen, alkyl, cycloalkylalkyl, or cyano;

each R$^7$ is independently selected from the group consisting of hydrogen, alkyl, trifluoromethyl, aryl, cycloalkyl, heteroaryl, heterocyclyl, hydroxyalkyl, cycloalkylalkyl or aralkyl; and each R$^8$ is independently a direct bond, an optionally substituted straight or branched alkylene chain, an optionally substituted straight or branched alkenylene chain or an optionally substituted straight or branched alkynylene chain;

as a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism and/or lipid homeostasis utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

It is understood that the scope of the invention as it relates to compounds of formula (I) is not intended to encompass compounds which are known, including, but not limited to, any specific compounds which are disclosed and/or claimed in the following publications:
PCT Published Patent Application, WO 00/25768;
PCT Published Patent Application, WO 99/47507;
PCT Published Patent Application, WO 01/60458;
PCT Published Patent Application, WO 01/60369;
PCT Published Patent Application, WO 94/26720;
European Published Patent Application, 0 438 230;
European Published Patent Application, 1 184 442;
CA 2,114,178; and U.S. Pat. No. 5,334,328;
U.S. Pat. No. 5,310,499; and
US Published Patent Application, 2003/0127627.

DETAILED DESCRIPTION OF THE INVENTION

Definitions

Certain chemical groups named herein are preceded by a shorthand notation indicating the total number of carbon atoms that are to be found in the indicated chemical group. For example, $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Cyano" refers to the —CN radical;
"Hydroxy" refers to the —OH radical;
"Nitro" refers to the —$NO_2$ radical;
"Amino" refers to the —$NR^{14}$ or $NR^{15}$ radical;
"Mercapto" refers to the —SR radical;
"Acid" refers to the —COOH radical;
"Trifluoromethyl" refers to the —$CF_3$ radical;

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one or more of the following groups: alkyl, alkenyl, halo, haloalkyl, cyano, aryl, cycloalkyl, heterocyclyl, heteroaryl, silyoxy, —$OR^{14}$, —OC(O)—$R^{14}$, —$N(R^{14})_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$), —S(O)$_t$O$R^{16}$, —S$R^{16}$, —S(O)$_t$$R^{16}$, —O—S(O)$_2$$R^{16}$, —O—Si($R^{16}$)$_3$ and —S(O)$_t$N($R^{14}$)$_2$, where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl cycloalkyl, cycloalkylalkyl, aryl, aralkyl (e.g. tolyl), heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms or two to six carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —$OR^{14}$, —OC(O)—$R^{14}$N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$), —S$R^{16}$, —S(O)$_t$O$R^{16}$, —S(O)$_t$$R^{16}$, and —S(O)$_t$N($R^{14}$)$_2$, where each $R^{14}$ is independently hydrogen, alkyl, haloalkyl, cycloalkyl, cycloalkylalkyl, aryl aralkyl, heterocyclyl, heterocyclylalkyl, heteroaryl, or heteroarylalkyl; and each $R^{16}$ is alkyl, cycloalkyl, cycloalkylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one triple bond, having from two to twelve carbon atoms, preferably two to eight carbon atoms or two to six carbon atoms and which is attached to the rest of the molecule by a single bond. Unless stated otherwise specifically in the specification, an alkynyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, —$OR^{14}$, —OC(O)—$R^{14}$N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$), —S$R^{16}$, —S(O)$_t$O$R^{16}$, —S(O)$_t$$R^{16}$, and —S(O)$_t$N($R^{14}$)$_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalky; and each $R^{16}$ is alkyl, cycloalkyl, cycloalkylalkyl, aryl, aralkyl, heterocyclyl, heterocyclylalkyl, heteroaryl or heteroarylalkyl.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms or two to six carbon atoms, e.g., ethenylene, propenylene, n-butenylene, and the like. Unless stated otherwise specifically in the specification, an alkenylene chain may be optionally substituted by one or more of the following groups: alkyl, alkenyl, halo, cyano, aryl, cycloalkyl, heterocyclyl, heteroaryl, —$OR^{14}$, —OC(O)—$R^{14}$, —N($R^{14}$)$_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$), —S—, —S(O)$_t$O$R^{16}$, —S(O)$_t$$R^{16}$, and —S(O)$_t$N($R^{14}$)$_2$, where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, cycloalkyl, cycloalkylalkyl, aryl, aralkyl, heterocyclyl, heterocyclylalkyl, heteroaryl or heteroarylalkyl.

"Alkynylene" and "Alkynylene chain" refer to a straight or branched divalent hydrocarbon chain linking the rest of the molecule to a radical group, consisting solely of carbon and hydrogen, containing at least one triple bond and having from two to twelve carbon atoms or two to six carbon atoms, e.g. propynylene, n butynylene, and the like. Unless stated otherwise specifically in the specification, an alkynylene chain may be optionally substituted by one or more of the following groups: alkyl, alkenyl, halo, cyano, aryl, cycloalkyl, heterocyclyl, heteroaryl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{16}$, $-N(R^{14})(S(O)_tR^{16})$, $-S-$, $-S(O)_tOR^{16}$, $-S(O)_tR^{16}$, and $-S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, cycloalkyl, cycloalkylalkyl, aryl, aralkyl, heterocyclyl, heterocyclylalkyl, heteroaryl or heteroarylalkyl.

"Alkoxy" refers to a radical of the formula $-OR_a$ where $R_a$ is an alkyl radical as generally defined above. The alkyl part of the alkoxy radical may be optionally substituted as defined above for an alkyl radical.

"Alkoxyalkyl" refers to a radical of the formula $-R_a-O-R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from six to nineteen carbon atoms, preferably six to ten carbon atoms, where the ring system may be partially saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include an radicals optionally substituted by one or more substituents selected from the group consisting of alkyl, alkenyl, alkynyl, halo, haloalkyl, cyano, nitro, aryl, aralkyl, cycloalkyl, cycloalkylalkyl, heterocyclyl, heterocyclylalkyl, heteroaryl, heteroarylalky, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$, $-R^{15}-SR^{16}$, $-R^{15}-S(O)_tOR^{16}$, $-R^{15}-S(O)_tR^{16}$, and $-R^{15}-S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Aralkyl" refers to a radical of the formula $-R_aR_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aralkyl" refers to a radical of the formula $-R_aR_b$ where $R_a$ is an alkylene chain as defined above and $R_b$ is one or more aryl radicals as defined above, e.g., benzyl, diphenylmethyl and the like. The aryl part of the aralkyl radical may be optionally substituted as described above for an aryl group. The alkylene chain part of the aralkyl radical may be optionally substituted as defined above for an alkyl group.

"Aralkenyl" refers to a radical of the formula $-R_aR_b$ where $R_a$ is an alkenylene chain as defined above and $R_b$ is one or more aryl radicals as defined above, which may be optionally substituted as described above. The aryl part of the aralkenyl radical may be optionally substituted as described above for an aryl group. The alkenylene chain of the aralkenyl radical may be optionally substituted as defined above for an alkenyl group.

"Aryloxy" refers to a radical of the formula $-OR_b$ where $R_b$ is an aryl group as defined above. The aryl part of the aryloxy radical may be optionally substituted as defined above.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms or from three to seven atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, alkynyl, halo, haloalkyl, cyano, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$, $-R^{15}-SR^{16}$, $-R^{15}-S(O)_tOR^{16}$, $-R^{15}-S(O)_tR^{16}$, and $-R^{15}-S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Cycloalkylalkyl" refers to a radical of the formula $-R_aR_d$ where $R_a$ is an alkyl radical as defined above and $R_d$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems, which may be partially unsaturated; and the nitrogen, carbon or sulfur atoms in the heterocyclyl radical may be optionally oxidized; the nitrogen atom may be optionally alkylated/substituted; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl, homopiperidinyl, homopiperazinyl, and quinuclidinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, cyano, oxo, thioxo, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$, $R^{15}-SR^{16}$, $-R^{15}-S(O)_tR^{16}$, and $-R^{15}-S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl, and where each of the above substituents is unsubstituted.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic or tricyclic ring system, which may include fused or bridged ring systems, which may be partially saturated; and the nitrogen, carbon or sulfur atoms in the heteroaryl radical may be optionally oxidized; the nitrogen atom may be optionally alkylated/substituted. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzopyranyl, benzofuranonyl, benzothienyl, benzo[b]thiophenyl, benzothiophenyl, benzotriazolyl, benzo[4,6]imidazo[1,2-a]pyridinyl, benzo[c][1,2,5]oxadiazolyl, benzo[c][1,2,5]thiadiazolyl, carbazolyl, cinnolinyl, dibenzofuranyl, furanyl, furanonyl, isoquinolinyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, alkynyl, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $R^{15}N(R^{14})_2$, $R^{15}-C(O)R^{14}$, $R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$, $R^{15}-SR^{16}$, $-R^{15}-S(O)_tOR^{16}$, $-R^{15}-S(O)_tR^{16}$, and $-R^{15}-S(O)_tN(R^{14})_2$, where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Heteroarylalkyl" refers to a radical of the formula —$R_aR_f$ where $R_a$ is an alkylene chain as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to each other through direct bonds or some or all of the rings may be fused to each other.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto or acid group is bonded to any group that, when the prodrug of the compound of the invention is administered to a mammalian subject, cleaves to form a free hydroxy, free amino or free mercapto or acid group, respectively. Examples of prodrugs include, but are not limited to, acetate, formate and benzoate derivatives of alcohol or amides of amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent. A skilled artisan will recognize unstable combinations of substituents.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients thereof.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age and body weight of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes: (i) preventing the disease or condition from occurring in a mammal, in particular, when such mammal is predisposed to the condition but has not yet been diagnosed as having it (ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

The chemical naming protocol and structure diagrams used herein employ and rely on the chemical naming features as utilized by Chemdraw version 10.0 (available from Cambridgesoft Corp., Cambridge, Mass.).

Embodiments of the Invention

One embodiment of the invention is the compounds of Formula (I) disclosed above in the Summary of the Invention.

Of the compounds of Formula (I) disclosed above in the Summary of the Invention, one embodiment of the compounds of Formula (I) is that embodiment wherein X is N, Y is S, Q is

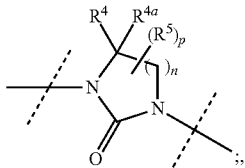

i.e., compound having the following Formula (Ia):

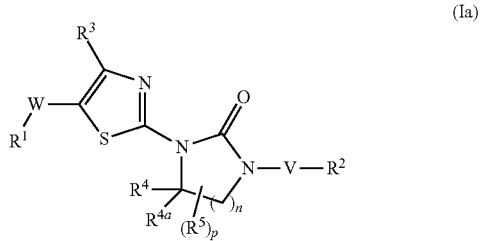

(Ia)

where n, p, V, W, $R^1$, $R^2$, $R^3$, $R^4$, $R^{4a}$ and $R^5$ are as defined above in the Summary of the Invention.

Of this group of compounds, a subgroup of compounds are those compounds wherein n is 1; p is 0; W is —N($R^6$)C(O)—, —C(O)—, —OC(O)— or a direct bond; V is —$R^8$—C(O)—, —$R^8$—C(O)O—, —$R^8$—C(O)N($R^6$)— or a direct bond; $R^1$ is halo, hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; $R^3$ is hydrogen, alkyl or haloalkyl; each of $R^4$ and $R^{4a}$ is independently hydrogen, hydroxyl or alkoxy; or $R^4$ and $R^{4a}$ are together to form an oxo (═O) group; each $R^6$ is independently hydrogen, alkyl, hydroxyalkyl, cycloalkylalkyl, aryl, heteroaryl, heterocyclyl or aralkyl; and each $R^8$ is a direct bond, an optionally substituted straight or branched alkylene chain, an optionally substituted straight or branched alkenylene chain or an optionally substituted straight or branched alkynylene chain.

Of this subgroup, a set of compounds are those compounds where W is —N($R^6$)C(O)—; V is —$R^8$—C(O)—, —$R^3$—C(O)O—, —$R^8$—C(O)N($R^6$)— or a direct bond; $R^3$ is alkyl; each of $R^4$ and $R^{4a}$ is hydrogen; each $R^6$ is hydrogen or alkyl; and each $R^8$ is a direct bond or an optionally substituted straight or branched alkylene chain.

Of this set of compounds, a subset of compounds are those compounds where W is —N(H)C(O)—; V is —$R^8$—C(O)N($R^6$)— or a direct bond; and $R^3$ is methyl.

Of this subset of compounds, a further subset of compounds are those compounds where each $R^1$ and $R^2$ is independently aralkyl.

Specific embodiments of this further subset of compounds include the following:
N-benzyl-2-(3-benzyl-2-oxoimidazolidin-1-yl)-4-methylthiazole-5-carboxamide;
2-(3-benzyl-2-oxoimidazolidin-1-yl)-N-(3-fluorobenzyl)-4-methylthiazole-5-carboxamide;
2-(3-benzyl-2-oxoimidazolidin-1-yl)-N-(4-fluorobenzyl)-4-methylthiazole-5-carboxamide;
2-(3-benzyl-2-oxoimidazolidin-1-yl)-N-(2-fluorobenzyl)-4-methylthiazole-5-carboxamide;
2-(3-benzyl-2-oxoimidazolidin-1-yl)-N-(2,5-difluorobenzyl)-4-methylthiazole-5-carboxamide;
2-(3-benzyl-2-oxoimidazolidin-1-yl)-N-(3,5-difluorobenzyl)-4-methylthiazole-5-carboxamide;
2-(3-benzyl-2-oxoimidazolidin-1-yl)-N-(2,4-difluorobenzyl)-4-methylthiazole-5-carboxamide;
2-(3-benzyl-2-oxoimidazolidin-1-yl)-N-(3,4-difluorobenzyl)-4-methylthiazole-5-carboxamide;
2-(3-benzyl-2-oxoimidazolidin-1-yl)-N-(3-chlorobenzyl)-4-methylthiazole-5-carboxamide;
N-benzyl-4-methyl-2-(2-oxo-3-phenethylimidazolidin-1-yl)thiazole-5-carboxamide;
N-benzyl-4-methyl-2-(2-oxo-3-(4-(trifluoromethyl)benzyl)imidazolidin-1-yl)thiazole-5-carboxamide;
N-(4-fluorobenzyl)-2-(3-(4-fluorobenzyl)-2-oxoimidazolidin-1-yl)-4-methylthiazole-5-carboxamide;
N-benzyl-2-(3-(4-fluorobenzyl)-2-oxoimidazolidin-1-yl)-4-methylthiazole-5-carboxamide;
N-benzyl-4-methyl-2-(2-oxo-3-(4-(trifluoromethoxy)benzyl)imidazolidin-1-yl)thiazole-5-carboxamide;
(R)—N-(2-hydroxy-2-phenylethyl)-4-methyl-2-(2-oxo-3-(4-(trifluoromethoxy)benzyl)imidazolidin-1-yl)thiazole-5-carboxamide;
4-methyl-2-(2-oxo-3-(4-(trifluoromethoxy)benzyl)imidazolidin-1-yl)-N-phenethylthiazole-5-carboxamide;
N-benzyl-2-(3-(4-cyanobenzyl)-2-oxoimidazolidin-1-yl)-4-methylthiazole-5-carboxamide;
N-benzyl-4-methyl-2-(2-oxo-3-(2-(trifluoromethyl)benzyl)imidazolidin-1-yl)thiazole-5-carboxamide;
ethyl 3-((3-(5-(benzylcarbamoyl)-4-methylthiazol-2-yl)-2-oxoimidazolidin-1-yl)methyl)benzoate;
N-benzyl-2-(3-(3-fluorobenzyl)-2-oxoimidazolidin-1-yl)-4-methylthiazole-5-carboxamide;
methyl 3-((3-(5-(benzylcarbamoyl)-4-methylthiazol-2-yl)-2-oxoimidazolidin-1-yl)methyl)benzoate;
methyl 2-((3-(5-(benzylcarbamoyl)-4-methylthiazol-2-yl)-2-oxoimidazolidin-1-yl)methyl)benzoate;

3-((3-(5-(benzylcarbamoyl)-4-methylthiazol-2-yl)-2-ox-
oimidazolidin-1-yl)methyl)benzoic acid;
N-benzyl-2-(3-(2-(4-fluorobenzylamino)-2-oxoethyl)-2-ox-
oimidazolidin-1-yl)-4-methylthiazole-5-carboxamide;
3-((3-(5-(benzylcarbamoyl)-4-methylthiazol-2-yl)-2-ox-
oimidazolidin-1-yl)methyl)benzoic acid; and
2-((3-(5-(benzylcarbamoyl)-4-methylthiazol-2-yl)-2-ox-
oimidazolidin-1-yl)methyl)benzoic acid.

Of the subset of compounds first set forth above, another further subset of compounds are those compounds where $R^1$ is alkyl and $R^2$ is aralkyl.

Specific embodiments of this further subset of compounds include the following:
N-ethyl-4-methyl-2-(2-oxo-3-(4-(trifluoromethoxy)benzyl)
imidazolidin-1-yl)thiazole-5-carboxamide; and
2-(3-(4-fluorobenzyl)-2-oxoimidazolidin-1-yl)-N,4-dimeth-
ylthiazole-5-carboxamide.

Of the subset of compounds first set forth above, another further subset of compounds are those compounds where $R^1$ is aralkyl and $R^2$ is cycloalkylalkyl.

Specific embodiments of this further subset of compounds include the following:
N-benzyl-2-(3-(cyclopropylmethyl)-2-oxoimidazolidin-1-
yl)-4-methylthiazole-5-carboxamide;
2-(3-(cyclopropylmethyl)-2-oxoimidazolidin-1-yl)-N-(4-
fluorobenzyl)-4-methylthiazole-5-carboxamide;
N-benzyl-2-(3-(2-cyclopropylethyl)-2-oxoimidazolidin-1-
yl)-4-methylthiazole-5-carboxamide; and
2-(3-(2-cyclopropylethyl)-2-oxoimidazolidin-1-yl)-N-(4-
fluorobenzyl)-4-methylthiazole-5-carboxamide.

Of the subset of compounds first set forth above, another further subset of compounds are those compounds where $R^1$ is aralkyl and $R^2$ is heteroarylalkyl.

Specific embodiments of this further subset of compounds include the following:
N-benzyl-4-methyl-2-(2-oxo-3-((5-(trifluoromethyl)furan-
2-yl)methyl)imidazolidin-1-yl)thiazole-5-carboxamide;
N-benzyl-4-methyl-2-(3-((5-methyl-1-phenyl-1H-1,2,4-
triazol-3-yl)methyl)-2-oxoimidazolidin-1-yl)thiazole-5-
carboxamide;
2-(3-(2-(1H-indol-3-yl)ethyl)-2-oxoimidazolidin-1-yl)-N-
benzyl-4-methylthiazole-5-carboxamide; N-benzyl-2-(3-
((2,3-dihydrobenzo[b][1,4]dioxin-2-yl)methyl)-2-ox-
oimidazolidin-1-yl)-4-methylthiazole-5-carboxamide;
and
N-benzyl-4-methyl-2-(2-oxo-3-(pyridin-3-ylmethyl)imida-
zolidin-1-yl)thiazole-5-carboxamide.

Of the subset of compounds first set forth above, another further subset of compounds are those compounds where $R^1$ is aralkyl and $R^2$ is aryl.

Specific embodiments of this further subset of compounds is N-benzyl-4-methyl-2-(2-oxo-3-phenylimidazolidin-1-yl)
thiazole-5-carboxamide.

Of the subset of compounds first set forth above, another further subset of compounds are those compounds where $R^1$ is cycloalkylalkyl and $R^2$ is aralkyl.

Specific embodiments of this further subset of compounds include the following:
N-(2-cyclopropylethyl)-4-methyl-2-(2-oxo-3-(4-(trifluo-
romethoxy)benzyl)imidazolidin-1-yl)thiazole-5-carboxa-
mide; and
N-(cyclopropylmethyl)-4-methyl-2-(2-oxo-3-(4-(trifluo-
romethoxy)benzyl)imidazolidin-1-yl)thiazole-5-carboxa-
mide.

Of the subset of compounds first set forth above, another further subset of compounds are those compounds where $R^1$ is heterocyclylalkyl and $R^2$ is aralkyl.

Specific embodiments of this further subset of compounds is 2-(3-(4-fluorobenzyl)-2-oxoimidazolidin-1-yl)-4-methyl-
N-(2-(pyrrolidin-1-yl)ethyl)thiazole-5-carboxamide.

Of the subset of compounds first set forth above, another further subset of compounds are those compounds where $R^1$ is heteroarylalkyl and $R^2$ is aralkyl.

Specific embodiments of this further subset of compounds include the following:
2-(3-benzyl-2-oxoimidazolidin-1-yl)-4-methyl-N-(pyridin-
3-ylmethyl)thiazole-5-carboxamide;
2-(3-benzyl-2-oxoimidazolidin-1-yl)-4-methyl-N-(pyridin-
2-ylmethyl)thiazole-5-carboxamide;
2-(3-benzyl-2-oxoimidazolidin-1-yl)-4-methyl-N-(pyridin-
4-ylmethyl)thiazole-5-carboxamide;
2-(3-benzyl-2-oxoimidazolidin-1-yl)-4-methyl-N-((5-meth-
ylfuran-2-yl)methyl)thiazole-5-carboxamide;
4-methyl-2-(2-oxo-3-(4-(trifluoromethyl)benzyl)imidazoli-
din-1-yl)-N-(pyridin-3-ylmethyl)thiazole-5-carboxamide;
2-(3-(4-fluorobenzyl)-2-oxoimidazolidin-1-yl)-4-methyl-N-
(pyridin-3-ylmethyl)thiazole-5-carboxamide;
4-methyl-2-(2-oxo-3-(4-(trifluoromethoxy)benzyl)imidazo-
lidin-1-yl)-N-(pyridin-3-ylmethyl)thiazole-5-carboxam-
ide;
2-(3-(4-(difluoromethoxy)benzyl)-2-oxoimidazolidin-1-yl)-
4-methyl-N-(pyridin-3-ylmethyl)thiazole-5-carboxam-
ide;
4-methyl-2-(2-oxo-3-(3-phenylpropyl)imidazolidin-1-yl)-
N-(pyridin-3-ylmethyl)thiazole-5-carboxamide;
2-(3-(4-chlorobenzyl)-2-oxoimidazolidin-1-yl)-4-methyl-
N-(pyridin-3-ylmethyl)thiazole-5-carboxamide;
4-methyl-2-(2-oxo-3-(4-(trifluoromethoxy)benzyl)imidazo-
lidin-1-yl)-N-(2-(pyridin-3-yl)ethyl)thiazole-5-carboxa-
mide;
4-methyl-N-((5-methylpyrazin-2-yl)methyl)-2-(2-oxo-3-(4-
(trifluoromethyl)benzyl)imidazolidin-1-yl)thiazole-5-car-
boxamide;
4-methyl-2-(2-oxo-3-(3-(trifluoromethyl)benzyl)imidazoli-
din-1-yl)-N-(pyridin-3-ylmethyl)thiazole-5-carboxamide;
N-((5-(difluoromethyl)furan-2-yl)methyl)-2-(3-(4-fluo-
robenzyl)-2-oxoimidazolidin-1-yl)-4-methylthiazole-5-
carboxamide;
2-(3-(4-fluorobenzyl)-2-oxoimidazolidin-1-yl)-4-methyl-N-
((5-methylpyrazin-2-yl)methyl)thiazole-5-carboxamide;
2-(3-(4-fluorobenzyl)-2-oxoimidazolidin-1-yl)-4-methyl-N-
(oxazol-2-ylmethyl)thiazole-5-carboxamide;
2-(3-(4-fluorobenzyl)-2-oxoimidazolidin-1-yl)-4-methyl-N-
((2-methylthiazol-5-yl)methyl)thiazole-5-carboxamide;
2-(3-(4-fluorobenzyl)-2-oxoimidazolidin-1-yl)-4-methyl-N-
((1-methyl-1H-pyrazol-4-yl)methyl)thiazole-5-carboxa-
mide;
2-(3-(4-fluorobenzyl)-2-oxoimidazolidin-1-yl)-4-methyl-N-
(pyrimidin-4-ylmethyl)thiazole-5-carboxamide;
2-(3-(4-fluorobenzyl)-2-oxoimidazolidin-1-yl)-4-methyl-N-
(pyridazin-3-ylmethyl)thiazole-5-carboxamide;
2-(3-(4-fluorobenzyl)-2-oxoimidazolidin-1-yl)-4-methyl-N-
(pyrimidin-2-ylmethyl)thiazole-5-carboxamide;
2-(3-(4-fluorobenzyl)-2-oxoimidazolidin-1-yl)-4-methyl-N-
(pyrazin-2-ylmethyl)thiazole-5-carboxamide;
2-(3-(4-fluorobenzyl)-2-oxoimidazolidin-1-yl)-4-methyl-N-
(pyridin-2-ylmethyl)thiazole-5-carboxamide; and
2-(3-(4-fluorobenzyl)-2-oxoimidazolidin-1-yl)-4-methyl-N-
(pyridin-4-ylmethyl)thiazole-5-carboxamide.

Of the subset of compounds first set forth above, another further subset of compounds are those compounds where $R^1$ is heteroarylalkyl and $R^2$ is cycloalkylalkyl.

Specific embodiments of this further subset of compounds include the following:

2-(3-(cyclopropylmethyl)-2-oxoimidazolidin-1-yl)-4-methyl-N-(pyridin-3-ylmethyl)thiazole-5-carboxamide;
2-(3-(2-cyclopropylethyl)-2-oxoimidazolidin-1-yl)-4-methyl-N-(pyridin-3-ylmethyl)thiazole-5-carboxamide;
2-(3-(cyclohexylmethyl)-2-oxoimidazolidin-1-yl)-4-methyl-N-(pyridin-3-ylmethyl)thiazole-5-carboxamide;
4-methyl-2-(2-oxo-3-((tetrahydro-2H-pyran-2-yl)methyl)imidazolidin-1-yl)-N-(pyridin-3-ylmethyl)thiazole-5-carboxamide;
2-(3-(cyclobutylmethyl)-2-oxoimidazolidin-1-yl)-4-methyl-N-(pyridin-3-ylmethyl)thiazole-5-carboxamide;
2-(3-(cyclopentylmethyl)-2-oxoimidazolidin-1-yl)-4-methyl-N-(pyridin-3-ylmethyl)thiazole-5-carboxamide; and
2-(3-(cyclopropylmethyl)-2-oxoimidazolidin-1-yl)-4-methyl-N-(pyridin-2-ylmethyl)thiazole-5-carboxamide.

Of the subset of compounds first set forth above, another further subset of compounds are those compounds where $R^1$ is aryl and $R^2$ is aralkyl.

Specific embodiments of this further subset of compounds is 4-methyl-2-(2-oxo-3-(4-(trifluoromethoxy)benzyl)imidazolidin-1-yl)-N-phenylthiazole-5-carboxamide.

Of the subset of compounds first set forth above, another further subset of compounds are those compounds where $R^1$ is heteroarylalkyl and $R^2$ is heterocyclylalkyl.

Specific embodiments of this further subset of compounds is 4-methyl-2-(2-oxo-3-((tetrahydro-2H-pyran-2-yl)methyl)imidazolidin-1-yl)-N-(pyridin-3-ylmethyl)thiazole-5-carboxamide.

Of the subset of compounds first set forth above, another further subset of compounds are those compounds where $R^1$ is heteroarylalkyl and $R^2$ is alkyl.

Specific embodiments of this further subset of compounds include the following:
2-(3-ethyl-2-oxoimidazolidin-1-yl)-4-methyl-N-(pyridin-3-ylmethyl)thiazole-5-carboxamide;
4-methyl-2-(2-oxo-3-propylimidazolidin-1-yl)-N-(pyridin-3-ylmethyl)thiazole-5-carboxamide;
2-(3-butyl-2-oxoimidazolidin-1-yl)-4-methyl-N-(pyridin-3-ylmethyl)thiazole-5-carboxamide; and
4-methyl-2-(2-oxo-3-pentylimidazolidin-1-yl)-N-(pyridin-3-ylmethyl)thiazole-5-carboxamide.

Of the subset of compounds first set forth above, another further subset of compounds are those compounds where each $R^1$ and $R^2$ is independently heteroarylalkyl.

Specific embodiments of this further subset of compounds include the following:
2-(3-((5-(difluoromethyl)furan-2-yl)methyl)-2-oxoimidazolidin-1-yl)-4-methyl-N-(pyridin-3-ylmethyl)thiazole-5-carboxamide
2-(3-((5-chlorobenzo[b]thiophen-3-yl)methyl)-2-oxoimidazolidin-1-yl)-4-methyl-N-(pyridin-3-ylmethyl)thiazole-5-carboxamide;
2-(3-(isoquinolin-1-ylmethyl)-2-oxoimidazolidin-1-yl)-4-methyl-N-(pyridin-3-ylmethyl)thiazole-5-carboxamide;
4-methyl-2-(2-oxo-3-(quinolin-8-ylmethyl)imidazolidin-1-yl)-N-(pyridin-3-ylmethyl)thiazole-5-carboxamide;
4-methyl-2-(3-((5-methylisoxazol-3-yl)methyl)-2-oxoimidazolidin-1-yl)-N-(pyridin-3-ylmethyl)thiazole-5-carboxamide;
4-methyl-2-(3-((3-methyl-5-phenylisoxazol-4-yl)methyl)-2-oxoimidazolidin-1-yl)-N-(pyridin-3-ylmethyl)thiazole-5-carboxamide;
4-methyl-2-(2-oxo-3-((5-phenyloxazol-4-yl)methyl)imidazolidin-1-yl)-N-(pyridin-3-ylmethyl)thiazole-5-carboxamide;
2-(3-(benzo[c][1,2,5]oxadiazol-5-ylmethyl)-2-oxoimidazolidin-1-yl)-4-methyl-N-(pyridin-3-ylmethyl)thiazole-5-carboxamide;
2-(3-(benzo[c][1,2,5]thiadiazol-5-ylmethyl)-2-oxoimidazolidin-1-yl)-4-methyl-N-(pyridin-3-ylmethyl)thiazole-5-carboxamide;
4-methyl-2-(2-oxo-3-(pyridin-2-ylmethyl)imidazolidin-1-yl)-N-(pyridin-3-ylmethyl)thiazole-5-carboxamide;
2-(3-(2-(1H-indol-3-yl)ethyl)-2-oxoimidazolidin-1-yl)-4-methyl-N-(pyridin-3-ylmethyl)thiazole-5-carboxamide; and
4-methyl-2-(2-oxo-3-(pyridin-4-ylmethyl)imidazolidin-1-yl)-N-(pyridin-3-ylmethyl)thiazole-5-carboxamide.

Of the subset of compounds first set forth above, another further subset of compounds are those compounds where each $R^1$ and $R^2$ is independently hydrogen or aralkyl.

Specific embodiments of this further subset of compounds include the following:
N-benzyl-4-methyl-2-(2-oxoimidazolidin-1-yl)thiazole-5-carboxamide; and
2-(3-(4-fluorobenzyl)-2-oxoimidazolidin-1-yl)-4-methylthiazole-5-carboxamide.

Of the subset of compounds first set forth above, another further subset of compounds are those compounds where $R^1$ is aralkyl and $R^2$ is heterocyclylalkyl.

Specific embodiments of this further subset of compounds is N-benzyl-4-methyl-2-(2-oxo-3-((tetrahydro-2H-pyran-2-yl)methyl)imidazolidin-1-yl)thiazole-5-carboxamide.

Of the set of compounds first set forth above, another subset of compounds are those compounds where W is —N($R^6$)C(O)—; V is —$R^8$—C(O)O—; and $R^3$ is methyl.

Of this subset of compounds, a further subset of compounds are those compounds where $R^1$ is aralkyl and $R^2$ is hydrogen or alkyl.

Specific embodiments of this further subset of compounds including the following:
ethyl 2-(3-(5-(benzylcarbamoyl)-4-methylthiazol-2-yl)-2-oxoimidazolidin-1-yl)acetate; and
2-(3-(5-(benzylcarbamoyl)-4-methylthiazol-2-yl)-2-oxoimidazolidin-1-yl)acetic acid.

Of the set of compounds first set forth above, another subset of compounds are those compounds where W is —N($R^6$)C(O)—; V is —$R^8$—C(O)—; and $R^3$ is methyl.

Of this subset of compounds, a further subset of compounds are those where $R^1$ is aralkyl and $R^2$ is alkyl.

Specific embodiments of this further subset of compounds is N-benzyl-2-(3-(4-fluorobenzoyl)-2-oxoimidazolidin-1-yl)-4-methylthiazole-5-carboxamide.

Of the set of compounds first set forth above, another subset of compounds are those compounds where W is —N($R^6$)C(O)—; V is a direct bond; and $R^3$ is methyl.

Of this subset of compounds, a further subset of compounds are those compounds where $R^1$ is alkyl or heteroarylalkyl and $R^2$ is aralkyl or alkyl.

Specific embodiments of this further subset of compounds is 2-(3-(4-fluorobenzyl)-2-oxoimidazolidin-1-yl)-N,N-4-trimethylthiazole-5-carboxamide.

Of the set of compounds first set forth above, another subset of compounds are those compounds where W is —OC(O)—; V is a direct bond; and $R^3$ is methyl.

Of this subset of compounds, a further subset of compounds are those compounds where $R^1$ is alkyl and $R^2$ is hydrogen.

Specific embodiments of this further subset of compounds is ethyl 4-methyl-2-(2-oxoimidazolidin-1-yl)thiazole-5-carboxylate.

Of this subset of compounds, a further subset of compounds are those compounds where $R^1$ is alkyl and $R^2$ is aryl.

Specific embodiments of this further subset of compounds is ethyl 4-methyl-2-(2-oxo-3-phenylimidazolidin-1-yl)thiazole-5-carboxylate.

Of this subset of compounds, a further subset of compounds are those compounds where $R^1$ is alkyl and $R^2$ is aralkyl.

Specific embodiments of this further subset of compounds include the following:
ethyl 2-(3-benzyl-2-oxoimidazolidin-1-yl)-4-methylthiazole-5-carboxylate;
ethyl 4-methyl-2-(2-oxo-3-phenethylimidazolidin-1-yl)thiazole-5-carboxylate;
ethyl 4-methyl-2-(2-oxo-3-(4-(trifluoromethyl)benzyl)imidazolidin-1-yl)thiazole-5-carboxylate;
ethyl 2-(3-(4-fluorobenzyl)-2-oxoimidazolidin-1-yl)-4-methylthiazole-5-carboxylate;
ethyl 4-methyl-2-(2-oxo-3-(4-(trifluoromethoxy)benzyl)imidazolidin-1-yl)thiazole-5-carboxylate;
ethyl 2-(3-(4-(difluoromethoxy)benzyl)-2-oxoimidazolidin-1-yl)-4-methylthiazole-5-carboxylate;
ethyl 4-methyl-2-(2-oxo-3-(3-(trifluoromethyl)benzyl)imidazolidin-1-yl)thiazole-5-carboxylate;
ethyl 4-methyl-2-(2-oxo-3-(3-phenylpropyl)imidazolidin-1-yl)thiazole-5-carboxylate;
ethyl 2-(3-(4-chlorobenzyl)-2-oxoimidazolidin-1-yl)-4-methylthiazole-5-carboxylate; and
ethyl 2-(3-(4-fluorobenzyl)-2-oxoimidazolidin-1-yl)-4-methylthiazole-5-carboxylate.

Of this subset of compounds, a further subset of compounds are those compounds where each $R^1$ and $R^2$ is independently alkyl.

Specific embodiments of this further subset of compounds include the following:
ethyl 2-(3-ethyl-2-oxoimidazolidin-1-yl)-4-methylthiazole-5-carboxylate;
ethyl 4-methyl-2-(2-oxo-3-propylimidazolidin-1-yl)thiazole-5-carboxylate;
ethyl 2-(3-butyl-2-oxoimidazolidin-1-yl)-4-methylthiazole-5-carboxylate; and
ethyl 4-methyl-2-(2-oxo-3-pentylimidazolidin-1-yl)thiazole-5-carboxylate.

Of this subset of compounds, a further subset of compounds are those compounds where $R^1$ is alkyl and $R^2$ is cycloalkylalkyl.

Specific embodiments of this further subset of compounds include the following:
ethyl 2-(3-(cyclopropylmethyl)-2-oxoimidazolidin-1-yl)-4-methylthiazole-5-carboxylate;
ethyl 2-(3-(2-cyclopropylethyl)-2-oxoimidazolidin-1-yl)-4-methylthiazole-5-carboxylate;
ethyl 2-(3-(cyclohexylmethyl)-2-oxoimidazolidin-1-yl)-4-methylthiazole-5-carboxylate;
ethyl 2-(3-(cyclobutylmethyl)-2-oxoimidazolidin-1-yl)-4-methylthiazole-5-carboxylate; and
ethyl 2-(3-(cyclopentylmethyl)-2-oxoimidazolidin-1-yl)-4-methylthiazole-5-carboxylate.

Of this subset of compounds, a further subset of compounds are those compounds where $R^1$ is hydrogen and $R^2$ is aryl.

Specific embodiments of this further subset of compounds is 4-methyl-2-(2-oxo-3-phenylimidazolidin-1-yl)thiazole-5-carboxylic acid.

Of this subset of compounds, a further subset of compounds are those compounds where $R^1$ is hydrogen and $R^2$ is aralkyl.

Specific embodiments of this further subset of compounds include the following:
2-(3-benzyl-2-oxoimidazolidin-1-yl)-4-methylthiazole-5-carboxylic acid;
4-methyl-2-(2-oxo-3-phenethylimidazolidin-1-yl)thiazole-5-carboxylic acid;
4-methyl-2-(2-oxo-3-(4-(trifluoromethyl)benzyl)imidazolidin-1-yl)thiazole-5-carboxylic acid;
2-(3-(4-fluorobenzyl)-2-oxoimidazolidin-1-yl)-4-methylthiazole-5-carboxylic acid;
4-methyl-2-(2-oxo-3-(4-(trifluoromethoxy)benzyl)imidazolidin-1-yl)thiazole-5-carboxylic acid;
2-(3-(4-(difluoromethoxy)benzyl)-2-oxoimidazolidin-1-yl)-4-methylthiazole-5-carboxylic acid;
4-methyl-2-(2-oxo-3-(3-phenylpropyl)imidazolidin-1-yl)thiazole-5-carboxylic acid;
2-(3-(4-chlorobenzyl)-2-oxoimidazolidin-1-yl)-4-methylthiazole-5-carboxylic acid;
4-methyl-2-(2-oxo-3-(3-(trifluoromethyl)benzyl)imidazolidin-1-yl)thiazole-5-carboxylic acid; and
2-(3-(4-fluorobenzyl)-2-oxoimidazolidin-1-yl)-4-methylthiazole-5-carboxylic acid.

Of this subset of compounds, a further subset of compounds are those compounds where $R^1$ is hydrogen and $R^2$ is cycloalkylalkyl.

Specific embodiments of this further subset of compounds include the following:
2-(3-(cyclopropylmethyl)-2-oxoimidazolidin-1-yl)-4-methylthiazole-5-carboxylic acid;
2-(3-(2-cyclopropylethyl)-2-oxoimidazolidin-1-yl)-4-methylthiazole-5-carboxylic acid;
2-(3-(cyclohexylmethyl)-2-oxoimidazolidin-1-yl)-4-methylthiazole-5-carboxylic acid;
2-(3-(cyclobutylmethyl)-2-oxoimidazolidin-1-yl)-4-methylthiazole-5-carboxylic acid; and
2-(3-(cyclopentylmethyl 1)-2-oxoimidazolidin-1-yl)-4-methylthiazole-5-carboxylic acid.

Of this subset of compounds, a further subset of compounds are those compounds where $R^1$ is hydrogen and $R^2$ is heteroarylalkyl.

Specific embodiments of this further subset of compounds include the following:
2-(3-((5-chlorobenzo[b]thiophen-3-yl)methyl)-2-oxoimidazolidin-1-yl)-4-methylthiazole-5-carboxylic acid;
2-(3-(2-(1H-indol-3-yl)ethyl)-2-oxoimidazolidin-1-yl)-4-methylthiazole-5-carboxylic acid;
2-(3-((5-(difluoromethyl)furan-2-yl)methyl)-2-oxoimidazolidin-1-yl)-4-methylthiazole-5-carboxylic acid;
2-(3-(isoquinolin-1-ylmethyl)-2-oxoimidazolidin-1-yl)-4-methylthiazole-5-carboxylic acid;
4-methyl-2-(2-oxo-3-(quinolin-8-ylmethyl)imidazolidin-1-yl)thiazole-5-carboxylic acid;
4-methyl-2-(3-((5-methylisoxazol-3-yl)methyl)-2-oxoimidazolidin-1-yl)thiazole-5-carboxylic acid;
4-methyl-2-(3-((3-methyl-5-phenylisoxazol-4-yl)methyl)-2-oxoimidazolidin-1-yl)thiazole-5-carboxylic acid;
4-methyl-2-(2-oxo-3-((5-phenyloxazol-4-yl)methyl)imidazolidin-1-yl)thiazole-5-carboxylic acid;
2-(3-(benzo[c][1,2,5]oxadiazol-5-ylmethyl)-2-oxoimidazolidin-1-yl)-4-methylthiazole-5-carboxylic acid;
2-(3-(benzo[c][1,2,5]thiadiazol-5-ylmethyl)-2-oxoimidazolidin-1-yl)-4-methylthiazole-5-carboxylic acid;
4-methyl-2-(2-oxo-3-(pyridin-2-ylmethyl)imidazolidin-1-yl)thiazole-5-carboxylic acid;
4-methyl-2-(2-oxo-3-(pyridin-4-ylmethyl)imidazolidin-1-yl)thiazole-5-carboxylic acid; and 4-methyl-2-(2-oxo-3-(pyridin-2-ylmethyl)imidazolidin-1-yl)thiazole-5-carboxylic acid.

Of this subset of compounds, a further subset of compounds are those compounds where $R^1$ is hydrogen and $R^2$ is heterocyclylalkyl.

Specific embodiments of this further subset of compounds is 4-methyl-2-(2-oxo-3-((tetrahydro-2H-pyran-2-yl)methyl)imidazolidin-1-yl)thiazole-5-carboxylic acid.

Of this subset of compounds, a further subset of compounds are those compounds where $R^1$ is hydrogen and $R^2$ is alkyl.

Specific embodiments of this further subset of compounds include the following:
2-(3-ethyl-2-oxoimidazolidin-1-yl)-4-methylthiazole-5-carboxylic acid;
4-methyl-2-(2-oxo-3-propylimidazolidin-1-yl)thiazole-5-carboxylic acid;
2-(3-butyl-2-oxoimidazolidin-1-yl)-4-methylthiazole-5-carboxylic acid; and
4-methyl-2-(2-oxo-3-pentylimidazolidin-1-yl)thiazole-5-carboxylic acid.

Of this subset of compounds, a further subset of compounds are those compounds where $R^1$ is alkyl and $R^2$ is heterocyclylalkyl.

Specific embodiments of this further subset of compounds is ethyl 4-methyl-2-(2-oxo-3-((tetrahydro-2H-pyran-2-yl)methyl)imidazolidin-1-yl)thiazole-5-carboxylate.

Of this subset of compounds, a further subset of compounds are those compounds where $R^1$ is alkyl and $R^2$ is heteroarylalkyl.

Specific embodiments of this further subset of compounds include the following:
ethyl 2-(3-((5-chlorobenzo[b]thiophen-3-yl)methyl)-2-oxoimidazolidin-1-yl)-4-methylthiazole-5-carboxylate;
ethyl 2-(3-(isoquinolin-1-ylmethyl)-2-oxoimidazolidin-1-yl)-4-methylthiazole-5-carboxylate;
ethyl 4-methyl-2-(2-oxo-3-(quinolin-8-ylmethyl)imidazolidin-1-yl)thiazole-5-carboxylate;
ethyl 4-methyl-2-(3-((5-methylisoxazol-3-yl)methyl)-2-oxoimidazolidin-1-yl)thiazole-5-carboxylate;
ethyl 4-methyl-2-(3-((3-methyl-5-phenylisoxazol-4-yl)methyl)-2-oxoimidazolidin-1-yl)thiazole-5-carboxylate;
ethyl 4-methyl-2-(2-oxo-3-((5-phenyloxazol-4-yl)methyl)imidazolidin-1-yl)thiazole-5-carboxylate;
ethyl 2-(3-(benzo[c][1,2,5]oxadiazol-5-ylmethyl)-2-oxoimidazolidin-1-yl)-4-methylthiazole-5-carboxylate;
ethyl 2-(3-(benzo[c][1,2,5]thiadiazol-5-ylmethyl)-2-oxoimidazolidin-1-yl)-4-methylthiazole-5-carboxylate;
ethyl 4-methyl-2-(2-oxo-3-(pyridin-2-ylmethyl)imidazolidin-1-yl)thiazole-5-carboxylate;
ethyl 4-methyl-2-(2-oxo-3-(pyridin-4-ylmethyl)imidazolidin-1-yl)thiazole-5-carboxylate;
ethyl 4-methyl-2-(2-oxo-3-(pyridin-2-ylmethyl)imidazolidin-1-yl)thiazole-5-carboxylate;
ethyl 2-(3-(2-(1H-indol-3-yl)ethyl)-2-oxoimidazolidin-1-yl)-4-methylthiazole-5-carboxylate; and
ethyl 2-(3-((5-(difluoromethyl)furan-2-yl)methyl)-2-oxoimidazolidin-1-yl)-4-methylthiazole-5-carboxylate.

Of the subgroup first set forth above, another set of compounds are those compounds where W is —C(O)—; V is direct bond; $R^3$ is alkyl; and each of $R^4$ and $R^{4a}$ is hydrogen; and each $R^6$ is hydrogen or alkyl.

Of this set of compounds, a subset of compounds are those compounds where W is —C(O)—; V is a direct bond; and $R^3$ is methyl.

Of this subset of compounds, a further subset of compounds are those compounds where $R^1$ is alkyl and $R^2$ is aralkyl.

Specific embodiments of this further subset of compounds including the following:
1-(5-acetyl-4-methylthiazol-2-yl)-3-(4-(trifluoromethyl)benzyl)imidazolidin-2-one;
methyl 4-((3-(5-acetyl-4-methylthiazol-2-yl)-2-oxoimidazolidin-1-yl)methyl)benzoate;
1-(5-acetyl-4-methylthiazol-2-yl)-3-(4-fluorobenzyl)imidazolidin-2-one;
methyl 3-((3-(5-acetyl-4-methylthiazol-2-yl)-2-oxoimidazolidin-1-yl)methyl)benzoate;
4-((3-(5-acetyl-4-methylthiazol-2-yl)-2-oxoimidazolidin-1-yl)methyl)benzoic acid;
3-((3-(5-acetyl-4-methylthiazol-2-yl)-2-oxoimidazolidin-1-yl)methyl)benzoic acid;
1-(5-acetyl-4-methylthiazol-2-yl)-3-(4-(piperidine-1-carbonyl)benzyl)imidazolidin-2-one;
4-((3-(5-acetyl-4-methylthiazol-2-yl)-2-oxoimidazolidin-1-yl)methyl)-N-methylbenzamide;
3-((3-(5-acetyl-4-methylthiazol-2-yl)-2-oxoimidazolidin-1-yl)methyl)-N-methylbenzamide;
1-(4-methyl-5-(1H-pyrazol-5-yl)thiazol-2-yl)-3-(4-(piperidine-1-carbonyl)benzyl)imidazolidin-2-one; and
N-methyl-3-((3-(4-methyl-5-(3-methyl-1H-pyrazol-5-yl)thiazol-2-yl)-2-oxoimidazolidin-1-yl)methyl)benzamide.

Of this subset of compounds, a further subset of compounds are those compounds where $R^1$ is alkyl and $R^2$ is hydrogen.

Specific embodiments of this further subset of compounds is 1-(5-acetyl-4-methylthiazol-2-yl)imidazolidin-2-one.

Of this subset of compounds, a further subset of compounds are those compounds where $R^1$ is alkenyl and $R^2$ is aralkyl.

Specific embodiments of this further subset of compounds include the following:
(E)-1-(5-(3-(dimethylamino)acryloyl)-4-methylthiazol-2-yl)-3-(4-(trifluoromethyl)benzyl)imidazolidin-2-one; and
(E)-1-(5-(3-(dimethylamino)but-2-enoyl)-4-methylthiazol-2-yl)-3-(4-(trifluoromethyl)benzyl)imidazolidin-2-one.

Of the subgroup first set forth above, another set of compounds are those where W is a direct bond; V is a direct bond; $R^3$ is alkyl; and each of $R^4$ and $R^{4a}$ is hydrogen; each $R^6$ is hydrogen or alkyl; and each $R^8$ is a direct bond or an optionally substituted straight or branched alkylene chain.

Of this set of compounds, a subset of compounds are those compounds where W is a direct bond; V is a direct bond; and $R^3$ is methyl.

Of this subset of compounds, a further subset of compounds are those compounds where $R^1$ and $R^2$ is hydrogen.

Specific embodiments of this further subset of compounds is 1-(4-methylthiazol-2-yl)imidazolidin-2-one.

Of this subset of compounds, a further subset of compounds are those compounds where $R^1$ is halo or hydrogen and $R^2$ is aralkyl.

Specific embodiments of this further subset of compounds include the following:
methyl 4-((3-(4-methylthiazol-2-yl)-2-oxoimidazolidin-1-yl)methyl)benzoate;
1-(4-methylthiazol-2-yl)-3-(4-(trifluoromethyl)benzyl)imidazolidin-2-one;
4-((3-(4-methylthiazol-2-yl)-2-oxoimidazolidin-1-yl)methyl)benzoic acid;
N-(4-fluorophenyl)-4-(3-(4-methylthiazol-2-yl)-2-oxoimidazolidin-1-yl)methyl)benzamide;

1-(4-(5-methyl-1H-pyrazole-1-carbonyl)benzyl)-3-(4-methylthiazol-2-yl)imidazolidin-2-one;
1-(5-bromo-4-methylthiazol-2-yl)-3-(4-(trifluoromethyl)-benzyl)imidazolidin-2-one;
N-benzyl-4-((3-(4-methylthiazol-2-yl)-2-oxoimidazolidin-1-yl)methyl)benzamide; and
N-(4-methylthiazol-2-yl)-4-(3-(4-methylthiazol-2-yl)-2-oxoimidazolidin-1-yl)methyl)benzamide;

Of this subset of compounds, a further subset of compounds are those compounds where $R^1$ is heteroarylalkyl and $R^2$ is aralkyl.

Specific embodiments of this further subset of compounds include the following:
1-(4-methyl-5-(1H-pyrazol-3-yl)thiazol-2-yl)-3-(4-(trifluoromethyl)-benzyl)imidazolidin-2-one;
1-(5-(isoxazol-5-yl)-4-methylthiazol-2-yl)-3-(4-(trifluoromethyl)benzyl)-imidazolidin-2-one;
1-(4-methyl-5-(5-methyl-1H-pyrazol-3-yl)thiazol-2-yl)-3-(4-(trifluoromethyl)benzyl)imidazolidin-2-one;
1-(4-methyl-5-(3-methylisoxazol-5-yl)thiazol-2-yl)-3-(4-(trifluoromethyl)benzyl)imidazolidin-2-one;
1-(4-methyl-5-(3-methyl-1H-pyrazol-5-yl)thiazol-2-yl)-3-(4-(piperidine-1-carbonyl)benzyl)imidazolidin-2-one;
1-(4-fluorobenzyl)-3-(4-methyl-5-(5-methyl-1H-pyrazol-3-yl)thiazol-2-yl)imidazolidin-2-one;
N-methyl-4-((3-(4-methyl-5-(3-methyl-1H-pyrazol-5-yl)thiazol-2-yl)-2-oxoimidazolidin-1-yl)methyl)benzamide;
1-(4-methyl-5-(oxazol-5-yl)thiazol-2-yl)-3-(4-(trifluoromethyl)benzyl)-imidazolidin-2-one; and
1-(4-methyl-5-(3-methyl-1,2,4-oxadiazol-5-yl)thiazol-2-yl)-3-(4-(trifluoromethyl)benzyl)imidazolidin-2-one.

Of this subset of compounds, a further subset of compounds are those compounds where $R^1$ is hydroxyalkyl and $R^2$ is aralkyl.

Specific embodiments of this further subset of compounds is 1-(5-(hydroxymethyl)-4-methylthiazol-2-yl)-3-(4-(trifluoromethyl)benzyl)imidazolidin-2-one.

Of the subgroup first set forth above, another set of compounds are those compounds where W is —N($R^6$)C(O)—; V is —$R^8$—C(O)—, —$R^8$—C(O)O— or a direct bond; $R^3$ is alkyl; $R^4$ is hydroxyl or alkoxy; $R^{4a}$ is hydrogen; each $R^6$ is hydrogen or alkyl; and each $R^8$ is a direct bond or an optionally substituted straight or branched alkylene chain.

Of this set of compounds, a subset of compounds are those compounds where W is —N(H)C(O)—; V is direct bond; $R^3$ is alkyl; $R^4$ is hydroxyl or methoxy; and $R^{4a}$ is hydrogen.

Of this subset of compounds, a further subset of compounds are those compounds where $R^1$ is aralkyl and $R^2$ is aryl.

Specific embodiments of this further subset of compounds include the following:
N-benzyl-2-(3-(4-fluorophenyl)-5-methoxy-2-oxoimidazolidin-1-yl)-4-methylthiazole-5-carboxamide; and
N-benzyl-2-(3-(4-fluorophenyl)-5-hydroxy-2-oxoimidazolidin-1-yl)-4-methylthiazole-5-carboxamide.

Of this subset of compounds, a further subset of compounds are those compounds where each $R^1$ and $R^2$ are independently aralkyl.

Specific embodiments of this further subset of compounds is N-benzyl-2-(3-(4-fluorobenzyl)-5-hydroxy-2-oxoimidazolidin-1-yl)-4-methylthiazole-5-carboxamide.

Of this subset of compounds, a further subset of compounds are those compounds where $R^1$ is heteroarylalkyl and $R^2$ is aralkyl.

Specific embodiments of this further subset of compounds include the following:
2-(3-(4-fluorophenethyl)-5-hydroxy-2-oxoimidazolidin-1-yl)-4-methyl-N-(pyridin-3-ylmethyl)thiazole-5-carboxamide;
2-(3-(4-fluorobenzyl)-5-hydroxy-2-oxoimidazolidin-1-yl)-4-methyl-N-(pyridin-3-ylmethyl)thiazole-5-carboxamide; and
2-(5-hydroxy-2-oxo-3-(4-(trifluoromethyl)benzyl)imidazolidin-1-yl)-4-methyl-N-(pyridin-3-ylmethyl)thiazole-5-carboxamide.

Of the subgroup first set forth above, another set of compounds are those compounds where W is —N($R^6$)C(O)—; V is —$R^8$—C(O)—, —$R^8$—C(O)O— or a direct bond; $R^3$ is alkyl; $R^4$ and $R^{4a}$ together form oxo; each $R^6$ is hydrogen or alkyl; and each $R^8$ is a direct bond or an optionally substituted straight or branched alkylene chain.

Of this set of compounds, a subset of compounds are those compounds where W is —N($R^6$)C(O)—; V is a direct bond; $R^3$ is methyl; and $R^4$ and $R^{4a}$ together form oxo.

Of this subset of compounds, a further subset of compounds are those compounds where $R^1$ is aralkyl and $R^2$ is alkyl.

Specific embodiments of this further subset of compounds is N-benzyl-2-(3-(4-fluorophenyl)-2,5-dioxoimidazolidin-1-yl)-4-methylthiazole-5-carboxamide.

Of the subgroup first set forth above, another set of compounds are those compounds where W is —N(H)C(O)—; V is a direct bond; $R^3$ is hydrogen or haloalkyl; each $R^4$ and $R^{4a}$ is independently hydrogen; each $R^6$ is hydrogen or alkyl; and each $R^8$ is a direct bond or an optionally substituted straight or branched alkylene chain.

Of this set of compounds, a subset of compounds are those compounds where $R^1$ is heteroarylalkyl and $R^2$ is cycloalkyl or aralkyl.

Specific embodiments of this subset of compounds includes the following:
2-(3-(cyclopropylmethyl)-2-oxoimidazolidin-1-yl)-N-(pyridin-3-ylmethyl)thiazole-5-carboxamide; and
2-(3-(4-fluorobenzyl)-2-oxoimidazolidin-1-yl)-N-(pyridin-3-ylmethyl)-4-(trifluoromethyl)thiazole-5-carboxamide.

Of the subgroup first set forth above, another set of compounds are those compounds where W is —OC(O)—; V is a direct bond; $R^3$ is hydrogen or haloalkyl; and each $R^4$ and $R^{4a}$ is independently hydrogen.

Of this set of compounds, a subset of compounds are those compounds where $R^1$ is hydrogen or aryl and $R^2$ is hydrogen, cycloalkylalkyl or aralkyl.

Specific embodiments of this subset of compounds includes the following:
2-(3-(cyclopropylmethyl)-2-oxoimidazolidin-1-yl)thiazole-5-carboxylic acid; and
2-(3-(4-fluorobenzyl)-2-oxoimidazolidin-1-yl)-4-(trifluoromethyl)thiazole-5-carboxylic acid.

Of this set of compounds, a subset of compounds are those compounds where $R^1$ is alkyl and $R^2$ is hydrogen, cycloalkylalkyl or aralkyl.

Specific embodiments of this subset of compounds includes the following:
methyl 2-(2-oxoimidazolidin-1-yl)thiazole-5-carboxylate;
ethyl 2-(2-oxoimidazolidin-1-yl)-4-(trifluoromethyl)thiazole-5-carboxylate;
methyl 2-(3-(cyclopropylmethyl)-2-oxoimidazolidin-1-yl)thiazole-5-carboxylate; and
ethyl 2-(3-(4-fluorobenzyl)-2-oxoimidazolidin-1-yl)-4-(trifluoromethyl)thiazole-5-carboxylate.

Of the group of compounds first set forth above, another subgroup of compounds are those compounds wherein X is N; Y is S; n is 2; p is 0; W is —N($R^6$)C(O)—, —C(O)—, —OC(O)— or a direct bond; V is —R$^8$—C(O)—, —R$^8$—C(O)O— or a direct bond; R$^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; R$^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; R$^3$ is hydrogen, alkyl or haloalkyl; each of R$^4$ and R$^{4a}$ is independently hydrogen, hydroxyl or alkoxy; or R$^4$ and R$^{4a}$ are together to form an oxo (=O) group; each R$^6$ is independently hydrogen, alkyl, hydroxyalkyl, cycloalkylalkyl, aryl, heteroaryl, heterocyclyl or aralkyl; and each R$^8$ is a direct bond, an optionally substituted straight or branched alkylene chain, an optionally substituted straight or branched alkenylene chain or an optionally substituted straight or branched alkynylene chain.

Of this subgroup, a set of compounds are those compounds where W is —N(R$^6$)C(O)— or —OC(O)—; V is a direct bond; R$^3$ is alkyl; each of R$^4$ and R$^{4a}$ is hydrogen; each R$^6$ is hydrogen or alkyl; and each R$^8$ is a direct bond or an optionally substituted straight or branched alkylene chain.

Of this set of compounds, a subset of compounds are those compounds where W is —N(H)C(O)—; V is a direct bond; and R$^3$ is methyl.

Of this subset of compounds, a further subset of compounds are those compounds where R$^1$ is heteroarylalkyl and R$^2$ is aralkyl or cycloalkylalkyl.

Specific embodiments of this further subset of compounds including the following:
2-(3-(4-fluorobenzyl)-2-oxotetrahydropyrimidin-1(2H)-yl)-4-methyl-N-(pyridin-3-ylmethyl)thiazole-5-carboxamide; and
2-(3-(cyclopropylmethyl)-2-oxotetrahydropyrimidin-1(2H)-yl)-4-methyl-N-(pyridin-3-ylmethyl)thiazole-5-carboxamide.

Of this set of compounds, another subset of compounds are those compounds where W is —OC(O)—; V is direct bond; and R$^3$ is methyl.

Of this subset of compounds, a further subset of compounds are those compounds where R$^1$ is hydrogen or alkyl and R$^2$ is hydrogen, aralkyl or cycloalkylalkyl.

Specific embodiments of this further subset of compounds including the following:
ethyl 4-methyl-2-(2-oxotetrahydropyrimidin-1(2H)-yl)thiazole-5-carboxylate;
ethyl 2-(3-(4-fluorobenzyl)-2-oxotetrahydropyrimidin-1(2H)-yl)-4-methylthiazole-5-carboxylate;
ethyl 2-(3-(cyclopropylmethyl)-2-oxotetrahydropyrimidin-1(2H)-yl)-4-methylthiazole-5-carboxylate; 2-(3-(4-fluorobenzyl)-2-oxotetrahydropyrimidin-1(2H)-yl)-4-methylthiazole-5-carboxylic acid; and
2-(3-(cyclopropylmethyl)-2-oxotetrahydropyrimidin-1(2H)-yl)-4-methylthiazole-5-carboxylic acid.

In another embodiment of the invention, a group of compounds of Formula (Ia) wherein n is 1; p is 1; W is —N(H)C(O)— or —OC(O)—; V is a direct bond; R$^1$ is hydrogen, alkyl or aralkyl; R$^2$ is hydrogen; R$^3$ is alkyl; each of R$^4$ and R$^{4a}$ is hydrogen; and R$^5$ is aralkyl.

Of this group of compounds, a subgroup of compounds are those compounds where W is —N(H)C(O)—, V is a direct bond; R$^1$ is aralkyl; R$^2$ is hydrogen; and R$^3$ is methyl.

Specific embodiments of this subgroup of compounds is (R)—N-benzyl-2-(4-benzyl-2-oxoimidazolidin-1-yl)-4-methylthiazole-5-carboxamide.

Of this group of compounds, another subgroup of compounds are those compounds where W is —OC(O)—; V is a direct bond; R$^1$ is hydrogen or alkyl; R$^2$ is hydrogen; and R$^3$ is methyl.

Specific embodiments of this subgroup of compounds include the following:
(R)-2-(4-benzyl-2-oxoimidazolidin-1-yl)-4-methylthiazole-5-carboxylic acid; and
(R)-ethyl 2-(4-benzyl-2-oxoimidazolidin-1-yl)-4-methylthiazole-5-carboxylate.

In yet another embodiment of the invention, a group of compounds of Formula (I) is directed to compounds wherein n is 0, p is 0, X is CH, Y is S, each of R$^4$ and R$^{4a}$ is hydrogen, Q is

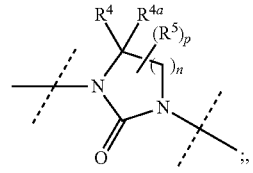

i.e., compound having the following Formula (Ib):

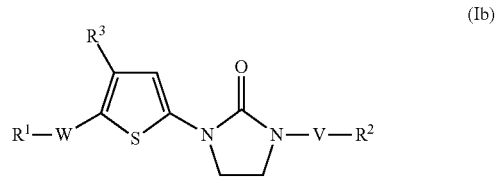

(Ib)

where W, V, R$^1$, R$^2$ and R$^3$ are as defined above in the Summary of the Invention.

Of this group of compounds, a subgroup of compounds are those compounds wherein W is —N(R$^6$)C(O)—, —C(O)—, —OC(O)— or a direct bond; V is —R$^8$—C(O)—, —R$^8$—C(O)O— or a direct bond; R$^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; R$^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; R$^3$ is hydrogen, alkyl or haloalkyl; each R$^6$ is independently hydrogen, alkyl, hydroxyalkyl, cycloalkylalkyl, aryl, heteroaryl, heterocyclyl or aralkyl; and each R$^8$ is a direct bond, an optionally substituted straight or branched alkylene chain, an optionally substituted straight or branched alkenylene chain or an optionally substituted straight or branched alkynylene chain.

Of this subgroup, a set of compounds are those compounds where W is —N(R$^6$)C(O)—; V is a direct bond; R$^1$ is heterocyclylalkyl or heteroarylalkyl; R$^2$ is alkyl, alkoxy, hydroxyalkyl, alkoxyalkyl, cycloalkylalkyl, haloalkyl or aralkyl; and R$^3$ is alkyl.

Of this set of compounds, a subset of compounds are those compounds where W is —N(H)C(O)—, R$^1$ is heteroarylalkyl; R$^2$ is aralkyl; and R$^3$ is methyl.

Specific embodiments of this subset of compounds include the following
3-methyl-5-(2-oxo-3-(4-(trifluoromethyl)benzyl)imidazolidin-1-yl)-N-(pyridin-3-ylmethyl)thiophene-2-carboxamide;

5-(3-benzyl-2-oxoimidazolidin-1-yl)-3-methyl-N-(pyridin-3-ylmethyl)thiophene-2-carboxamide;
5-(3-(4-fluorobenzyl)-2-oxoimidazolidin-1-yl)-3-methyl-N-(pyridin-3-ylmethyl)thiophene-2-carboxamide;
3-methyl-5-(2-oxo-3-phenethylimidazolidin-1-yl)-N-(pyridin-3-ylmethyl)thiophene-2-carboxamide;
5-(3-(4-carbamoylbenzyl)-2-oxoimidazolidin-1-yl)-3-methyl-N-(pyridin-3-ylmethyl)thiophene-2-carboxamide;
tert-butyl 4-((3-(4-methyl-5-(pyridin-3-ylmethylcarbamoyl)thiophen-2-yl)-2-oxoimidazolidin-1-yl)methyl)phenylcarbamate;
N-((1H-benzo[d]imidazol-2-yl)methyl)-5-(3-(4-fluorobenzyl)-2-oxoimidazolidin-1-yl)-3-methylthiophene-2-carboxamide;
5-(3-(4-fluorobenzyl)-2-oxoimidazolidin-1-yl)-3-methyl-N-(thiophen-2-ylmethyl)thiophene-2-carboxamide;
5-(3-(4-fluorobenzyl)-2-oxoimidazolidin-1-yl)-3-methyl-N-((6-(trifluoromethyl)pyridin-3-yl)methyl)thiophene-2-carboxamide;
5-(3-(4-fluorobenzyl)-2-oxoimidazolidin-1-yl)-3-methyl-N-((3-methylthiophen-2-yl)methyl)thiophene-2-carboxamide;
N-(benzo[b]thiophen-2-ylmethyl)-5-(3-(4-fluorobenzyl)-2-oxoimidazolidin-1-yl)-3-methylthiophene-2-carboxamide;
N-(benzo[d]thiazol-2-ylmethyl)-5-(3-(4-fluorobenzyl)-2-oxoimidazolidin-1-yl)-3-methylthiophene-2-carboxamide;
N-(benzo[d]oxazol-2-ylmethyl)-5-(3-(4-fluorobenzyl)-2-oxoimidazolidin-1-yl)-3-methylthiophene-2-carboxamide;
N-((1H-indol-2-yl)methyl)-5-(3-(4-fluorobenzyl)-2-oxoimidazolidin-1-yl)-3-methylthiophene-2-carboxamide;
5-(3-(4-fluorobenzyl)-2-oxoimidazolidin-1-yl)-3-methyl-N-((1-methyl-1H-pyrrol-2-yl)methyl)thiophene-2-carboxamide;
5-(3-(4-fluorobenzyl)-2-oxoimidazolidin-1-yl)-3-methyl-N-((5-phenyl-1,3,4-oxadiazol-2-yl)methyl)thiophene-2-carboxamide;
ethyl 5-((5-(3-(4-fluorobenzyl)-2-oxoimidazolidin-1-yl)-3-methylthiophene-2-carboxamido)methyl)furan-2-carboxylate;
N-((6-chloropyridin-3-yl)methyl)-5-(3-(4-fluorobenzyl)-2-oxoimidazolidin-1-yl)-3-methylthiophene-2-carboxamide;
N-((1H-pyrazol-3-yl)methyl)-5-(3-(4-fluorobenzyl)-2-oxoimidazolidin-1-yl)-3-methylthiophene-2-carboxamide;
5-(3-(4-fluorobenzyl)-2-oxoimidazolidin-1-yl)-3-methyl-N-((5-methylfuran-2-yl)methyl)thiophene-2-carboxamide;
5-(3-(4-fluorobenzyl)-2-oxoimidazolidin-1-yl)-3-methyl-N-((4-methylthiophen-2-yl)methyl)thiophene-2-carboxamide;
5-(3-(4-fluorobenzyl)-2-oxoimidazolidin-1-yl)-3-methyl-N-(thiazol-2-ylmethyl)thiophene-2-carboxamide;
N-((1,5-dimethyl-1H-pyrrol-2-yl)methyl)-5-(3-(4-fluorobenzyl)-2-oxoimidazolidin-1-yl)-3-methylthiophene-2-carboxamide;
5-(3-(4-fluorobenzyl)-2-oxoimidazolidin-1-yl)-3-methyl-N-((5-methylthiophen-2-yl)methyl)thiophene-2-carboxamide;
5-(3-(4-fluorobenzyl)-2-oxoimidazolidin-1-yl)-3-methyl-N-((1-methyl-1H-imidazol-5-yl)methyl)thiophene-2-carboxamide;
5-(3-(4-fluorobenzyl)-2-oxoimidazolidin-1-yl)-3-methyl-N-((1-methyl-1H-imidazol-4-yl)methyl)thiophene-2-carboxamide;
5-(3-(4-fluorobenzyl)-2-oxoimidazolidin-1-yl)-3-methyl-N-((5-methylpyrazin-2-yl)methyl)thiophene-2-carboxamide;
5-(3-(4-fluorobenzyl)-2-oxoimidazolidin-1-yl)-3-methyl-N-((2-methylthiazol-4-yl)methyl)thiophene-2-carboxamide;
5-(3-(4-fluorobenzyl)-2-oxoimidazolidin-1-yl)-3-methyl-N-((1-methyl-1H-pyrazol-4-yl)methyl)thiophene-2-carboxamide;
5-(3-(4-fluorobenzyl)-2-oxoimidazolidin-1-yl)-3-methyl-N-(oxazol-2-ylmethyl)thiophene-2-carboxamide;
N-((3,5-dimethyl-1H-pyrazol-4-yl)methyl)-5-(3-(4-fluorobenzyl)-2-oxoimidazolidin-1-yl)-3-methylthiophene-2-carboxamide;
N-((5-tert-butyl-1H-pyrazol-3-yl)methyl)-5-(3-(4-fluorobenzyl)-2-oxoimidazolidin-1-yl)-3-methylthiophene-2-carboxamide;
5-(3-(4-fluorobenzyl)-2-oxoimidazolidin-1-yl)-3-methyl-N-(quinolin-3-ylmethyl)thiophene-2-carboxamide;
4-((3-(4-methyl-5-(pyridin-3-ylmethylcarbamoyl)thiophen-2-yl)-2-oxoimidazolidin-1-yl)methyl)benzoic acid;
5-(3-(2-hydroxy-2-phenylethyl)-2-oxoimidazolidin-1-yl)-3-methyl-N-(pyridin-3-ylmethyl)thiophene-2-carboxamide; and
5-(3-(4-aminobenzyl)-2-oxoimidazolidin-1-yl)-3-methyl-N-(pyridin-3-ylmethyl)thiophene-2-carboxamide.

Of this set of compounds, another subset of compounds are those compounds where W is —N(H)C(O)—; $R^1$ is heteroarylalkyl; $R^2$ is alkyl or cycloalkylalkyl; and $R^3$ is methyl.

Specific embodiments of this subset of compounds include the following:
5-(3-(cyclopropylmethyl)-2-oxoimidazolidin-1-yl)-3-methyl-N-(pyridin-3-ylmethyl)thiophene-2-carboxamide; and
3-methyl-5-(2-oxo-3-(2-phenoxyethyl)imidazolidin-1-yl)-N-(pyridin-3-ylmethyl)thiophene-2-carboxamide.

Of this set of compounds, another subset of compounds are those compounds where W is —N(H)C(O)—; $R^1$ is aryl or heterocyclylalkyl; $R^2$ is aralkyl; and $R^3$ is methyl.

Specific embodiments of this subset of compounds include the following:
N-(2,3-dihydro-1H-inden-2-yl)-5-(3-(4-fluorobenzyl)-2-oxoimidazolidin-1-yl)-3-methylthiophene-2-carboxamide; and
N-(benzo[d][1,3]dioxol-5-ylmethyl)-5-(3-(4-fluorobenzyl)-2-oxoimidazolidin-1-yl)-3-methylthiophene-2-carboxamide.

Of the subgroup of compounds first set forth above, another set of compounds are those compounds where W is —OC(O)—; V is —$R^8$—C(O)— or a direct bond; $R^1$ is hydrogen or alkyl; $R^2$ is hydrogen, alkyl, alkoxy, hydroxyalkyl, alkoxyalkyl, cycloalkylalkyl, aryl, haloalkyl or aralkyl, and $R^3$ is alkyl.

Of this set of compounds, a subset of compounds are those compounds where $R^1$ is hydrogen or alkyl; $R^2$ is hydrogen, alkyl, cycloalkylalkyl, hydroxyalkyl, aryl or aralkyl; and $R^3$ is methyl.

Specific embodiments of this subset of compounds include the following:
ethyl 3-methyl-5-(2-oxoimidazolidin-1-yl)thiophene-2-carboxylate;
ethyl 3-methyl-5-(2-oxo-3-(4-(trifluoromethyl)benzyl)imidazolidin-1-yl)thiophene-2-carboxylate;
ethyl 5-(3-benzyl-2-oxoimidazolidin-1-yl)-3-methylthiophene-2-carboxylate;
ethyl 5-(3-(4-fluorobenzyl)-2-oxoimidazolidin-1-yl)-3-methylthiophene-2-carboxylate;

ethyl 3-methyl-5-(2-oxo-3-phenethylimidazolidin-1-yl)thiophene-2-carboxylate;

ethyl 5-(3-(4-cyanobenzyl)-2-oxoimidazolidin-1-yl)-3-methylthiophene-2-carboxylate;

ethyl 5-(3-(4-(tert-butoxycarbonylamino)benzyl)-2-oxoimidazolidin-1-yl)-3-methylthiophene-2-carboxylate;

ethyl 5-(3-(cyclopropylmethyl)-2-oxoimidazolidin-1-yl)-3-methylthiophene-2-carboxylate;

ethyl 3-methyl-5-(2-oxo-3-(2-oxo-2-phenylethyl)imidazolidin-1-yl)thiophene-2-carboxylate;

3-methyl-5-(2-oxo-3-(2-oxo-2-phenylethyl)imidazolidin-1-yl)thiophene-2-carboxylic acid;

ethyl 3-methyl-5-(2-oxo-3-(2-(tosyloxy)ethyl)imidazolidin-1-yl)thiophene-2-carboxylate;

ethyl 5-(3-(2-(tert-butyldimethylsilyloxy)ethyl)-2-oxoimidazolidin-1-yl)-3-methylthiophene-2-carboxylate;

ethyl 5-(3-(2-hydroxyethyl)-2-oxoimidazolidin-1-yl)-3-methylthiophene-2-carboxylate; and ethyl 3-methyl-5-(2-oxo-3-(2-phenoxyethyl)imidazolidin-1-yl)thiophene-2-carboxylate.

Of this set of compounds, another subset of compounds are those compounds where $R^1$ is hydrogen; $R^2$ is alkyl, cycloalkylalkyl, hydroxyalkyl or aralkyl; and $R^3$ is methyl.

Specific embodiments of this subset of compounds include the following:

3-methyl-5-(2-oxo-3-(4-(trifluoromethyl)benzyl)imidazolidin-1-yl)thiophene-2-carboxylic acid;

5-(3-benzyl-2-oxoimidazolidin-1-yl)-3-methylthiophene-2-carboxylic acid;

5-(3-(4-fluorobenzyl)-2-oxoimidazolidin-1-yl)-3-methylthiophene-2-carboxylic acid;

3-methyl-5-(2-oxo-3-phenethylimidazolidin-1-yl)thiophene-2-carboxylic acid;

5-(3-(4-carbamoylbenzyl)-2-oxoimidazolidin-1-yl)-3-methylthiophene-2-carboxylic acid;

5-(3-(4-(tert-butoxycarbonylamino)benzyl)-2-oxoimidazolidin-1-yl)-3-methylthiophene-2-carboxylic acid;

5-(3-(cyclopropylmethyl)-2-oxoimidazolidin-1-yl)-3-methylthiophene-2-carboxylic acid; and 3-methyl-5-(2-oxo-3-(2-phenoxyethyl)imidazolidin-1-yl)thiophene-2-carboxylic acid.

Of the subgroup of compounds first set forth above, another set of compounds are those compounds where W is a direct bond; V is —$R^8$—C(O)— or a direct bond; $R^1$ is heterocyclylalkyl or heteroarylalkyl; $R^2$ is aryl or aralkyl, and $R^3$ is alkyl.

Specific embodiments of this set of compounds include the following:

1-(5-(4-benzyl-4,5-dihydro-1H-imidazol-2-yl)-4-methylthiophen-2-yl)-3-(4-fluorobenzyl)imidazolidin-2-one;

3-methyl-5-(2-oxo-3-(2-oxo-2-phenylethyl)imidazolidin-1-yl)-N-(pyridin-3-ylmethyl)thiophene-2-carboxamide; and 1-(5-(4-benzyl-1H-imidazol-2-yl)-4-methylthiophen-2-yl)-3-(4-fluorobenzyl)imidazolidin-2-one.

In yet another embodiment of the invention, a group of compounds of Formula (I) is directed to compounds wherein Q is

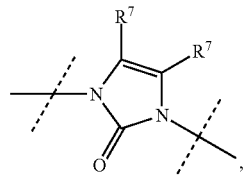

i.e., compound having the following Formula (Ic):

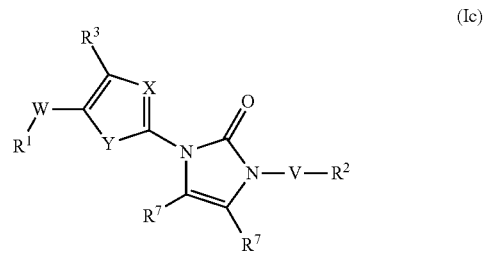

(Ic)

where V, W, X, Y, $R^1$, $R^2$, $R^3$ and $R^7$ are as defined above in the Summary of the Invention.

Of this group of compounds, a subgroup of compounds are those compounds wherein X is N; Y is S; W is —N($R^6$)C(O)—; V is a direct bond; $R^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; $R^3$ is hydrogen or alkyl; each $R^6$ is independently hydrogen or alkyl; each $R^7$ is independently hydrogen, alkyl, trifluoromethyl or aryl; and each $R^8$ is a direct bond, an optionally substituted straight or branched alkylene chain, an optionally substituted straight or branched alkenylene chain or an optionally substituted straight or branched alkynylene chain.

Of this subgroup, a set of compounds are those compounds where W is —N(H)C(O)—; V is a direct bond; each of $R^1$ and $R^2$ is independently aralkyl; $R^3$ is alkyl; and each $R^7$ is hydrogen.

Specific embodiments of this set of compounds is N-benzyl-2-(3-(4-fluorobenzyl)-2-oxo-2,3-dihydro-1H-imidazol-1-yl)-4-methylthiazole-5-carboxamide.

Of this subgroup, another set of compounds are those compounds where W is —N(H)C(O)—; V is a direct bond; $R^1$ is heteroarylalkyl; $R^2$ is aralkyl; $R^3$ is alkyl; and each $R^7$ is hydrogen.

Specific embodiments of this set of compounds include the following:

2-(3-(4-fluorophenethyl)-2-oxo-2,3-dihydro-1H-imidazol-1-yl)-4-methyl-N-(pyridin-3-ylmethyl)thiazole-5-carboxamide;

2-(3-(4-fluorobenzyl)-2-oxo-2,3-dihydro-1H-imidazol-1-yl)-4-methyl-N-(pyridin-3-ylmethyl)thiazole-5-carboxamide; and 4-methyl-2-(2-oxo-3-(4-(trifluoromethyl)benzyl)-2,3-dihydro-1H-imidazol-1-yl)-N-(pyridin-3-ylmethyl)thiazole-5-carboxamide.

In yet another embodiment of the invention, a group of compounds of Formula (I) is directed to compounds wherein Q is

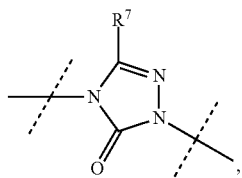

i.e., compound having the following Formula (Id):

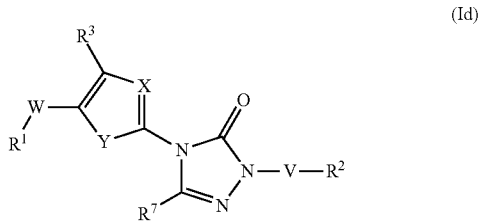

where V, W, X, Y, R¹, R², R³ and R⁷ are as defined above in the Summary of the Invention.

Of this group of compounds, a subgroup of compounds are those compounds wherein X is N; Y is S; W is —N(R⁶)C(O)— or —OC(O)—; V is —R⁸—OC(O)N(R⁶)—, —R⁸—C(O)N(R⁶)— or a direct bond; R¹ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; R² is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; R³ is hydrogen or alkyl; each R⁶ is independently hydrogen or alkyl; and each R⁷ is independently hydrogen, alkyl, trifluoromethyl or aryl.

Of this subgroup of compounds, a set of compounds are those compounds where W is —OC(O)—; V is a direct bond; R¹ is hydrogen or alkyl; R² is hydrogen, alkyl, alkoxy, hydroxyalkyl, alkoxyalkyl, cycloalkylalkyl, haloalkyl, aralkyl or heteroarylalkyl; R³ is alkyl; and R⁷ is hydrogen.

Of this set of compounds, a subset of compounds are those compounds where R¹ is alkyl; R² is hydrogen; and R³ is methyl.

Specific embodiments of this subset of compounds is ethyl 4-methyl-2-(5-oxo-1H-1,2,4-triazol-4(5H)-yl)thiazole-5-carboxylate.

Of this set of compounds, another subset of compounds are those compounds where R¹ is alkyl; R² is aralkyl; and R³ is methyl.

Specific embodiments of this subset of compounds include the following:
ethyl 4-methyl-2-(5-oxo-1-(4-(trifluoromethyl)benzyl)-1H-1,2,4-triazol-4(5H)-yl)thiazole-5-carboxylate;
ethyl 2-(1-(4-fluorobenzyl)-5-oxo-1H-1,2,4-triazol-4(5H)-yl)-4-methylthiazole-5-carboxylate; and
ethyl 2-(1-(4-(difluoromethoxy)benzyl)-5-oxo-1H-1,2,4-triazol-4(5H)-yl)-4-methylthiazole-5-carboxylate.

Of this set of compounds, another subset of compounds are those compounds where R¹ is alkyl; R² is heteroarylalkyl or cycloalkylalkyl; and R³ is methyl.

Specific embodiments of this subset of compounds is ethyl 4-methyl-2-(5-oxo-1-((5-(trifluoromethyl)furan-2-yl)methyl)-1H-1,2,4-triazol-4(5H)-yl)thiazole-5-carboxylate; and ethyl 2-(1-(cyclopropylmethyl)-5-oxo-1H-1,2,4-triazol-4(5H)-yl)-4-methylthiazole-5-carboxylate.

Of this set of compounds, another subset of compounds are those compounds where R¹ is alkyl; R² is haloalkyl, alkyl or hydroxyalkyl; and R³ is methyl.

Specific embodiments of this subset of compounds include the following:
ethyl 4-methyl-2-(5-oxo-1-(4,4,4-trifluorobutyl)-1H-1,2,4-triazol-4(5H)-yl)thiazole-5-carboxylate; and
ethyl 2-(1-(2-(4-fluorophenoxy)ethyl)-5-oxo-1H-1,2,4-triazol-4(5H)-yl)-4-methylthiazole-5-carboxylate.

Of this set of compounds, another subset of compounds are those compounds where R¹ is hydrogen; R² is hydrogen, cycloalkylalkyl or heteroarylalkyl; and R³ is methyl.

Specific embodiments of this subset of compounds include the following:
4-methyl-2-(5-oxo-1H-1,2,4-triazol-4(5H)-yl)thiazole-5-carboxylic acid;
2-(1-(cyclopropylmethyl)-5-oxo-1H-1,2,4-triazol-4(5H)-yl)-4-methylthiazole-5-carboxylic acid; and
4-methyl-2-(5-oxo-1-((5-(trifluoromethyl)furan-2-yl)methyl)-1H-1,2,4-triazol-4(5H)-yl)thiazole-5-carboxylic acid.

Of this set of compounds, another subset of compounds are those compounds where R¹ is hydrogen; R² is aralkyl; and R³ is methyl.

Specific embodiments of this subset of compounds include the following:
4-methyl-2-(5-oxo-1-(4-(trifluoromethyl)benzyl)-1H-1,2,4-triazol-4(5H)-yl)thiazole-5-carboxylic acid;
2-(1-(4-(difluoromethoxy)benzyl)-5-oxo-1H-1,2,4-triazol-4(5H)-yl)-4-methylthiazole-5-carboxylic acid; and
2-(1-(4-fluorobenzyl)-5-oxo-1H-1,2,4-triazol-4(5H)-yl)-4-methylthiazole-5-carboxylic acid.

Of this set of compounds, another subset of compounds are those compounds where R¹ is hydrogen; R² is alkyl or haloalkyl; and R³ is methyl.

Specific embodiments of this subset of compounds include the following:
2-(1-(2-(4-fluorophenoxy)ethyl)-5-oxo-1H-1,2,4-triazol-4(5H)-yl)-4-methylthiazole-5-carboxylic acid; and
4-methyl-2-(5-oxo-1-(4,4,4-trifluorobutyl)-1H-1,2,4-triazol-4(5H)-yl)thiazole-5-carboxylic acid.

Of the subgroup of compounds first set forth above, another set of compounds are those compounds wherein W is —N(H)C(O)—; V is —R⁸—OC(O)N(R⁶)—, —R⁸—C(O)N(R⁶)— or a direct bond; R¹ is heteroarylalkyl; R² is hydrogen, alkyl, alkoxy, hydroxyalkyl, alkoxyalkyl, cycloalkylalkyl, haloalkyl, aralkyl or heteroarylalkyl; R³ is alkyl; and R⁷ is hydrogen.

Of this set of compounds, a subset of compounds are those compounds where R¹ is hetearoarylalkyl; R² is aralkyl; and R³ is methyl.

Specific embodiments of this subset of compounds include the following:
4-methyl-2-(5-oxo-1-(4-(trifluoromethyl)benzyl)-1H-1,2,4-triazol-4(5H)-yl)-N-(pyridin-3-ylmethyl)thiazole-5-carboxamide;
2-(1-(4-(difluoromethoxy)benzyl)-5-oxo-1H-1,2,4-triazol-4(5H)-yl)-4-methyl-N-(pyridin-3-ylmethyl)thiazole-5-carboxamide;
2-(1-(4-fluorobenzyl)-5-oxo-1H-1,2,4-triazol-4(5H)-yl)-4-methyl-N-(pyridin-3-ylmethyl)thiazole-5-carboxamide;
2-(1-(4-fluorobenzyl)-5-oxo-1H-1,2,4-triazol-4(5H)-yl)-4-methyl-N-(oxazol-2-ylmethyl)thiazole-5-carboxamide;
N-((1H-pyrazol-3-yl)methyl)-2-(1-(4-fluorobenzyl)-5-oxo-1H-1,2,4-triazol-4(5H)-yl)-4-methylthiazole-5-carboxamide;

2-(1-(4-fluorobenzyl)-5-oxo-1H-1,2,4-triazol-4(5H)-yl)-4-methyl-N-((1-methyl-1H-pyrazol-4-yl)methyl)thiazole-5-carboxamide;

2-(1-(4-fluorobenzyl)-5-oxo-1H-1,2,4-triazol-4(5H)-yl)-4-methyl-N-((2-methylthiazol-5-yl)methyl)thiazole-5-carboxamide;

2-(1-(4-fluorobenzyl)-5-oxo-1H-1,2,4-triazol-4(5H)-yl)-4-methyl-N-(thiazol-2-ylmethyl)thiazole-5-carboxamide;

2-(1-(4-fluorobenzyl)-5-oxo-1H-1,2,4-triazol-4(5H)-yl)-4-methyl-N-(oxazol-4-ylmethyl)thiazole-5-carboxamide;

2-(1-(2-(4-chlorophenylamino)-2-oxoethyl)-5-oxo-1H-1,2,4-triazol-4(5H)-yl)-4-methyl-N-(pyridin-3-ylmethyl)thiazole-5-carboxamide;

2-(1-(4-fluorobenzyl)-5-oxo-1H-1,2,4-triazol-4(5H)-yl)-4-methyl-N-((1-methyl-1H-imidazol-4-yl)methyl)thiazole-5-carboxamide; and 2-(1-(4-fluorobenzyl)-5-oxo-1H-1,2,4-triazol-4(5H)-yl)-4-methyl-N-((5-methylpyrazin-2-yl)methyl)thiazole-5-carboxamide.

Of this set of compounds, another subset of compounds are those compounds where $R^1$ is heteroarylalkyl; $R^2$ is alkyl, hydroxyalkyl, alkoxy or haloalkyl; and $R^3$ is methyl.

Specific embodiments of this subset of compounds include the following:

2-(1-(2-hydroxyethyl)-5-oxo-1H-1,2,4-triazol-4(5H)-yl)-4-methyl-N-(pyridin-3-ylmethyl)thiazole-5-carboxamide.

2-(1-(2-(4-fluorophenoxy)ethyl)-5-oxo-1H-1,2,4-triazol-4(5H)-yl)-4-methyl-N-(pyridin-3-ylmethyl)thiazole-5-carboxamide;

4-methyl-2-(5-oxo-1-(4,4,4-trifluorobutyl)-1H-1,2,4-triazol-4(5H)-yl)-N-(pyridin-3-ylmethyl)thiazole-5-carboxamide;

2-(1-(2-(4-fluorobenzylamino)ethyl)-5-oxo-1H-1,2,4-triazol-4(5H)-yl)-4-methyl-N-(pyridin-3-ylmethyl)thiazole-5-carboxamide;

2-(4-(4-methyl-5-(pyridin-3-ylmethylcarbamoyl)thiazol-2-yl)-5-oxo-4,5-dihydro-1H-1,2,4-triazol-1-yl)ethyl methanesulfonate;

2-(1-(2-(4-fluorophenylamino)ethyl)-5-oxo-1H-1,2,4-triazol-4(5H)-yl)-4-methyl-N-(pyridin-3-ylmethyl)thiazole-5-carboxamide; and 2-(1-(2-(4-fluorobenzyloxy)ethyl)-5-oxo-1H-1,2,4-triazol-4(5H)-yl)-4-methyl-N-(pyridin-3-ylmethyl)thiazole-5-carboxamide.

Of this set of compounds, another subset of compounds are those compounds where $R^1$ is heteroarylalkyl; $R^2$ is heteroarylalkyl; and $R^3$ is methyl.

Specific embodiments of this subset of compounds include the following:

2-(1-((3,5-dimethylisoxazol-4-yl)methyl)-5-oxo-1H-1,2,4-triazol-4(5H)-yl)-4-methyl-N-(pyridin-3-ylmethyl)thiazole-5-carboxamide;

2-(4-(4-methyl-5-(pyridin-3-ylmethylcarbamoyl)thiazol-2-yl)-5-oxo-4,5-dihydro-1H-1,2,4-triazol-1-yl)ethyl 4-fluorobenzylcarbamate;

4-methyl-2-(1-((2-methylthiazol-4-yl)methyl)-5-oxo-1H-1,2,4-triazol-4(5H)-yl)-N-(pyridin-3-ylmethyl)thiazole-5-carboxamide; and 4-methyl-2-(5-oxo-1-((5-(trifluoromethyl)furan-2-yl)methyl)-1H-1,2,4-triazol-4(5H)-yl)-N-(pyridin-3-ylmethyl)thiazole-5-carboxamide.

Of this set of compounds, another subset of compounds are those compounds where $R^1$ is heteroarylalkyl; $R^2$ is hydrogen or cycloalkylalkyl; and $R^3$ is methyl.

Specific embodiments of this subset of compounds include the following:

2-(1-(cyclopropylmethyl)-5-oxo-1H-1,2,4-triazol-4(5H)-yl)-4-methyl-N-(pyridin-3-ylmethyl)thiazole-5-carboxamide; and 4-methyl-2-(5-oxo-1H-1,2,4-triazol-4(5H)-yl)-N-(pyridin-3-ylmethyl)thiazole-5-carboxamide.

In yet another embodiment of the invention, a group of compounds of Formula (Id) is directed to compounds wherein X is CH; Y is S; W is —N($R^6$)C(O)— or —OC(O)—; V is a direct bond; $R^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; $R^3$ is hydrogen or alkyl; each $R^6$ is independently hydrogen or alkyl; and each $R^7$ is independently hydrogen, alkyl, trifluoromethyl or aryl.

Of this group of compounds, a subgroup of compounds are those compounds where W is —OC(O)—; V is a direct bond; $R^1$ is hydrogen or alkyl; $R^2$ is hydrogen, cycloalkylalkyl or aralkyl; $R^3$ is alkyl; and $R^7$ is hydrogen.

Of this subgroup of compounds, a set of compounds are those compounds where $R^1$ is alkyl; $R^2$ is hydrogen or cycloalkylalkyl; and $R^3$ is methyl.

Specific embodiments of this set of compounds include the following:

ethyl 3-methyl-5-(5-oxo-1H-1,2,4-triazol-4(5H)-yl)thiophene-2-carboxylate; and ethyl 5-(1-(2-cyclopropylethyl)-5-oxo-1H-1,2,4-triazol-4(5H)-yl)-3-methylthiophene-2-carboxylate.

Of this subgroup of compounds, another set of compounds are those compounds where $R^1$ is alkyl; $R^2$ is aralkyl; and $R^3$ is methyl.

Specific embodiments of this set of compounds include the following:

ethyl 5-(1-(4-fluorobenzyl)-5-oxo-1H-1,2,4-triazol-4(5H)-yl)-3-methylthiophene-2-carboxylate;

ethyl 5-(1-benzyl-5-oxo-1H-1,2,4-triazol-4(5H)-yl)-3-methylthiophene-2-carboxylate;

ethyl 3-methyl-5-(5-oxo-1-(4-(trifluoromethyl)benzyl)-1H-1,2,4-triazol-4(5H)-yl)thiophene-2-carboxylate; and ethyl 3-methyl-5-(1-(4-(methylsulfonyl)benzyl)-5-oxo-1H-1,2,4-triazol-4(5H)-yl)thiophene-2-carboxylate.

Of this subgroup of compounds, another set of compounds are those compounds where $R^1$ is hydrogen; $R^2$ is aralkyl; and $R^3$ is methyl.

Specific embodiments of this set of compounds include the following:

5-(1-(4-fluorobenzyl)-5-oxo-1H-1,2,4-triazol-4(5H)-yl)-3-methylthiophene-2-carboxylic acid;

5-(1-benzyl-5-oxo-1H-1,2,4-triazol-4(5H)-yl)-3-methylthiophene-2-carboxylic acid;

3-methyl-5-(5-oxo-1-(4-(trifluoromethyl)benzyl)-1H-1,2,4-triazol-4(5H)-yl)thiophene-2-carboxylic acid; and 3-methyl-5-(1-(4-(methylsulfonyl)benzyl)-5-oxo-1H-1,2,4-triazol-4(5H)-yl)thiophene-2-carboxylic acid.

Of this subgroup of compounds, another set of compounds are those compounds where $R^1$ is hydrogen; $R^2$ is cycloalkylalkyl; and $R^3$ is methyl.

Specific embodiments of this set of compounds is 5-(1-(2-cyclopropylethyl)-5-oxo-1H-1,2,4-triazol-4(5H)-yl)-3-methylthiophene-2-carboxylic acid.

Of the group of compounds first noted above, another subgroup of compounds are those compounds where W is —N(H)C(O)—; V is a direct bond; $R^1$ is heteroarylalkyl; $R^2$ is cycloalkylalkyl or aralkyl; $R^3$ is alkyl; and $R^7$ is hydrogen.

Of this subgroup of compounds, a set of compounds are those compounds where $R^1$ is heteroarylalkyl; $R^2$ is aralkyl; and $R^3$ is methyl.

Specific embodiments of this set of compounds include the following:

5-(1-(4-fluorobenzyl)-5-oxo-1H-1,2,4-triazol-4(5H)-yl)-3-methyl-N-(pyridin-3-ylmethyl)thiophene-2-carboxamide;

5-(1-benzyl-5-oxo-1H-1,2,4-triazol-4(5H)-yl)-3-methyl-N-(pyridin-3-ylmethyl)thiophene-2-carboxamide;

3-methyl-5-(5-oxo-1-(4-(trifluoromethyl)benzyl)-1H-1,2,4-triazol-4(5H)-yl)-N-(pyridin-3-ylmethyl)thiophene-2-carboxamide;

3-methyl-5-(1-(4-(methylsulfonyl)benzyl)-5-oxo-1H-1,2,4-triazol-4(5H)-yl)-N-(pyridin-3-ylmethyl)thiophene-2-carboxamide;

5-(1-(4-fluorobenzyl)-5-oxo-1H-1,2,4-triazol-4(5H)-yl)-3-methyl-N-((5-methylpyrazin-2-yl)methyl)thiophene-2-carboxamide;

5-(1-(4-fluorobenzyl)-5-oxo-1H-1,2,4-triazol-4(5H)-yl)-3-methyl-N-(oxazol-2-ylmethyl)thiophene-2-carboxamide;

5-(1-(4-fluorobenzyl)-5-oxo-1H-1,2,4-triazol-4(5H)-yl)-3-methyl-N-((1-methyl-1H-pyrazol-4-yl)methyl)thiophene-2-carboxamide; and 5-(1-(4-fluorobenzyl)-5-oxo-1H-1,2,4-triazol-4(5H)-yl)-3-methyl-N-((2-methylthiazol-4-yl)methyl)thiophene-2-carboxamide.

Of this subgroup of compounds, another set of compounds are those compounds where $R^1$ is heteroarylalkyl; $R^2$ is cycloalkylalkyl; and $R^3$ is methyl.

Specific embodiments of this set of compounds is 5-(1-(2-cyclopropylethyl)-5-oxo-1H-1,2,4-triazol-4(5H)-yl)-3-methyl-N-(pyridin-3-ylmethyl)thiophene-2-carboxamide.

In yet another embodiment of the invention, a group of compounds of Formula (Id) wherein W is —OC(O)—; V is a direct bond; $R^1$ is heteroarylalkyl; $R^2$ is alkyl; $R^3$ is methyl; and $R^6$ is alkyl.

Specific embodiments of this group of compounds is 2-(1-(2-(4-fluorophenylamino)ethyl)-5-oxo-1H-1,2,4-triazol-4(5H)-yl)-N,4-dimethyl-N-(pyridin-3-ylmethyl)thiazole-5-carboxamide.

In yet another embodiment of the invention, a group of compounds of Formula (I) is directed to compounds wherein Q is

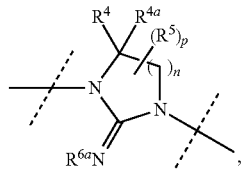

i.e., compound having the following Formula (Ie):

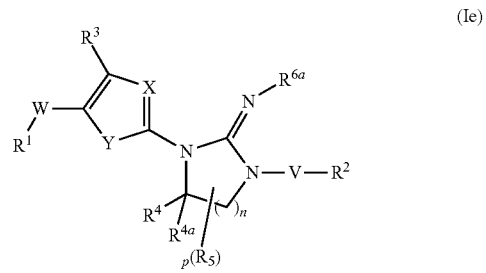

where n, p, V, W, X, Y, $R^1$, $R^2$, $R^3$, $R^4$, $R^{4a}$, $R^5$ and $R^{6a}$ are as defined above in the Summary of the Invention.

Of this group of compounds, a subgroup of compounds are those compounds wherein n is 1; p is 0; X is N; Y is S; W is —N($R^6$)C(O)— or —OC(O)—; V is a direct bond; $R^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; $R^3$ is hydrogen or alkyl; each $R^4$ and $R^{4a}$ is hydrogen; $R^{6a}$ is independently hydrogen or cyano; and $R^6$ is independently hydrogen or alkyl.

Of this subgroup of compounds, a set of compounds are those compounds where W is —N(H)C(O)—; V is a direct bond; $R^1$ is aralkyl; $R^2$ is aralkyl; $R^3$ is alkyl; and $R^{6a}$ is hydrogen or cyano.

Specific embodiments of this set of compounds include the following:

N-benzyl-2-(3-benzyl-2-(cyanoimino)imidazolidin-1-yl)-4-methylthiazole-5-carboxamide;

N-benzyl-2-(3-benzyl-2-iminoimidazolidin-1-yl)-4-methylthiazole-5-carboxamide;

2-(3-benzyl-2-iminoimidazolidin-1-yl)-N-(4-fluorobenzyl)-4-methylthiazole-5-carboxamide; and 2-(3-benzyl-2-iminoimidazolidin-1-yl)-N-(3,4-difluorobenzyl)-4-methylthiazole-5-carboxamide.

In yet another embodiment of the invention, a group of compounds of Formula (I) is directed to compounds where Q is

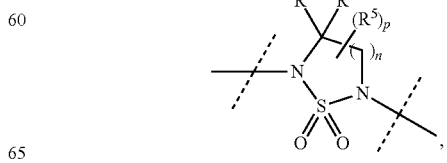

i.e., compound having the following Formula (If):

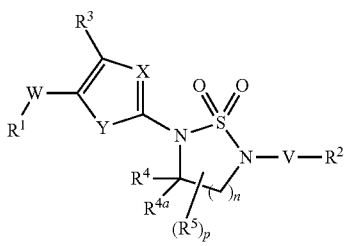

where n, p, V, W, X, Y, $R^1$, $R^2$, $R^3$, $R^4$, $R^{4a}$ and $R^5$ are as defined above in the Summary of the Invention.

Of this group of compounds, a subgroup of compounds are those compounds wherein n is 1; p is 0; X is N; Y is S; W is —N($R^6$)C(O)—; V is a direct bond; $R^1$ is hydrogen, alkyl, alkenyl, alkynyl, alkoxy, hydroxyalkyl, alkoxyalkyl, cycloalkyl, cycloalkylalkyl, aryl, aralkyl, heterocyclyl, heterocyclylalkyl, heteroaryl or heteroarylalkyl; $R^2$ is hydrogen, alkyl, alkenyl, alkynyl, alkoxy, hydroxyalkyl, alkoxyalkyl, cycloalkyl, cycloalkylalkyl, aryl, haloalkyl, aralkyl, heterocyclyl, heterocyclylalkyl, heteroaryl or heteroarylalkyl; $R^3$ is hydrogen or alkyl; each $R^4$ and $R^{4a}$ is hydrogen; and $R^6$ is independently hydrogen or alkyl.

Of this subgroup of compounds, a set of compounds are those compounds where W is —N(H)C(O)—; V is a direct bond; $R^1$ is aralkyl or heteroarylalkyl; $R^2$ is aralkyl; and $R^3$ is alkyl.

Of this set of compounds, a subset of compounds are those compounds where $R^1$ is heteroarylalkyl; $R^2$ is aralkyl; and $R^3$ is methyl.

Specific embodiments of this subset of compounds is 2-(5-benzyl-1,1-dioxido-1,2,5-thiadiazolidin-2-yl)-4-methyl-N-(pyridin-3-ylmethyl)-1,3-thiazole-5-carboxamide.

Of this set of compounds, another subset of compounds are those compounds where $R^1$ is aralkyl; $R^2$ is aralkyl; and $R^3$ is methyl.

Specific embodiments of this subset of compounds is N-benzyl-2-(5-benzyl-1,1-dioxido-1,2,5-thiadiazolidin-2-yl)-4-methyl-1,3-thiazole-5-carboxamide. In yet another embodiment is a group of compounds represented by Formula (II):

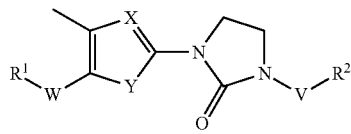

wherein
V is selected from aryl or a direct bond;
W is selected from —N($R^6$)C(O)—, —C(O)N($R^6$)—, —C(O)O— or a direct bond;
X is N or CH;
Y is S;
$R^1$ is selected from the group consisting of hydrogen, alkyl, aryl, aralkyl, cycloalkyl, cycloalkylalkyl, heterocyclyl, heterocyclylalkyl, heteroaryl, and heteroarylalkyl;
$R^2$ is selected from the group consisting of aryl, aralkyl, heteroaryl and heteroarylalkyl; and
$R^6$ is hydrogen or $C_{1-4}$alkyl.

In yet another embodiment is a group of compounds represented by Formula (II) wherein
V is selected from aryl or a direct bond;
W is selected from —N($R^6$)C(O)—, or —C(O)O—;
X is N or CH;
Y is S;
$R^1$ is selected from the group consisting of aralkyl, and heteroarylalkyl;
$R^2$ is selected from the group consisting of aryl and aralkyl; and
$R^6$ is hydrogen.

In yet another embodiment is a group of compounds of represented by Formula (II)
wherein
V is a direct bond;
W is —N($R^6$)C(O)—;
X is N or CH;
Y is S;
$R^1$ is select aralkyl or heteroarylalkyl;
$R^2$ is selected from the group consisting of an and aralkyl; and
$R^6$ is hydrogen.

In yet another embodiment is a group of compounds represented by Formula (III):

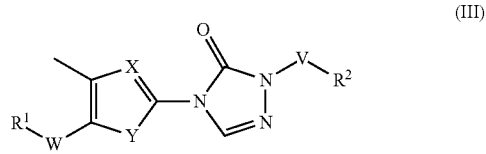

wherein
V is selected from aryl or a direct bond;
W is selected from —N($R^6$)C(O)—, —C(O)N($R^6$)—, —C(O)O— or a direct bond;
X is N or CH;
Y is S;
$R^1$ is selected from the group consisting of hydrogen, alkyl, aryl, aralkyl, cycloalkyl, cycloalkylalkyl, heterocyclyl, heterocyclylalkyl, heteroaryl, and heteroarylalkyl;
$R^2$ is selected from the group consisting of aryl, aralkyl, heteroaryl and heteroarylalkyl; and
$R^6$ is hydrogen or $C_{1-4}$alkyl.

In yet another embodiment is a group of compounds represented by Formula (III) wherein
V is selected from aryl or a direct bond;
W is selected from —N($R^6$)C(O)—, or —C(O)O—;
X is N or CH;
Y is S;
$R^1$ is selected from the group consisting of aralkyl, and heteroarylalkyl;
$R^2$ is selected from the group consisting of aryl and aralkyl; and
$R^6$ is hydrogen.

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome, dermatological disorders and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome, dermatological disorders and the like, by administering to a patient in need of such treatment an effective amount of an SCD modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 63.

Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)), and Sprague Dawley rats (Charles Rivers), as used in models for diet-induced obesity (Ghibaudi, L. et al., (2002), *Obes. Res.* Vol. 10, pp. 956-963). Similar models have also been developed for mice and Lewis rat.

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition is defined as any disease or condition in which the activity of SCD is elevated and/or where inhibition of SCD activity can be demonstrated to bring about symptomatic improvements for the individual so treated. As defined herein, an SCD-mediated disease or condition includes, but is not limited to, a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport)), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin-related diseases. In a preferred embodiment, compounds of the invention will be used to treat diabetes mellitus and/or obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaernia, hypercoagulability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids, wax esters, and the like. Preferably, the compounds of the invention will prevent or attenuate keloid scar formation by reduction of excessive sebum production that typically results in their formation.

The investigation of the role of SCD inhibitors in the treatment of acne was advanced by the discovery that rodents lacking a functional SCD1 gene had changes to the condition of their eyes, skin, coat (Zheng Y., et al. "SCD1 is expressed in sebaceous glands and is disrupted in the asebia mouse", *Nat. Genet.* (1999) 23:268-270. Miyazaki, M., "Targeted Disruption of Stearoyl-CoA Desaturase1 Gene in Mice Causes Atrophy of Sebaceous and Meibomian Glands and Depletion of Wax Esters in the Eyelid", *J. Nutr.* (2001), Vol. 131, pp 2260-68., Binczek, E. et al., "Obesity resistance of the stearoyl-CoA desaturase-deficient mouse results from disruption of the epidermal lipid barrier and adaptive thermoregulation", *Biol. Chem.* (2007) Vol. 388 No. 4, pp 405-18).

An SCD-mediated disease or condition also includes inflammation, sinusitis, asthma, pancreatitis, osteoarthritis, rheumatoid arthritis, cystic fibrosis, and premenstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition that is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, ITheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POCYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA), which is accomplished by delta-9 desaturases, such as stearoyl-CoA desaturase 1 (SCD1). As such, these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 20 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ ("Inhibitory Concentration of 50%") in a 15 minute microsomal assay of preferably less than 10 mM, less than 5 µM, less than 2.5 µM, less than 1 µM, less than 750 nM, less than 500 nM, less than 250 nM, less than 100 nM, less than 50 nM, and most preferably less than 20 nM. Compounds of the invention may show reversible inhibition (i.e., competitive inhibition) and preferably do not inhibit other iron binding proteins.

The identification of compounds of the invention as SCD inhibitors was readily accomplished using the SCD enzyme and microsomal assay procedure described in Shanklin J. and Summerville C., *Proc. Natl. Acad. Sci. USA* (1991), Vol. 88, pp. 2510-2514. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain-groups tend to provide more potent inhibitory compounds. SAR analysis is one of the tools those skilled in the art may employ to identify preferred embodiments of the compounds of the invention for use as therapeutic agents. Other methods of testing the compounds disclosed herein are also readily available to those skilled in the art. Thus, in addition, the determination of the ability of a compound to inhibit SCD may be accomplished in vivo. In one such embodiment this is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (-TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase or other enzymes containing iron at the active site.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available. Rabbits and hamsters are also useful as animal models, especially those expressing CETP (cholesterol ester transfer protein).

Another suitable method for determining the in vivo efficacy of the compounds of the invention is to indirectly measure their impact on inhibition of SCD enzyme by measuring a subject's Desaturation Index after administration of the compound.

"Desaturation Index" as employed in this specification means the ratio of the product over the substrate for the SCD enzyme as measured from a given tissue sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate).

Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, with a subsequent modulation of the activity of multiple enzymes present within the membrane, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented.

For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Alternatively, another format can be used to measure the effect of SCD inhibition on sebaceous gland function. In a typical study using ridnets, oral, intravenous or topical formulations of the SCD inhibitor are administered to a rodent for a period of 1 to 8 days. Skin samples are taken and prepared for histological assessment to determine sebaceous gland number, size, or lipid content. A reduction of sebaceous gland size, number or function would indicate that the SCD inhibitor would have a beneficial impact on acne vulgaris, (Clark, S. B. et al. "Pharmacological modulation of sebaceous gland activity: mechanisms and clinical applications", *Dermatol. Clin.* (2007) Vol. 25, No. 2, pp 137-46. Geiger, J. M., "Retinoids and sebaceous gland activity" *Dermatology* (1995), Vol. 191, No. 4, pp 305-10).

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are familiar with how to determine suitable doses of the compounds for use in treating the diseases and disorders contemplated herein.

Therapeutic doses are generally identified through a dose ranging study in humans based on preliminary evidence derived from animal studies. Doses must be sufficient to result in a desired therapeutic benefit without causing unwanted side effects for the patient. The preferred dosage range for an animal is 0.001 mg/Kg to 10,000 mg/Kg, including 0.5 mg/Kg, 1.0 mg/Kg, 2.0 mg/Kg 5.0 mg/Kg, 10 mg/Kg and 20 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, transdermal, topical, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

The pharmaceutical compositions according to the invention are those suitable for enteral, such as oral or rectal, transdermal and parenteral administration to mammals, including man, to inhibit stearoyl-CoA desaturase, and for the treatment of conditions associated with stearoyl desaturase activity. In general, the pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. For enteral or parenteral application, it is preferred to administer an effective amount of a pharmaceutical composition according to the invention as tablets or gelatin capsules. Such pharmaceutical compositions may comprise, for example, the active ingredient together with diluents (e.g., lactose, dextrose, sucrose, mannitol, sorbitol, cellulose and/or glycine), lubricants (e.g., silica, talcum, stearic acid, its magnesium or calcium salt and/or polyethyleneglycol), and for tablets also comprises binders (e.g., magnesium aluminum silicate, starch paste, gelatin, tragacanth, methylcellulose, sodium carboxymethylcellulose and/or polyvinylpyrrolidone) and disintegrants (e.g., starches, agar, alginic acid or its sodium salt) or effervescent mixtures and absorbents, colorants, flavors and sweeteners.

In another aspect of the present invention the compounds may be in the form of injectable compositions, e.g. preferably aqueous isotonic solutions or suspensions, and suppositories, which can be advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions may be prepared according to conventional mixing, granulating or coating methods, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate-controlling barrier to deliver the compound of the skin of the host at a controlled and pre-determined rate over a prolonged period of time, and means to secure the device to the skin.

The most suitable route will depend on the nature and severity of the condition being treated. Those skilled in the art are also familiar with determining administration methods, dosage forms, suitable pharmaceutical excipients and other matters relevant to the delivery of the compounds to a subject in need thereof.

The compounds of the invention may be usefully combined with one or more other therapeutic agents for the treatment of SCD-mediated diseases and conditions. Preferably, the other therapeutic agent is selected from antidiabetics, hypolipidemic agents, anti-obesity agents, anti-hypertensive agents or inotropic agents.

Thus, an additional aspect of the present invention concerns a pharmaceutical composition comprising a therapeutically effective amount of a compound of the invention in combination with one or more other therapeutic agents. For example, the composition can be formulated to comprise a therapeutically effective amount of a compound of the invention as defined above, in combination with another therapeutic agent, each at an effective therapeutic dose as reported in the art. Such therapeutic agents may, for example, include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARγ and/or PPARα (peroxisome proliferator-activated receptor) ligands such as MCC-555, MK767, L-165041, GW7282 or thiazolidinediones such as rosiglitazone, pioglitazone, troglitazone; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441, N,N-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237 (Vildagliptin); hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perindopril, quinapril, ramipril and trandolapril; inhibitors of the Na—K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (*Expert Opin Investig Drugs*. (2003)

April; 12 (4):623-33) in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the active agents identified by code numbers (nos.), generic or trade names may be taken from the actual edition of the standard compendium "The Merck Index" or from databases, e.g. Patents International (e.g. IMS World Publications). The corresponding content thereof is hereby incorporated by reference.

In another aspect is the use of the pharmaceutical composition as described above for production of a medicament for the treatment of SCD-mediated disease or conditions. In another aspect is the use of a pharmaceutical composition or combination as described above for the preparation of a medicament for the treatment of conditions associated with stearoyl-CoA desaturase activity.

A pharmaceutical composition as described above for the treatment of conditions associated with the inhibition of stearoyl-CoA desaturase.

Preparations of Compounds

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wuts, *Protective Groups in Organic Synthesis* (2006), 4th Ed., Wiley. The protecting group may also be a polymer resin such as a Wang resin or a 2-chlorotritylchloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. $R^1$, $R^2$, $R^3$, $R^4$, $R^5$, X, W and V are defined as in the Specification unless specifically defined. R' is a protecting group.

In general, the cyclized urea compounds of Formula (I) of this invention can be synthesized following the general procedure as described in Scheme 1 where Q is

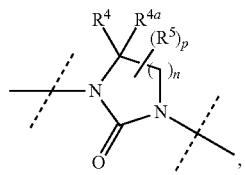

$R^4$, $R^{4a}$ and $R^5$ are hydrogen, W is —N($R^6$)C(O)— and V is a direct bond.

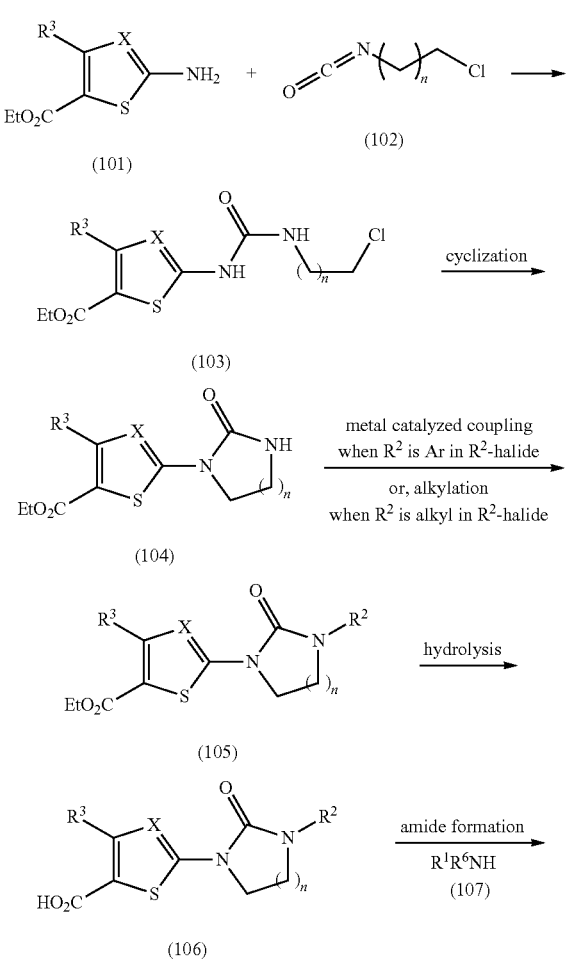

-continued

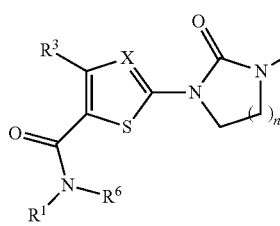

Formula (I), R² is alkyl or aryl

The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (101) reacts with isocyanate (102) to generate compound (103) which undergoes intramolecular cyclization in the presence of a base, such as, but not limited to, potassium carbonate, to afford the cyclized compound (104). Compound (104) reacts with an aryl halide or heteroaryl halide compound under metal catalyzed coupling reaction conditions to afford compound (105) where R² is an aryl or heteroaryl. Alternatively, compound (104) reacts with an alkyl halide under alkylation conditions to generate compound (105) where R² is an alkyl. Compound (105) undergoes standard hydrolysis known to one skilled in the art to generate compound (106). Compound (106) then undergoes a standard amide formation reaction with an amine compound (107) to afford the compound of Formula (I) of the invention where R² is alkyl, or aryl or heteroaryl, Q is

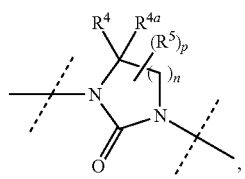

R⁴, R⁴ᵃ and R⁵ are hydrogen, W is —N(R⁶)C(O)— and V is a direct bond.

Alternatively, the cyclized urea compounds of Formula (I) of this invention can be synthesized following the general procedure as described in Scheme 2 where Q is

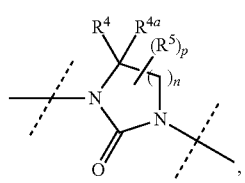

R⁴, R⁴ᵃ and R⁵ are hydrogen, W is —N(R⁶)C(O)— and V is a direct bond.

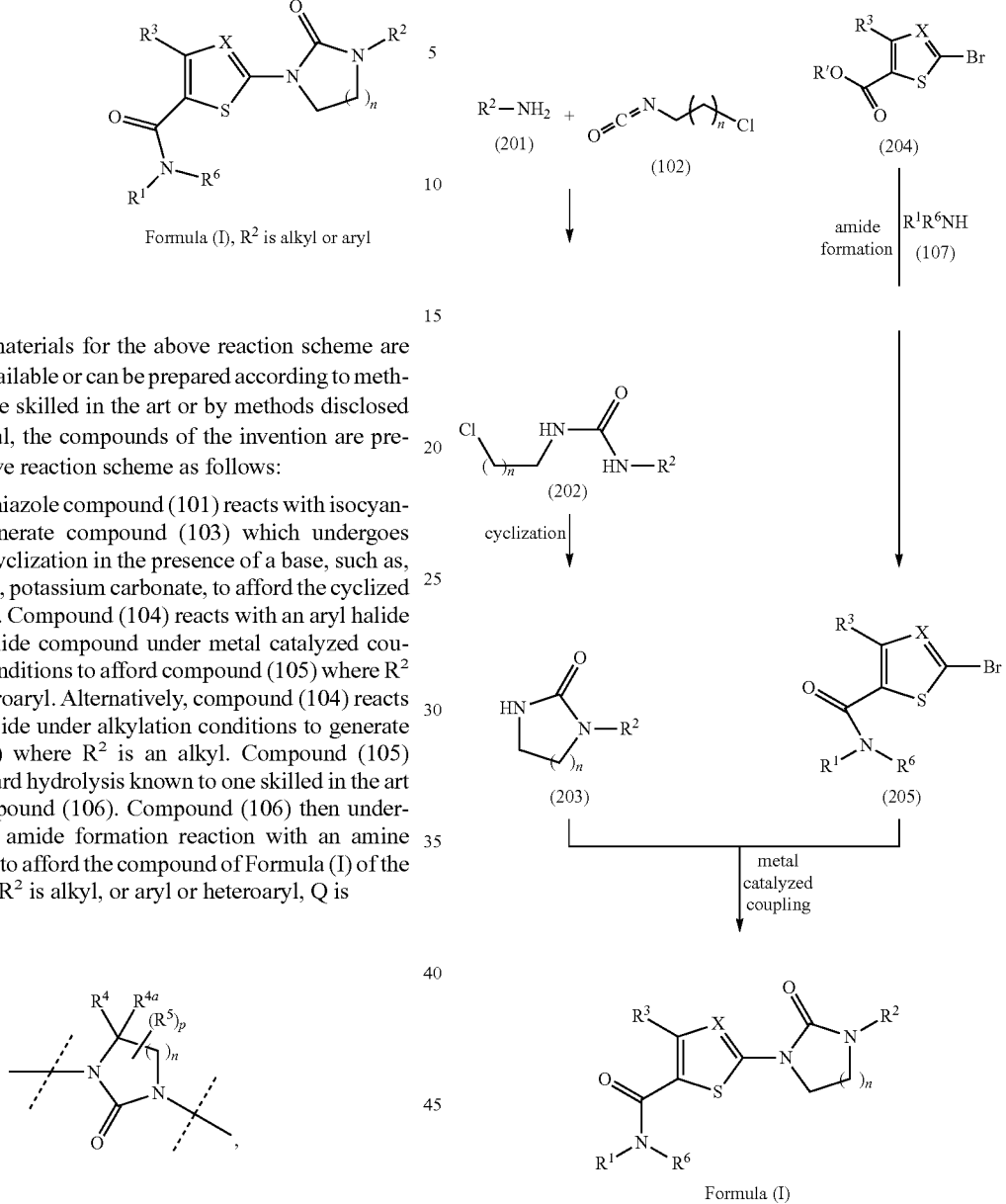

Scheme 2

Formula (I)

The starting materials for the above reaction scheme are commercially available or can be prepared according to methods known to one skilled in the art or by methods disclosed herein. In general, the compounds of the invention are prepared in the above reaction scheme as follows:

The amine compound (201) reacts with isocyanate (102) to generate compound (202) which undergoes intramolecular cyclization in the presence of a base, such as, but not limited to, potassium carbonate, to afford the cyclized compound (203). In parallel, the bromo compound (204) is coupled with the amine compound (107) under standard amide formation conditions to generate compound (205). Compound (203) is coupled with compound (205) under metal catalyzed coupling reaction conditions to afford compound

51
of Formula (I) of the invention where Q is
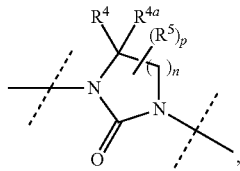
$R^4$, $R^{4a}$ and $R^5$ are hydrogen, W is —N($R^6$)C(O)— and V is a direct bond.
52
Alternatively, the cyclized urea compounds of Formula (I) of this invention can be synthesized following the general procedure as described in Scheme 3 where Q is
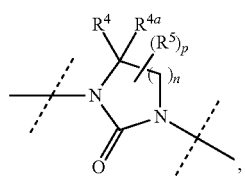
$R^4$, $R^{4a}$ and $R^5$ are hydrogen, W is —N($R^6$)C(O)— and V is a direct bond.
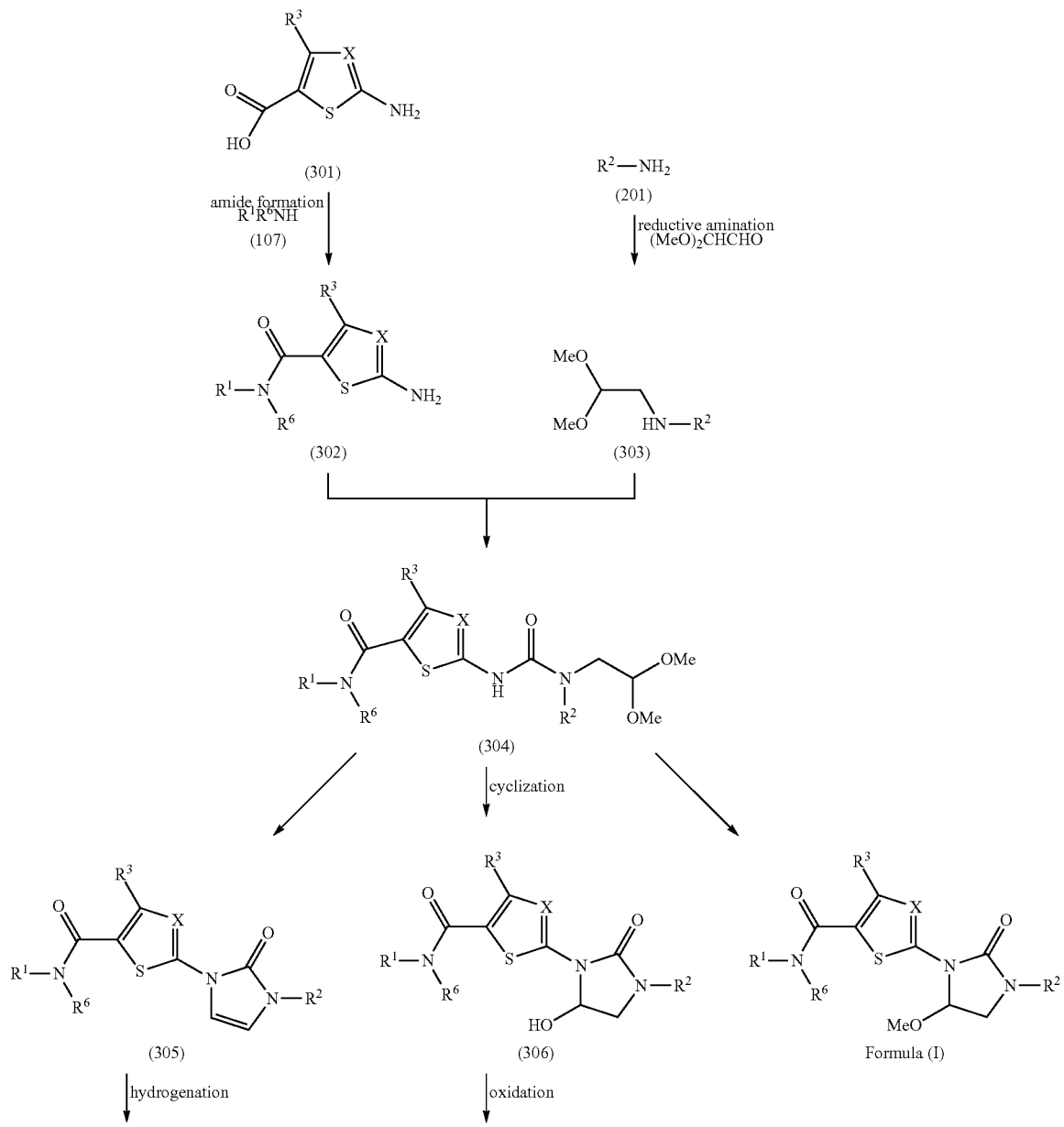
Scheme 3

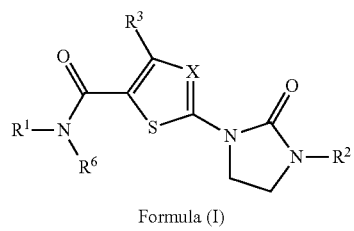

Formula (I)

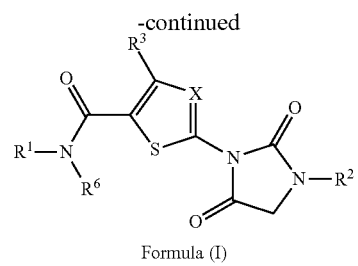

-continued

Formula (I)

The starting materials for the above reaction scheme are commercially available or can be prepared according to methods known to one skilled in the art or by methods disclosed herein. In general, the compounds of the invention are prepared in the above reaction scheme as follows:

Compound (301) is coupled with amine (107) under standard amide formation conditions known to the one skilled in the art to generate compound (302). In parallel, amine (201) is subjected to reductive amination conditions to generate compound (303). Under urea formation conditions in the presence of a coupling reagent, such as, but not limited to, 1,1-carbonyldiimidazole, compounds (302) and (303) are coupled to generate the urea compound (304) which undergoes cyclization under different acidic conditions to generate compound (305), compound (306) (a compound of Formula (I) where $R^4$ is hydroxyl, $R^{4a}$ is hydrogen, W is —N($R^6$)C(O)— and V is a direct bond, and a compound of Formula (I) where $R^4$ is hydrogen, $R^{4a}$ is methoxy, W is —N($R^6$)C(O)— and V is a direct bond, respectively). Compound (306) can be reduced by hydrogenation to afford compound of Formula (I) where $R^4$ and $R^{4a}$ are H, W is —N($R^6$)C(O)— and V is a direct bond. Compound (306) could be oxidized to generate compound of Formula (I) where $R^4$ and $R^{4a}$ together to form an oxo (=O), W is —N($R^6$)C(O)— and V is a direct bond.

Alternatively, the cyclized urea compounds of Formula (I) of this invention can be synthesized following the general procedure as described in Scheme 4 where Q is

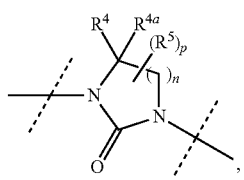

, $R^4$, $R^{4a}$ and $R^5$ are hydrogen, W is —N($R^6$)C(O)— and V is a direct bond.

Scheme 4

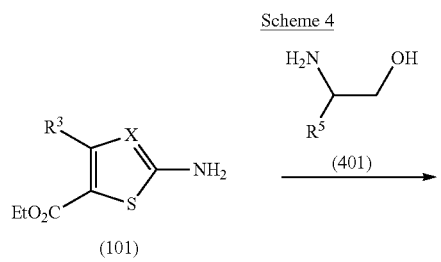

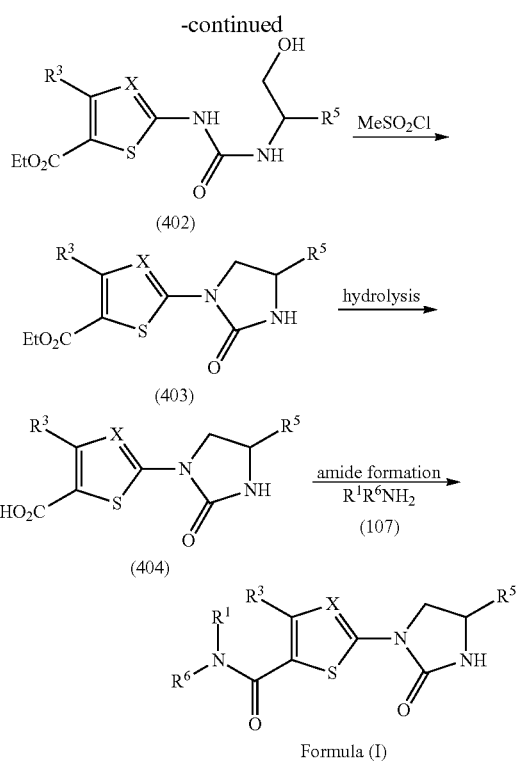

Formula (I)

The starting materials for the above reaction scheme are commercially available or can be prepared according to methods known to one skilled in the art or by methods disclosed herein. In general, the compounds of the invention are prepared in the above reaction scheme as follows:

The amine compounds (101) and (401) are coupled in the presence of a urea forming reagent, such as, but not limited to, 1,1-carbonyldiimidazole to generate the urea compound (402), which undergoes cyclization with the treatment of methanesulfonyl chloride (or similar activating group), in the presence of a base such as, but not limited to, N,N-diisopropylethylamine or potassium carbonate, through a two-step process to generate the cyclized urea compound (403). Compound (403) undergoes a standard hydrolysis known to one skilled in the art, to afford the carboxylic acid (404). The coupling between the carboxylic acid (404) and an amine (107) under standard amide formation conditions known to the one skilled in the art to afford the compound Formula (I) of the invention where $R^2$, $R^4$ and $R^{4a}$ are hydrogen, W is —N($R^6$)C(O)— and V is a direct bond. This compound can be further derivatized to generate other compounds following the conditions outlined in Scheme 1 for alkylation or metal catalyzed coupling reactions.

Alternatively, the triazolone compounds of Formula (I) of this invention can be synthesized following the general procedure as described in Scheme 5 where Q is

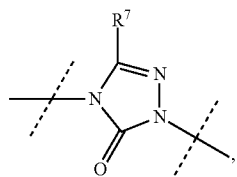

$R^7$ is hydrogen, W is —$N(R^6)C(O)$— and V is a direct bond.

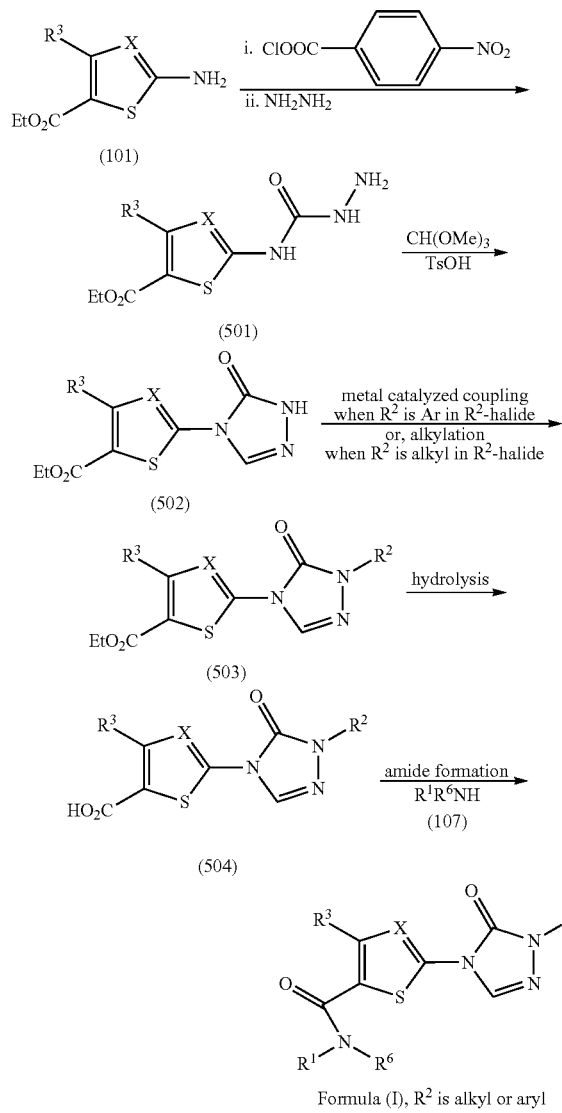

The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (101) reacts with chloroformate and then hydrazine to generate compound (501) which is cyclized using trimethyl orthoformate in the presence of p-toluenesulfonic acid to afford the cyclized compound (502). Compound (502) reacts with an aryl halide or heteroaryl halide compound under metal catalyzed coupling reaction conditions to afford compound (503) where $R^2$ is an aryl or heteroaryl. Alternatively, compound (502) reacts with an alkyl halide under alkylation conditions to generate compound (503) where $R^2$ is an alkyl. Compound (503) undergoes standard hydrolysis known to one skilled in the art to generate compound (504). Compound (504) then undergoes a standard amide formation reaction with an amine compound to afford the compound of Formula (I) of the invention where $R^2$ is alkyl, or aryl or heteroaryl, where Q is

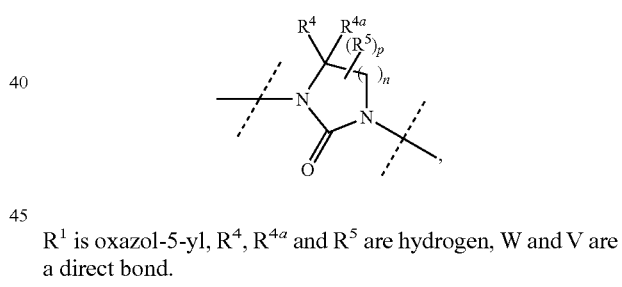

$R^7$ is hydrogen, W is —$N(R^6)C(O)$— and V is a direct bond.

Alternatively, the cyclized urea compounds of Formula (I) of this invention can be synthesized following the general procedure as described in Scheme 6 where Q is $R^1$ is oxazol-5-yl, $R^4$, $R^{4a}$ and $R^5$ are hydrogen, W and V are a direct bond.

Scheme 6

-continued

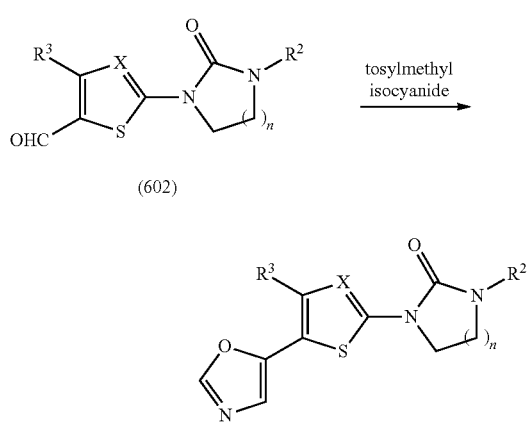

Formula (I), R² is alkyl or aryl

The starting materials for the above reaction scheme are commercially available or can be prepared according to methods known to one skilled in the art or by methods disclosed herein. In general, the compounds of the invention are prepared in the above reaction scheme as follows:

The ester intermediate (105) is reduced by a reducing agent, such as, but not limited to, lithium borohydride to generate the alcohol compound of formula (601) which is oxidized by an oxidation reagent, such as, but not limited to, Dess-Martin periodinane to generate the aldehyde compound of formula (602). Cyclization of the aldehyde of formula (602) with tosylmethyl isocyanide to generate the compound of formula (I) of the invention where Q is

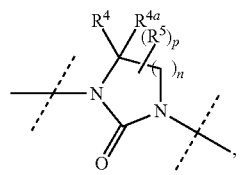

$R^1$ is oxazol-5-yl, $R^4$, $R^{4a}$ and $R^5$ are hydrogen, W and V are a direct bond.

Alternatively, the cyclized urea compounds of Formula (I) of this invention can be synthesized following the general procedure as described in Scheme 7 where Q is

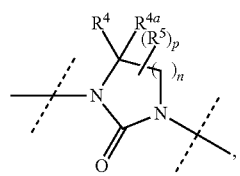

$R^4$, $R^{4a}$ and $R^5$ are hydrogen, V is a direct bond.

Scheme 7

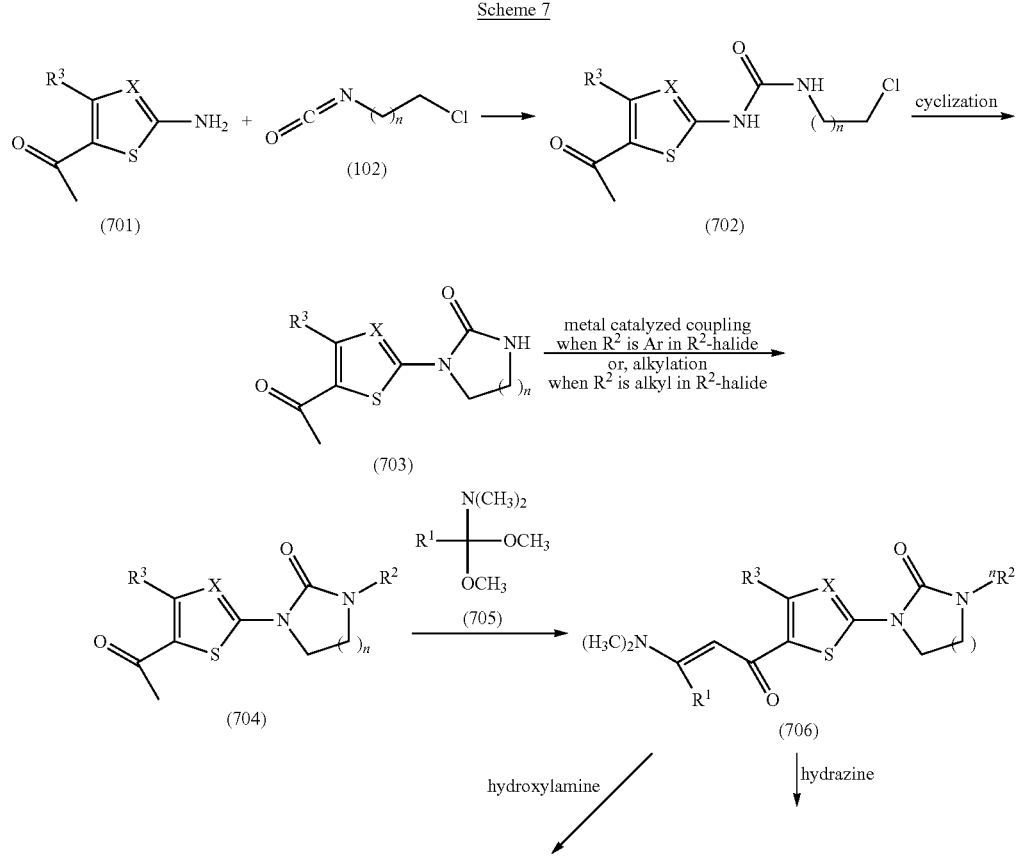

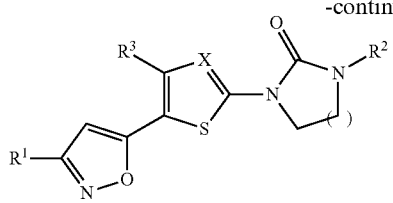

Formula (I), $R^2$ is alkyl or aryl

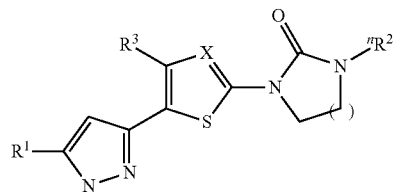

Formula (I), $R^2$ is alkyl or aryl

The starting materials for the above reaction scheme are commercially available or can be prepared according to methods known to one skilled in the art or by methods disclosed herein. In general, the compounds of the invention are prepared in the above reaction scheme as follows:

The 2-aminothiazole compound (701) reacts with isocyanate (102) to generate compound (702) which undergoes intramolecular cyclization in the presence of a base, such as, but not limited to, potassium carbonate, to afford the cyclized compound (703). Compound (703) reacts with an aryl halide or heteroaryl halide compound under metal catalyzed coupling reaction conditions to afford compound (704) where $R^2$ is an aryl or heteroaryl. Alternatively, compound (703) reacts with an alkyl halide under alkylation conditions to generate compound (704) where $R^2$ is an alkyl. Compound (704) reacts with dimethyl acetal of formula (705) under heating to generate the intermediate (706). Compound (706) is cyclized with hydrazine to generate compound of formula (I) where Q is

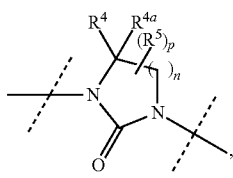

$R^4$, $R^{4a}$ and $R^5$ are hydrogen, W is

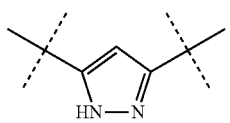

and V is a direct bond. Alternatively, compound (706) is cyclized with hydroxylamine to generate compound of formula (I) where Q is

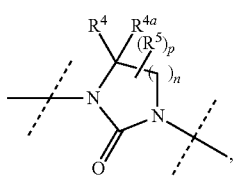

$R^4$, $R^{4a}$ and $R^5$ are hydrogen, W is

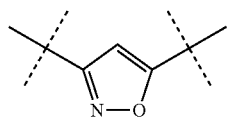

and V is a direct bond.

Alternatively, the cyclized urea compounds of Formula (I) of this invention can be synthesized following the general procedure as described in Scheme 8 where Q is

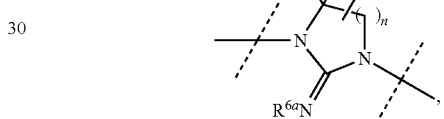

$R^4$, $R^{4a}$ and $R^5$ are hydrogen, W is —N($R^6$)C(O)— and V is a direct bond.

Scheme 8

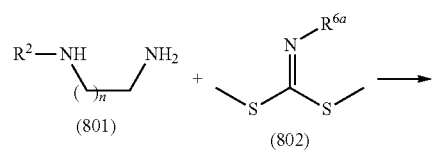

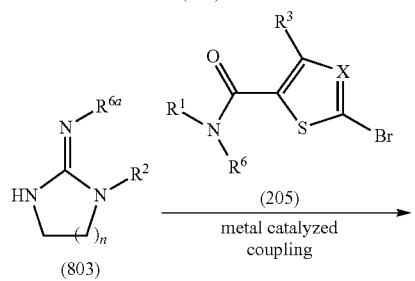

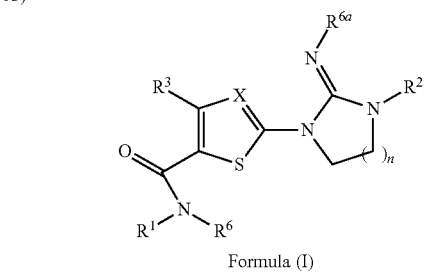

Formula (I)

The starting materials for the above reaction scheme are commercially available or can be prepared according to methods known to one skilled in the art or by methods disclosed herein. In general, the compounds of the invention are prepared in the above reaction scheme as follows:

Compound (801) is cyclized with compound (802) under reflux to afford compound (803). Compound (803) is coupled with compound (205) under metal catalyzed coupling reaction conditions to afford compound of Formula (I) of the invention where Q is

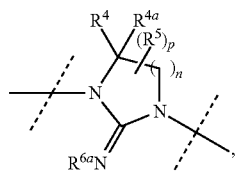

$R^4$, $R^{4a}$ and $R^5$ are hydrogen, W is —N($R^6$)C(O)— and V is a direct bond.

Alternatively, the cyclized urea compounds of Formula (I) of this invention can be synthesized following the general procedure as described in Scheme 9 where Q is

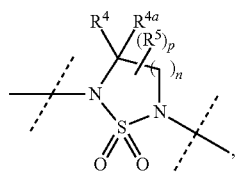

$R^4$, $R^{4a}$ and $R^5$ are hydrogen, W is —N($R^6$)C(O)— and V is a direct bond.

Scheme 9

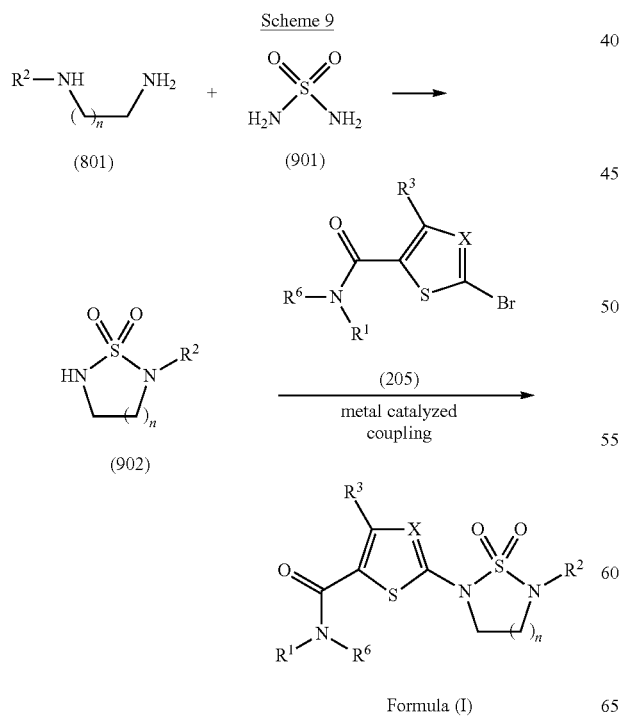

The starting materials for the above reaction scheme are commercially available or can be prepared according to methods known to one skilled in the art or by methods disclosed herein. In general, the compounds of the invention are prepared in the above reaction scheme as follows:

Compound (801) is cyclized with sulfuric diamide (901) under reflux to afford compound (902). Compound (902) is coupled with compound (205) under metal catalyzed coupling reaction conditions to afford compound of Formula (I) of the invention where Q is

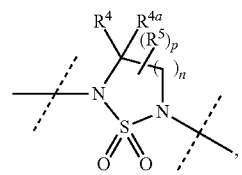

$R^4$, $R^{4a}$ and $R^5$ are hydrogen, W is —N($R^6$)C(O)— and V is a direct bond.

Preparation 1

Preparation of 2-amino-N-benzyl-4-methylthiazole-5-carboxamide

A. A mixture of ethyl 2-amino-4-methylthiazole-5-carboxylate (6.58 g, 35.5 mmol) and NaOH (5.40 g, 135 mmol) in tetrahydrofuran (60 mL) and water (30 mL) was heated to reflux overnight. Tetrahydrofuran was removed in vacuo, and the residue was neutralized with 5% hydrochloric acid solution to pH 5~6. The precipitate obtained was collected by filtration and dried to afford the crude 2-amino-4-methylthiazole-5-carboxylic acid (5.20 g, 94%): $^1$H NMR (300 MHz, DMSO-$d_6$) δ 7.63 (s, 2H), 2.30 (s, 3H); MS (ES+) m/z 159.1 (M+1).

B. To a suspension of 2-amino-4-methylthiazole-5-carboxylic acid (5.20 g, 32.9 mmol) and N,N-diisopropylethylamine (15 mL, 86.70 mmol) in N,N-dimethylformamide (40 mL) was added N-(3-dimethylaminopropyl)-N'-ethylcarbodiimide hydrochloride (8.18 g, 42.7 mmol). The resulting mixture was stirred for 30 min, then 1-hydroxybenzotriazole hydrate (5.78 g, 42.7 mmol) was added, followed by the addition of benzylamine (4.3 mL, 39.3 mmol). The reaction mixture was stirred at ambient temperature for 2 days, then diluted with ethyl acetate, washed with water and brine, dried over anhydrous sodium sulfate and filtered. The filtrate was concentrated in vacuo. The residue was purified by column chromatography to afford the title compound in 60% yield (4.90 g): $^1$H NMR (300 MHz, DMSO-$d_6$) δ 7.36-7.25 (m, 5H), 5.79 (br s, 1H), 5.36 (br s, 2H), 4.54 (d, J=5.7 Hz, 2H), 2.47 (s, 3H); MS (ES+) m/z 248.4 (M+1).

Preparation 2

Preparation of N-benzyl-2-(3-(2,2-dimethoxyethyl)-3-(4-fluorophenyl)ureido)-4-methylthiazole-5-carboxamide A. To a solution of 4-fluoroaniline (2.00 mL, 21.1 mmol) and dimethoxyacetaldehyde (60% solution in water, 3.30 mL, 21.9 mmol) in tetrahydrofuran (100 mL) was added sodium triacetoxyborohydride (6.70 g, 30.0 mmol) at ambient temperature. The resulting reaction mixture was stirred at ambient temperature for 12 hours, followed by the addition of brine (50 mL) then extraction with ethyl acetate (3×100 mL). The combined organic solution was dried over anhydrous sodium sulfate and filtered. The filtrate was concentrated in vacuo, and the residue was purified by column chromatography to afford N-(2,2-dimethoxyethyl)-4-fluoroaniline (2.30 g, 57%): MS (ES+) m/z 200.6 (M+1).

B. To a solution of 2-amino-N-benzyl-4-methylthiazole-5-carboxamide (0.37 g, 1.50 mmol) in tetrahydrofuran (20 mL) was added 1,1'-carbonyldiimidazole (0.31 g, 1.91 mmol) at ambient temperature. The resulting reaction mixture was stirred at ambient temperature for 11 hours, followed by the addition of N-(2,2-dimethoxyethyl)-4-fluoroaniline (0.40 g, 2.00 mmol). The reaction mixture was kept stirring for 17 hour at ambient temperature. The solvent was removed in vacuo, and the residue was purified by column chromatography to afford the title compound in 68% yield (0.48 g): $^1$H NMR (300 MHz, CDCl$_3$) δ 7.36-7.12 (m, 10H), 5.89 (t, J=5.7 Hz, 1H), 4.61 (t, J=5.4 Hz, 1H), 4.53 (d, J=5.4 Hz, 2H), 3.76 (t, J=5.7 Hz, 2H), 3.31 (s, 6H), 2.51 (s, 3H); MS (ES+) m/z 473.4 (M+1).

Preparation 2.1

Preparation of 2-(3-(2,2-dimethoxyethyl)-3-(4-fluorobenzyl)ureido)-4-methyl-N-(pyridin-3-ylmethyl)thiazole-5-carboxamide A. Following the procedure as described in step A of Preparation 2, making variations as required to replace 4-fluoroaniline with 4-fluorobenzylamine to react with dimethoxyacetaldehyde followed by the imine reduction with sodium triacetoxyborohydride, N-(4-fluorobenzyl)-2,2-dimethoxyethanamine was obtained in 71% yield: $^1$H NMR (300 MHz, CDCl$_3$) δ 7.24-7.19 (m, 2H), 6.97-6.89 (m, 2H), 4.43-4.39 (m, 1H), 3.70 (s, 2H), 3.30 (s, 6H), 2.67 (dd, J=5.4, 1.5 Hz, 2H); MS (ES+) m/z 214.3 (M+1).

B. Following the procedure as described in step B of Preparation 2, making variations as required to replace N-(2,2-dimethoxyethyl)-4-fluoroaniline with N-(4-fluorobenzyl)-2,2-dimethoxyethanamine to react with 2-amino-4-methyl-N-(pyridin-3-ylmethyl)thiazole-5-carboxamide, 2-(3-(2,2-dimethoxyethyl)-3-(4-fluorobenzyl)ureido)-4-methyl-N-(pyridin-3-ylmethyl)thiazole-5-carboxamide was obtained in 69% yield: MS (ES+) m/z 488.4 (M+1).

Preparation 2.2

Preparation of 2-(3-(2,2-dimethoxyethyl)-3-(4-(trifluoromethyl)benzyl)ureido)-4-methyl-N-(pyridin-3-ylmethyl)thiazole-5-carboxamide A. Following the procedure as described in step A of Preparation 2, making variations as required to replace 4-fluoroaniline with 4-(trifluoromethyl)benzylamine to react with dimethoxyacetaldehyde followed by the imine reduction with sodium triacetoxyborohydride, 2,2-dimethoxy-N-(4-(trifluoromethyl)benzyl)ethanamine was obtained in 67% yield: $^1$H NMR (300 MHz, CDCl$_3$) δ 7.52 (d, J=8.1 Hz, 2H), 7.39 (d, J=8.1 Hz, 2H), 4.43 (t, J=2.7 Hz, 1H), 3.81 (s, 2H), 3.38 (s, 6H), 2.67 (dd, J=2.7, 2.5 Hz, 2H); MS (ES+) m/z 264.3 (M+1).

B. Following the procedure as described in step B of Preparation 2, making variations as required to replace N-(2,2-dimethoxyethyl)-4-fluoroaniline with 2,2-dimethoxy-N-(4-(trifluoromethyl)benzyl)ethanamine to react with 2-amino-4-methyl-N-(pyridin-3-ylmethyl)thiazole-5-carboxamide, 2-(3-(2,2-dimethoxyethyl)-3-(4-(trifluoromethyl)benzyl) ureido)-4-methyl-N-(pyridin-3-ylmethyl)thiazole-5-carboxamide was obtained in 52% yield: $^1$H NMR (300 MHz, CDCl$_3$) δ 8.49 (d, J=1.5 Hz, 1H), 8.39-8.37 (m, 1H), 7.76-7.60 (m, 3H), 7.45 (d, J=8.1 Hz, 2H), 7.27 (d, J=8.1 Hz, 2H), 7.19-7.15 (m, 1H), 4.71-4.40 (m, 5H), 3.40 (d, J=4.8 Hz, 2H), 3.27 (s, 6H), 2.51 (s, 3H); MS (ES+) m/z 538.5 (M+1).

Preparation 3

Preparation of (R)-ethyl 2-(3-(1-hydroxy-3-phenylpropan-2-yl)ureido)-4-methylthiazole-5-carboxylate To a solution of ethyl 2-amino-4-methylthiazole-5-carboxylate (1.86 g, 10.0 mmol) in tetrahydrofuran (50 mL) was added 1,1'-carbonyldiimidazole (1.95 g, 12.0 mmol) at ambient temperature. The resulting reaction mixture was stirred at ambient temperature for 17 hours, followed by the addition of (R)-(+)-2-amino-3-phenyl-1-propanol (2.00 g, 13.2 mmol). The reaction mixture was kept stirring at ambient temperature for 50 hours. The solvent was removed in vacuo. The residue was dissolved in ethyl acetate (200 mL) and washed with water and brine. The organic solution was dried over anhydrous sodium sulfate and filtered. The filtrate was concentrated in vacuo to afford the title compound in 88% (3.20 g): MS (ES+) m/z 364.4 (M+1).

Preparation 4

Preparation of ethyl 5-(3-(2-chloroethyl)ureido)-3-methylthiophene-2-carboxylate A. Ethyl 5-amino-3-methylthiophene-2-carboxylate hydrochloride (5.80 g, 26.2 mmol) was suspended in dichloromethane (200 mL). To the suspension was added saturated aqueous sodium bicarbonate solution (250 mL). The resulting mixture was stirred for 15 minutes, then the two layers were separated. The aqueous layer was extracted with dichloromethane (100 mL). The combined organic layer was dried over sodium sulphate, filtered and concentrated in vacuo to afford ethyl 5-amino-3-methylthiophene-2-carboxylate (4.75 g, 98%).

B. A mixture of ethyl 5-amino-3-methylthiophene-2-carboxylic acid ethyl ester (4.75 g, 25.6 mmol) and 2-chloroethyl-isocyanate (2.63 ml, 30.8 mmol) in anhydrous acetonitrile (50 mL) was stirred under nitrogen atmosphere at 70° C. for 20 h, then was cooled to ambient temperature and concentrated in vacuo. The residue was triturated with hexanes/ethyl acetate to afford an off-white solid. The filtrate was concentrated in vacuo, and the residue was triturated with hexanes/ethyl acetate to afford an off white solid. The combined solid was dried to afford the title compound in 82% yield (6.11 g): $^1$H NMR (300 MHz, CDCl$_3$) δ 7.73 (br s, 1H), 6.31 (s, 1H), 5.60 (t, J=5.0 Hz, 1H), 4.27 (q, J=7.1 Hz, 2H), 3.69-3.59 (m, 4H), 2.44 (s, 3H), 1.33 (t, J=7.1 Hz, 3H); MS (ES+) m/z 291.2 (M+1).

Preparation 5

Preparation of N-benzyl-2-(3-(2,2-dimethoxyethyl)-3-(4-fluorobenzyl)ureido)-4-methylthiazole-5-carboxamide A. To a solution of 4-fluorobenzylamine (2.00 mL, 17.6 mmol) and dimethoxyacetaldehyde (60% solution in water, 3.00 mL, 19.9 mmol) in tetrahydrofuran (100 mL) was added sodium triacetoxyborohydride (5.90 g, 26.4 mmol) at ambient temperature. The resulting reaction mixture was stirred at ambient temperature for 5 hours, followed by the addition of saturated sodium bicarbonate (50 mL) and extraction with ethyl acetate (3×100 mL). The combined organic solution was dried over anhydrous sodium sulfate and filtered. The filtrate was concentrated and the residue was purified by column chromatography to afford N-(4-fluorobenzyl)-2,2-dimethoxyethanamine (2.70 g, 71%): $^1$H NMR (300 MHz, CDCl$_3$) δ 7.24-7.19 (m, 2H), 6.97-6.89 (m, 2H), 4.43-4.39 (m, 1H), 3.70 (s, 2H), 3.30 (s, 6H), 2.67 (dd, J=5.4, 1.5 Hz, 2H); MS (ES+) m/z 214.3 (M+1).

B. To a solution of 2-amino-N-benzyl-4-methylthiazole-5-carboxamide (0.31 g, 1.25 mmol) in tetrahydrofuran (20 mL) was added 1,1'-carbonyldiimidazole (0.24 g, 1.50 mmol) at ambient temperature. The resulting reaction mixture was stirred at ambient temperature for 6 hours, and N-(4-fluorobenzyl)-2,2-dimethoxyethanamine (0.35 g, 1.65 mmol) was added. The reaction mixture was stirred at ambient temperature for 17 hour. The solvent was removed in vacuo, and the residue was purified by column chromatography to afford the title compound in 77% yield (0.47 g): MS (ES+) m/z 487.4 (M+1).

Preparation 6

Preparation of ethyl 2-(hydrazinecarboxamido)-4-methylthiazole-5-carboxylate

To a solution of ethyl 2-amino-4-methylthiazole-5-carboxylate (0.50 g, 2.68 mmol) and pyridine (0.32 mL, 4.03 mmol) in tetrahydrofuran (25 mL) and dichloromethane (25 mL) was added 4-nitrophenyl chloroformate (0.65 g, 3.22 mmol) at 0° C. The resulting reaction mixture was stirred at ambient temperature for 1 hour, followed by the addition of hydrazine monohydrate (3.00 mL, 59.9 mmol). The reaction mixture was stirred at ambient temperature for 18 hours and quenched with water (100 mL). The solid precipitated was filtered, washed with water and ethyl acetate and dried to afford the title compound in 78% yield (0.51 g): MS (ES+) m/z 245.2 (M+1).

Preparation 7

Preparation of N-(1-benzylimidazolidin-2-ylidene)cyanamide

To a solution of N-benzylethane-1,2-diamine (3.00 g, 19.96 mmol) in anhydrous dioxane (15 mL) was added dimethyl cyanocarbonimidodithioate (3.50 g, 23.96 mmol). The mixture was refluxed for 16 hours, then diluted with dichloromethane (200 mL), washed with water (200 mL) and brine (100 mL). The organic layer was dried over anhydrous sodium sulfate, filtered and concentrated in vacuo. The residue was purified by column chromatography eluted with ethyl acetate/hexane (1/4) to afford the title compound as a colorless solid in 95% yield (3.88 g): mp 120-122° C. (ethyl acetate/hexanes); $^1$H NMR (300 MHz, CDCl$_3$) δ 7.36-7.22 (m, 5H), 6.86 (br s, 1H), 4.38 (s, 2H), 3.58-3.52 (m, 2H), 3.44-3.88 (m, 2H); $^{13}$C NMR (75 MHz, CDCl$_3$) δ 164.0, 135.5, 128.8, 128.1, 127.9, 119.4, 48.3, 46.1, 40.2; MS (ES+) m/z 201.2 (M+1).

Preparation 8

Preparation of N-benzyl-2-bromo-4-methylthiazole-5-carboxamide

To a solution of 2-bromo-4-methylthiazole-5-carboxylic acid (9.00 g, 40.0 mmol) in anhydrous tetrahydrofuran (140 mL) was added N,N-diisopropylethylamine (20.76 mL, 121.0 mmol) and 1-ethyl-3-(3-dimethylaminopropyl)carbodiimide hydrochloride (10.87 g, 56.0 mmol). The reaction mixture was stirred at ambient temperature for 0.5 hours and 1-hydroxybenzotriazole (7.60 g, 56.0 mmol) and benzyl amine (6.00 g, 56.0 mmol) were added. The resulting mixture was stirred at ambient temperature for 18 hours, then concentrated to half volume in vacuo, diluted with dichloromethane (400 mL), and washed with water (400 mL) and brine (150 mL). The organic layer was dried over anhydrous sodium sulfate, filtered and concentrated in vacuo. The residue was purified by column chromatography eluted with ethyl acetate/hexane (1/1) to afford the title compound as a colorless solid in 70% yield (8.89 g): mp 92-94° C. (ethyl acetate/hexanes); $^1$H NMR (300 MHz, CDCl$_3$) δ 7.41-7.23 (m, 5H), 5.94 (br s, 1H), 4.57 (d, J=5.6 Hz, 2H), 2.64 (s, 3H); MS (ES+) m/z 311.0 (M+1), 313.1 (M+3).

Preparation 8.1

Preparation of 2-bromo-N-(3,4-difluorobenzyl)-4-methylthiazole-5-carboxamide

Following the procedure as described in Preparation 8, making variations as required to replace benzyl amine with (3,4-difluorophenyl)methanamine to react with 2-bromo-4-methylthiazole-5-carboxylic acid, the title compound was obtained as a colorless solid in 61% yield: $^1$H NMR (300 MHz, CDCl$_3$) δ 7.16-7.01 (m, 3H), 6.08-5.94 (m, 1H), 4.52 (d, J=5.9 Hz, 2H), 2.64 (s, 3H); MS (ES+) m/z 347.2 (M+1), 349.2 (M+3).

Preparation 9

Preparation of 2-benzyl-1,2,5-thiadiazolidine 1,1-dioxide

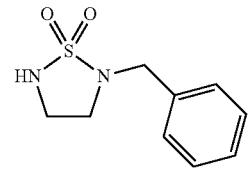

To a solution of N-benzylethane-1,2-diamine (1.00 g, 6.65 mmol) in pyridine (10 mL) was added sulfamide (0.77 g, 7.98 mmol). The mixture was refluxed for 16 hours. The solvent was removed in vacuo. The residue was diluted with ethyl acetate (100 mL), washed with water (200 mL) and brine (100 mL). The organic layer was dried over anhydrous sodium sulfate, filtered and concentrated in vacuo. The residue was purified by column chromatography eluted with ethyl acetate/hexane (1/4) to afford the title compound as an oily solid in 40% yield (0.57 g): $^1$H NMR (300 MHz, CDCl$_3$) δ 7.35-7.27 (m, 5H), 4.59 (br s, 1H), 4.15 (s, 2H), 3.48-3.42 (m, 2H), 3.27-3.22 (m, 2H); MS (ES+) m/z 213.2 (M+1).

Preparation 10

Preparation of 1-benzylimidazolidin-2-imine

To a solution of N-benzylethane-1,2-diamine (1.00 g, 6.65 mmol) in absolute ethanol (25 mL) was added cyanogen bromide (0.92 g, 8.65 mmol). The reaction mixture was stirred at ambient temperature for 1 hour, then cooled in an ice water bath. The pH of the solution was adjusted to ~10 by the addition of 1 M sodium hydroxide solution dropwise. The solvent was concentrated in vacuo. The residue was diluted with ethyl acetate (100 mL), washed with water (200 mL) and brine (100 mL). The organic layer was dried over anhydrous sodium sulfate, filtered and the concentrated in vacuo. The residue was recrystallized in ethyl acetate and hexane to yield the title compound as a colorless solid in 96% yield (1.12 g): mp 165-167° C. (ethyl acetate/hexanes); $^1$H NMR (300 MHz, DMSO-d$_6$) δ 7.39-7.24 (m, 6H), 4.47 (s, 2H), 3.49-3.33 (m, 4H); $^{13}$C NMR (75 MHz, DMSO-d$_6$) δ 159.4, 136.0, 129.1, 128.2, 128.1, 48.1, 47.4, 41.3; MS (ES+) m/z 176.3 (M+1).

Preparation 11

Preparation of 2-(3-(2,2-dimethoxyethyl)-3-(4-fluorophenethyl)ureido)-4-methyl-N-(pyridin-3-ylmethyl)thiazole-5-carboxamide A. To a solution of 4-fluorophenethylamine (2.00 mL, 15.0 mmol) and dimethoxyacetaldehyde (60% solution in water, 2.53 mL, 16.83 mmol) in tetrahydrofuran (100 mL) was added sodium triacetoxyborohydride (4.28 g, 20.20 mmol) at ambient temperature. The resulting reaction mixture was stirred at ambient temperature for 16 hours. The reaction was quenched by the addition of saturated sodium bicarbonate (50 mL). The mixture was extracted with ethyl acetate (3×100 mL) and the combined organic solution was dried over anhydrous sodium sulfate, filtered, and concentrated. The residue was purified by column chromatography eluted with ethyl acetate/hexane to afford N-(4-fluorophenethyl)-2,2-dimethoxyethanamine as a colorless oil in 52% yield (1.78 g): $^1$H NMR (300 MHz, CDCl$_3$) δ 7.14-7.10 (m, 2H), 6.97-6.91 (m, 2H), 4.43-4.40 (m, 1H), 3.35 (s, 6H), 2.89-2.81 (m, 2H), 2.76-2.71 (m, 4H); MS (ES+) m/z 228.2 (M+1).

B. To a solution of 2-amino-4-methyl-N-(pyridin-3-ylmethyl)thiazole-5-carboxamide (0.50 g, 2.01 mmol) in tetrahydrofuran (30 mL) was added 1,1% carbonyldiimidazole (0.39 g, 2.41 mmol) at ambient temperature. The resulting reaction mixture was stirred at ambient temperature for 6 hours and N-(4-fluorophenethyl)-2,2-dimethoxyethanamine (0.59 g, 2.61 mmol) was added. The reaction mixture was stirred for 17 hour at ambient temperature. The solvent was removed in vacuo, and the residue was purified by column chromatography eluted with dichloromethane/methanol (4/1) to afford 2-(3-(2,2-dimethoxyethyl)-3-(4-fluorophenethyl)ureido)-4-methyl-N-(pyridin-3-ylmethyl)thiazole-5-carboxamide as an oil in 19% yield (0.19 g): MS (ES+) m/z 502.4 (M+1).

Preparation 12

Preparation of ethyl 5-(hydrazinecarboxamido)-3-methylthiophene-2-carboxylate

A. A mixture of ethyl 5-(tert-butoxycarbonylamino)-3-methylthiophene-2-carboxylate (25.00 g, 87.61 mmol) and trifluoroacetic acid (50 mL) in dichloromethane (100 mL) was stirred at 0° C. for 2 h, then concentrated in vacuo. The residue was partitioned between ethyl acetate (300 mL) and 1 N aqueous sodium hydroxide (300 mL). The aqueous layer was extracted with ethyl acetate (200 mL), and the combined organic layer was dried over sodium sulfate, filtered and concentrated in vacuo. The residue was purified by column chromatography eluted with 40% ethyl acetate in hexanes to afford ethyl 5-amino-3-methylthiophene-2-carboxylate as a beige solid (14.44 g, 89%): $^1$H NMR (300 MHz, CDCl$_3$) δ 5.95 (s, 1H), 4.25 (q, J=7.1 Hz, 2H), 2.41 (s, 3H), 1.32 (t, J=7.1 Hz, 3H); MS (ES+) m/z 186.2 (M+1).

B. To a stirred mixture of 5-amino-3-methylthiophene-2-carboxylate (11.87 g, 64.08 mmol) and pyridine (5.70 mL, 70.48 mml) in dichloromethane (140 mL) at 0° C. was added dropwise phenyl chloroformate (8.90 mL, 70.71 mmol). The resulting reaction mixture was stirred at ambient temperature for 30 minutes, and then quenched with water (200 mL). The aqueous layer was extracted with dichloromethane (2×200 mL), and the combined organic layer was dried over sodium sulfate, filtered and concentrated in vacuo. The residue was triturated with dichloromethane in hexanes to afford ethyl 3-methyl-5-(phenoxycarbonylamino)thiophene-2-carboxylate as a colorless solid (18.89 g, 96%): MS (ES+) m/z 306.1 (M+1).

C. To a stirred suspension of ethyl 3-methyl-5-(phenoxycarbonylamino)-thiophene-2-carboxylate (18.89 g, 61.86 mmol) in tetrahydrofuran (130 mL) was added hydrazine monohydrate (19.0 mL, 391.7 mmol). The resulting reaction mixture was stirred for 2.5 h, and then concentrated in vacuo. The residue was triturated with ethyl acetate to afford ethyl 5-(hydrazinecarboxamido)-3-methylthiophene-2-carboxylate as a yellowish solid in 89% yield (13.30 g): MS (ES+) m/z 244.2 (M+1).

Preparation 13

Preparation of 2-amino-4-methyl-N-(pyridin-3-ylmethyl)thiazole-5-carboxamide

A. A solution of ethyl 2-amino-4-methylthiazole-5-carboxylate (6.58 g, 35.00 mmol) and sodium hydroxide (5.40 g, 135.00 mmol) in the mixture of tetrahydrofuran (60 mL) and water (30 mL) was heated at reflux for 18 hours. The tetrahydrofuran was removed in vacuo, and the aqueous solution was neutralized with 5% HCl solution to pH 5-6. The precipitated solid was collected by filtration, washed with water and dried to afford 2-amino-4-methylthiazole-5-carboxylic acid as a white solid in 94% yield (5.20 g): $^1$H NMR (300 MHz, DMSO-d$_6$) δ 7.63 (s, 2H), 2.30 (s, 3H); MS (ES+) m/z 159.1 (M+1).

B. To a solution of 2-amino-4-methylthiazole-5-carboxylic acid (8.30 g, 52.0 mmol), 1-(3-dimethylaminopropyl)-3-ethylcarbodiimide hydrochloride (13.01 g, 68.00 mmol) and N,N-diisopropylethylamine (12.90 mL, 68.00 mmol) in N,N-dimethylformamide (150 mL) was added 1-hydroxybenzotriazole (18.34 g, 136.0 mmol). The resulting mixture was stirred at ambient temperature for 15 minutes followed by the addition of 3-(aminomethyl)pyridine (6.30 mL, 63.00 mmol). The reaction mixture was stirred at ambient temperature for 17 hours. The solvent was removed in vacuo at 60° C. and the residue was partition between water and ethyl acetate. The organic layer was washed once with saturated sodium bicarbonate, dried over anhydrous sodium sulphate, filtered and concentrated in vacuo. The residue was triturated with mixture of ethyl acetate and methanol (99/1) to afford a white solid (4.60 g). The aqueous layer was left to stand at ambient temperature for 24 hours. The precipitated solid was collected by filtration and dried to afford a white solid (4.00 g). Both solids were combined to afford the title compound as a white solid in 67% yield (8.60 g); $^1$H NMR (300 MHz, CDCl$_3$) δ 8.47 (s, 1H), 8.41 (s, 1H), 8.04 (t, J=5.9 Hz, 1H), 7.67-7.61 (m, 1H), 7.36 (s, 2H), 7.34-7.28 (m, 1H), 4.32 (d, J=5.9 Hz, 2H), 2.30 (s, 3H); $^{13}$C NMR (75 MHz, CDCl$_3$) 167.73, 162.03, 153.79, 148.74, 147.88, 135.47, 135.05, 123.42, 111.74, 40.30, 17.21; MS (ES+) m/z 249.2 (M+1).

Preparation 14

Synthesis of pyrimidin-4-ylmethanamine

A. A solution of 4-(chloromethyl)pyrimidine (4.10 g, 31.9 mmol, prepared according to R. W. Carling et al., *J. Med. Chem.*, (2004), Vol. 47, pp. 1807-1822) and potassium phthalimide (5.91 g, 31.89 mmol) in N,N-dimethylformamide (60 mL) was heated to 110° C. for 16 hours. The reaction mixture was cooled to ambient temperature, and concentrated in vacuo. The residue was dissolved in dichloromethane (100 mL), washed with water (50 mL) and brine (50 ml). The organic layer was dried over anhydrous sodium sulphate, filtered and concentrated in vacuo. The residue was purified by column chromatography eluted with 40-50% ethyl acetate in hexanes to afford 2-(pyrimidin-4-ylmethyl)isoindoline-1,3-dione in 40% yield (3.0 g): $^1$H NMR (300 MHz, CDCl$_3$) δ 9.13 (s, 1H), 8.70 (br s, 1H), 7.93-7.86 (m, 2H), 7.79-7.75 (m, 2H), 7.30 (d, J=6.0 Hz, 1H), 4.99 (s, 2H); MS (ES+) m/z 240.1 (M+1).

B. A solution of 2-(pyrimidin-4-ylmethyl)isoindoline-1,3-dione (1.00 g, 4.18 mmol) in 5 N sodium hydroxide solution (50 mL) was refluxed for 1 h. The resulting solution was cooled to ambient temperature and extracted with dichloromethane (3×30 mL). The combined organic layer was dried over anhydrous sodium sulphate, filtered and the filtrate was used without further purification for the next step reaction: MS (ES+) m/z 110.9 (M+1).

Preparation 14.1

Synthesis of pyridazin-3-ylmethanamine

A. Following the procedure as described in step A of Preparation 14, making variations as required to replace 4-(chloromethyl)pyrimidine with 3-(chloromethyl)pyridazine (prepared according to R. W. Carling, et al., *J. Med. Chem.*, (2004), Vol. 47, pp. 1807-1822) to react with potassium phthalimide, 2-(pyridazin-3-ylmethyl)isoindoline-1,3-dione was obtained as a colorless solid in 17% yield: $^1$H NMR (300 MHz, CDCl$_3$) δ 9.12 (d, J=3.0 Hz, 1H), 7.90-7.85 (m, 2H), 7.78-7.72 (m, 2H), 7.51-7.43 (m, 2H), 5.21 (s, 2H); MS (ES+) m/z 240.1 (M+1).

B. Following the procedure as described in step B of Preparation 14, making variations as required to replace 2-(pyrimidin-4-ylmethyl)isoindoline-1,3-dione with 2-(pyridazin-3-ylmethyl)isoindoline-1,3-dione, pyridazin-3-ylmethanamine was obtained as an oil: MS (ES+) m/z 110.0 (M+1).

Preparation 14.2

Synthesis of pyrazin-2-ylmethanamine

A. Following the procedure as described in step A of Preparation 14, making variations as required to replace 4-(chloromethyl)pyrimidine with 2-(chloromethyl)pyrazine (prepared according to R. W. Carling, et al., J. Med. Chem., (2004), Vol. 47, pp. 1807-1822) to react with potassium phthalimide, 2-(pyrazin-2-ylmethyl)isoindoline-1,3-dione was obtained as a colorless solid in 46% yield: mp 141-143° C.; $^1$H NMR (300 MHz, CDCl$_3$) δ 8.65 (s, 1H), 8.47 (s, 2H), 7.90-7.87 (m, 2H), 7.76-7.73 (m, 2H), 5.05 (s, 2H); MS (ES+) m/z 240.1 (M+1).

B. Following the procedure as described in step B of Preparation 14, making variations as required to replace 2-(pyrimidin-4-ylmethyl)isoindoline-1,3-dione with 2-(pyrazin-2-ylmethyl)isoindoline-1,3-dione, pyridazin-2-ylmethanamine was obtained as an oil: MS (ES+) m/z 110.9 (M+1).

Preparation 15

Preparation of tert-butyl 4-(chloromethyl)phenylcarbamate

A. To a stirred solution of 4-aminobenzyl alcohol (1.50 g, 12.18 mmol) in 1,4-dioxane (30 mL) was added sodium hydroxide (0.49 g, 12.2 mmol) in water (30 mL). The mixture was cooled to 0° C., and di-tert-butyl dicarbonate (2.93 g, 13.4 mmol) was added in portions. The resulting reaction mixture was stirred at ambient temperature for 1.5 h, and diluted with ethyl acetate (75 mL). The organic layer was washed with 10% aqueous hydrochloric acid (2×35 mL) and water, dried over sodium sulfate, filtered and concentrated in vacuo to afford tert-butyl 4-(hydroxymethyl)phenylcarbamate as a viscous yellowish liquid in 87% yield (2.36 g): $^1$H NMR (300 MHz, CDCl$_3$) δ 7.37-7.26 (m, 4H), 6.52 (br s, 1H), 4.63 (s, 2H), 1.52 (s, 9H); MS (ES+) m/z 246.3 (M+23).

B. To a stirred solution of tert-butyl 4-(hydroxymethyl) phenylcarbamate (0.50 g, 2.24 mmol) in dichloromethane was added pyridine (3 drops), followed by the dropwise addition of thionyl chloride (0.35 mL, 4.98 mmol). The resulting reaction mixture was stirred for 30 minutes, and then quenched with water (25 mL). The aqueous layer was extracted with dichloromethane (50 mL), and the organic layer was dried over sodium sulfate, filtered and concentrated in vacuo to afford tert-butyl 4-(chloromethyl)-phenylcarbamate as an orange solid in 50% yield (0.27 g, 50%): $^1$H NMR (300 MHz, CDCl$_3$) δ 7.38-7.28 (m, 4H), 6.51 (br s, 1H), 4.55 (s, 2H), 1.52 (s, 9H).

Preparation 16

Preparation of quinolin-3-ylmethanaminium chloride

A. To a stirred solution of 3-quinolinecarbonitrile (1.00 g, 6.49 mmol) in methanol (50 mL) at 0° C. was added di-tert-butyl dicarbonate (2.83 g, 12.97 mmol), followed by the addition of nickel chloride hexahydrate (0.15 g, 0.65 mmol). Sodium borohydride was then added in small portions over 20 minutes. The resulting reaction mixture was stirred at ambient temperature for 1 h. Diethylenetriamine (0.70 mL) was added, and the mixture was stirred for 30 minutes. The solvent was removed in vacuo. The residue was taken up in saturated aqueous sodium bicarbonate solution (100 mL) and extracted with dichloromethane (2×100 mL). The combined organic layer was dried over sodium sulfate, filtered and concentrated in vacuo. The residue was purified by column chromatography eluted with 60% ethyl acetate in hexanes, and then triturated with dichloromethane. The insoluble material was filtered off, and the filtrate was concentrated in vacuo to afford tert-butyl quinolin-3-ylcarbamate as a colorless solid in 13% yield (0.21 g): $^1$H NMR (300 MHz, CDCl$_3$) δ 8.86 (d, J=1.8 Hz, 1H), 8.10 (d, J=8.3 Hz, 1H), 8.05 (s, 1H), 7.80 (d, J=8.3 Hz, 1H), 7.74-7.66 (m, 1H), 7.59-7.51 (m, 1H), 5.04 (br s, 1H), 4.51 (d, J=5.8 Hz, 2H), 1.47 (s, 9H); MS (ES+) m/z 259.2 (M+1).

B. A mixture of tert-butyl quinolin-3-ylcarbamate (0.21 g, 0.81 mmol) and trifluoroacetic acid (1 mL) in dichloromethane (4 mL) was stirred for 1 h, and then concentrated in vacuo. The residue was taken up in dichloromethane (4 mL) and acidified with hydrogen chloride (4.0 M in dioxane, 0.5 mL). The solvent was removed in vacuo, and the residue was dissolved in methanol and triturated with ethyl acetate to afford quinolin-3-ylmethanaminium chloride as a beige solid in 95% yield (0.15 g): $^1$H NMR (300 MHz, CDCl$_3$) δ 9.35 (d, J=1.7 Hz, 1H), 9.03 (s, 1H), 8.85 (br s, 3H), 8.32 (d, J=8.2 Hz, 1H), 8.22 (d, J=8.2 Hz, 1H), 8.10-8.03 (m, 1H), 7.92-7.85 (m, 1H), 4.36 (d, J=5.6 Hz, 2H); MS (ES+) m/z 159.1 (M+1).

Preparation 17

Preparation of (S)-3-phenylpropane-1,2-diamine

A. A mixture of L-phenylalanine methyl ester hydrochloride (6.50 g, 30.1 mmol) and ammonium hydroxide solution (28% in water, 15 mL) in water (60 mL) was stirred at ambient temperature for 64 h. The aqueous layer was extracted with dichloromethane (6×100 mL), and the combined organic layer was dried over sodium sulfate, filtered and concentrated in vacuo to afford (S)-2-amino-3-phenylpropanamide as a colorless solid in 59% yield (2.92 g): $^1$H NMR (300 MHz, DMSO-d$_6$) δ 7.38-7.21 (m, 5H), 7.12 (br s, 1H), 5.44 (br s, 1H), 3.63 (dd, J=9.5, 3.9 Hz, 1H), 3.28 (dd, J=13.7, 3.9 Hz, 1H), 2.72 (dd, J=13.7, 9.5 Hz, 1H), 1.41 (br s, 2H).

B. To a stirred solution of (S)-2-amino-3-phenylpropanamide (2.92 g, 17.78 mmol) in tetrahydrofuran (50 mL) at 0° C. under nitrogen atmosphere was dropwise added lithium aluminum hydride (18.0 mL of 2.0 M solution in tetrahydrofuran, 36.0 mmol). The resulting reaction mixture was stirred at reflux for 2 h, and then cooled to 0° C. and quenched with sodium sulfate decahydrate. The resulting precipitate was filtered, and the filter cake was washed with ethyl acetate (250 mL). The filtrate was concentrated in vacuo to afford (S)-3-phenylpropane-1,2-diamine as yellowish oil in 97% yield (2.60 g): $^1$H NMR (300 MHz, CDCl$_3$) δ 7.35-7.17 (m, 5H), 3.02-2.92 (m, 1H), 2.85-2.74 (m, 2H), 2.60-2.45 (m, 2H), 1.47 (br s, 4H).

Preparation 18

Preparation of (5-(difluoromethyl)furan-2-yl)methanamine

A. To the solution of (5-formylfuran-2-yl)methyl acetate (6.70 g, 39.8 mmol) in anhydrous dichloromethane (50 mL) was added dropwise (diethylamino)sulfur trifluoride (5.22 mL, 39.85 mmol) at 0° C. The reaction mixture was stirred at ambient temperature for 20 hours, quenched with saturated sodium bicarbonate solution and extracted with dichloromethane (3×50 mL). The organic solutions were combined, dried over anhydrous sodium sulphate, filtered and concentrated in vacuo. The residue was purified by column chromatography eluted with ethyl acetate/hexane (3/7) to afford (5-(difluoromethyl)furan-2-yl)methyl acetate as a colorless oil in 55% yield (4.21 g): $^1$H NMR (300 MHz, CDCl$_3$) δ 6.61-6.59 (m, 1H), 5.57 (t, J$_{H-F}$=54.4 Hz, 1H), 6.45-6.30 (m, 1H), 5.04 (s, 2H), 2.07 (s, 3H).

B. To a suspension of potassium carbonate in anhydrous methanol (10%, 50 mL) was added (5-(difluoromethyl)furan-2-yl)methyl acetate (4.21 g, 22.16 mmol). The reaction mixture was stirred at ambient temperature for 20 minutes, filtered and concentrated in vacuo. The residue was purified by column chromatography eluted with ethyl acetate/hexane (3/7) to afford (5-(difluoromethyl)furan-2-yl)methanol as a yellow oil in 96% yield (3.15 g): $^1$H NMR (300 MHz, CDCl$_3$) δ 6.55 (t, J$_{H-F}$=54.2 Hz, 1H), 6.58-6.55 (m, 1H), 6.34-6.26 (m, 1H), 4.59 (d. J=5.9 Hz, 2H).

C. To a solution of (5-(difluoromethyl)furan-2-yl)methanol (0.55 g, 3.72 mmol), triphenylphosphine (1.07 g, 4.09 mmol) and diethylazodicarboxylate (0.64 mL, 4.09 mmol) in anhydrous tetrahydrofuran (20 mL) was added diphenylphosphorylazide (0.88 mL, 4.09 mmol). The reaction mixture was stirred at ambient temperature for 18 hours, diluted with dichloromethane (40 mL) and washed with water and brine. The organic solution was dried over anhydrous sodium sulphate, filtered and concentrated in vacuo. The residue was purified by column chromatography eluted with ethyl acetate/hexane (1/9) to afford 2-(azidomethyl)-5-(difluoromethyl)furan as a yellow oil in 77% yield (0.50 g): $^1$H NMR (300 MHz, CDCl$_3$) δ 6.61 (d, J=3.3 Hz, 1H), 6.58 (t, J=54.3 Hz, 1H), 6.37 (d, J=3.3 Hz, 1H), 4.30 (s, 2H); MS (ES+) m/z 172.2 (M+1).

D. To a solution of 2-(azidomethyl)-5-(difluoromethyl)furan (0.50 g, 2.92 mmol) in a mixture of tetrahydrofuran (10 mL) and water (1 mL) was added triphenylphosphine (1.15 g, 4.39 mmol). The reaction mixture was stirred at ambient temperature for 18 hours. The solvent was removed in vacuo and the residue was purified on strong cation exchange column to afford (5-(difluoromethyl)furan-2-yl)methanamine as a yellow oil in 70% yield (0.30 g): MS (ES+) m/z 3148.2 (M+1).

Preparation 19

Preparation of 2-bromo-4-methyl-N-(pyridin-3-ylmethyl)thiazole-5-carboxamide

To a solution of 2-bromo-4-methylthiazole-5-carboxylic acid (10.00 g, 45.00 mmol) and 4-methylmorpholine (6.5 mL, 59.0 mmol) in tetrahydrofuran (150 mL) was added isobutyl chloroformate (6.5 mL, 49.6 mmol) at 0° C. The resulting mixture was stirred at room temperature for 1 hour and 3-(aminomethyl)pyridine (5.2 mL, 51.4 mmol) was added. The reaction mixture was stirred at ambient temperature for 17 hours, and then concentrated in vacuo. The residue was purified by column chromatography to afford 2-bromo-4-methyl-N-(pyridin-3-ylmethyl)thiazole-5-carboxamide in 52% yield (7.3 g): $^1$H NMR (300 MHz, CDCl$_3$) δ 8.39-8.80 (m, 2H), 7.80-7.72 (m, 1H), 7.40-7.35 (m, 1H), 6.47 (br s, 1H), 4.60 (d, J=6.0 Hz, 2H), 2.64 (s, 3H); MS (ES+) m/z 312.1 (M+1), 314.1 (M+1).

Preparation 20

Preparation of 2-bromo-N-(4-fluorobenzyl)-4-methylthiazole-5-carboxamide

To a solution of 2-bromo-4-methylthiazole-5-carboxylic acid (2.00 g, 9.00 mmol), 1-(3-dimethylaminopropyl)-3-ethylcarbodiimide hydrochloride (2.41 g, 12.6 mmol) and N,N-diisopropylethylamine (4.67 mL, 27.0 mmol) in tetrahydrofuran (40 mL) was added 1-hydroxybenzotriazole (1.70 g, 12.6 mmol). The resulting mixture was stirred at ambient temperature for 30 minutes and 4-fluorobenzylamine (1.43 mL, 12.6 mmol) was added. The reaction mixture was kept stirring for 17 hours, then concentrated in vacuo. The residue was dissolved ethyl acetate and washed with water and brine. The organic solution was dried over anhydrous sodium sulfate, filtered and concentrated in vacuo. The residue was purified by column chromatography to afford 2-bromo-N-(4-fluorobenzyl)-4-methylthiazole-5-carboxamide in 81% yield (2.38 g): $^1$H NMR (300 MHz, CDCl$_3$) δ 7.30-7.26 (m, 2H), 7.05-7.00 (m, 2H), 5.99-5.87 (m, 1H), 4.54 (d, J=5.7 Hz, 2H), 2.63 (s, 3H).

Example 1

Synthesis of N-benzyl-2-(3-(4-fluorophenyl)-5-methoxy-2-oxoimidazolidin-1-yl)-4-methylthiazole-5-carboxamide and N-benzyl-2-(3-(4-fluorophenyl)-5-hydroxy-2-oxoimidazolidin-1-yl)-4-methylthiazole-5-carboxamide

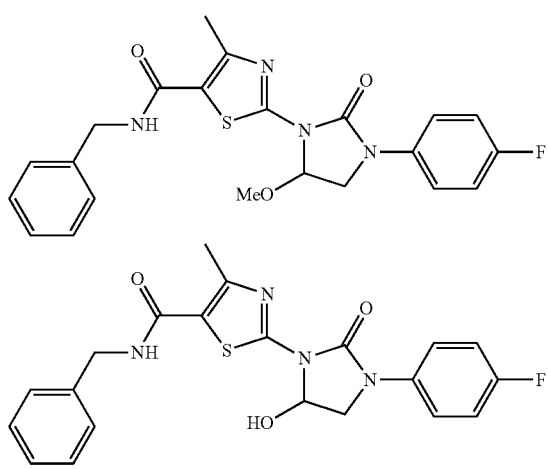

To a solution of N-benzyl-2-(3-(2,2-dimethoxyethyl)-3-(4-fluorophenyl)ureido)-4-methylthiazole-5-carboxamide (0.48 g, 1.01 mmol) in tetrahydrofuran (20 mL) was added 2.0 M sulfuric acid (5.00 mL) at ambient temperature. The resulting reaction mixture was stirred at ambient temperature for 53 hours. The solvent was removed in vacuo, and the residue was dissolved in ethyl acetate (200 mL) and washed with saturated sodium bicarbonate solution and brine. The organic solution was dried over anhydrous sodium sulfate and filtered. The filtrate was concentrated in vacuo, and the residue was purified by column chromatography to afford two products. The first fraction: N-benzyl-2-(3-(4-fluorophenyl)-5-methoxy-2-oxoimidazolidin-1-yl)-4-methylthiazole-5-carboxamide (0.31 g, 69%): mp 162-163° C.; $^1$H NMR (300 MHz, DMSO-d$_6$) δ 8.59 (t, J=6.0 Hz, 1H), 7.64-7.59 (m, 2H), 7.34-7.17 (m, 7H), 5.90 (d, J=6.6 Hz, 1H), 4.36 (d, J=6.0 Hz, 2H), 4.21 (dd, J=10.8, 6.6 Hz, 1H), 3.92 (d, J=10.8 Hz, 1H), 3.41 (s, 3H), 2.48 (s, 3H); $^{13}$C NMR (75 MHz, DMSO-d$_6$) δ 162.0, 160.5, 157.3, 156.5, 152.5, 151.1, 140.0, 135.2, 135.1, 128.7, 127.6, 127.1, 120.8, 120.7, 119.8, 116.2, 115.9, 82.7, 55.7, 50.2, 43.1, 17.6; MS (ES+) m/z 441.2 (M+1). The second fraction: N-benzyl-2-(3-(4-fluorophenyl)-5-hydroxy-2-oxoimidazolidin-1-yl)-4-methylthiazole-5-carboxamide (0.10 g, 23%): mp 186-187° C.; $^1$H NMR (300 MHz, DMSO-d$_6$) δ 8.57 (t, J=5.7 Hz, 1H), 7.65-7.60 (m, 2H), 7.34-7.15 (m, 7H), 7.09 (d, J=7.2 Hz, 1H), 6.01 (t, J=6.6 Hz, 1H), 4.36 (d, J=6.0 Hz, 2H), 4.24 (dd, J=10.5, 6.6 Hz, 1H), 3.71 (d, J=10.5 Hz, 1H), 2.49 (s, 3H); $^{13}$C NMR (75 MHz, DMSO-d$_6$) δ 162.1, 160.3, 157.1, 156.3, 152.3, 151.3, 140.0, 135.6, 135.5, 128.7, 127.7, 127.1, 120.5, 120.4, 119.4, 116.2, 115.9, 75.7, 52.8, 43.1, 17.6; MS (ES+) m/z 427.2 (M+1).

Example 2

Synthesis of N-benzyl-2-(3-(4-fluorophenyl)-2,5-dioxoimidazolidin-1-yl)-4-methylthiazole-5-carboxamide

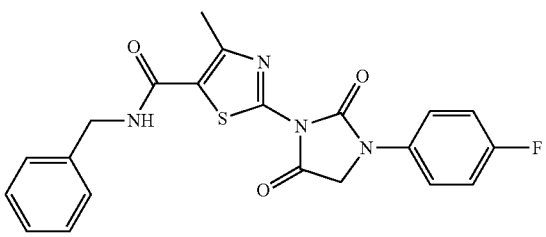

To a solution of 2-[3-(4-fluorophenyl)-5-hydroxy-2-oxo-imidazolidin-1-yl]-4-methylthiazole-5-carboxylic acid benzylamide (0.07 g, 0.17 mmol) and tetrapropylammonium perruthenate (0.003 g, 0.008 mmol) in chloroform (15 mL) was added 4-methylmorpholine N-oxide (0.03 g, 0.22 mmol) at ambient temperature. The resulting reaction mixture was stirred at ambient temperature for 1 hour, and filtered through a bed of celite. The filtrate was concentrated in vacuo, and the residue was purified by column chromatography to afford the title compound in 18% yield (0.14 g): mp 217-219° C.; $^1$H NMR (300 MHz, CDCl$_3$) δ 7.54-7.07 (m, 9H), 6.12 (t, J=5.1 Hz, 1H), 4.55 (d, J=5.1 Hz, 2H), 4.47 (s, 2H), 2.70 (s, 3H); MS (ES+) m/z 425.3 (M+1).

Example 3

Synthesis of ethyl 4-methyl-2-(2-oxoimidazolidin-1-yl)thiazole-5-carboxylate

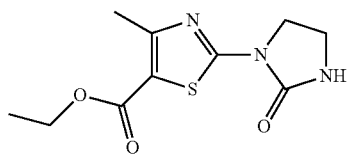

To a solution of ethyl 2-amino-4-methylthiazole-5-carboxylate (9.31 g, 49.99 mmol) in tetrahydrofuran (200 mL) was added 2-chloroethyl isocyanate (5.50 mL, 64.0 mmol) at ambient temperature. The resulting reaction mixture was heated to reflux for 7 hours, followed by the addition of potassium carbonate (8.30 g, 60.0 mmol) and tetra-n-butylammonium iodide (0.50 g, 1.35 mmol) and the resulting mixture was heated to reflux for 23 hours. The solvent was removed in vacuo, and the residue was washed with water (200 mL) and ethyl acetate (50 mL) to afford the title compound in 71% yield (9.10 g): mp 197-199° C.; $^1$H NMR (300 MHz, DMSO-d$_6$) δ 7.83 (s, 1H), 4.20-3.93 (m, 4H), 3.49-3.43 (m, 2H), 2.46 (s, 3H), 1.20 (t, J=6.9 Hz, 3H); MS (ES+) m/z 256.3 (M+1).

Example 3.1

Synthesis of methyl 2-(2-oxoimidazolidin-1-yl)thiazole-5-carboxylate

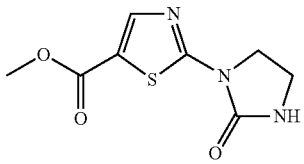

Following the procedure as described in Example 3, making variations as required to replace ethyl 2-amino-4-methylthiazole-5-carboxylate with methyl 2-aminothiazole-5-carboxylate to react with 2-chloroethyl isocyanate, the title compound was obtained as a colorless solid in 44% yield: mp 205-208° C. (ethyl acetate/hexanes); $^1$H NMR (300 MHz, CDCl$_3$) δ 8.02 (s, 1H), 5.55 (s, 1H), 4.25-4.19 (m, 2H), 3.84 (s, 3H), 3.72-3.67 (m, 2H); $^{13}$C NMR (75 MHz, CDCl$_3$) δ 162.8, 162.5, 157.0, 145.1, 122.2, 52.1, 44.4, 38.1; MS (ES+) m/z 228.2 (M+1).

Example 3.2

Synthesis of ethyl 2-(2-oxoimidazolidin-1-yl)-4-(trifluoromethyl)thiazole-5-carboxylate

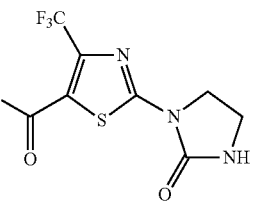

Following the procedure as described in Example 3, making variations as required to replace ethyl 2-amino-4-methylthiazole-5-carboxylate with ethyl 2-amino-4-(trifluoromethyl)thiazole-5-carboxylate to react with 2-chloroethyl isocyanate, the title compound was obtained as a colorless solid in 30% yield: mp 185-187° C. (ethyl acetate/hexanes); $^1$H NMR (300 MHz, CDCl$_3$) δ 5.54 (s, 1H), 4.36-4.21 (m, 4H), 3.74-3.68 (m, 2H), 1.36-1.31 (m, 3H); $^{13}$C NMR (75 MHz, CDCl$_3$) δ 159.8, 157.0, 125.4, 122.6, 121.8, 118.2, 62.0, 44.2, 43.8, 14.0; MS (ES+) m/z 310.2 (M+1).

Example 3.3

Synthesis of 1-(4-methylthiazol-2-yl)imidazolidin-2-one

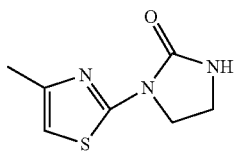

Following the procedure as described in Example 3, making variations as required to replace ethyl 2-amino-4-methylthiazole-5-carboxylate with 2-amino-4-methylthiazole to react with 2-chloroethyl isocyanate, the title compound was obtained as a colorless solid in 90% yield: $^1$H NMR (300 MHz, CDCl$_3$) δ 6.41 (s, 1H), 5.79 (br s, 1H), 4.20-4.14 (m, 2H), 3.67-3.61 (m, 2H), 2.29 (s, 3H); MS (ES+) m/z 184.1.1 (M+1).

Example 3.4

Synthesis of ethyl 4-methyl-2-(2-oxotetrahydropyrimidin-1(2H)-yl)thiazole-5-carboxylate

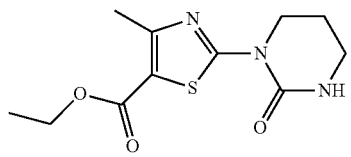

Following the procedure as described in Example 3, making variations as required to replace 2-chloroethyl isocyanate with 3-chloropropyl isocyanate to react with ethyl 2-amino-4-methylthiazole-5-carboxylate, the title compound was obtained as a brown solid in 32% yield: $^1$H NMR (300 MHz, DMSO-d$_6$) δ 8.21 (s, 1H), 4.75 (q, J=7.1 Hz, 2H), 4.57 (t, J=5.9 Hz, 2H), 3.80-3.75 (m, 2H), 3.05 (s, 3H), 2.54-2.46 (m, 2H), 1.81 (t, J=7.1 Hz, 3H); MS (ES+) m/z 270.2 (M+1).

Example 4

Synthesis of ethyl 4-methyl-2-(2-oxo-3-phenylimidazolidin-1-yl)thiazole-5-carboxylate

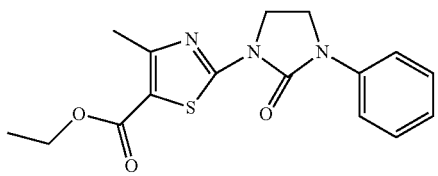

To a degassed solution of ethyl 4-methyl-2-(2-oxoimidazolidin-1-yl)thiazole-5-carboxylate (1.28 g, 5.00 mmol), iodobenzene (0.70 mL, 6.15 mmol), potassium carbonate (0.83 g, 6.00 mmol) and rac-trans-N,N'-dimethylcyclohexane-1,2-diamine (0.08 mL, 0.50 mmol) in dioxane (50 mL) was added copper(I) iodide (0.10 g, 0.50 mmol). The reaction mixture was heated to reflux for 16 hours. The solvent was removed in vacuo, and the residue was suspended in water and filtered. The solid was collected and washed with water (200 mL) and t-butyl methyl ether (100 mL) to afford the title compound in 89% yield (1.49 g): $^1$H NMR (300 MHz, DMSO-d$_6$) δ 7.69-7.08 (m, 5H), 4.28-4.13 (m, 6H), 2.62 (s, 3H), 1.30 (t, J=6.9 Hz, 3H); MS (ES+) m/z 332.4 (M+1).

Example 5

Synthesis of ethyl 2-(3-benzyl-2-oxoimidazolidin-1-yl)-4-methylthiazole-5-carboxylate

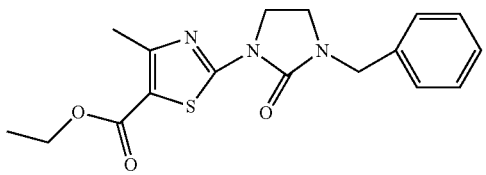

To a suspension of ethyl 4-methyl-2-(2-oxoimidazolidin-1-yl)thiazole-5-carboxylate (0.51 g, 2.00 mmol) and potassium carbonate (0.49 g, 3.54 mmol) in acetone (30 mL) was added benzyl bromide (0.30 mL, 0.25 mmol). The reaction mixture was heated to reflux for 16 hours. The solvent was removed in vacuo, and the residue was washed with water (100 mL) and hexanes (30 mL) to afford the title compound in 93% yield (0.65 g): mp 122-124° C.; $^1$H NMR (300 MHz, DMSO-$d_6$) δ 7.35-7.26 (m, 5H), 4.40 (s, 2H), 4.19 (q, J=7.2 Hz, 2H), 3.97 (t, J=7.5 Hz, 2H), 3.42 (t, J=7.5 Hz, 2H), 2.48 (s, 3H), 1.23 (t, J=7.2 Hz, 3H); MS (ES+) m/z 346.0 (M+1).

Example 5.1

Synthesis of ethyl 4-methyl-2-(2-oxo-3-phenethylimidazolidin-1-yl)thiazole-5-carboxylate

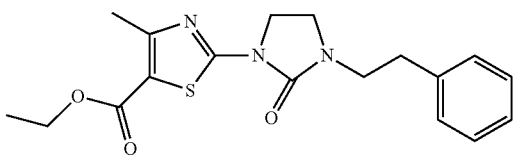

Following the procedure as described in Example 5, making variations to replace benzyl bromide with (2-iodoethyl)benzene to react with ethyl 4-methyl-2-(2-oxoimidazolidin-1-yl)thiazole-5-carboxylate, the title compound was obtained in 35% yield: $^1$H NMR (300 MHz, CDCl$_3$) δ 7.31-7.20 (m, 5H), 4.25 (q, J=7.2 Hz, 2H), 4.02 (t, J=7.8 Hz, 2H), 3.57 (t, J=7.2 Hz, 2H), 3.42 (t, J=7.8 Hz, 2H), 2.89 (t, J=7.2 Hz, 2H), 2.59 (s, 3H), 1.31 (t, J=7.2 Hz, 3H); MS (ES+) m/z 360.2 (M+1).

Example 5.2

Synthesis of ethyl 4-methyl-2-(2-oxo-3-(4-(trifluoromethyl)benzyl)imidazolidin-1-yl)thiazole-5-carboxylate

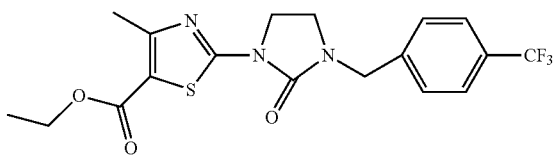

Following the procedure as described in Example 5, making variations to replace benzyl bromide with 4-(trifluoromethyl)benzyl bromide to react with ethyl 4-methyl-2-(2-oxoimidazolidin-1-yl)thiazole-5-carboxylate, the title compound was obtained in 92% yield: mp 126-127° C.; $^1$H NMR (300 MHz, DMSO-$d_6$) δ 7.70 (d, J=8.1 Hz, 2H), 7.51 (d, J=8.1 Hz, 2H), 4.51 (s, 2H), 4.17 (q, J=6.9 Hz, 2H), 4.00 (t, J=8.1 Hz, 2H), 3.47 (t, J=8.1 Hz, 2H), 2.49 (s, 3H), 1.23 (t, J=6.9 Hz, 3H); MS (ES+) m/z 414.1 (M+1).

Example 5.3

Synthesis of ethyl 2-(3-(4-fluorobenzyl)-2-oxoimidazolidin-1-yl)-4-methylthiazole-5-carboxylate

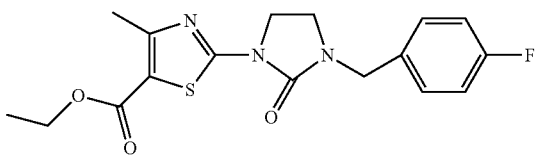

Following the procedure as described in Example 5, making variations to replace benzyl bromide with 4-fluorobenzyl bromide to react with ethyl 4-methyl-2-(2-oxoimidazolidin-1-yl)thiazole-5-carboxylate, the title compound was obtained in 98% yield: MS (ES+) m/z 364.2 (M+1).

Example 5.4

Synthesis of ethyl 4-methyl-2-(2-oxo-3-(4-(trifluoromethoxy)benzyl)imidazolidin-1-yl)thiazole-5-carboxylate

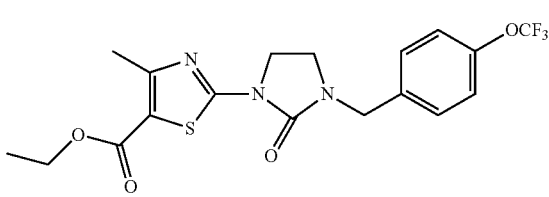

Following the procedure as described in Example 5, making variations to replace benzyl bromide with 4-(trifluoromethoxy)benzyl bromide to react with ethyl 4-methyl-2-(2-oxoimidazolidin-1-yl)thiazole-5-carboxylate, the title compound was obtained in 90% yield: $^1$H NMR (300 MHz, DMSO-$d_6$) δ 7.32 (d, J=8.7 Hz, 2H), 7.18 (d, J=8.7 Hz, 2H), 4.48 (s, 2H), 4.27 (q, J=7.2 Hz, 2H), 4.08 (t, J=7.8 Hz, 2H), 3.46 (t, J=7.8 Hz, 2H), 2.60 (s, 3H), 1.32 (t, J=7.2 Hz, 3H); MS (ES+) m/z 430.2 (M+1).

Example 5.5

Synthesis of ethyl 2-(3-(4-(difluoromethoxy)benzyl)-2-oxoimidazolidin-1-yl)-4-methylthiazole-5-carboxylate

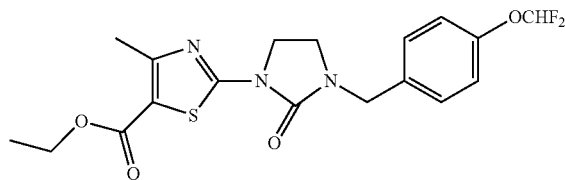

Following the procedure as described in Example 5, making variations to replace benzyl bromide with 4-(difluoromethoxy)benzyl bromide to react with ethyl 4-methyl-2-(2-oxoimidazolidin-1-yl)thiazole-5-carboxylate, the title compound was obtained in 88% yield: $^1$H NMR (300 MHz, DMSO-$d_6$) δ 7.37 (d, J=8.1 Hz, 2H), 7.29 (d, J=8.1 Hz, 2H), 6.48 (t, $J_{F-H}$=73.8 Hz, 1H), 4.46 (s, 2H), 4.26 (q, J=7.2 Hz, 2H), 4.07 (t, J=7.8 Hz, 2H), 3.45 (t, J=7.8 Hz, 2H), 2.56 (s, 3H), 1.30 (t, J=7.2 Hz, 3H); MS (ES+) m/z 412.2 (M+1).

Example 5.6

Synthesis of ethyl 2-(3-ethyl-2-oxoimidazolidin-1-yl)-4-methylthiazole-5-carboxylate

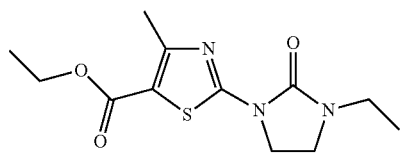

Following the procedure as described in Example 5, making variations to replace benzyl bromide with iodoethane to react with ethyl 4-methyl-2-(2-oxoimidazolidin-1-yl)thiazole-5-carboxylate, the title compound was obtained in 58% yield: $^1$H NMR (300 MHz, CDCl$_3$) δ 4.29-4.04 (m, 4H), 3.64-3.33 (m, 4H), 2.63 (s, 3H), 1.38-1.05 (m, 6H); MS (ES+) m/z 284.3 (M+1).

Example 5.7

Synthesis of ethyl 4-methyl-2-(2-oxo-3-propylimidazolidin-1-yl)thiazole-5-carboxylate

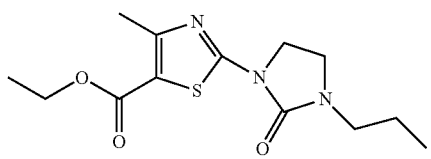

Following the procedure as described in Example 5, making variations to replace benzyl bromide with 1-iodopropane to react with ethyl 4-methyl-2-(2-oxoimidazolidin-1-yl)thiazole-5-carboxylate, the title compound was obtained in 60% yield: $^1$H NMR (300 MHz, CDCl$_3$) δ 4.18 (q, J=7.2 Hz, 2H), 4.07-3.94 (m, 2H), 3.53-3.48 (m, 2H), 3.20 (t, J=7.2 Hz, 2H), 2.52 (s, 3H), 1.58-1.46 (m, 2H), 1.24 (t, J=7.2 Hz, 3H), 0.82 (t, J=7.2 Hz, 3H); MS (ES+) m/z 298.3 (M+1).

Example 5.8

Synthesis of ethyl 2-(3-butyl-2-oxoimidazolidin-1-yl)-4-methylthiazole-5-carboxylate

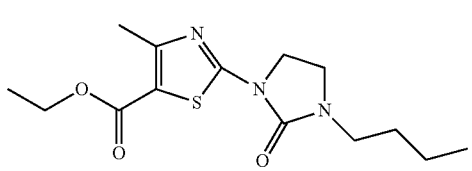

Following the procedure as described in Example 5, making variations to replace benzyl bromide with 1-iodobutane to react with ethyl 4-methyl-2-(2-oxoimidazolidin-1-yl)thiazole-5-carboxylate, the title compound was obtained in 73% yield: $^1$H NMR (300 MHz, CDCl$_3$) δ 4.08 (q, J=7.2 Hz, 2H), 3.99-3.85 (m, 2H), 3.47-3.33 (m, 2H), 3.11 (t, J=7.5 Hz, 2H), 2.38 (s, 3H), 1.41-1.22 (m, 7H), 0.74 (t, J=7.2 Hz, 3H); MS (ES+) m/z 312.3 (M+1).

Example 5.9

Synthesis of ethyl 4-methyl-2-(2-oxo-3-pentylimidazolidin-1-yl)thiazole-5-carboxylate

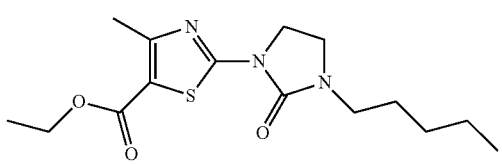

Following the procedure as described in Example 5, making variations to replace benzyl bromide with 1-iodopentane to react with ethyl 4-methyl-2-(2-oxoimidazolidin-1-yl)thiazole-5-carboxylate, the title compound was obtained in 69% yield: $^1$H NMR (300 MHz, CDCl$_3$) δ 4.23 (q, J=7.2 Hz, 2H), 4.11-3.87 (m, 2H), 3.64-3.43 (m, 2H), 3.26 (t, J=7.5 Hz, 2H), 2.63 (s, 3H), 1.61-1.18 (m, 9H), 0.74 (t, J=7.2 Hz, 3H); MS (ES+) m/z 326.3 (M+1).

Example 5.10

Synthesis of 1-(5-acetyl-4-methylthiazol-2-yl)-3-(4-(trifluoromethyl)benzyl)imidazolidin-2-one

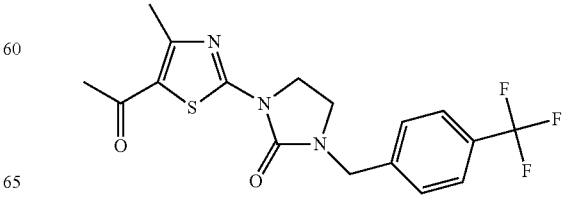

Following the procedure as described in Example 5, making variations to replace benzyl bromide with 4-(trifluoromethyl)benzyl bromide to react with 1-(5-acetyl-4-methylthiazol-2-yl)imidazolidin-2-one, the title compound was obtained in 74% yield: mp 141-142° C. (ethyl acetate/hexanes); $^1$H NMR (300 MHz, CDCl$_3$) δ 7.60 (d, J=8.1 Hz, 2H), 7.41 (d, J=8.1 Hz, 2H), 4.54 (s, 2H), 4.13-4.07 (m, 2H), 3.50-3.41 (m, 2H), 2.66 (s, 3H), 2.25 (s, 3H); $^{13}$C NMR (75 MHz, CDCl$_3$) δ 190.6, 159.6, 155.9, 155.4, 139.6, 130.2, 128.5, 126.0, 124.8, 122.1, 47.6, 42.0, 41.8, 30.5, 18.2; MS (ES+) m/z 384.1 (M+1).

Example 5.11

Synthesis of methyl 4-((3-(5-acetyl-4-methylthiazol-2-yl)-2-oxoimidazolidin-1-yl)methyl)benzoate

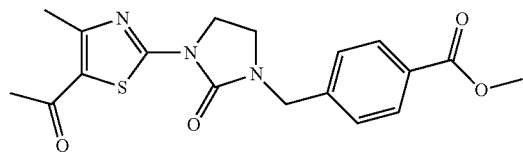

Following the procedure as described in Example 5, making variations to replace benzyl bromide with methyl 4-(bromomethyl)benzoate to react with 1-(5-acetyl-4-methylthiazol-2-yl)imidazolidin-2-one, the title compound was obtained in 60% yield: mp 174-175° C. (ethyl acetate/hexanes); $^1$H NMR (300 MHz, CDCl$_3$) δ 8.02 (d, J=7.5 Hz, 2H), 7.35 (d, J=7.5 Hz, 2H), 4.53 (s, 2H), 4.12-4.03 (m, 2H), 3.96 (s, 3H), 3.49-3.44 (m, 2H), 2.60 (s, 3H), 2.39 (s, 3H); MS (ES+) m/z 374.1 (M+1).

Example 5.12

Synthesis of 1-(5-acetyl-4-methylthiazol-2-yl)-3-(4-fluorobenzyl)imidazolidin-2-one

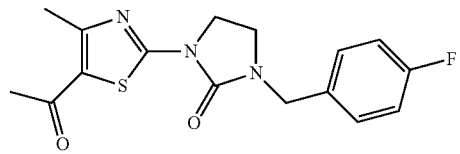

Following the procedure as described in Example 5, making variations to replace benzyl bromide with 4-fluorobenzyl bromide to react with 1-(5-acetyl-4-methylthiazol-2-yl)imidazolidin-2-one, the title compound was obtained in 98% yield: $^1$H NMR (300 MHz, CDCl$_3$) δ 7.32-7.22 (m, 2H), 7.07-6.97 (m, 2H), 4.45 (s, 2H), 4.10-4.04 (m, 2H), 3.48-3.37 (m, 2H), 2.67 (s, 3H), 2.38 (s, 3H); MS (ES+) m/z 334.1 (M+1).

Example 5.13

Synthesis of methyl 4-((3-(4-methylthiazol-2-yl)-2-oxoimidazolidin-1-yl)methyl)benzoate

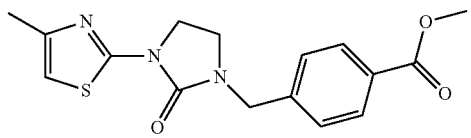

Following the procedure as described in Example 5, making variations to replace benzyl bromide with methyl (4-bromomethyl)benzoate to react with 1-(4-methylthiazol-2-yl)imidazolidin-2-one, the title compound was obtained in 67% yield: mp 157-158° C. (ethyl acetate/hexanes); $^1$H NMR (300 MHz, CDCl$_3$) δ 8.00 (d, J=8.1 Hz, 2H), 7.35 (d, J=8.1 Hz, 2H), 6.43 (s, 1H), 4.52 (s, 2H), 4.14-4.02 (m, 2H), 3.89 (s, 3H), 3.63-3.40 (m, 2H), 2.30 (s, 3H); MS (ES+) m/z 332.3 (M+1).

Example 5.14

Synthesis of 1-(4-methylthiazol-2-yl)-3-(4-(trifluoromethyl)benzyl)imidazolidin-2-one

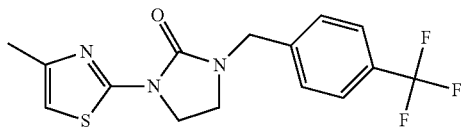

Following the procedure as described in Example 5, making variations to replace benzyl bromide with 4-(trifluoromethyl)benzyl bromide to react with 1-(4-methylthiazol-2-yl)imidazolidin-2-one, the title compound was obtained in 42% yield: mp 102-103° C. (ethyl acetate/hexanes); $^1$H NMR (300 MHz, CDCl$_3$) δ 7.58 (d, J=8.1 Hz, 2H), 7.39 (d, J=8.1 Hz, 2H), 6.42 (s, 1H), 4.51 (s, 2H), 4.10-4.04 (m, 2H), 3.45-3.39 (m, 2H), 2.29 (s, 3H); MS (ES+) m/z 342.2 (M+1).

Example 5.15

Synthesis of ethyl 4-methyl-2-(2-oxo-3-(3-(trifluoromethyl)benzyl)imidazolidin-1-yl)thiazole-5-carboxylate

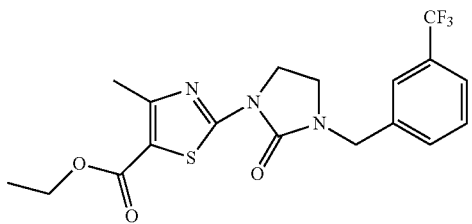

Following the procedure as described in Example 5, making variations to replace benzyl bromide with 1-(chloromethyl)-3-(trifluoromethyl)benzene to react with 1-(4-methylthiazol-2-yl)imidazolidin-2-one, the title compound was obtained as a white solid in 33% yield: $^1$H NMR (300 MHz, CDCl$_3$) δ 7.61-7.43 (m, 4H), 4.54 (s, 2H), 4.26 (q, J=7.1 Hz, 2H), 4.14-4.05 (m, 2H), 3.52-3.43 (m, 2H), 2.61 (s, 3H), 1.33 (t, J=7.1 Hz, 3H); MS (ES+) m/z 414.3 (M+1).

Example 5.16

Synthesis of ethyl 2-(3-(5-(benzylcarbamoyl)-4-methylthiazol-2-yl)-2-oxoimidazolidin-1-yl)acetate

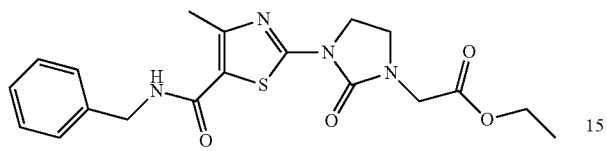

Following the procedure as described in Example 5, making variations to replace benzyl bromide with ethyl bromoacetate to react with N-benzyl-4-methyl-2-(2-oxoimidazolidin-1-yl)thiazole-5-carboxamide, the title compound was obtained as a white solid in 38% yield: $^1$H NMR (300 MHz, CDCl$_3$) δ 7.39-7.27 (m, 5H), 5.87 (t, J=5.4 Hz, 1H), 4.57 (d, J=5.4 Hz, 2H), 4.27-4.13 (m, 4H), 4.08 (s, 2H), 3.76-3.68 (m, 2H), 2.63 (s, 3H), 1.29 (t, J=7.1 Hz, 3H); MS (ES+) m/z 403.2 (M+1).

Example 5.17

Synthesis of methyl 3-((3-(5-acetyl-4-methylthiazol-2-yl)-2-oxoimidazolidin-1-yl)methyl)benzoate

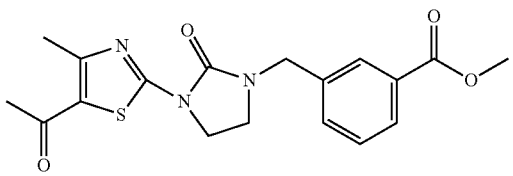

Following the procedure as described in Example 5, making variations to replace benzyl bromide with methyl 3-(bromomethyl)benzoate to react with 1-(5-acetyl-4-methylthiazol-2-yl)imidazolidin-2-one, the title compound was obtained as a white solid in 64% yield: mp 122-124° C. (ethyl acetate/hexanes); $^1$H NMR (300 MHz, CDCl$_3$) δ 7.99-7.93 (m, 2H), 7.52-7.40 (m, 2H), 4.53 (s, 2H), 4.11-4.05 (m, 2H), 3.96 (s, 3H), 3.49-3.43 (m, 2H), 2.59 (s, 3H), 2.49 (s, 3H); MS (ES+) m/z 374.1 (M+1).

Example 6

Synthesis of 4-methyl-2-(2-oxo-3-phenylimidazolidin-1-yl)thiazole-5-carboxylic acid

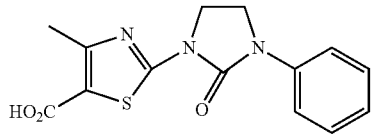

To a solution of ethyl 4-methyl-2-(2-oxo-3-phenylimidazolidin-1-yl)thiazole-5-carboxylate (1.49 g, 4.49 mmol) in tetrahydrofuran (30 mL), methanol (10 mL) and water (10 mL) was added lithium hydroxide monohydrate (0.38 g, 9.00 mmol) at ambient temperature. The resulting reaction mixture was heated to reflux for 14 hours. The solvent was removed in vacuo, and the residue was neutralized to pH 4~5 with 10% hydrochloric acid. The resulting precipitate was filtered and dried to afford the title compound in 93% yield (1.27 g): mp 286-289° C.; $^1$H NMR (300 MHz, DMSO-d$_6$) δ 7.88-7.34 (m, 5H), 4.10-3.76 (m, 4H), 2.49 (s, 3H); MS (ES+) m/z 304.3 (M+1).

Example 6.1

Synthesis of 2-(3-(cyclopropylmethyl)-2-oxoimidazolidin-1-yl)-4-methylthiazole-5-carboxylic acid

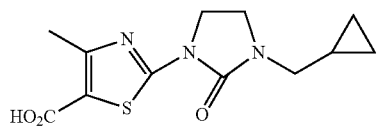

Following the procedure as described in Example 6, making variations as required to replace ethyl 4-methyl-2-(2-oxo-3-phenylimidazolidin-1-yl)thiazole-5-carboxylate with ethyl 2-(3-(cyclopropylmethyl)-2-oxoimidazolidin-1-yl)-4-methylthiazole-5-carboxylate, the title compound was obtained in 82% yield: $^1$H NMR (300 MHz, DMSO-d$_6$) δ 3.96 (t, J=7.8 Hz, 2H), 3.67 (t, J=7.8 Hz, 2H), 3.06 (d, J=6.9 Hz, 2H), 2.52 (s, 3H), 0.97-0.84 (m, 1H), 0.53-0.37 (m, 2H), 0.20-0.11 (m, 2H); MS (ES+) m/z 282.2 (M+1).

Example 6.2

Synthesis of 2-(3-benzyl-2-oxoimidazolidin-1-yl)-4-methylthiazole-5-carboxylic acid

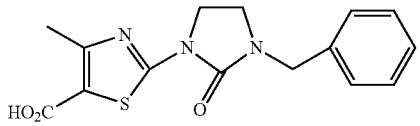

Following the procedure as described in Example 6, making variations as required to replace ethyl 4-methyl-2-(2-oxo-3-phenylimidazolidin-1-yl)thiazole-5-carboxylate with ethyl 2-(3-benzyl-2-oxoimidazolidin-1-yl)-4-methylthiazole-5-carboxylate, the title compound was obtained in 84% yield: mp 248-249° C.; $^1$H NMR (300 MHz, DMSO-d$_6$) δ 7.36-7.22 (m, 5H), 4.47 (s, 2H), 3.97 (t, J=7.5 Hz, 2H), 3.42 (t, J=7.5 Hz, 2H), 2.49 (s, 3H); MS (ES+) m/z 318.3 (M+1).

Example 6.3

Synthesis of 2-(3-(2-cyclopropylethyl)-2-oxoimidazolidin-1-yl)-4-methylthiazole-5-carboxylic acid

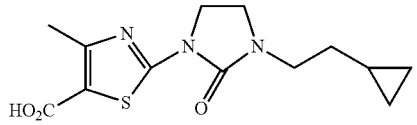

Following the procedure as described in Example 6, making variations as required to replace ethyl 4-methyl-2-(2-oxo-3-phenylimidazolidin-1-yl)thiazole-5-carboxylate with ethyl 2-(3-(2-cyclopropylethyl)-2-oxoimidazolidin-1-yl)-4-methylthiazole-5-carboxylate, the title compound was obtained in 88% yield: $^1$H NMR (300 MHz, DMSO-$d_6$) δ 4.20-3.04 (m, 6H), 2.45 (s, 3H), 1.50-1.41 (m, 2H), 0.78-0.54 (m, 1H), 0.43-0.28 (m, 2H), 0.10-0.96 (m, 2H); MS (ES+) m/z 296.2 (M+1).

Example 6.4

Synthesis of 4-methyl-2-(2-oxo-3-phenethylimidazolidin-1-yl)thiazole-5-carboxylic acid

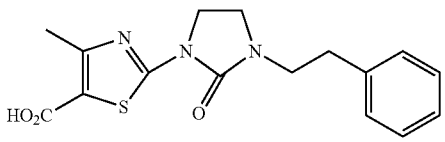

Following the procedure as described in Example 5, making variations as required to replace ethyl 4-methyl-2-(2-oxo-3-phenylimidazolidin-1-yl)thiazole-5-carboxylate with ethyl 4-methyl-2-(2-oxo-3-phenethylimidazolidin-1-yl)thiazole-5-carboxylate, the title compound was obtained in 92% yield: $^1$H NMR (300 MHz, DMSO-$d_6$) δ 7.29-7.14 (m, 5H), 3.92 (t, J=7.2 Hz, 2H), 3.53-3.41 (m, 4H), 2.79 (t, J=7.8 Hz, 2H), 2.46 (s, 3H); MS (ES+) m/z 332.2 (M+1).

Example 6.5

Synthesis of 4-methyl-2-(2-oxo-3-(4-(trifluoromethyl)benzyl)imidazolidin-1-yl)thiazole-5-carboxylic acid

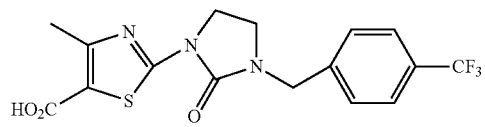

Following the procedure as described in Example 6, making variations as required to replace ethyl 4-methyl-2-(2-oxo-3-phenylimidazolidin-1-yl)thiazole-5-carboxylate with ethyl 4-methyl-2-(2-oxo-3-(4-(trifluoromethyl)benzyl)imidazolidin-1-yl)thiazole-5-carboxylate, the title compound was obtained in 85% yield: mp 195-197° C.; $^1$H NMR (300 MHz, DMSO-$d_6$) δ 7.74 (d, J=11.4 Hz, 2H), 7.60 (d, J=11.4 Hz, 2H), 4.51 (s, 2H), 4.00 (t, J=8.1 Hz, 2H), 3.47 (t, J=8.1 Hz, 2H), 2.47 (s, 3H); MS (ES+) m/z 386.2 (M+1).

Example 6.6

Synthesis of 2-(3-(4-fluorobenzyl)-2-oxoimidazolidin-1-yl)-4-methylthiazole-5-carboxylic acid

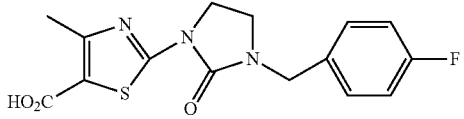

Following the procedure as described in Example 6, making variations as required to replace ethyl 4-methyl-2-(2-oxo-3-phenylimidazolidin-1-yl)thiazole-5-carboxylate with ethyl 2-(3-(4-fluorobenzyl)-2-oxoimidazolidin-1-yl)-4-methylthiazole-5-carboxylate, the title compound was obtained in 97% yield: $^1$H NMR (300 MHz, DMSO-$d_6$) δ 7.84-7.07 (m, 4H), 4.32 (s, 2H), 3.93 (t, J=8.1 Hz, 2H), 3.22 (t, J=8.1 Hz, 2H), 2.46 (s, 3H); MS (ES+) m/z 336.2 (M+1).

Example 6.7

Synthesis of 4-methyl-2-(2-oxo-3-(4-(trifluoromethoxy)benzyl)imidazolidin-1-yl)thiazole-5-carboxylic acid

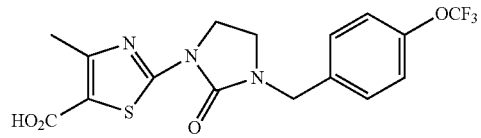

Following the procedure as described in Example 6, making variations as required to replace ethyl 4-methyl-2-(2-oxo-3-phenylimidazolidin-1-yl)thiazole-5-carboxylate with ethyl 4-methyl-2-(2-oxo-3-(4-(trifluoromethoxy)benzyl)imidazolidin-1-yl)thiazole-5-carboxylate, the title compound was obtained in 64% yield: $^1$H NMR (300 MHz, DMSO-$d_6$) δ 7.42 (d, J=8.4 Hz, 2H), 7.32 (d, J=8.4 Hz, 2H), 4.43 (s, 2H), 3.98 (t, J=8.1 Hz, 2H), 3.44 (t, J=8.1 Hz, 2H), 2.46 (s, 3H); MS (ES+) m/z 402.1 (M+1).

Example 6.8

Synthesis of 2-(3-(4-(difluoromethoxy)benzyl)-2-oxoimidazolidin-1-yl)-4-methylthiazole-5-carboxylic acid

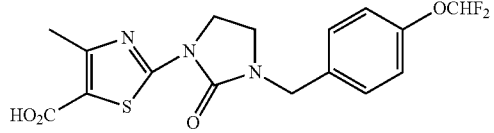

Following the procedure as described in Example 6, making variations as required to replace ethyl 4-methyl-2-(2-oxo-3-phenylimidazolidin-1-yl)thiazole-5-carboxylate with ethyl 2-(3-(4-(difluoromethoxy)benzyl)-2-oxoimidazolidin-1-yl)-4-methylthiazole-5-carboxylate, the title compound was obtained in 88% yield: $^1$H NMR (300 MHz, DMSO-$d_6$) δ

7.43-6.94 (m, 5H), 4.39 (s, 2H), 3.97 (t, J=8.1 Hz, 2H), 3.42 (t, J=8.1 Hz, 2H), 2.46 (s, 3H); MS (ES+) m/z 384.2 (M+1).

Example 6.9

Synthesis of (R)-2-(4-benzyl-2-oxoimidazolidin-1-yl)-4-methylthiazole-5-carboxylic acid

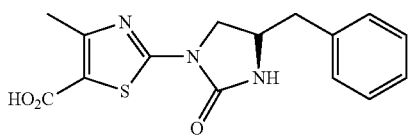

Following the procedure as described in Example 6, making variations as required to replace ethyl 4-methyl-2-(2-oxo-3-phenylimidazolidin-1-yl)thiazole-5-carboxylate with (R)-ethyl 2-(4-benzyl-2-oxoimidazolidin-1-yl)-4-methylthiazole-5-carboxylate, the title compound was obtained in 83% yield: MS (ES+) m/z 318.1 (M+1).

Example 6.10

Synthesis of 2-(3-((5-chlorobenzo[b]thiophen-3-yl)methyl)-2-oxoimidazolidin-1-yl)-4-methylthiazole-5-carboxylic acid

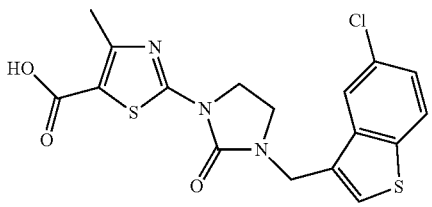

Following the procedure as described in Example 6, making variations as required to replace ethyl 4-methyl-2-(2-oxo-3-phenylimidazolidin-1-yl)thiazole-5-carboxylate with ethyl 2-(3-((5-chlorobenzo[b]thiophen-3-yl)methyl)-2-oxoimidazolidin-1-yl)-4-methylthiazole-5-carboxylate, the title compound was obtained in 59% yield: $^1$H NMR (300 MHz, DMSO-$d_6$) δ 12.86 (s, 1H), 8.06 (d, J=6.0 Hz, 1H), 7.98 (d, J=3.0 Hz, 1H), 7.90 (s, 1H), 7.45-7.41 (m, 1H), 4.69 (s, 2H), 4.00 (t, J=6.0 Hz, 2H), 3.48 (t, J=6.0 Hz, 2H), 2.50 (s, 3H); MS (ES+) m/z 408.1 (M+1).

Example 6.11

Synthesis of 2-(3-(2-(1H-indol-3-yl)ethyl)-2-oxoimidazolidin-1-yl)-4-methylthiazole-5-carboxylic acid

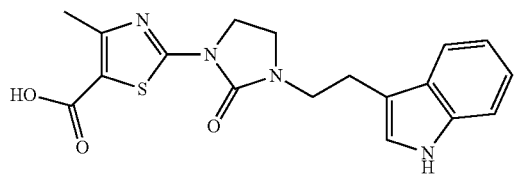

Following the procedure as described in Example 6, making variations as required to replace ethyl 4-methyl-2-(2-oxo-3-phenylimidazolidin-1-yl)thiazole-5-carboxylate with ethyl 2-(3-(2-(1H-indol-3-yl)ethyl)-2-oxoimidazolidin-1-yl)-4-methylthiazole-5-carboxylate, the title compound was obtained in 86% yield: $^1$H NMR (300 MHz, DMSO-$d_6$) δ 10.89 (s, 1H), 7.56 (d, J=9.0 Hz, 1H), 7.34 (d, J=9.0 Hz, 1H), 7.20 (s, 1H), 7.09-695 (m, 2H), 3.98 (t, J=6.0 Hz, 2H), 3.61-3.50 (m, 4H), 2.94 (t, J=6.0 Hz, 2H), 2.49 (s, 3H); MS (ES+) m/z 371.1 (M+1).

Example 6.12

Synthesis of 4-methyl-2-(2-oxo-3-(3-phenylpropyl)imidazolidin-1-yl)thiazole-5-carboxylic acid

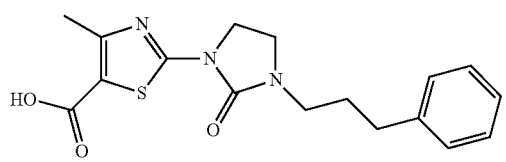

Following the procedure as described in Example 6, making variations as required to replace ethyl 4-methyl-2-(2-oxo-3-phenylimidazolidin-1-yl)thiazole-5-carboxylate with ethyl 4-methyl-2-(2-oxo-3-(3-phenylpropyl)imidazolidin-1-yl)thiazole-5-carboxylate, the title compound was obtained in 99% yield: mp 218-221° C.; $^1$H NMR (300 MHz, DMSO-$d_6$) δ 7.25-7.10 (m, 5H), 3.94-3.89 (m, 2H), 3.53-3.48 (m, 2H), 3.22 (t, J=6.9 Hz, 2H), 2.55 (t, J=7.5 Hz, 2H), 2.46 (s, 3H), 1.83-1.73 (m, 2H); MS (ES+) m/z 346.2 (M+1).

Example 6.13

Synthesis of 2-(3-(4-chlorobenzyl)-2-oxoimidazolidin-1-yl)-4-methylthiazole-5-carboxylic acid

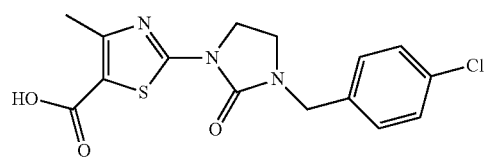

Following the procedure as described in Example 6, making variations as required to replace ethyl 4-methyl-2-(2-oxo-3-phenylimidazolidin-1-yl)thiazole-5-carboxylate with ethyl 2-(3-(4-chlorobenzyl)-2-oxoimidazolidin-1-yl)-4-methylthiazole-5-carboxylate, the title compound was obtained in 96% yield: $^1$H NMR (300 MHz, DMSO-$d_6$) δ 7.45 (d, J=7.2 Hz, 2H), 7.29 (d, J=7.2 Hz, 2H), 4.39 (s, 2H), 4.06-3.91 (m, 2H), 3.51-3.39 (m, 2H), 2.53 (s, 3H); MS (ES+) m/z 352.2 (M+1), 354.2 (M+1).

Example 6.14

Synthesis of 2-(3-(cyclohexylmethyl)-2-oxoimidazolidin-1-yl)-4-methylthiazole-5-carboxylic acid

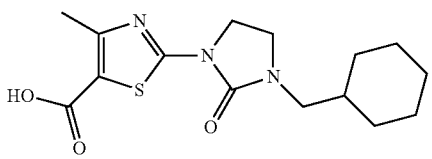

Following the procedure as described in Example 6, making variations as required to replace ethyl 4-methyl-2-(2-oxo-3-phenylimidazolidin-1-yl)thiazole-5-carboxylate with ethyl 2-(3-(cyclohexylmethyl)-2-oxoimidazolidin-1-yl)-4-methylthiazole-5-carboxylate, the title compound was obtained in 86% yield: $^1$H NMR (300 MHz, DMSO-$d_6$) δ 4.06-3.82 (m, 2H), 3.52-3.42 (m, 2H), 298 (d, J=6.9 Hz, 2H), 2.52 (s, 3H), 1.73-1.52 (m, 6H), 1.27-1.08 (m, 3H), 0.90-0.72 (m, 2H); MS (ES+) m/z 324.2 (M+1).

Example 6.15

Synthesis of 4-methyl-2-(2-oxo-3-((tetrahydro-2H-pyran-2-yl)methyl)imidazolidin-1-yl)thiazole-5-carboxylic acid

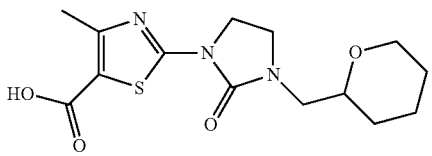

Following the procedure as described in Example 6, making variations as required to replace ethyl 4-methyl-2-(2-oxo-3-phenylimidazolidin-1-yl)thiazole-5-carboxylate with ethyl 4-methyl-2-(2-oxo-3-((tetrahydro-2H-pyran-2-yl)methyl)imidazolidin-1-yl)thiazole-5-carboxylate, the title compound was obtained in 84% yield: $^1$H NMR (300 MHz, DMSO-$d_6$) δ 3.96-3.91 (m, 2H), 3.85-3.78 (m, 1H), 3.65-3.54 (m, 2H), 3.46-3.34 (m, 1H), 3.32-3.24 (m, 1H), 3.17-3.09 (m, 2H), 2.47 (s, 3H), 1.86-1.70 (m, 1H), 1.49-1.37 (m, 4H), 1.18-1.04 (m, 1H); MS (ES+) m/z 326.3 (M+1).

Example 6.16

Synthesis of 2-(3-(cyclobutylmethyl)-2-oxoimidazolidin-1-yl)-4-methylthiazole-5-carboxylic acid

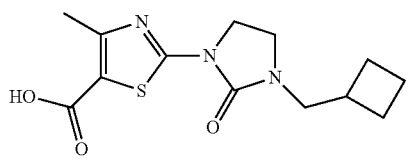

Following the procedure as described in Example 6, making variations as required to replace ethyl 4-methyl-2-(2-oxo-3-phenylimidazolidin-1-yl)thiazole-5-carboxylate with ethyl 2-(3-(cyclobutylmethyl)-2-oxoimidazolidin-1-yl)-4-methylthiazole-5-carboxylate, the title compound was obtained in 77% yield: MS (ES+) m/z 296.2 (M+1).

Example 6.17

Synthesis of 2-(3-(cyclopentylmethyl)-2-oxoimidazolidin-1-yl)-4-methylthiazole-5-carboxylic acid

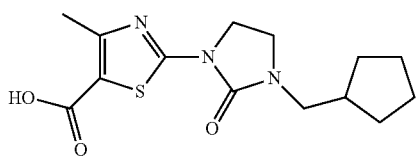

Following the procedure as described in Example 6, making variations as required to replace ethyl 4-methyl-2-(2-oxo-3-phenylimidazolidin-1-yl)thiazole-5-carboxylate with ethyl 2-(3-(cyclopentylmethyl)-2-oxoimidazolidin-1-yl)-4-methylthiazole-5-carboxylate, the title compound was obtained in 97% yield: MS (ES+) m/z 310.2 (M+1).

Example 6.18

Synthesis of 2-(3-ethyl-2-oxoimidazolidin-1-yl)-4-methylthiazole-5-carboxylic acid

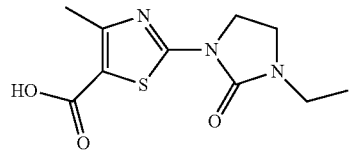

Following the procedure as described in Example 6, making variations as required to replace ethyl 4-methyl-2-(2-oxo-3-phenylimidazolidin-1-yl)thiazole-5-carboxylate with 2-(3-ethyl-2-oxoimidazolidin-1-yl)-4-methylthiazole-5-carboxylate, the title compound was obtained in 80% yield: $^1$H NMR (300 MHz, DMSO-$d_6$) δ 3.97-3.91 (m, 2H), 3.54-3.48 (m, 2H), 3.23 (q, J=7.2 Hz, 2H), 2.49 (s, 3H), 0.98 (t, J=7.2 Hz, 3H); MS (ES+) m/z 256.3 (M+1).

Example 6.19

Synthesis of 4-methyl-2-(2-oxo-3-propylimidazolidin-1-yl)thiazole-5-carboxylic acid

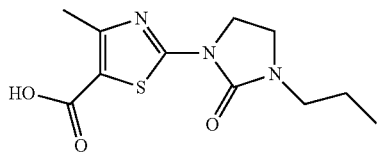

Following the procedure as described in Example 6, making variations as required to replace ethyl 4-methyl-2-(2-oxo-3-phenylimidazolidin-1-yl)thiazole-5-carboxylate with ethyl 4-methyl-2-(2-oxo-3-propylimidazolidin-1-yl)thiazole-5-carboxylate, the title compound was obtained in 94% yield:

¹H NMR (300 MHz, DMSO-d₆) δ 3.98-3.89 (m, 2H), 3.57-3.44 (m, 2H), 3.14 (t, J=7.2 Hz, 2H), 2.45 (s, 3H), 1.54-1.42 (m, 2H), 0.79 (t, J=7.2 Hz, 3H); MS (ES+) m/z 270.2 (M+1).

Example 6.20

Synthesis of 2-(3-butyl-2-oxoimidazolidin-1-yl)-4-methylthiazole-5-carboxylic acid

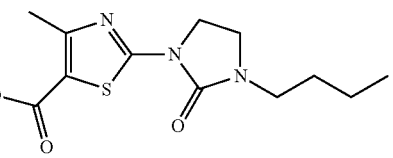

Following the procedure as described in Example 6, making variations as required to replace ethyl 4-methyl-2-(2-oxo-3-phenylimidazolidin-1-yl)thiazole-5-carboxylate with ethyl 2-(3-butyl-2-oxoimidazolidin-1-yl)-4-methylthiazole-5-carboxylate, the title compound was obtained in 94% yield: MS (ES+) m/z 284.2 (M+1).

Example 6.21

Synthesis of 4-methyl-2-(2-oxo-3-pentylimidazolidin-1-yl)thiazole-5-carboxylic acid

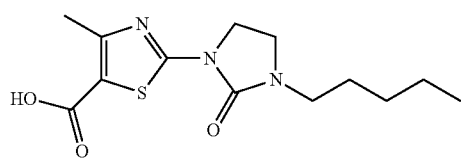

Following the procedure as described in Example 6, making variations as required to replace ethyl 4-methyl-2-(2-oxo-3-phenylimidazolidin-1-yl)thiazole-5-carboxylate with ethyl 4-methyl-2-(2-oxo-3-pentylimidazolidin-1-yl)thiazole-5-carboxylate, the title compound was obtained in 65% yield: MS (ES+) m/z 298.3 (M+1).

Example 6.22

Synthesis of 4-((3-(5-acetyl-4-methylthiazol-2-yl)-2-oxoimidazolidin-1-yl)methyl)benzoic acid

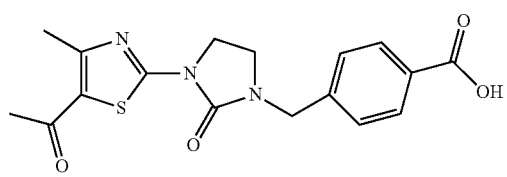

Following the procedure as described in Example 6, making variations as required to replace ethyl 4-methyl-2-(2-oxo-3-phenylimidazolidin-1-yl)thiazole-5-carboxylate with methyl 4-((3-(5-acetyl-4-methylthiazol-2-yl)-2-oxoimidazolidin-1-yl)methyl)benzoate, the title compound was obtained in 85% yield: ¹H NMR (300 MHz, DMSO-d₆) δ 12.89 (br s, 1H), 7.90 (d, J=7.5 Hz, 2H), 7.39 (d, J=7.5 Hz, 2H), 4.49 (s, 2H), 4.05-3.90 (m, 2H), 3.52-3.40 (m, 2H), 2.51 (s, 3H), 2.42 (s, 3H); MS (ES+) m/z 360.1 (M+1).

Example 6.23

Synthesis of 4-((3-(4-methylthiazol-2-yl)-2-oxoimidazolidin-1-yl)methyl)benzoic acid

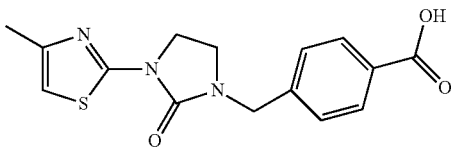

Following the procedure as described in Example 6, making variations as required to replace ethyl 4-methyl-2-(2-oxo-3-phenylimidazolidin-1-yl)thiazole-5-carboxylate with methyl 4-((3-(4-methylthiazol-2-yl)-2-oxoimidazolidin-1-yl)methyl)benzoate, the title compound was obtained in 65% yield: mp 222-224° C.; ¹H NMR (300 MHz, CDCl₃) δ 7.89 (d, J=8.4 Hz, 2H), 7.38 (d, J=8.4 Hz, 2H), 6.65 (s, 1H), 4.52 (s, 2H), 3.98-3.93 (m, 2H), 3.45-3.40 (m, 2H), 2.19 (s, 3H); MS (ES+) m/z 318.2 (M+1).

Example 6.24

Synthesis of 4-methyl-2-(2-oxo-3-(3-(trifluoromethyl)benzyl)imidazolidin-1-yl)thiazole-5-carboxylic acid

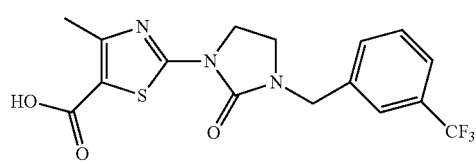

Following the procedure as described in Example 6, making variations as required to replace ethyl 4-methyl-2-(2-oxo-3-phenylimidazolidin-1-yl)thiazole-5-carboxylate with ethyl 4-methyl-2-(2-oxo-3-(3-(trifluoromethyl)benzyl)imidazolidin-1-yl)thiazole-5-carboxylate, the title compound was obtained as a white solid in 96% yield: MS (ES+) m/z 386.3 (M+1).

Example 6.25

Synthesis of 2-(3-((5-(difluoromethyl)furan-2-yl)methyl)-2-oxoimidazolidin-1-yl)-4-methylthiazole-5-carboxylic acid

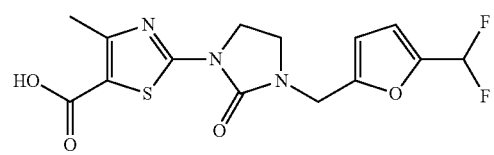

Following the procedure as described in Example 6, making variations as required to replace ethyl 4-methyl-2-(2-oxo-3-phenylimidazolidin-1-yl)thiazole-5-carboxylate with ethyl 2-(3-((5-(difluoromethyl)furan-2-yl)methyl)-2-oxoimidazolidin-1-yl)-4-methylthiazole-5-carboxylate, the title compound was obtained as a white solid in 58% yield: MS (ES+) m/z 358.2 (M+1).

Example 6.26

Synthesis of 3-((3-(5-acetyl-4-methylthiazol-2-yl)-2-oxoimidazolidin-1-yl)methyl)benzoic acid

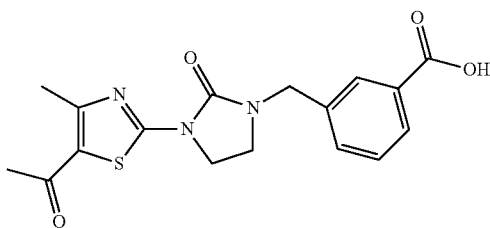

Following the procedure as described in Example 6, making variations as required to replace ethyl 4-methyl-2-(2-oxo-3-phenylimidazolidin-1-yl)thiazole-5-carboxylate with methyl 3-((3-(5-acetyl-4-methylthiazol-2-yl)-2-oxoimidazolidin-1-yl)methyl)benzoate, the title compound was obtained as a white solid in 89% yield: MS (ES+) m/z 360.1 (M+1).

Example 7

Synthesis of N-benzyl-4-methyl-2-(2-oxo-3-phenylimidazolidin-1-yl)thiazole-5-carboxamide

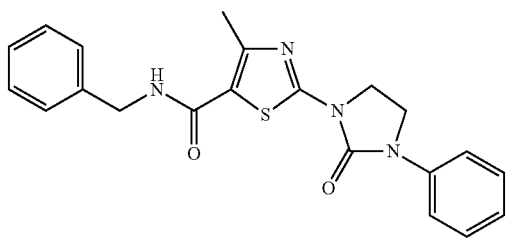

To a solution of 4-methyl-2-(2-oxo-3-phenylimidazolidin-1-yl)thiazole-5-carboxylic acid (0.30 g, 1.00 mmol) and 4-methylmorpholine (0.15 mL, 1.10 mmol) in tetrahydrofuran (50 mL) was added isobutyl chloroformate (0.15 mL, 1.3 mmol) at 0° C. The resulting mixture was stirred at ambient temperature for 2 hours and benzylamine (0.20 mL, 1.80 mmol) was added. The reaction mixture was kept stirring for 17 hours at ambient temperature. The solvent was removed in vacuo, and the residue was purified by column chromatography to afford the title compound as a white powder in 7% yield (0.030 g): mp 234-236° C.; $^1$H NMR (300 MHz, DMSO-$d_6$) δ 8.54 (d, J=5.7 Hz, 1H), 7.60 (d, J=7.8 Hz, 2H), 7.39-7.12 (m, 8H), 4.35 (d, J=5.7 Hz, 2H), 4.14-3.92 (m, 4H), 2.46 (s, 3H); $^{13}$C NMR (75 MHz, DMSO-$d_6$) δ 161.6, 156.7, 152.7, 150.7, 139.5, 138.9, 128.8, 128.1, 127.1, 126.6, 123.3, 118.3, 117.8, 42.4, 42.3, 41.2, 17.0; MS (ES+) m/z 393.3 (M+1).

Example 8

Synthesis of N-benzyl-2-(3-benzyl-2-oxoimidazolidin-1-yl)-4-methylthiazole-5-carboxamide

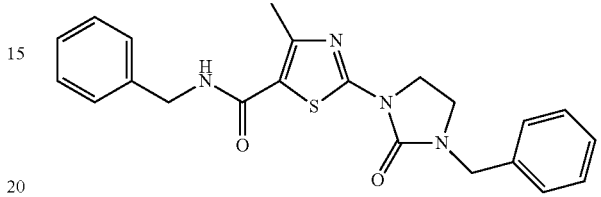

To a solution of 2-(3-benzyl-2-oxoimidazolidin-1-yl)-4-methylthiazole-5-carboxylic acid (0.21 g, 0.66 mmol) and 4-methylmorpholine (0.08 mL, 0.72 mmol) in tetrahydrofuran (50 mL) was added isobutyl chloroformate (0.09 mL, 0.68 mmol) at 0° C. The resulting mixture was stirred at ambient temperature for 2 hours and benzylamine (0.08 mL, 0.73 mmol) was added. The reaction mixture was kept stirring for 14 hour at ambient temperature. The solvent was removed in vacuo, and the residue was purified by column chromatography to afford the title compound as a white powder in 20% yield (0.050 g): mp 169-171° C.; $^1$H NMR (300 MHz, DMSO-$d_6$) δ 8.49 (t, J=5.7 Hz, 1H), 7.35-7.19 (m, 10H), 4.39 (s, 2H), 4.35 (d, J=5.7 Hz, 2H), 3.96 (t, J=7.5 Hz, 2H), 3.41 (t, J=7.5 Hz, 2H), 2.44 (s, 3H); $^{13}$C NMR (75 MHz, DMSO-$d_6$) δ 162.2, 157.8, 155.5, 151.4, 140.1, 136.7, 129.1, 128.7, 128.2, 127.9, 127.6, 127.1, 118.2, 47.3, 43.0, 42.4, 42.0, 17.5; MS (ES+) m/z 407.3 (M+1).

Example 8.1

Synthesis of 2-(3-benzyl-2-oxoimidazolidin-1-yl)-N-(3-fluorobenzyl)-4-methylthiazole-5-carboxamide

Following the procedure as describe in Example 8, making variations as required to replace benzylamine with 3-fluorobenzylamine to react with 2-(3-benzyl-2-oxoimidazolidin-1-yl)-4-methylthiazole-5-carboxylic acid, the title compound was obtained as a white powder in 14% yield: mp 169-171° C.; $^1$H NMR (300 MHz, DMSO-$d_6$) δ 8.51 (t, J=5.7 Hz, 1H), 7.50-7.00 (m, 9H), 4.54-4.34 (m, 4H), 3.97 (t, J=7.5 Hz, 2H), 3.42 (t, J=7.5 Hz, 2H), 2.44 (s, 3H); $^{13}$C NMR (75 MHz, DMSO-$d_6$) δ 164.2, 162.3, 161.0, 157.8, 155.5, 151.6, 143.1, 130.6, 129.1, 128.2, 127.9, 123.6, 118.0, 114.4, 114.1, 47.3, 42.6, 42.4, 42.0, 17.5; MS (ES+) m/z 425.3 (M+1).

Example 8.2

Synthesis of N-ethyl-4-methyl-2-(2-oxo-3-(4-(trifluoromethoxy)benzyl)imidazolidin-1-yl)thiazole-5-carboxamide

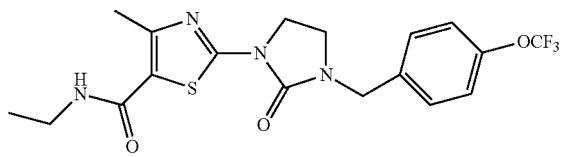

Following the procedure as describe in Example 8, making variations as required to replace benzylamine with ethylamine to react with 4-methyl-2-(2-oxo-3-(4-(trifluoromethoxy)benzyl)imidazolidin-1-yl)thiazole-5-carboxylic acid, the title compound was obtained as a white powder in 25% yield: mp 218-219° C. (ethyl acetate/hexanes); $^1$H NMR (300 MHz, CDCl$_3$) δ 7.32 (d, J=8.4 Hz, 2H), 7.18 (d, J=8.4 Hz, 2H), 5.60 (s, 1H), 4.47 (s, 2H), 4.10-4.04 (m, 2H), 3.51-3.35 (m, 4H), 2.57 (s, 3H), 1.18 (t, J=7.5 Hz, 3H); $^{13}$C NMR (75 MHz, CDCl$_3$) δ 162.3, 157.0, 155.4, 152.3, 148.9, 134.4, 129.7, 121.4, 120.4, 117.8, 47.3, 42.0, 41.8, 35.1, 34.8, 17.0, 14.8; MS (ES+) m/z 429.2 (M+1).

Example 8.3

Synthesis of N-(2-cyclopropylethyl)-4-methyl-2-(2-oxo-3-(4-(trifluoromethoxy)benzyl)imidazolidin-1-yl)thiazole-5-carboxamide

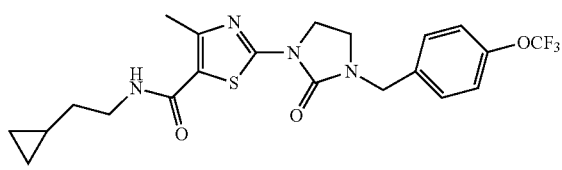

Following the procedure as describe in Example 8, making variations as required to replace benzylamine with 2-cyclopropylethylamine to react with 4-methyl-2-(2-oxo-3-(4-(trifluoromethoxy)benzyl)imidazolidin-1-yl)thiazole-5-carboxylic acid, the title compound was obtained as a white powder in 26% yield: mp 195-196° C. (ethyl acetate/hexanes); $^1$H NMR (300 MHz, CDCl$_3$) δ 7.32 (d, J=8.4 Hz, 2H), 7.18 (d, J=8.4 Hz, 2H), 5.76 (s, 1H), 4.47 (s, 2H), 4.12-4.07 (m, 2H), 3.49-3.42 (m, 4H), 2.59 (s, 3H), 1.50-1.43 (m, 2H), 0.72-0.62 (m, 1H), 0.47-0.41 (m, 2H), 0.14-0.02 (m, 2H); $^{13}$C NMR (75 MHz, CDCl$_3$) δ 162.3, 157.1, 155.4, 152.0, 148.9, 134.3, 129.7, 121.4, 120.4, 118.0, 47.3, 42.1, 41.8, 40.2, 34.3, 17.0, 8.6, 4.1; MS (ES+) m/z 469.3 (M+1).

Example 8.4

Synthesis of 2-(3-(4-fluorobenzyl)-2-oxoimidazolidin-1-yl)-4-methyl-N-(2-(pyrrolidin-1-yl)ethyl)thiazole-5-carboxamide

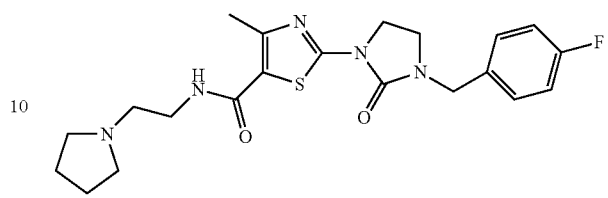

Following the procedure as describe in Example 8, making variations as required to replace benzylamine with 1-(2-aminoethyl)pyrrolidine to react with 2-(3-(4-fluorobenzyl)-2-oxoimidazolidin-1-yl)-4-methylthiazole-5-carboxylic acid, the title compound was obtained as a white powder in 17% yield: mp 183-184° C. (ethyl acetate/hexanes); $^1$H NMR (300 MHz, CDCl$_3$) δ 7.27-7.22 (m, 2H), 7.04-6.97 (m, 2H), 6.33 (br s, 1H), 4.43 (s, 2H), 4.07-4.01 (m, 2H), 3.47-3.32 (m, 4H), 2.64-2.50 (m, 9H), 1.85-1.70 (m, 4H); $^{13}$C NMR (75 MHz, CDCl$_3$) δ 162.6, 162.5 (d, $J_{C-F}$=245.2 Hz), 157.3, 155.4, 152.0, 131.4 (d, $J_{C-F}$=3.0 Hz), 130.0 (d, $J_{C-F}$=8.2 Hz), 118.3, 115.8 (d, $J_{C-F}$=21.0 Hz), 54.3, 53.8, 47.2, 42.0, 41.6, 38.4, 23.5, 17.1; MS (ES+) m/z 432.4 (M+1).

Example 8.5

Synthesis of 1-(5-acetyl-4-methylthiazol-2-yl)-3-(4-(piperidine-1-carbonyl)benzyl)imidazolidin-2-one

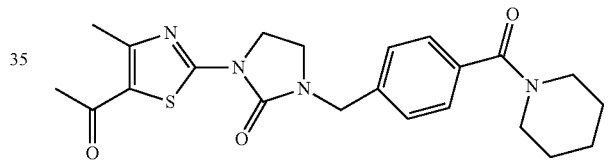

Following the procedure as describe in Example 8, making variations as required to replace benzylamine with piperidine to react with 4-((3-(5-acetyl-4-methylthiazol-2-yl)-2-oxoimidazolidin-1-yl)methyl)benzoic acid, the title compound was obtained as a white powder in 54% yield: $^1$H NMR (300 MHz, CDCl$_3$) δ 7.45-7.22 (m, 4H), 4.50 (s, 2H), 4.15-4.01 (m, 2H), 3.69-3.32 (m, 6H), 2.60 (s, 3H), 2.40 (s, 3H), 1.71-1.20 (m, 6H); MS (ES+) m/z 427.1 (M+1).

Example 8.6

Synthesis of 4-((3-(5-acetyl-4-methylthiazol-2-yl)-2-oxoimidazolidin-1-yl)methyl)-N-methylbenzamide

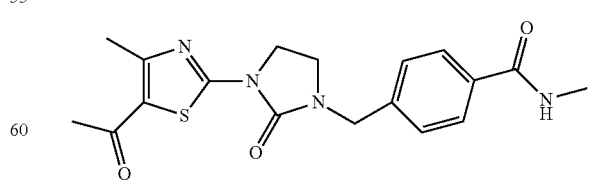

Following the procedure as describe in Example 8, making variations as required to replace benzylamine with methylamine to react with 4-((3-(5-acetyl-4-methylthiazol-2-yl)-2-oxoimidazolidin-1-yl)methyl)benzoic acid, the title compound was obtained as a white powder in 43% yield: mp 173-175° C. (ethyl acetate); $^1$H NMR (300 MHz, CDCl$_3$) δ 7.73 (d, J=8.4 Hz, 2H), 7.35 (d, J=8.4 Hz, 2H), 6.12 (br s, 1H), 4.52 (s, 2H), 4.12-4.06 (m, 2H), 3.49-3.43 (m, 2H), 3.00 (d, J=4.2 Hz, 3H), 2.67 (s, 3H), 2.46 (s, 3H); MS (ES+) m/z 373.2 (M+1).

Example 8.7

Synthesis of N-(4-fluorophenyl)-4-((3-(4-methylthiazol-2-yl)-2-oxoimidazolidin-1-yl)methyl)benzamide

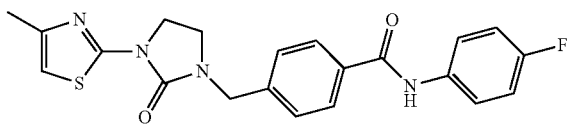

Following the procedure as describe in Example 8, making variations as required to replace benzylamine with 4-fluoroaniline to react with 4-((3-(4-methylthiazol-2-yl)-2-oxoimidazolidin-1-yl)methyl)benzoic acid, the title compound was obtained as a white powder in 16% yield: mp 206-207° C. (ethyl acetate/hexanes); $^1$H NMR (300 MHz, CDCl$_3$) δ 7.74 (d, J=7.2 Hz, 2H), 7.52-7.44 (m, 2H), 7.23 (d, J=7.2 Hz, 2H), 6.90-6.85 (m, 2H), 6.33 (s, 1H), 4.37 (s, 2H), 3.95-3.90 (m, 2H), 3.37-3.31 (m, 2H), 2.16 (s, 3H); $^{13}$C NMR (75 MHz, CDCl$_3$) δ 161.0, 155.9, 146.7, 139.5, 134.2, 127.9, 127.8, 122.6, 115.3, 115.1, 106.9, 47.3, 42.2, 41.8, 16.5; MS (ES+) m/z 411.1 (M+1).

Example 8.8

Synthesis of 1-(4-(5-methyl-1H-pyrazole-1-carbonyl)benzyl)-3-(4-methylthiazol-2-yl)imidazolidin-2-one

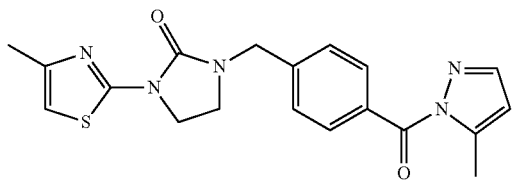

Following the procedure as describe in Example 8, making variations as required to replace benzylamine with 3-methylpyrazole to react with 4-((3-(4-methylthiazol-2-yl)-2-oxoimidazolidin-1-yl)methyl)benzoic acid, the title compound was obtained as a white powder in 24% yield: mp 96-97° C. (ethyl acetate/hexanes); $^1$H NMR (300 MHz, CDCl$_3$) δ 8.28 (d, J=2.7 Hz, 1H), 8.09 (d, J=8.4 Hz, 2H), 7.43 (d, J=8.4 Hz, 2H), 6.42 (d, J=0.9 Hz, 1H), 6.30 (d, J=2.7 Hz, 1H), 4.53 (s, 2H), 4.10-4.05 (m, 2H), 3.48-3.42 (m, 2H), 2.31 (s, 3H), 2.30 (s, 3H); $^{13}$C NMR (75 MHz, CDCl$_3$) δ 165.5, 158.7, 155.9, 154.6, 147.2, 141.1, 132.1, 131.3, 131.1, 127.7, 110.4, 106.9, 47.7, 42.3, 42.0, 17.3, 14.1; MS (ES+) m/z 382.2 (M+1).

Example 8.9

Synthesis of N-benzyl-4-((3-(4-methylthiazol-2-yl)-2-oxoimidazolidin-1-yl)methyl)benzamide

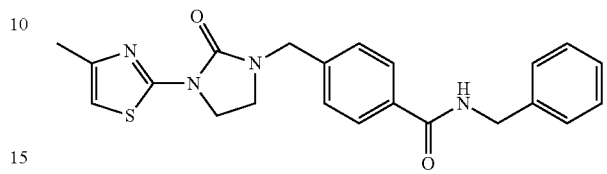

Following the procedure as describe in Example 8, making variations as required to replace 2-(3-benzyl-2-oxoimidazolidin-1-yl)-4-methylthiazole-5-carboxylic acid with 4-((3-(4-methylthiazol-2-yl)-2-oxoimidazolidin-1-yl)methyl)benzoic acid to react with benzylamine, the title compound was obtained as a white powder in 60% yield: mp 185-186° C. (ethyl acetate/hexanes); $^1$H NMR (300 MHz, CDCl$_3$) δ 7.76 (d, J=9.0 Hz, 2H), 7.30-7.28 (m, 6H), 6.73 (t, J=6.0 Hz, 2H), 6.41 (s, 1H), 4.59 (d, J=6.0 Hz, 2H), 4.44 (s, 2H), 4.05-4.00 (m, 2H), 3.40-3.35 (m, 2H), 2.29 (s, 3H); $^{13}$C NMR (75 MHz, CDCl$_3$) δ 166.8, 158.7, 155.9, 147.2, 139.6, 138.2, 134.0, 128.7, 128.3, 127.9, 127.6, 127.5, 106.9, 47.6, 44.0, 42.3, 41.9, 17.3; MS (ES+) m/z 407.2 (M+1).

Example 8.10

Synthesis of N-(4-methylthiazol-2-yl)-4-((3-(4-methylthiazol-2-yl)-2-oxoimidazolidin-1-yl)methyl)benzamide

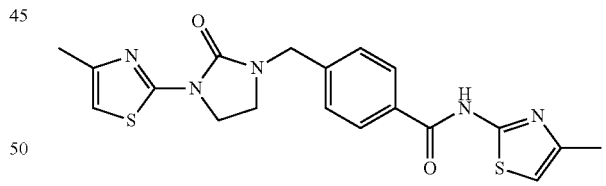

Following the procedure as describe in Example 8, making variations as required to replace benzylamine with 2-amino-4-methylthiazole to react with 4-((3-(4-methylthiazol-2-yl)-2-oxoimidazolidin-1-yl)methyl)benzoic acid, the title compound was obtained as a white powder in 41% yield: mp 197-198° C. (ethyl acetate/hexanes); $^1$H NMR (300 MHz, CDCl$_3$) δ 11.54 (br s, 1H), 7.87 (d, J=6.0 Hz, 2H), 7.37 (d, J=6.0 Hz, 2H), 6.52 (s, 1H), 6.43 (s, 1H), 4.53 (s, 2H), 4.11-4.06 (m, 2H), 3.46-3.41 (m, 2H), 2.30 (s, 3H), 1.97 (s, 3H); $^{13}$C NMR (75 MHz, CDCl$_3$) δ 164.8, 158.9, 158.7, 156.0, 147.3, 146.9, 141.2, 132.1, 128.5, 128.3, 108.6, 106.9, 47.7, 42.3, 42.0, 17.3, 16.6; MS (ES+) m/z 414.1 (M+1).

Example 8.11

Synthesis of 3-((3-(5-acetyl-4-methylthiazol-2-yl)-2-oxoimidazolidin-1-yl)methyl)-N-methylbenzamide

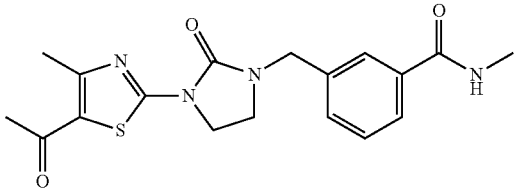

Following the procedure as describe in Example 8, making variations as required to replace benzylamine with methylamine monohydrochloride to react with 3-((3-(5-acetyl-4-methylthiazol-2-yl)-2-oxoimidazolidin-1-yl)methyl)benzoic acid, the title compound was obtained as a white powder in 85% yield: $^1$H NMR (300 MHz, CDCl$_3$) δ 7.73-7.62 (m, 2H), 7.42-7.34 (m, 2H), 6.32 (br s, 1H), 4.51 (s, 2H), 4.13-4.04 (m, 2H), 3.49-3.41 (m, 2H), 2.97 (d, J=4.8 Hz, 3H), 2.60 (s, 3H), 2.45 (s, 3H); MS (ES+) m/z 373.1 (M+1).

Example 8.12

Synthesis of N-(cyclopropylmethyl)-4-methyl-2-(2-oxo-3-(4-(trifluoromethoxy)benzyl)imidazolidin-1-yl)thiazole-5-carboxamide

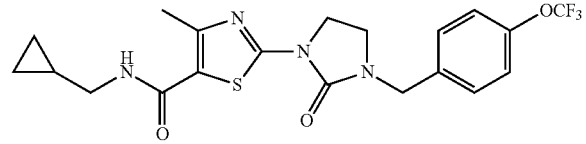

Following the procedure as describe in Example 8, making variations as required to replace benzylamine with 2-cyclopropylmethylamine to react with 4-methyl-2-(2-oxo-3-(4-(trifluoromethoxy)benzyl)imidazolidin-1-yl)thiazole-5-carboxylic acid, the title compound was obtained as a white powder in 15% yield: mp 184-186° C.; $^1$H NMR (300 MHz, CDCl$_3$) δ 7.32 (d, J=8.4 Hz, 2H), 7.18 (d, J=8.4 Hz, 2H), 5.70 (s, 1H), 4.48 (s, 2H), 4.08 (t, J=8.4 Hz, 2H), 3.46 (t, J=8.4 Hz, 2H), 3.24-3.20 (m, 2H), 2.58 (s, 3H), 1.03-0.92 (m, 1H), 0.55-0.44 (m, 2H), 0.29-0.27 (m, 2H); $^{13}$C NMR (75 MHz, CDCl$_3$) δ 162.3, 156.9, 155.5, 152.7, 148.9, 134.4, 129.7, 121.4, 120.4, 117.6, 47.3, 44.8, 42.0, 41.8, 17.1, 10.6, 3.5; MS (ES+) m/z 455.3 (M+1).

Example 9

Synthesis of 2-(3-benzyl-2-oxoimidazolidin-1-yl)-N-(4-fluorobenzyl)-4-methylthiazole-5-carboxamide

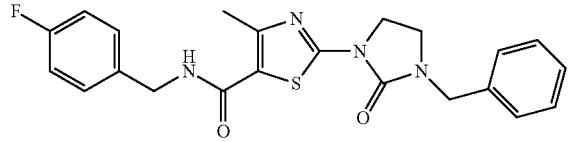

To a solution of 2-(3-benzyl-2-oxoimidazolidin-1-yl)-4-methylthiazole-5-carboxylic acid (0.32 g, 1.00 mmol), 1-(3-dimethylaminopropyl)-3-ethylcarbodiimide hydrochloride (0.20 g, 1.30 mmol) and N,N-diisopropylethylamine (0.50 mL, 2.80 mmol) in N,N-dimethylformamide (20 mL) was added 1-hydroxybenzotriazole (0.16 g, 1.20 mmol). The resulting mixture was stirred at ambient temperature for 15 minutes and 4-fluorobenzylamine (0.17 mL, 1.45 mmol) was added. The reaction mixture was kept stirring for 27 hours at ambient temperature, then was diluted with ethyl acetate (300 mL) and washed with water and brine. The organic solution was dried over anhydrous sodium sulfate and filtered. The filtrate was concentrated in vacuo, and the residue was purified by column chromatography to afford the title compound as a white powder in 58% yield (0.25 g): mp 147-148° C.; $^1$H NMR (300 MHz, DMSO-d$_6$) δ 7.35-7.20 (m, 7H), 7.02-6.96 (m, 2H), 6.00 (s, 1H), 4.55-4.44 (m, 4H), 4.04 (t, J=7.5 Hz, 2H), 3.42 (t, J=7.5 Hz, 2H), 2.59 (s, 3H); $^{13}$C NMR (75 MHz, DMSO-d$_6$) δ 163.8, 162.4, 160.5, 157.3, 155.3, 153.2, 135.5, 133.8, 129.4, 128.9, 128.2, 117.0, 115.7, 47.9, 43.2, 42.0, 41.6, 17.1; MS (ES+) m/z 425.2 (M+1).

Example 9.1

Synthesis of 2-(3-benzyl-2-oxoimidazolidin-1-yl)-N-(2-fluorobenzyl)-4-methylthiazole-5-carboxamide

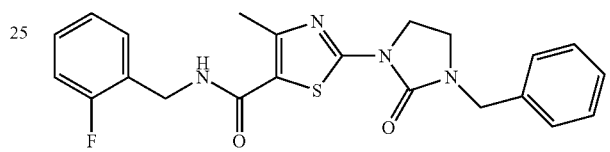

Following the procedure as describe in Example 9, making variations as required to replace 4-fluorobenzylamine with 2-fluorobenzylamine to react with 2-(3-benzyl-2-oxoimidazolidin-1-yl)-4-methylthiazole-5-carboxylic acid, the title compound was obtained as a white powder in 44% yield: mp 167-168° C.; $^1$H NMR (300 MHz, DMSO-d$_6$) δ 7.39-7.20 (m, 7H), 7.11-7.00 (m, 2H), 6.03 (s, 1H), 4.59 (d, J=5.7 Hz, 2H), 4.45 (s, 2H), 4.07-4.00 (m, 2H), 3.46-3.40 (m, 2H), 2.58 (s, 3H); $^{13}$C NMR (75 MHz, DMSO-d$_6$) δ 162.4, 159.4 157.4, 155.4, 153.0, 135.5, 130.3, 129.4, 129.3, 128.9, 125.4, 124.4, 117.2, 115.5, 115.8, 47.9, 42.0, 41.6, 38.7, 17.1; MS (ES+) m/z 425.2 (M+1).

Example 9.2

Synthesis of 2-(3-benzyl-2-oxoimidazolidin-1-yl)-N-(2,5-difluorobenzyl)-4-methylthiazole-5-carboxamide

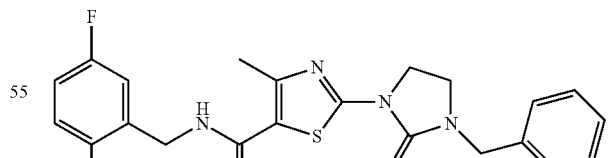

Following the procedure as describe in Example 9, making variations as required to replace 4-fluorobenzylamine with 2,5-difluorobenzylamine to react with 2-(3-benzyl-2-oxoimidazolidin-1-yl)-4-methylthiazole-5-carboxylic acid, the title compound was obtained as a white powder in 76% yield: mp 176-177° C.; $^1$H NMR (300 MHz, DMSO-d$_6$) δ 7.37-6.87 (m, 8H), 6.06 (t, J=5.7 Hz, 1H), 4.56 (d, J=5.7 Hz, 2H), 4.46 (s, 2H), 4.05 (t, J=8.1 Hz, 2H), 3.44 (t, J=8.1 Hz, 2H), 2.58 (s, 3H); $^{13}$C NMR (75 MHz, DMSO-d$_6$) δ 162.5, 158.4, 157.4, 155.3, 155.2, 153.5, 135.5, 128.9, 128.3, 128.0, 127.0, 126.8, 116.8, 115.4, 48.0, 42.0, 41.6, 37.6, 17.2; MS (ES+) m/z 443.2 (M+1).

Example 9.3

Synthesis of 2-(3-benzyl-2-oxoimidazolidin-1-yl)-N-(3,5-difluorobenzyl)-4-methylthiazole-5-carboxamide

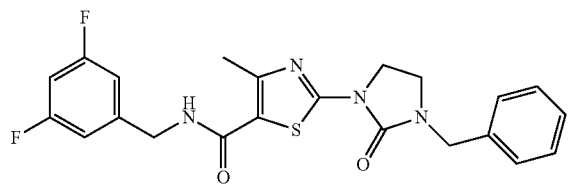

Following the procedure as describe in Example 9, making variations as required to replace 4-fluorobenzylamine with 3,5-difluorobenzylamine to react with 2-(3-benzyl-2-oxoimidazolidin-1-yl)-4-methylthiazole-5-carboxylic acid, the title compound was obtained as a white powder in 45% yield: mp 208-209° C.; $^1$H NMR (300 MHz, DMSO-d$_6$) δ 7.35-7.23 (m, 5H), 6.82 (s, 1H), 6.80 (s, 1H), 6.66 (t, J=8.7 Hz, 1H), 6.24 (t, J=5.7 Hz, 1H), 4.51 (d, J=5.7 Hz, 2H), 4.44 (s, 2H), 4.03 (t, J=8.4 Hz, 2H), 3.43 (t, J=8.4 Hz, 2H), 2.58 (s, 3H); $^{13}$C NMR (75 MHz, DMSO-d$_6$) δ 164.6, 162.6, 161.5, 161.4, 157.4, 155.3, 142.3, 135.4, 128.9, 128.2, 128.0, 116.7, 110.3, 102.8, 47.9, 43.0, 42.0, 41.6, 17.2; MS (ES+) m/z 443.2 (M+1).

Example 9.4

Synthesis of 2-(3-benzyl-2-oxoimidazolidin-1-yl)-N-(2,4-difluorobenzyl)-4-methylthiazole-5-carboxamide

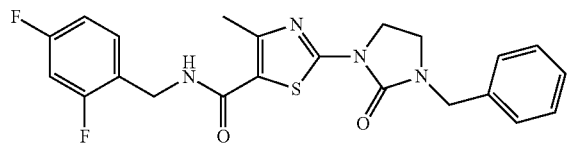

Following the procedure as describe in Example 9, making variations as required to replace 4-fluorobenzylamine with 2,4-difluorobenzylamine to react with 2-(3-benzyl-2-oxoimidazolidin-1-yl)-4-methylthiazole-5-carboxylic acid, the title compound was obtained as a white powder in 45% yield: mp 157-158° C.; $^1$H NMR (300 MHz, DMSO-d$_6$) δ 7.39-7.23 (m, 6H), 6.84-6.74 (m, 2H), 6.06 (t, J=5.7 Hz, 1H), 4.53 (d, J=5.7 Hz, 2H), 4.49 (s, 2H), 4.03 (t, J=8.4 Hz, 2H), 3.43 (t, J=8.4 Hz, 2H), 2.57 (s, 3H); $^{13}$C NMR (75 MHz, DMSO-d$_6$) δ 164.1, 162.7, 160.8, 157.4, 155.3, 153.3, 135.5, 131.2, 128.9, 128.3, 128.0, 121.2, 117.0, 111.5, 103.9, 47.9, 42.0, 41.6, 37.4, 17.2; MS (ES+) m/z 443.2 (M+1).

Example 9.5

Synthesis of 2-(3-benzyl-2-oxoimidazolidin-1-yl)-N-(3,4-difluorobenzyl)-4-methylthiazole-5-carboxamide

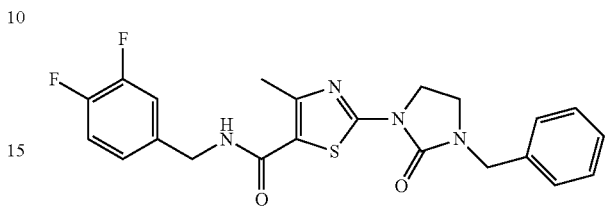

Following the procedure as describe in Example 9, making variations as required to replace 4-fluorobenzylamine with 3,4-difluorobenzylamine to react with 2-(3-benzyl-2-oxoimidazolidin-1-yl)-4-methylthiazole-5-carboxylic acid, the title compound was obtained as a white powder in 43% yield: mp 152-153° C.; $^1$H NMR (300 MHz, DMSO-d$_6$) δ 7.36-7.00 (m, 8H), 6.05 (s, 1H), 4.49 (d, J=5.7 Hz, 2H), 4.45 (s, 2H), 4.05 (t, J=8.4 Hz, 2H), 3.44 (t, J=8.4 Hz, 2H), 2.58 (s, 3H); $^{13}$C NMR (75 MHz, DMSO-d$_6$) δ 162.5, 157.3, 155.3, 153.6, 152.0, 148.6, 135.2, 128.9, 128.2, 128.1, 123.6, 117.5, 116.8, 116.7, 116.6, 47.9, 42.9, 42.0, 41.6, 17.2; MS (ES+) m/z 443.0 (M+1).

Example 9.6

Synthesis of 2-(3-benzyl-2-oxoimidazolidin-1-yl)-N-(3-chlorobenzyl)-4-methylthiazole-5-carboxamide

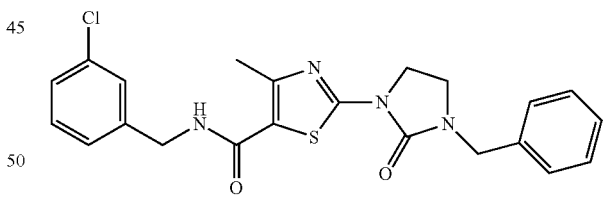

Following the procedure as describe in Example 9, making variations as required to replace 4-fluorobenzylamine with 3-chlorobenzylamine to react with 2-(3-benzyl-2-oxoimidazolidin-1-yl)-4-methylthiazole-5-carboxylic acid, the title compound was obtained as a white powder in 46% yield: mp 178-179° C.; $^1$H NMR (300 MHz, DMSO-d$_6$) δ 7.33-7.19 (m, 9H), 6.10 (s, 1H), 4.51 (d, J=5.7 Hz, 2H), 4.44 (s, 2H), 4.03 (t, J=8.4 Hz, 2H), 3.43 (t, J=8.4 Hz, 2H), 2.59 (s, 3H); $^{13}$C NMR (75 MHz, DMSO-d$_6$) δ 162.5, 157.3, 155.3, 153.4, 140.2, 135.5, 134.5, 130.0, 128.9, 128.3, 128.0, 127.8, 127.7, 125.8, 116.9, 47.9, 43.3, 42.0, 41.6, 17.2; MS (ES+) m/z 441.0 (M+1), 443.0 (M+1).

Example 9.7

Synthesis 2-(3-benzyl-2-oxoimidazolidin-1-yl)-4-methyl-N-(pyridin-3-ylmethyl)thiazole-5-carboxamide

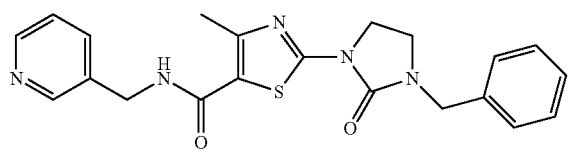

Following the procedure as describe in Example 9, making variations as required to replace 4-fluorobenzylamine with 3-(aminomethyl)pyridine to react with 2-(3-benzyl-2-oxoimidazolidin-1-yl)-4-methylthiazole-5-carboxylic acid, the title compound was obtained as a white powder in 57% yield: mp 153-154° C.; $^1$H NMR (300 MHz, DMSO-$d_6$) δ 8.56-8.40 (m, 3H), 7.66 (d, J=7.8 Hz, 1H), 7.35-7.19 (m, 6H), 4.46-4.35 (m, 4H), 3.96 (t, J=7.5 Hz, 2H), 3.41 (t, J=7.5 Hz, 2H), 2.50 (s, 3H); $^{13}$C NMR (75 MHz, DMSO-$d_6$) δ 162.3, 157.8, 155.5, 151.7, 149.3, 148.4, 136.7, 135.6, 135.5, 129.1, 128.2, 127.9, 123.9, 117.9, 47.3, 42.9, 42.4, 40.8, 14.5; MS (ES+) m/z 408.1 (M+1).

Example 9.8

Synthesis of 2-(3-benzyl-2-oxoimidazolidin-1-yl)-4-methyl-N-(pyridin-2-ylmethyl)thiazole-5-carboxamide

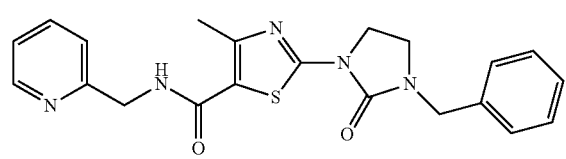

Following the procedure as describe in Example 9, making variations as required to replace 4-fluorobenzylamine with 2-(aminomethyl)pyridine to react with 2-(3-benzyl-2-oxoimidazolidin-1-yl)-4-methylthiazole-5-carboxylic acid, the title compound was obtained as a white powder in 43% yield: mp 149-151° C.; $^1$H NMR (300 MHz, DMSO-$d_6$) δ 8.52-8.46 (m, 2H), 7.72 (t, J=5.7 Hz, 1H), 7.39-7.19 (m, 7H), 4.49 (d, J=5.7 Hz, 2H), 4.40 (s, 2H), 3.97 (t, J=7.5 Hz, 2H), 3.42 (t, J=7.5 Hz, 2H), 2.46 (s, 3H); $^{13}$C NMR (75 MHz, DMSO-$d_6$) δ 162.4, 159.1, 157.9, 155.5, 151.5, 149.2, 137.1, 136.7, 129.1, 128.2, 127.9, 122.4, 121.2, 118.2, 47.3, 45.0, 42.4, 42.0, 17.6; MS (ES+) m/z 408.3 (M+1).

Example 9.9

Synthesis of 2-(3-benzyl-2-oxoimidazolidin-1-yl)-4-methyl-N-(pyridin-4-ylmethyl)thiazole-5-carboxamide

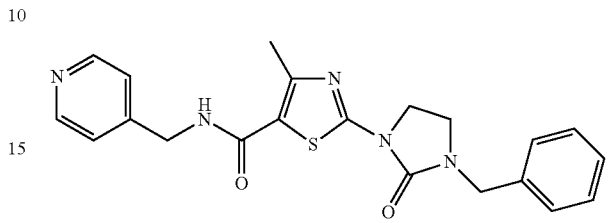

Following the procedure as describe in Example 9, making variations as required to replace 4-fluorobenzylamine with 4-(aminomethyl)pyridine to react with 2-(3-benzyl-2-oxoimidazolidin-1-yl)-4-methylthiazole-5-carboxylic acid, the title compound was obtained as a white powder in 49% yield: mp 96-97° C.; $^1$H NMR (300 MHz, DMSO-$d_6$) δ 8.47 (d, J=4.8 Hz, 2H), 7.31-7.19 (m, 7H), 6.52 (t, J=5.7 Hz, 1H), 4.53 (d, J=5.7 Hz, 2H), 4.35 (s, 2H), 4.02 (t, J=7.5 Hz, 2H), 3.41 (t, J=7.5 Hz, 2H), 2.56 (s, 3H); $^{13}$C NMR (75 MHz, DMSO-$d_6$) δ 162.8, 157.5, 155.3, 153.7, 149.7, 147.7, 135.4, 128.9, 128.2, 128.0, 122.3, 116.7, 47.9, 42.6, 42.0, 41.6, 17.3; MS (ES+) m/z 408.3 (M+1).

Example 9.10

Synthesis of 2-(3-benzyl-2-oxoimidazolidin-1-yl)-4-methyl-N-((5-methylfuran-2-yl)methyl)thiazole-5-carboxamide

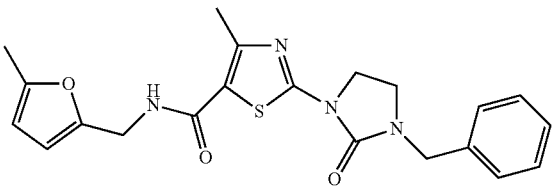

Following the procedure as describe in Example 9, making variations as required to replace 4-fluorobenzylamine with 5-methylfurfurylamine to react with 2-(3-benzyl-2-oxoimidazolidin-1-yl)-4-methylthiazole-5-carboxylic acid, the title compound was obtained as a white powder in 29% yield: mp 138-139° C.; $^1$H NMR (300 MHz, DMSO-$d_6$) δ 7.36-7.25 (m, 5H), 6.10 (d, J=2.7 Hz, 1H), 5.90-5.86 (m, 2H), 4.50-4.44 (m, 4H), 4.04 (t, J=8.1 Hz, 2H), 3.43 (t, J=8.1 Hz, 2H), 2.58 (s, 3H), 2.24 (s, 3H); $^{13}$C NMR (75 MHz, DMSO-$d_6$) δ 162.1, 157.3, 155.4, 153.1, 152.1, 148.9, 135.5, 128.8, 128.3, 128.0, 117.1, 108.5, 106.3, 47.9, 42.0, 41.6, 37.0, 17.1, 13.5; MS (ES+) m/z 411.3 (M+1).

Example 9.11

Synthesis of N-benzyl-4-methyl-2-(2-oxo-3-phenethylimidazolidin-1-yl)thiazole-5-carboxamide

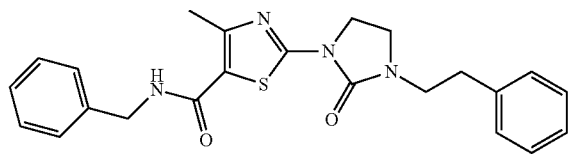

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-phenethylimidazolidin-1-yl)thiazole-5-carboxylic acid to react with benzylamine, the title compound was obtained as a white powder in 26% yield: mp 156-157° C.; $^1$H NMR (300 MHz, CDCl$_3$) δ 7.36-7.18 (m, 10H), 5.93 (s, 1H), 4.54 (d, J=5.7 Hz, 2H), 3.99 (t, J=7.8 Hz, 2H), 3.54 (t, J=7.2 Hz, 2H), 3.41 (t, J=7.8 Hz, 2H), 2.87 (t, J=7.2 Hz, 2H), 2.59 (s, 3H); $^{13}$C NMR (75 MHz, CDCl$_3$) δ 162.4, 157.3, 155.3, 153.0, 151.7, 138.2, 137.9, 128.7, 128.6, 127.8, 127.6, 126.7, 117.1, 45.3, 44.0, 42.7, 42.0, 34.0, 17.2; MS (ES+) m/z 421.2 (M+1).

Example 9.12

Synthesis of 4-methyl-2-(2-oxo-3-(4-(trifluoromethyl)benzyl)imidazolidin-1-yl)-N-(pyridin-3-ylmethyl)thiazole-5-carboxamide

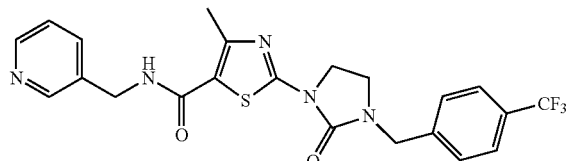

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethyl)benzyl)imidazolidin-1-yl)thiazole-5-carboxylic acid to react with 3-(aminomethyl)pyridine in place of benzylamine, the title compound was obtained as a white powder in 49% yield: mp 107-108° C.; $^1$H NMR (300 MHz, CDCl$_3$) δ 8.56 (s, 1H), 8.44 (s, 1H), 7.66 (d, J=7.8 Hz, 1H), 7.56 (d, J=8.1 Hz, 2H), 7.35 (d, J=8.1 Hz, 2H), 7.23-7.19 (m, 1H), 5.59 (s, 1H), 4.55 (d, J=5.7 Hz, 2H), 4.47 (s, 2H), 4.04 (t, J=8.1 Hz, 2H), 3.43 (t, J=8.1 Hz, 2H), 2.55 (s, 3H); $^{13}$C NMR (75 MHz, CDCl$_3$) δ 162.6, 157.2, 155.4, 153.5, 149.1, 148.6, 139.6, 135.8, 134.1, 130.5, 128.4, 125.8, 123.6, 122.1, 117.1, 47.5, 42.0, 41.8, 41.3, 17.2; MS (ES+) m/z 476.3 (M+1).

Example 9.13

Synthesis of N-benzyl-4-methyl-2-(2-oxo-3-(4-(trifluoromethyl)benzyl)imidazolidin-1-yl)thiazole-5-carboxamide

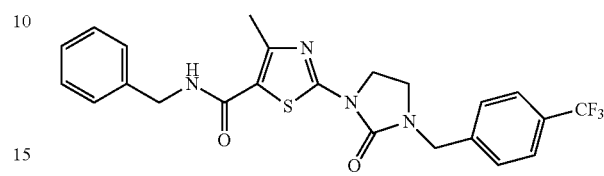

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethyl)benzyl)imidazolidin-1-yl)thiazole-5-carboxylic acid to react with benzylamine, the title compound was obtained as a white powder in 44% yield: mp 127-128° C.; $^1$H NMR (300 MHz, CDCl$_3$) δ 7.60 (d, J=8.1 Hz, 2H), 7.41-7.26 (m, 7H), 5.90 (t, J=5.7 Hz, 1H), 4.55 (d, J=5.7 Hz, 2H), 4.51 (s, 2H), 4.09 (t, J=8.1 Hz, 2H), 3.46 (t, J=8.1 Hz, 2H), 2.60 (s, 3H); $^{13}$C NMR (75 MHz, CDCl$_3$) δ 162.2, 157.2, 155.4, 152.8, 139.6, 137.9, 130.2, 128.8, 128.5, 127.8, 127.6, 125.8, 122.1, 117.5, 47.6, 44.0, 42.1, 41.9, 17.1; MS (ES+) m/z 475.0 (M+1).

Example 9.14

Synthesis of N-benzyl-2-(3-(cyclopropylmethyl)-2-oxoimidazolidin-1-yl)-4-methylthiazole-5-carboxamide

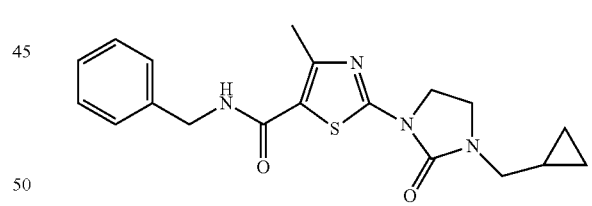

Following the procedure as describe in Example 9, making variations as required to replace 2-(3-benzyl-2-oxoimidazolidin-1-yl)-4-methylthiazole-5-carboxylic acid with 2-(3-(cyclopropylmethyl)-2-oxoimidazolidin-1-yl)-4-methylthiazole-5-carboxylic acid to react with benzylamine, the title compound was obtained as a white powder in 26% yield: mp 142-143° C.; $^1$H NMR (300 MHz, DMSO-d$_6$) δ 7.36-7.25 (m, 5H), 5.90 (s, 1H), 4.54 (d, J=5.7 Hz, 2H), 4.09 (t, J=8.4 Hz, 2H), 3.67 (t, J=8.4 Hz, 2H), 3.15 (d, J=7.2 Hz, 2H), 2.60 (s, 3H), 0.97-0.86 (m, 1H), 0.58-0.49 (m, 2H), 0.25-0.19 (m, 2H); $^{13}$C NMR (75 MHz, DMSO-d$_6$) δ 162.4, 157.4, 155.2, 153.0, 137.9, 128.7, 127.8, 127.6, 117.0, 48.6, 44.0, 42.2, 42.1, 17.1, 8.9, 3.4; MS (ES+) m/z 371.1 (M+1).

Example 9.15

Synthesis of 2-(3-(cyclopropylmethyl)-2-oxoimidazolidin-1-yl)-N-(4-fluorobenzyl)-4-methylthiazole-5-carboxamide

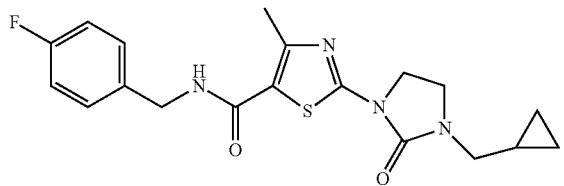

Following the procedure as describe in Example 9, making variations as required to replace 2-(3-benzyl-2-oxoimidazolidin-1-yl)-4-methylthiazole-5-carboxylic acid with 2-(3-(cyclopropylmethyl)-2-oxoimidazolidin-1-yl)-4-methylthiazole-5-carboxylic acid to react with 4-fluorobenzylamine in place of benzylamine, the title compound was obtained as a white powder in 76% yield: mp 146-147° C.; $^1$H NMR (300 MHz, DMSO-d$_6$) δ 7.27-7.23 (m, 2H), 7.00-6.94 (m, 2H), 6.01 (t, J=5.4 Hz, 1H), 4.48 (d, J=5.4 Hz, 2H), 4.06 (t, J=8.4 Hz, 2H), 3.67 (t, J=8.4 Hz, 2H), 3.13 (d, J=7.2 Hz, 2H), 2.57 (s, 3H), 0.95-0.84 (m, 1H), 0.56-0.48 (m, 2H), 0.23-0.18 (m, 2H); $^{13}$C NMR (75 MHz, DMSO-d$_6$) δ 162.5, 162.1, 157.4, 155.2, 153.2, 133.9, 129.5, 116.8, 115.6, 48.6, 43.2, 42.2, 42.1, 17.2, 8.9, 3.4; MS (ES+) m/z 389.2 (M+1).

Example 9.16

Synthesis of 2-(3-(cyclopropylmethyl)-2-oxoimidazolidin-1-yl)-4-methyl-N-(pyridin-3-ylmethyl)thiazole-5-carboxamide

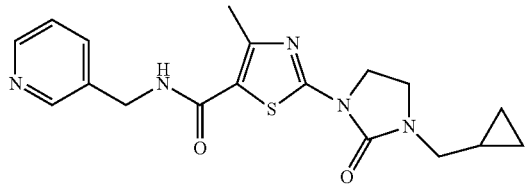

Following the procedure as describe in Example 9, making variations as required to replace 2-(3-benzyl-2-oxoimidazolidin-1-yl)-4-methylthiazole-5-carboxylic acid with 2-(3-(cyclopropylmethyl)-2-oxoimidazolidin-1-yl)-4-methylthiazole-5-carboxylic acid to react with 3-(aminomethyl)pyridine in place of benzylamine, the title compound was obtained as a white powder in 33% yield: mp 157-158° C.; $^1$H NMR (300 MHz, DMSO-d$_6$) δ 8.53-8.47 (m, 2H), 8.42-8.40 (m, 1H), 7.68-7.64 (m, 1H), 7.33-7.29 (m, 1H), 4.34 (d, J=5.7 Hz, 2H), 3.99 (t, J=7.2 Hz, 2H), 3.61 (t, J=7.2 Hz, 2H), 3.05 (d, J=6.9 Hz, 2H), 2.43 (s, 3H), 1.03-0.88 (m, 1H), 0.53-0.37 (m, 2H), 0.25-0.12 (m, 2H); $^{13}$C NMR (75 MHz, DMSO-d$_6$) δ 162.3, 157.9, 155.2, 151.7, 149.3, 148.5, 135.6, 135.5, 123.9, 117.7, 48.2, 42.5, 42.3, 41.5, 17.6, 9.3, 3.6; MS (ES+) m/z 372.3 (M+1).

Example 9.17

Synthesis of N-benzyl-2-(3-(2-cyclopropylethyl)-2-oxoimidazolidin-1-yl)-4-methylthiazole-5-carboxamide

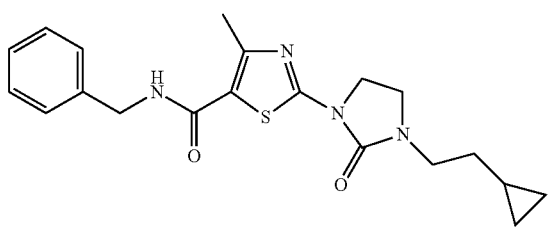

Following the procedure as describe in Example 9, making variations as required to replace 2-(3-benzyl-2-oxoimidazolidin-1-yl)-4-methylthiazole-5-carboxylic acid with 2-(3-(2-cyclopropylethyl)-2-oxoimidazolidin-1-yl)-4-methylthiazole-5-carboxylic acid to react with benzylamine, the title compound was obtained as a white powder in 15% yield: mp 137-138° C.; $^1$H NMR (300 MHz, CDCl$_3$) δ 7.36-7.25 (m, 5H), 5.88 (s, 1H), 4.54 (d, J=5.7 Hz, 2H), 4.09 (t, J=7.8 Hz, 2H), 3.58 (t, J=8.7 Hz, 2H), 3.37 (t, J=7.8 Hz, 2H), 2.60 (s, 3H), 1.46 (m, 2H), 0.70-0.58 (m, 1H), 0.46-0.37 (m, 2H), 0.13-0.03 (m, 2H); $^{13}$C NMR (75 MHz, CDCl$_3$) δ 162.4, 155.3, 153.0, 137.9, 128.7, 127.8, 127.6, 44.8, 44.0, 42.5, 42.0, 32.4, 17.1, 8.4, 4.3; MS (ES+) m/z 385.2 (M+1).

Example 9.18

Synthesis of 2-(3-(2-cyclopropylethyl)-2-oxoimidazolidin-1-yl)-N-(4-fluorobenzyl)-4-methylthiazole-5-carboxamide

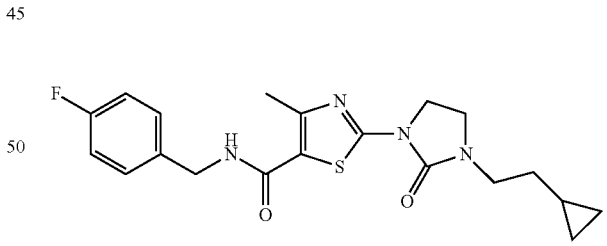

Following the procedure as describe in Example 9, making variations as required to replace 2-(3-benzyl-2-oxoimidazolidin-1-yl)-4-methylthiazole-5-carboxylic acid with 2-(3-(2-cyclopropylethyl)-2-oxoimidazolidin-1-yl)-4-methylthiazole-5-carboxylic acid to react with 4-fluorobenzylamine in place of benzylamine, the title compound was obtained as a white powder in 34% yield: mp 122-123° C.; $^1$H NMR (300 MHz, CDCl$_3$) δ 7.27-7.23 (m, 2H), 7.00-6.94 (m, 2H), 5.98 (s, 1H), 4.48 (d, J=5.7 Hz, 2H), 4.05 (t, J=7.8 Hz, 2H), 3.56 (t, J=8.7 Hz, 2H), 3.35 (t, J=7.8 Hz, 2H), 2.57 (s, 3H), 1.47-1.40 (m, 2H), 0.67-0.56 (m, 1H), 0.46-0.37 (m, 2H), 0.06-0.01 (m, 2H); $^{13}$C NMR (75 MHz, CDCl$_3$) δ 163.8, 162.5, 157.4, 155.3, 153.2, 133.9, 129.5, 116.8, 115.6, 44.0, 43.2, 42.7, 42.0, 32.4, 17.2, 8.4, 4.3; MS (ES+) m/z 403.2 (M+1).

Example 9.19

Synthesis of 2-(3-(4-fluorobenzyl)-2-oxoimidazolidin-1-yl)-4-methyl-N-(pyridin-3-ylmethyl)thiazole-5-carboxamide

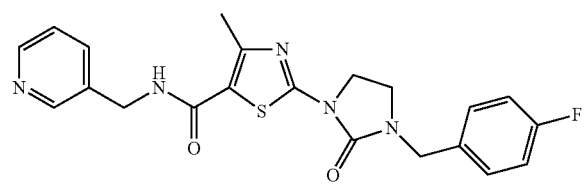

Following the procedure as describe in Example 9, making variations as required to replace 2-(3-benzyl-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with 3-(aminomethyl)pyridine in place of benzylamine, the title compound was obtained as a white powder in 33% yield: mp 177-179° C.; $^1$H NMR (300 MHz, CDCl$_3$) δ 8.59 (s, 1H), 8.50 (d, J=3.9 Hz, 1H), 7.70 (d, J=8.1 Hz, 1H), 7.29-7.21 (m, 3H), 7.04-6.97 (m, 2H), 6.26 (t, J=5.7 Hz, 1H), 4.57 (d, J=5.7 Hz, 2H), 4.42 (s, 2H), 4.04 (t, J=8.1 Hz, 2H), 3.43 (t, J=8.1 Hz, 2H), 2.58 (s, 3H); $^{13}$C NMR (75 MHz, CDCl$_3$) δ 164.1, 162.6, 160.8, 157.3, 155.3, 153.6, 148.5, 136.0, 134.1, 131.3, 129.9, 123.7, 116.9, 115.9, 115.6, 47.2, 42.0, 41.6, 41.3, 17.2; MS (ES+) m/z 475.0 (M+1).

Example 9.20

Synthesis of N-(4-fluorobenzyl)-2-(3-(4-fluorobenzyl)-2-oxoimidazolidin-1-yl)-4-methylthiazole-5-carboxamide

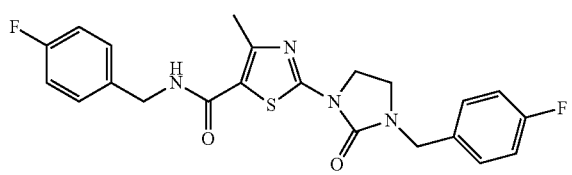

Following the procedure as describe in Example 9, making variations as required to replace 2-(3-benzyl-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with 4-fluorobenzylamine in place of benzylamine, the title compound was obtained as a white powder in 38% yield: mp 177-178° C.; $^1$H NMR (300 MHz, CDCl$_3$) δ 7.29-7.21 (m, 4H), 7.04-6.96 (m, 4H), 5.98 (s, 1H), 4.50 (d, J=5.7 Hz, 2H), 4.41 (s, 2H), 4.03 (t, J=8.1 Hz, 2H), 3.42 (t, J=8.1 Hz, 2H), 2.58 (s, 3H); $^{13}$C NMR (75 MHz, CDCl$_3$) δ 164.1, 162.4, 160.8, 155.3, 153.2, 133.8, 131.3, 129.9, 129.5, 117.2, 115.7, 115.4, 47.2, 43.2, 42.0, 41.6, 17.2; MS (ES+) m/z 443.2 (M+1).

Example 9.21

Synthesis of N-benzyl-2-(3-(4-fluorobenzyl)-2-oxoimidazolidin-1-yl)-4-methylthiazole-5-carboxamide

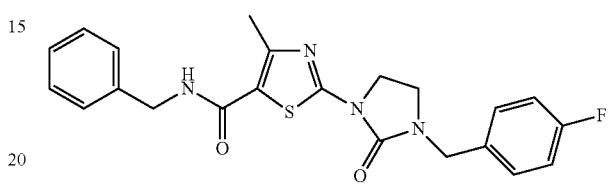

Following the procedure as describe in Example 9, making variations as required to replace 2-(3-benzyl-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with benzylamine, the title compound was obtained as a white powder in 16% yield: mp 192-193° C.; $^1$H NMR (300 MHz, CDCl$_3$) δ 7.37-7.21 (m, 7H), 7.04-6.98 (m, 2H), 5.95 (s, 1H), 4.54 (d, J=5.7 Hz, 2H), 4.41 (s, 2H), 4.03 (t, J=8.1 Hz, 2H), 3.42 (t, J=8.1 Hz, 2H), 2.58 (s, 3H); $^{13}$C NMR (75 MHz, CDCl$_3$) δ 164.1, 162.3, 157.2, 155.3, 152.9, 137.9, 133.8, 131.3, 129.9, 128.7, 127.7, 117.3, 115.9, 47.2, 44.0, 42.0, 41.6, 17.2; MS (ES+) m/z 425.2 (M+1).

Example 9.22

Synthesis of 4-methyl-2-(2-oxo-3-(4-(trifluoromethoxy)benzyl)imidazolidin-1-yl)-N-(pyridin-3-ylmethyl)thiazole-5-carboxamide

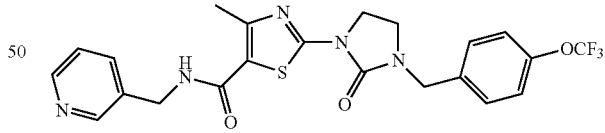

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethoxy)benzyl)imidazolidin-1-yl)thiazole-5-carboxylic acid to react with 3-(aminomethyl)pyridine in place of benzylamine, the title compound was obtained as a white powder in 77% yield: mp 165-166° C.; $^1$H NMR (300 MHz, CDCl$_3$) δ 8.57 (s, 1H), 8.46 (d, J=4.5 Hz, 1H), 7.67 (d, J=8.1 Hz, 1H), 7.29-7.14 (m, 5H), 6.46 (t, J=5.4 Hz, 1H), 4.56 (d, J=5.4 Hz, 2H), 4.43 (s, 2H), 4.04 (t, J=8.1 Hz, 2H), 3.43 (t, J=8.1 Hz, 2H), 2.56 (s, 3H); $^{13}$C NMR (75 MHz, CDCl$_3$) δ 162.6, 157.2, 155.4, 153.5, 149.0, 148.0, 135.8, 134.3, 129.6, 118.6, 117.0, 47.2, 42.0, 41.7, 41.3, 17.2; MS (ES+) m/z 492.3 (M+1).

Example 9.23

Synthesis of N-benzyl-4-methyl-2-(2-oxo-3-(4-(trifluoromethoxy)benzyl)imidazolidin-1-yl)thiazole-5-carboxamide

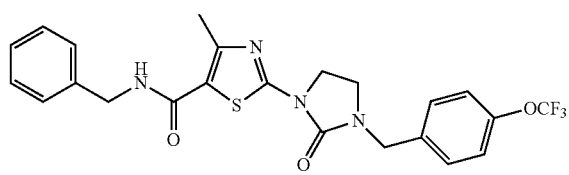

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethoxy)benzyl)imidazolidin-1-yl)thiazole-5-carboxylic acid to react with benzylamine, the title compound was obtained as a white powder in 54% yield: mp 197-198° C.; $^1$H NMR (300 MHz, CDCl$_3$) δ 7.36-7.16 (m, 9H), 5.97 (t, J=5.4 Hz, 1H), 4.54 (d, J=5.4 Hz, 2H), 4.44 (s, 2H), 4.05 (t, J=8.1 Hz, 2H), 3.44 (t, J=8.1 Hz, 2H), 2.59 (s, 3H); $^{13}$C NMR (75 MHz, CDCl$_3$) δ 162.3, 157.2, 155.4, 152.9, 148.9, 137.9, 134.3, 129.7, 128.7, 127.8, 127.6, 121.4, 120.8, 117.4, 47.2, 44.0, 42.0, 41.7, 17.2; MS (ES+) m/z 491.3 (M+1).

Example 9.24

Synthesis of 2-(3-(4-(difluoromethoxy)benzyl)-2-oxoimidazolidin-1-yl)-4-methyl-N-(pyridin-3-ylmethyl)thiazole-5-carboxamide

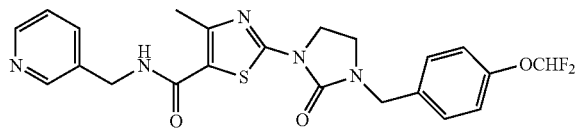

Following the procedure as describe in Example 9, making variations as required to replace 2-(3-benzyl-2-oxoimidazolidin-1-yl)-4-methylthiazole-5-carboxylic acid with 2-(3-(4-(difluoromethoxy)benzyl)-2-oxoimidazolidin-1-yl)-4-methylthiazole-5-carboxylic acid to react with 3-(aminomethyl)pyridine in place of benzylamine, the title compound was obtained as a white powder in 65% yield: mp 166-167° C.; $^1$H NMR (300 MHz, CDCl$_3$) δ 8.55-8.40 (m, 3H), 7.67 (d, J=7.8 Hz, 1H), 7.43-6.94 (m, 6H), 4.45-4.35 (m, 4H), 3.97 (t, J=8.1 Hz, 2H), 3.39 (t, J=8.1 Hz, 2H), 2.46 (s, 3H); $^{13}$C NMR (75 MHz, CDCl$_3$) δ 162.3, 157.8, 155.5, 151.7, 150.7, 149.3, 148.4, 135.6, 133.8, 130.0, 123.9, 120.1, 119.4, 117.9, 115.0, 46.6, 42.4, 42.0, 40.8, 17.5; MS (ES+) m/z 474.3 (M+1).

Example 9.25

Synthesis of (R)—N-benzyl-2-(4-benzyl-2-oxoimidazolidin-1-yl)-4-methylthiazole-5-carboxamide

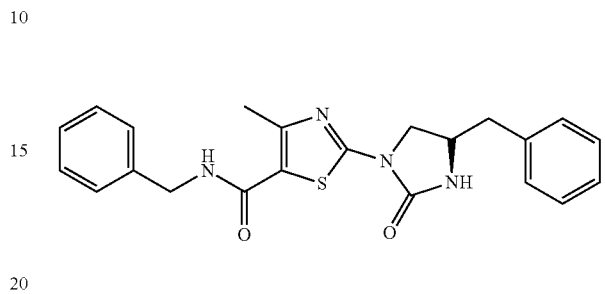

Following the procedure as describe in Example 9, making variations as required to replace 2-(3-benzyl-2-oxoimidazolidin-1-yl)-4-methylthiazole-5-carboxylic acid with (R)-2-(4-benzyl-2-oxoimidazolidin-1-yl)-4-methylthiazole-5-carboxylic acid to react with benzylamine, the title compound was obtained as a white powder in 10% yield: mp 212-214° C.; $^1$H NMR (300 MHz, DMSO-d$_6$) δ 8.43 (t, J=5.7 Hz, 1H), 8.02 (br s, 1H), 7.30-7.01 (m, 10H), 4.31 (d, J=5.7 Hz, 2H), 4.14-4.05 (m, 1H), 3.91 (t, J=10.2 Hz, 1H), 3.69-3.64 (m, 1H), 2.90-2.73 (m, 2H), 2.39 (s, 3H); $^{13}$C NMR (75 MHz, DMSO-d$_6$) δ 162.1, 157.4, 156.2, 151.4, 140.1, 136.9, 129.8, 128.8, 128.6, 127.6, 127.1, 127.0, 118.0, 50.4, 48.9, 43.0, 41.1, 17.4; MS (ES+) m/z 407.0 (M+1).

Example 9.26

Synthesis of 2-(3-(2-cyclopropylethyl)-2-oxoimidazolidin-1-yl)-4-methyl-N-(pyridin-3-ylmethyl)thiazole-5-carboxamide

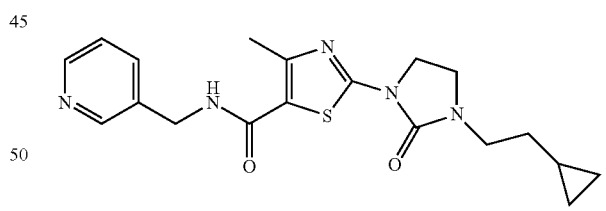

Following the procedure as describe in Example 9, making variations as required to replace 2-(3-benzyl-2-oxoimidazolidin-1-yl)-4-methylthiazole-5-carboxylic acid with 2-(3-(2-cyclopropylethyl)-2-oxoimidazolidin-1-yl)-4-methylthiazole-5-carboxylic acid to react with 3-(aminomethyl)pyridine, the title compound was obtained as a white powder in 40% yield: mp 146-147° C. (ethyl acetate/hexanes); $^1$H NMR (300 MHz, CDCl$_3$) d 8.54 (s, 1H), 8.43 (d, J=3.0 Hz, 1H), 7.63 (d, J=7.8 Hz, 1H), 7.23-7.17 (m, 1H), 6.55 (t, J=5.7 Hz, 1H), 4.52 (d, J=5.7 Hz, 2H), 4.06-3.99 (m, 2H), 3.57-3.52 (m, 2H), 3.32 (t, J=7.2 Hz, 2H), 2.54 (s, 3H), 1.44-1.37 (m, 2H), 0.65-0.54 (m, 1H), 0.43-0.35 (m, 2H), 0.06-0.01 (m, 2H); $^{13}$C NMR (75 MHz, CDCl$_3$) d 162.7, 157.5, 155.3, 153.5, 149.0, 148.6, 135.7, 134.1, 123.6, 116.7, 44.0, 42.4, 42.0, 41.2, 32.4, 17.2, 8.4, 4.3; MS (ES+) m/z 386.3 (M+1)

Example 9.27

Synthesis of 4-methyl-2-(2-oxo-3-(3-phenylpropyl) imidazolidin-1-yl)-N-(pyridin-3-ylmethyl)thiazole-5-carboxamide

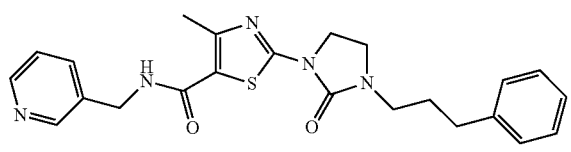

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(3-phenylpropyl)imidazolidin-1-yl)thiazole-5-carboxylic acid to react with 3-(aminomethyl)pyridine, the title compound was obtained as a white powder in 62% yield: mp 127-128° C. (ethyl acetate/hexanes); $^1$H NMR (300 MHz, CDCl$_3$) 8.57 (s, 1H), 8.45 (d, J=4.2 Hz, 1H), 7.66 (d, J=7.5 Hz, 1H), 7.22-7.07 (m, 6H), 6.51 (t, J=5.7 Hz, 1H), 4.54 (d, J=5.7 Hz, 2H), 3.98-3.92 (m, 2H), 3.49-3.43 (m, 2H), 3.31 (t, J=6.9 Hz, 2H), 2.61-2.50 (m, 5H), 1.91-1.82 (m, 2H); $^{13}$C NMR (75 MHz, CDCl$_3$) δ 162.7, 157.4, 155.3, 153.6, 149.0, 148.6, 141.0, 135.8, 134.2, 128.4, 128.2, 126.1, 123.6, 116.7, 43.6, 42.1, 41.9, 41.3, 33.0, 28.7, 17.3; MS (ES+) m/z 436.3 (M+1).

Example 9.28

Synthesis of 2-(3-(4-chlorobenzyl)-2-oxoimidazolidin-1-yl)-4-methyl-N-(pyridin-3-ylmethyl)thiazole-5-carboxamide

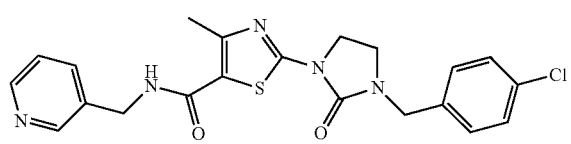

Following the procedure as describe in Example 9, making variations as required to replace 2-(3-benzyl-2-oxoimidazolidin-1-yl)-4-methylthiazole-5-carboxylic acid with 2-(3-(4-chlorobenzyl)-2-oxoimidazolidin-1-yl)-4-methylthiazole-5-carboxylic acid to react with 3-(aminomethyl)pyridine, the title compound was obtained as a white powder in 32% yield: mp 178-179° C. (ethyl acetate/hexanes); $^1$H NMR (300 MHz, CDCl$_3$) δ 8.58 (s, 1H), 8.48 (s, 1H), 7.68 (d, J=7.8 Hz, 1H), 7.30-7.16 (m, 5H), 6.42 (t, J=5.7 Hz, 1H), 4.56 (d, J=5.7 Hz, 2H), 4.40 (s, 2H), 4.09-3.97 (m, 2H), 3.44-3.39 (m, 2H), 2.57 (s, 3H); $^{13}$C NMR (75 MHz, CDCl$_3$) d 162.6, 157.3, 155.4, 153.6, 149.0, 148.5, 135.9, 134.0, 133.9, 129.6, 129.0, 123.7, 117.0, 47.3, 42.0, 41.7, 41.3, 17.2; MS (ES+) m/z 442.3 (M+1), 444.3 (M+1).

Example 9.29

Synthesis of (R)—N-(2-hydroxy-2-phenylethyl)-4-methyl-2-(2-oxo-3-(4-(trifluoromethoxy)benzyl) imidazolidin-1-yl)thiazole-5-carboxamide

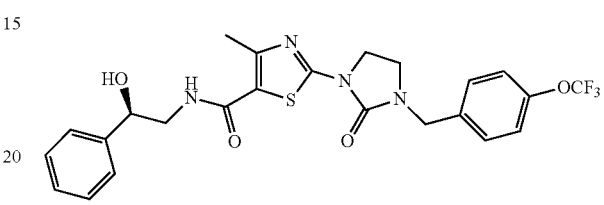

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethoxy)benzyl)imidazolidin-1-yl)thiazole-5-carboxylic acid to react with (R)-(−)-2-amino-1-phenylethanol, the title compound was obtained as a white powder in 67% yield: mp 149-151° C. (ethyl acetate/hexanes); $^1$H NMR (300 MHz, CDCl$_3$) δ 7.38-7.16 (m, 9H), 6.24 (br s, 1H), 4.92-4.89 (m, 1H), 4.44 (s, 2H), 4.28-4.02 (m, 2H), 3.85-3.41 (m, 2H), 3.57-3.38 (m, 3H), 2.54 (s, 3H); $^{13}$C NMR (75 MHz, CDCl$_3$) δ 163.6, 157.5, 155.4, 152.8, 148.9, 141.7, 134.3, 129.7, 128.5, 127.8, 125.8, 121.4, 117.6, 73.5, 47.8, 47.2, 42.0, 41.7, 17.1; MS (ES+) m/z 521.3 (M+1).

Example 9.30

Synthesis of 4-methyl-2-(2-oxo-3-(4-(trifluoromethoxy)benzyl)imidazolidin-1-yl)-N-phenylthiazole-5-carboxamide

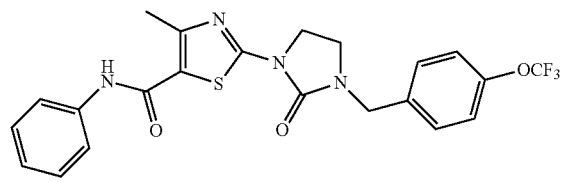

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethoxy)benzyl)imidazolidin-1-yl)thiazole-5-carboxylic acid to react with aniline, the title compound was obtained as a white powder in 67% yield: mp 187-188° C. (ethyl acetate/hexanes); $^1$H NMR (300 MHz, CDCl$_3$) δ 7.54 (d, J=6.0 Hz, 2H), 7.42 (br s, 1H), 7.36-7.28 (m, 4H), 7.19 (d, J=6.0 Hz, 2H), 7.15-7.08 (m, 1H), 4.47 (s, 2H), 4.12-4.07 (m, 2H), 3.50-3.44 (m, 2H), 2.63 (s, 3H); $^{13}$C NMR (75 MHz, CDCl$_3$) δ 160.6, 157.3, 155.4, 154.1, 149.0, 137.8, 134.3, 129.7, 129.0, 124.4, 121.4, 120.3, 120.2, 117.5, 47.3, 42.0, 41.8, 17.3; MS (ES+) m/z 477.3 (M+1).

Example 9.31

Synthesis of 4-methyl-2-(2-oxo-3-(4-(trifluoromethoxy)benzyl)imidazolidin-1-yl)-N-phenethylthiazole-5-carboxamide

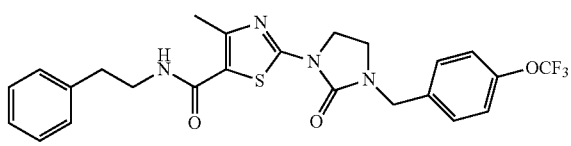

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethoxy)benzyl)imidazolidin-1-yl)thiazole-5-carboxylic acid to react with phenethylamine, the title compound was obtained as a white powder in 7% yield: mp 184-185° C. (ethyl acetate/hexanes); $^1$H NMR (300 MHz, CDCl$_3$) δ 7.32-7.17 (m, 9H), 5.62 (br s, 1H), 4.47 (s, 2H), 4.09-4.03 (m, 2H), 3.67-3.60 (m, 2H), 3.47-3.42 (m, 2H), 2.88 (d, J=6.9 Hz, 2H), 2.52 (s, 3H); $^{13}$C NMR (75 MHz, CDCl$_3$) δ 162.5, 157.2, 155.4, 152.3, 148.9, 138.7, 134.4, 129.7, 128.8, 128.7, 126.6, 122.1, 121.4, 118.0, 47.3, 42.0, 41.8, 41.1, 35.7, 17.1; MS (ES+) m/z 505.4 (M+1).

Example 9.32

Synthesis of 4-methyl-2-(2-oxo-3-(4-(trifluoromethoxy)benzyl)imidazolidin-1-yl)-N-(2-(pyridin-3-yl)ethyl)thiazole-5-carboxamide

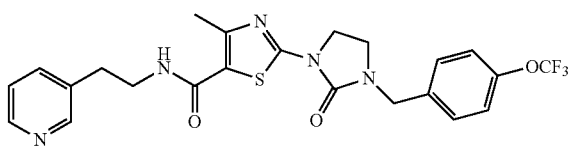

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethoxy)benzyl)imidazolidin-1-yl)thiazole-5-carboxylic acid to react with 3-(2-aminoethyl)pyridine, the title compound was obtained as a white powder in 21% yield: mp 172-173° C. (ethyl acetate/hexanes); $^1$H NMR (300 MHz, CDCl$_3$) δ 8.46 (s, 2H), 7.53 (d, J=7.8 Hz, 1H), 7.35-7.16 (m, 5H), 5.81 (br s, 1H), 4.46 (s, 2H), 4.08-4.03 (m, 2H), 3.65-3.59 (m, 2H), 3.47-3.42 (m, 2H), 2.92-2.87 (m, 2H), 2.53 (s, 3H); $^{13}$C NMR (75 MHz, CDCl$_3$) δ 162.6, 157.2, 155.4, 152.8, 150.1, 148.9, 148.1, 136.2, 134.3, 134.2, 129.6, 123.5, 121.4, 117.5, 47.2, 42.0, 41.8, 40.9, 33.0, 17.1; MS (ES+) m/z 506.4 (M+1).

Example 9.33

Synthesis of 4-methyl-N-((5-methylpyrazin-2-yl)methyl)-2-(2-oxo-3-(4-(trifluoromethyl)benzyl)imidazolidin-1-yl)thiazole-5-carboxamide

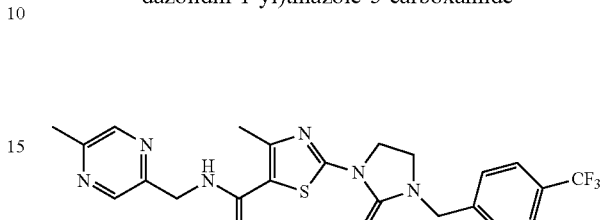

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(4-(trifluoromethyl)benzyl)imidazolidin-1-yl)thiazole-5-carboxylic acid to react with 2-(aminomethyl)-5-methylpyrazine, the title compound was obtained as a white powder in 42% yield: mp 172-173° C. (ethyl acetate/hexanes); $^1$H NMR (300 MHz, CDCl$_3$) δ 8.49 (s, 1H), 8.36 (s, 1H), 7.63 (d, J=7.8 Hz, 2H), 7.42 (d, J=7.8 Hz, 2H), 6.77 (t, J=4.8 Hz, 1H), 4.68 (d, J=4.8 Hz, 2H), 4.59 (s, 2H), 4.11-4.05 (m, 2H), 3.49-3.43 (m, 2H), 2.59 (s, 3H), 2.47 (s, 3H); $^{13}$C NMR (75 MHz, CDCl$_3$) δ 162.5, 157.5, 155.5, 153.0, 152.6, 148.7, 143.4, 142.7, 139.7, 130.6, 130.2, 128.5, 125.9, 125.8, 122.1, 117.7, 47.6, 42.3, 42.0, 41.9, 21.2, 17.3; MS (ES+) m/z 491.2 (M+1).

Example 9.34

Synthesis of 2-(3-(cyclopropylmethyl)-2-oxoimidazolidin-1-yl)-4-methyl-N-((5-methylpyrazin-2-yl)methyl)thiazole-5-carboxamide

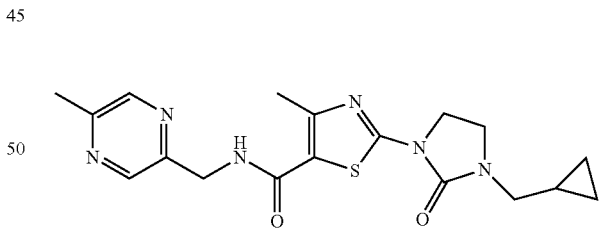

Following the procedure as describe in Example 9, making variations as required to replace 2-(3-benzyl-2-oxoimidazolidin-1-yl)-4-methylthiazole-5-carboxylic acid with 2-(3-(cyclopropylmethyl)-2-oxoimidazolidin-1-yl)-4-methylthiazole-5-carboxylic acid to react with 2-(aminomethyl)-5-methylpyrazine, the title compound was obtained as a white powder in 43% yield: mp 161-163° C. (ethyl acetate/hexanes); $^1$H NMR (300 MHz, CDCl$_3$) δ 8.46 (s, 1H), 8.33 (s, 1H), 6.77 (t, J=4.8 Hz, 1H), 4.64 (d, J=4.8 Hz, 2H), 4.09-4.01 (m, 2H), 3.68-3.58 (m, 2H), 3.14 (d, J=7.2 Hz, 2H), 2.57 (s, 3H), 2.50 (s, 3H), 0.96-0.85 (m, 1H), 0.55-0.49 (m, 2H), 0.23-0.18 (m, 2H); $^{13}$C NMR (75 MHz, CDCl$_3$) δ 162.7, 157.7, 155.2, 153.1, 152.5, 148.8, 143.4, 142.7, 117.2, 48.6, 42.3, 42.2, 42.1, 21.2, 17.3, 8.9, 3.5; MS (ES+) m/z 387.2 (M+1).

Example 9.35

Synthesis of 2-(3-(cyclohexylmethyl)-2-oxoimidazolidin-1-yl)-4-methyl-N-(pyridin-3-ylmethyl)thiazole-5-carboxamide

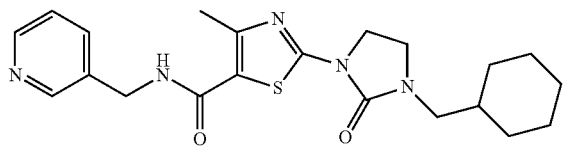

Following the procedure as describe in Example 9, making variations as required to replace 2-(3-benzyl-2-oxoimidazolidin-1-yl)-4-methylthiazole-5-carboxylic acid with 2-(3-(cyclohexylmethyl)-2-oxoimidazolidin-1-yl)-4-methylthiazole-5-carboxylic acid to react with 3-(aminomethyl)pyridine, the title compound was obtained as a white powder in 52% yield: mp 134-136° C. (ethyl acetate/hexanes); $^1$H NMR (300 MHz, CDCl$_3$) δ 8.57-8.47 (m, 2H), 7.68 (d, J=7.2 Hz, 1H), 7.27 (s, 1H), 6.31 (br s, 1H), 4.55 (d, J=5.7 Hz, 2H), 4.11-4.03 (m, 2H), 3.57 (m, 2H), 3.09 (d, J=7.2 Hz, 2H), 2.57 (s, 3H), 1.84-1.56 (m, 5H), 1.24-0.84 (m 6H); $^{13}$C NMR (75 MHz, CDCl$_3$) δ 162.7, 157.5, 155.6, 153.6, 148.9, 148.5, 135.9, 134.2, 123.7, 116.5, 50.3, 43.0, 42.0, 41.3, 36.0, 30.7, 26.2, 25.6, 17.2; MS (ES+) m/z 414.3 (M+1).

Example 9.36

Synthesis of 4-methyl-2-(2-oxo-3-((tetrahydro-2H-pyran-2-yl)methyl)imidazolidin-1-yl)-N-(pyridin-3-ylmethyl)thiazole-5-carboxamide

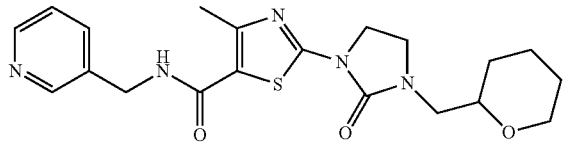

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-((tetrahydro-2H-pyran-2-yl)methyl)imidazolidin-1-yl)thiazole-5-carboxylic acid to react with 3-(aminomethyl)pyridine, the title compound was obtained as a white powder in 40% yield: mp 174-175° C. (ethyl acetate/hexanes); $^1$H NMR (300 MHz, CDCl$_3$) 8.51-8.40 (m, 2H), 7.61-7.59 (m, 1H), 7.20-7.14 (m, 1H), 6.58 (br s, 1H), 4.53 (s, 2H), 4.06-3.86 (m, 3H), 3.74-3.58 (m, 2H), 3.44-3.29 (m, 3H), 3.17-3.09 (m, 1H), 2.52 (s, 3H), 1.79-1.74 (m, 1H), 1.51-1.32 (m, 4H), 1.27-1.14 (m, 1H); $^{13}$C NMR (75 MHz, CDCl$_3$) δ 162.7, 157.5, 155.5, 153.4, 149.2, 148.7, 135.5, 134.1, 123.5, 116.7, 76.6, 68.2, 49.0, 44.0, 42.2, 41.2, 28.9, 25.6, 22.8, 17.2; MS (ES+) m/z 416.3 (M+1).

Example 9.37

Synthesis of 2-(3-(cyclobutylmethyl)-2-oxoimidazolidin-1-yl)-4-methyl-N-(pyridin-3-ylmethyl)thiazole-5-carboxamide

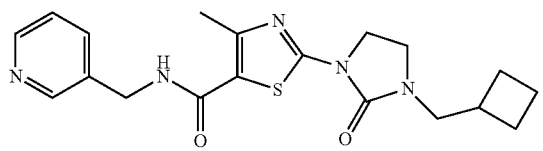

Following the procedure as describe in Example 9, making variations as required to replace 2-(3-benzyl-2-oxoimidazolidin-1-yl)-4-methylthiazole-5-carboxylic acid with 2-(3-(cyclobutylmethyl)-2-oxoimidazolidin-1-yl)-4-methylthiazole-5-carboxylic acid to react with 3-(aminomethyl)pyridine, the title compound was obtained as a white powder in 32% yield: mp 136-137° C. (ethyl acetate/hexanes); $^1$H NMR (300 MHz, CDCl$_3$) 8.53-8.41 (m, 2H), 7.63-7.61 (m, 1H), 7.20-7.16 (m, 1H), 6.51-6.17 (m, 1H), 4.60-4.46 (m, 2H), 4.08-3.93 (m, 2H), 3.53-3.41 (m, 2H), 3.39-3.20 (m, 2H), 2.60-2.45 (m, 4H), 2.03-1.98 (m, 2H), 1.88-1.79 (in 2H), 1.74-1.65 (m, 2H); $^{13}$C NMR (75 MHz, CDCl$_3$) δ 162.7, 157.5, 155.5, 153.5, 149.2, 148.7, 135.5, 134.0, 123.5, 116.7, 49.3, 42.5, 42.0, 41.3, 33.7, 26.2, 18.3, 17.2; MS (ES+) m/z 386.3 (M+1).

Example 9.38

Synthesis of 2-(3-(cyclopentylmethyl)-2-oxoimidazolidin-1-yl)-4-methyl-N-(pyridin-3-ylmethyl)thiazole-5-carboxamide

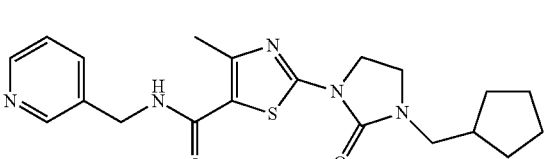

Following the procedure as describe in Example 9, making variations as required to replace 2-(3-benzyl-2-oxoimidazolidin-1-yl)-4-methylthiazole-5-carboxylic acid with 2-(3-(cyclopentylmethyl)-2-oxoimidazolidin-1-yl)-4-methylthiazole-5-carboxylic acid to react with 3-(aminomethyl)pyridine, the title compound was obtained as a white powder in 61% yield: mp 142-143° C. (ethyl acetate/hexanes); $^1$H NMR (300 MHz, CDCl$_3$) 8.54-8.43 (m, 2H), 7.63 (d, J=7.2 Hz, 1H), 7.27-7.18 (m, 1H), 6.45 (br s, 1H), 4.53 (d, J=5.7 Hz, 2H), 4.09-4.00 (m, 2H), 3.58-3.52 (m, 2H), 3.17 (d, J=7.2 Hz, 2H), 2.54 (s, 3H), 2.16-1.98 (m, 1H), 1.68-1.49 (m, 6H), 1.19-1.17 (m, 2H); $^{13}$C NMR (75 MHz, CDCl$_3$) δ 162.7, 157.5, 155.5, 153.6, 149.2, 148.8, 135.5, 134.0, 123.5, 116.6, 48.9, 42.6, 42.0, 41.3, 37.9, 30.3, 25.6, 17.2; MS (ES+) m/z 400.3 (M+1).

Example 9.39

Synthesis of 2-(3-ethyl-2-oxoimidazolidin-1-yl)-4-methyl-N-(pyridin-3-ylmethyl)thiazole-5-carboxamide

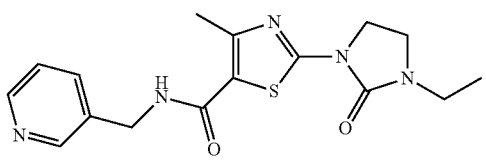

Following the procedure as describe in Example 9, making variations as required to replace 2-(3-benzyl-2-oxoimidazolidin-1-yl)-4-methylthiazole-5-carboxylic acid with 2-(3-ethyl-2-oxoimidazolidin-1-yl)-4-methylthiazole-5-carboxylic acid to react with 3-(aminomethyl)pyridine, the title compound was obtained as a white powder in 16% yield: mp 163-164° C. (ethyl acetate/hexanes); $^1$H NMR (300 MHz, CDCl$_3$) δ 8.56-8.48 (m, 2H), 7.66 (d, J=7.8 Hz, 1H), 7.28-7.17 (m, 1H), 6.23 (t, J=5.7 Hz, 1H), 4.55 (d, J=5.7 Hz, 2H), 4.12-4.03 (m, 2H), 3.58-3.53 (m, 2H), 3.35 (q, J=7.2 Hz, 2H), 2.58 (s, 3H), 1.18 (t, J=7.2 Hz, 3H); $^{13}$C NMR (75 MHz, CDCl$_3$) δ 162.7, 157.5, 155.1, 153.6, 149.2, 148.8, 135.6, 133.9, 123.6, 116.6, 42.0, 41.5, 41.3, 38.5, 17.2, 12.5; MS (ES+) m/z 346.3 (M+1).

Example 9.40

Synthesis of 4-methyl-2-(2-oxo-3-propylimidazolidin-1-yl)-N-(pyridin-3-ylmethyl)thiazole-5-carboxamide

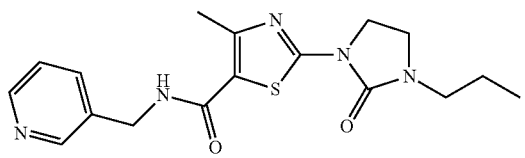

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-propylimidazolidin-1-yl)thiazole-5-carboxylic acid to react with 3-(aminomethyl)pyridine, the title compound was obtained as a white powder in 46% yield: mp 109-111° C. (ethyl acetate/hexanes); $^1$H NMR (300 MHz, CDCl$_3$) δ 8.52-8.42 (m, 2H), 7.63 (d, J=7.8 Hz, 1H), 7.24-7.17 (m, 1H), 6.54 (t, J=6.0 Hz, 1H), 4.52 (d, J=6.0 Hz, 2H), 4.05-4.00 (m, 2H), 3.55-3.49 (m, 2H), 3.20 (t, J=7.5 Hz, 2H), 2.60 (s, 3H), 1.59-1.49 (m, 2H), 0.85 (t, J=7.5 Hz, 3H); $^{13}$C NMR (75 MHz, CDCl$_3$) δ 162.8, 157.5, 155.4, 153.5, 149.1, 148.6, 135.6, 134.1, 123.6, 116.7, 45.4, 42.1, 42.0, 41.2, 20.5, 17.2, 11.1; MS (ES+) m/z 360.3 (M+1).

Example 9.41

Synthesis of 2-(3-butyl-2-oxoimidazolidin-1-yl)-4-methyl-N-(pyridin-3-ylmethyl)thiazole-5-carboxamide

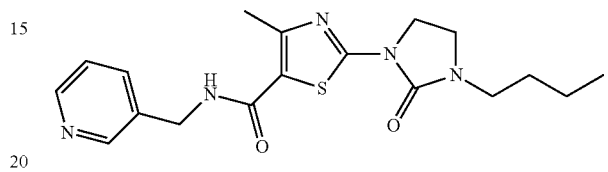

Following the procedure as describe in Example 9, making variations as required to replace 2-(3-benzyl-2-oxoimidazolidin-1-yl)-4-methylthiazole-5-carboxylic acid with 2-(3-butyl-2-oxoimidazolidin-1-yl)-4-methylthiazole-5-carboxylic acid to react with 3-(aminomethyl)pyridine, the title compound was obtained as a white powder in 33% yield: mp 109-111° C. (ethyl acetate/hexanes); $^1$H NMR (300 MHz, CDCl$_3$) δ 8.55-8.45 (m, 2H), 7.63 (d, J=7.8 Hz, 1H), 7.24-7.19 (m, 1H), 6.45 (br s, 1H), 4.52 (d, J=5.8 Hz, 2H), 4.05-4.00 (m, 2H), 3.55-3.49 (m, 2H), 3.31-3.18 (m, 2H), 2.55 (s, 3H), 1.53-1.20 (m, 4H), 0.88 (t, J=7.5 Hz, 3H); $^{13}$C NMR (75 MHz, CDCl$_3$) δ 162.7, 157.5, 155.4, 153.6, 149.2, 148.8, 135.5, 134.0, 123.6, 116.6, 43.5, 42.1, 42.0, 41.3, 29.3, 19.8, 17.2, 13.6; MS (ES+) m/z 374.3 (M+1).

Example 9.42

Synthesis of 4-methyl-2-(2-oxo-3-pentylimidazolidin-1-yl)-N-(pyridin-3-ylmethyl)thiazole-5-carboxamide

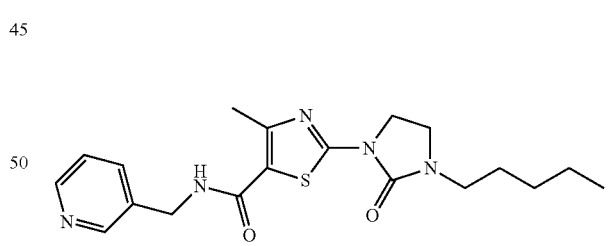

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-pentylimidazolidin-1-yl)thiazole-5-carboxylic acid to react with 3-(aminomethyl)pyridine, the title compound was obtained as a white powder in 40% yield: mp 102-103° C. (ethyl acetate/hexanes); $^1$H NMR (300 MHz, CDCl$_3$) δ 8.54-8.43 (m, 2H), 7.63 (d, J=7.5 Hz, 1H), 7.21-7.17 (m, 1H), 6.50 (br s, 1H), 4.54 (J=5.8 Hz, 2H), 4.05-3.97 (m, 2H), 3.55-3.47 (m, 2H), 3.26-3.14 (m, 2H), 2.55 (s, 3H), 1.52-1.46 (m, 2H), 1.30-1.20 (m, 4H), 0.84 (t, J=6.6 Hz, 3H); $^{13}$C NMR (75 MHz, CDCl$_3$) δ 162.7, 157.5, 155.4, 153.6, 149.2, 148.8, 135.5, 134.0, 123.6, 116.6, 43.8, 42.1, 42.0, 41.3, 28.8, 26.9, 22.3, 17.3, 14.0; MS (ES+) m/z 388.3 (M+1).

Example 9.43

Synthesis of 4-methyl-2-(2-oxo-3-(3-(trifluoromethyl)benzyl)imidazolidin-1-yl)-N-(pyridin-3-ylmethyl)thiazole-5-carboxamide

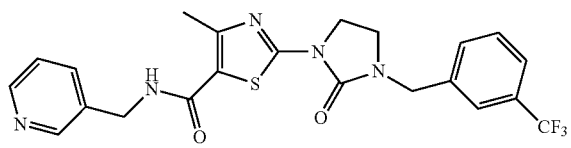

Following the procedure as describe in Example 9, making variations as required to replace 2-(3-benzyl-2-oxoimidazolidin-1-yl)-4-methylthiazole-5-carboxylic acid with 4-methyl-2-(2-oxo-3-(3-(trifluoromethyl)benzyl)imidazolidin-1-yl)thiazole-5-carboxylic acid to react with 3-(aminomethyl)pyridine, the title compound was obtained as a white powder in 81% yield: mp 175-176° C. (diethyl ether); $^1$H NMR (300 MHz, CDCl$_3$) 8.58 (s, 1H), 8.50 (d, J=4.8 Hz, 1H), 7.67 (d, J=7.8 Hz, 1H), 7.61-7.54 (m, 1H), 7.53-7.44 (m, 3H), 7.29-7.21 (m, 1H), 6.21 (t, J=5.6 Hz, 1H), 4.57 (d, J=5.6 Hz, 2H), 4.51 (s, 2H), 4.14-4.02 (m, 2H), 3.52-3.41 (m, 2H), 2.59 (s, 3H); $^{13}$C NMR (75 MHz, CDCl$_3$) δ 162.6, 157.2, 155.5, 153.7, 149.3, 149.0, 136.7, 135.6, 133.9, 131.6, 131.5, 131.1, 129.5, 125.0, 124.9, 123.6, 117.1, 47.7, 42.0, 41.9, 41.4, 17.3; MS (ES+) m/z 476.4 (M+1).

Example 9.44

Synthesis of N-((5-(difluoromethyl)furan-2-yl)methyl)-2-(3-(4-fluorobenzyl)-2-oxoimidazolidin-1-yl)-4-methylthiazole-5-carboxamide

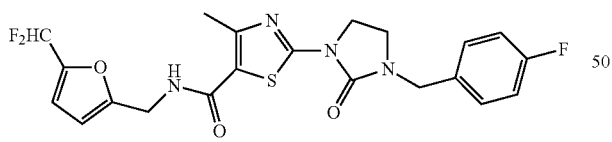

Following the procedure as describe in Example 9, making variations as required to replace 2-(3-benzyl-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with (5-(difluoromethyl)furan-2-yl)methanamine, the title compound was obtained as a white powder in 47% yield: mp 173-174° C. (diethyl ether); $^1$H NMR (300 MHz, CDCl$_3$) δ 7.28-7.22 (m, 2H), 7.05-6.99 (m, 2H), 6.59-6.56 (m, 1H), 6.55 (t, J$_{H-F}$=54.4 Hz, 1H), 6.32-6.29 (m, 1H), 6.01 (t, J=5.4 Hz, 1H), 4.56 (d, J=5.4 Hz, 2H), 4.43 (s, 2H), 4.08-4.02 (m, 2H), 3.46-3.40 (m, 2H), 2.58 (s, 3H); $^{13}$C NMR (75 MHz, CDCl$_3$) δ 164.2, 162.3, 160.9, 157.5, 155.4, 153.6, 153.3, 146.2, 130.3, 116.9, 115.8, 111.3, 108.4, 105.3, 47.3, 42.0, 41.7, 36.6, 17.3; MS (ES+) m/z 465.3 (M+1).

Example 9.45

Synthesis of 2-(3-((5-(difluoromethyl)furan-2-yl)methyl)-2-oxoimidazolidin-1-yl)-4-methyl-N-(pyridin-3-ylmethyl)thiazole-5-carboxamide

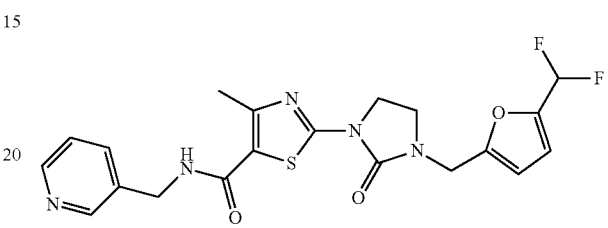

Following the procedure as describe in Example 9, making variations as required to replace 2-(3-benzyl-2-oxoimidazolidin-1-yl)-4-methylthiazole-5-carboxylic acid with 2-(3-((5-(difluoromethyl)furan-2-yl)methyl)-2-oxoimidazolidin-1-yl)-4-methylthiazole-5-carboxylic acid to react with 3-(aminomethyl)pyridine, the title compound was obtained as a white powder in 59% yield: mp 142-143° C. (diethyl ether); $^1$H NMR (300 MHz, CDCl$_3$) δ 8.60-8.53 (m, 1H), 8.51-8.44 (m, 1H), 7.72-7.62 (m, 1H), 7.28-7.19 (m, 1H), 6.59-6.57 (m, 1H), 6.54 (t, J$_{H-F}$=54.2 Hz, 1H), 6.33-6.59 (m, 1H), 4.56 (d, J=5.8 Hz, 2H), 4.46 (s, 2H), 4.10-4.03 (m, 2H), 3.61-3.53 (m, 2H), 2.57 (s, 3H); $^{13}$C NMR (75 MHz, CDCl$_3$) δ 162.6, 157.2, 155.1, 153.5, 151.4, 149.2, 148.8, 135.6, 133.9, 123.6, 117.1, 111.3, 109.7, 108.1, 105.0, 42.3, 42.0, 41.3, 40.4, 17.2; MS (ES+) m/z 448.3 (M+1).

Example 10

Synthesis of ethyl 2-(3-(cyclopropylmethyl)-2-oxoimidazolidin-1-yl)-4-methylthiazole-5-carboxylate

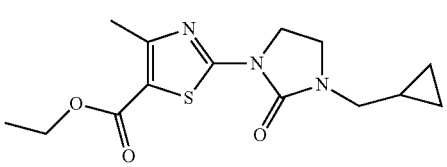

To a suspension of ethyl 4-methyl-2-(2-oxoimidazolidin-1-yl)thiazole-5-carboxylate (1.02 g, 4.00 mmol), tetra-n-butylammonium iodide (0.10 g) and potassium carbonate (0.90 g, 6.50 mmol) in acetone (80 mL) was added cyclopropylmethyl bromide (0.6 mL, 6.18 mmol). The reaction mixture was heated to reflux for 72 hours. The solvent was removed in vacuo, and the residue was washed with water (100 mL) and hexanes (30 mL) to afford the title compound in 96% yield (1.20 g): $^1$H NMR (300 MHz, CDCl$_3$) δ 4.23 (q, J=7.2 Hz, 2H), 4.07 (t, J=7.8 Hz, 2H), 3.67 (t, J=7.8 Hz, 2H), 3.16 (d, J=6.9 Hz, 2H), 2.58 (s, 3H), 1.28 (t, J=7.2 Hz, 3H), 0.97-0.88 (m, 1H), 0.59-0.42 (m, 2H), 0.25-0.12 (m, 2H); MS (ES+) m/z 310.3 (M+1).

Example 10.1

Synthesis of ethyl 2-(3-(2-cyclopropylethyl)-2-oxoimidazolidin-1-yl)-4-methylthiazole-5-carboxylate

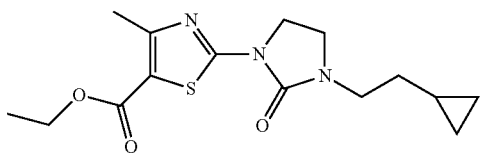

Following the procedure as described in Example 10, making variations as required to replace cyclopropylmethyl bromide with 2-cyclopropylethyl 4-methylbenzenesulfonate to react with ethyl 4-methyl-2-(2-oxoimidazolidin-1-yl)thiazole-5-carboxylate, the title compound was obtained in 60% yield: $^1$H NMR (300 MHz, CDCl$_3$) δ 4.13 (q, J=7.2 Hz, 2H), 3.65 (t, J=7.4 Hz, 2H), 3.43 (t, J=7.8 Hz, 2H), 3.22 (t, J=7.8 Hz, 2H), 2.34 (s, 3H), 1.44-1.15 (m, 5H), 0.57-0.51 (m, 1H), 0.32-0.22 (m, 2H), −0.07-0.11 (m, 2H); MS (ES+) m/z 324.3 (M+1).

Example 10.2

Synthesis of ethyl 4-methyl-2-(2-oxo-3-(3-phenylpropyl)imidazolidin-1-yl)thiazole-5-carboxylate

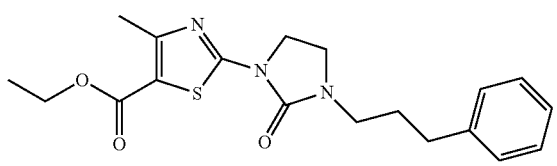

Following the procedure as described in Example 10, making variations as required to replace cyclopropylmethyl bromide with 1-bromo-3-phenylpropane to react with ethyl 4-methyl-2-(2-oxoimidazolidin-1-yl)thiazole-5-carboxylate, the title compound was obtained in 61% yield: $^1$H NMR (300 MHz, DMSO-d$_6$) δ 7.27-7.13 (m, 5H), 4.27 (q, J=7.2 Hz, 2H), 4.02-3.96 (m, 2H), 3.52-3.46 (m, 2H), 3.37 (t, J=7.2 Hz, 2H), 2.63 (t, J=7.5 Hz, 2H), 2.59 (s, 3H), 1.95-1.88 (m, 2H), 1.23 (t, J=7.2 Hz, 3H); MS (ES+) m/z 374.2 (M+1).

Example 10.3

Synthesis of ethyl 2-(3-(4-chlorobenzyl)-2-oxoimidazolidin-1-yl)-4-methylthiazole-5-carboxylate

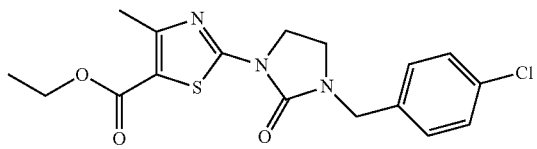

Following the procedure as described in Example 10, making variations as required to replace cyclopropylmethyl bromide with 4-chlorobenzyl chloride to react with ethyl 4-methyl-2-(2-oxoimidazolidin-1-yl)thiazole-5-carboxylate, the title compound was obtained in 84% yield: mp 117-119° C. (ethyl acetate/hexanes); $^1$H NMR (300 MHz, DMSO-d$_6$) δ 7.31 (d, J=7.2 Hz, 2H), 7.22 (d, J=7.2 Hz, 2H), 4.51 (s, 2H), 4.27 (q, J=7.8 Hz, 2H), 4.09-4.04 (m, 2H), 3.44-3.41 (m, 2H), 2.59 (s, 3H), 1.25 (t, J=7.8 Hz, 3H); MS (ES+) m/z 380.2 (M+1), 382.2 (M+1).

Example 10.4

Synthesis of ethyl 2-(3-(cyclohexylmethyl)-2-oxoimidazolidin-1-yl)-4-methylthiazole-5-carboxylate

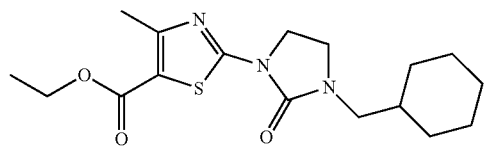

Following the procedure as described in Example 10, making variations as required to replace cyclopropylmethyl bromide with (bromomethyl)cyclohexane to react with ethyl 4-methyl-2-(2-oxoimidazolidin-1-yl)thiazole-5-carboxylate, the title compound was obtained in 76% yield: $^1$H NMR (300 MHz, CDCl$_3$) δ 4.27 (q, J=7.2 Hz, 2H), 4.09-3.99 (m, 2H), 3.57-3.40 (m, 2H), 3.11 (d, J=6.9 Hz, 2H), 2.59 (s, 3H), 1.86-1.55 (m, 5H), 1.31-1.11 (m, 7H), 0.97-0.82 (m, 2H); MS (ES+) m/z 352.3 (M+1).

Example 10.5

Synthesis of ethyl 4-methyl-2-(2-oxo-3-((tetrahydro-2H-pyran-2-yl)methyl)imidazolidin-1-yl)thiazole-5-carboxylate

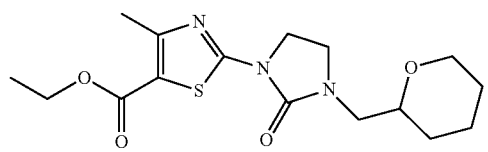

Following the procedure as described in Example 10, making variations as required to replace cyclopropylmethyl bromide with (bromomethyl)tetrahydro-2H-pyran to react with ethyl 4-methyl-2-(2-oxoimidazolidin-1-yl)thiazole-5-carboxylate, the title compound was obtained in 39% yield: $^1$H NMR (300 MHz, CDCl$_3$) δ 4.26 (q, J=7.2 Hz, 2H), 4.11-4.05 (m, 2H), 3.97-3.92 (m, 1H), 3.83-3.62 (m, 2H), 3.55-3.34 (m, 2H), 3.22-3.15 (m, 1H), 2.60 (s, 3H), 1.85-1.82 (m, 1H), 1.57-1.44 (m, 4H), 1.31-1.22 (m, 5H); MS (ES+) m/z 354.3 (M+1).

Example 10.6

Synthesis of ethyl 2-(3-(cyclobutylmethyl)-2-oxoimidazolidin-1-yl)-4-methylthiazole-5-carboxylate

Following the procedure as described in Example 10, making variations as required to replace cyclopropylmethyl bromide with (bromomethyl)cyclobutane to react with ethyl 4-methyl-2-(2-oxoimidazolidin-1-yl)thiazole-5-carboxylate, the title compound was obtained in 88% yield: $^1$H NMR (300 MHz, CDCl$_3$) δ 4.29-3.96 (m, 4H), 3.60-3.23 (m, 4H), 2.63-2.48 (m, 4H), 2.09-2.02 (m, 2H), 1.93-1.83 (m, 2H), 1.77-1.68 (m, 2H), 1.26 (t, J=7.3 Hz, 3H); MS (ES+) m/z 324.3 (M+1).

Example 10.7

Synthesis of ethyl 2-(3-(cyclopentylmethyl)-2-oxoimidazolidin-1-yl)-4-methylthiazole-5-carboxylate

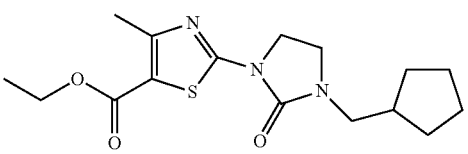

Following the procedure as described in Example 10, making variations as required to replace cyclopropylmethyl bromide with cyclopentylmethyl 4-methylbenzenesulfonate to react with ethyl 4-methyl-2-(2-oxoimidazolidin-1-yl)thiazole-5-carboxylate, the title compound was obtained in 62% yield: $^1$H NMR (300 MHz, CDCl$_3$) δ 4.20 (q, J=7.2 Hz, 2H), 4.04-3.99 (m, 2H), 3.52-3.41 (m, 2H), 3.17 (d, J=7.5 Hz, 2H), 2.46 (s, 3H), 2.16-1.08 (m, 12H); MS (ES+) m/z 338.3 (M+1).

Example 11

Synthesis of (R)-ethyl 2-(4-benzyl-2-oxoimidazolidin-1-yl)-4-methylthiazole-5-carboxylate

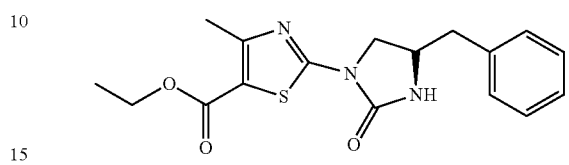

To a solution of (R)-ethyl 2-(3-(1-hydroxy-3-phenylpropan-2-yl)ureido)-4-methylthiazole-5-carboxylate (3.20 g, 8.80 mmol) and N,N-diisopropylethylamine (2.70 mL, 115.50 mmol) in tetrahydrofuran (50 mL) was added methanesulfonyl chloride (0.82 mL, 10.50 mmol) at 0° C. The reaction mixture was stirred at ambient temperature for 2 hours. To this reaction mixture was added potassium carbonate (1.38 g, 10.00 mmol), and heated to reflux for 17 hours. The solvent was removed in vacuo, the residue was dissolved in ethyl acetate (300 mL) and washed with water and brine. The organic solution was dried over anhydrous sodium sulfate and filtered. The filtrate was concentrated in vacuo and the residue was purified by column chromatography to afford the title compound in 47% yield (1.43 g): mp 102-103° C.; $^1$H NMR (300 MHz, acetone-d$_6$) δ 9.38 (s, 1H), 7.37-7.23 (m, 5H), 4.60-4.17 (m, 5H), 3.07-2.95 (m, 2H), 2.44 (s, 3H) 1.26 (t, J=7.2 Hz, 3H); $^{13}$C NMR (75 MHz, acetone-d$_6$) δ 174.9, 162.1, 161.7, 157.1, 136.9, 129.2, 128.7, 126.8, 113.0, 70.4, 60.1, 56.4, 40.3, 16.6, 13.7; MS (ES+) m/z 346.4 (M+1).

Example 12

Synthesis of ethyl 3-methyl-5-(2-oxoimidazolidin-1-yl)thiophene-2-carboxylate

A mixture of ethyl 5-(3-(2-chloroethyl)ureido)-3-methylthiophene-2-carboxylate (6.11 g, 21.02 mmol) and potassium carbonate (2.91 g, 21.0 mmol) in anhydrous acetonitrile (60 mL) was stirred under nitrogen atmosphere at 70° C. for 5 h, and then was allowed to cool to ambient temperature and was partitioned between ethyl acetate (200 mL) and water (100 mL). The aqueous layer was extracted with 10% methanol in dichloromethane (2×100 mL). The combined organic layer was dried over sodium sulfate, filtered and concentrated in vacuo. The residue was triturated with 20% ethyl acetate in hexanes to afford the title compound as a cream solid in 88% yield (4.70 g): $^1$H NMR (300 MHz, CDCl$_3$) δ 6.16 (s, 1H), 5.15 (br s, 1H), 4.28 (q, J=7.1 Hz, 2H), 3.97-3.89 (m, 2H), 3.71-3.64 (m, 2H), 2.50 (s, 3H), 1.34 (t, J=7.1 Hz, 3H); MS (ES+) m/z 255.2 (M+1).

Example 13

Synthesis of ethyl 3-methyl-5-(2-oxo-3-(4-(trifluoromethyl)benzyl)imidazolidin-1-yl)thiophene-2-carboxylate

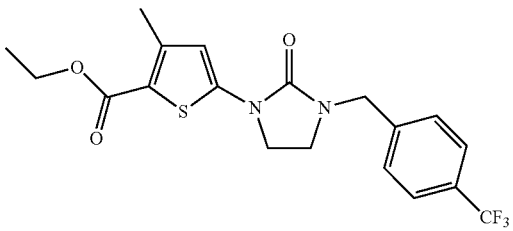

To a stirred suspension of ethyl 3-methyl-5-(2-oxoimidazolidin-1-yl)thiophene-2-carboxylate (3.00 g, 11.8 mmol) in anhydrous N,N-dimethylformamide (20 mL) under nitrogen atmosphere was added in one portion sodium hydride (60% in mineral oil, 0.57 g, 14.15 mmol). The mixture was stirred for 1 hour, then 4-(trifluoromethyl)benzyl bromide (3.39 g, 14.16 mmol) in anhydrous N,N-dimethylformamide (10 mL) was added. The resulting reaction mixture was stirred for 16 hours, then was partitioned between ethyl acetate (200 mL), water (100 mL) and brine (50 mL). The aqueous layer was extracted with ethyl acetate (200 mL) and the combined organic layer was dried over sodium sulfate, filtered and concentrated in vacuo. The residue was triturated with 10% ethyl acetate in hexanes to afford the title compound as a cream solid in 89% yield (4.32 g): $^1$H NMR (300 MHz, CDCl$_3$) δ 7.61 (d, J=8.1 Hz, 2H), 7.43 (d, J=8.1 Hz, 2H), 6.17 (s, 1H), 4.53 (s, 2H), 4.28 (q, J=7.1 Hz, 2H), 3.86-3.79 (m, 2H), 3.50-3.43 (m, 2H), 2.50 (s, 3H), 1.34 (t, J=7.1 Hz, 3H); MS (ES+) m/z 413.3 (M+1).

Example 13.1

Synthesis of ethyl 5-(3-benzyl-2-oxoimidazolidin-1-yl)-3-methylthiophene-2-carboxylate

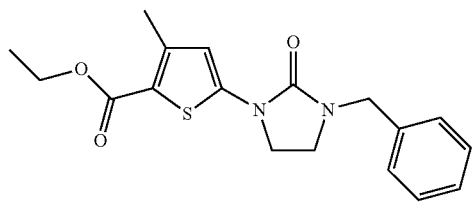

Following the procedure as described in Example 13, making variations as required to replace 4-(trifluoromethyl)benzyl bromide with benzyl bromide to react with ethyl 3-methyl-5-(2-oxoimidazolidin-1-yl)thiophene-2-carboxylate, the title compound was obtained as a colorless solid in 94% yield: $^1$H NMR (300 MHz, CDCl$_3$) δ 7.39-7.25 (m, 5H), 6.15 (s, 1H), 4.48 (s, 2H), 4.28 (q, J=7.1 Hz, 2H), 3.83-3.75 (m, 2H), 3.48-3.40 (m, 2H), 2.49 (s, 3H), 1.34 (t, J=7.1 Hz, 3H); MS (ES+) m/z 345.3 (M+1).

Example 13.2

Synthesis of ethyl 5-(3-(4-fluorobenzyl)-2-oxoimidazolidin-1-yl)-3-methylthiophene-2-carboxylate

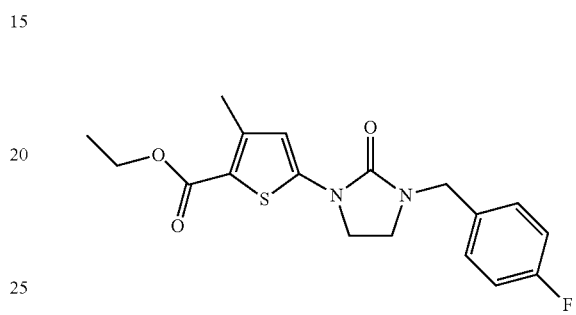

Following the procedure as described in Example 13, making variations as required to replace 4-(trifluoromethyl)benzyl bromide with 4-fluorobenzyl bromide to react with ethyl 3-methyl-5-(2-oxoimidazolidin-1-yl)thiophene-2-carboxylate, the title compound was obtained as a colorless solid in 95% yield: $^1$H NMR (300 MHz, CDCl$_3$) δ 7.31-7.25 (m, 2H), 7.04 (t, J=8.6 Hz, 2H), 6.15 (s, 1H), 4.44 (s, 2H), 4.28 (q, J=7.1 Hz, 2H), 3.84-3.76 (m, 2H), 3.48-3.40 (m, 2H), 2.49 (s, 3H), 1.34 (t, J=7.1 Hz, 3H); MS (ES+) m/z 363.2 (M+1).

Example 13.3

Synthesis of ethyl 5-(3-(cyclopropylmethyl)-2-oxoimidazolidin-1-yl)-3-methylthiophene-2-carboxylate

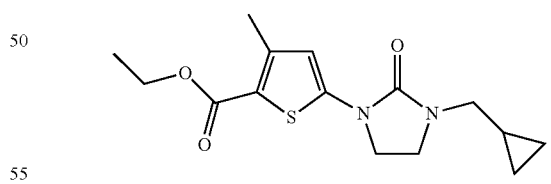

Following the procedure as described in Example 13, making variations as required to replace 4-(trifluoromethyl)benzyl bromide with (bromomethyl)cyclopropane to react with ethyl 3-methyl-5-(2-oxoimidazolidin-1-yl)thiophene-2-carboxylate, the title compound was obtained as a colorless solid in 80% yield: $^1$H NMR (300 MHz, CDCl$_3$) δ 6.14 (s, 1H), 4.26 (q, J=7.1 Hz, 2H), 3.87-3.79 (m, 2H), 3.72-3.64 (m, 2H), 3.18 (d, J=7.1 Hz, 2H), 2.49 (s, 3H), 1.33 (t, J=7.1 Hz, 3H), 1.02-0.87 (m, 1H), 0.60-0.52 (m, 2H), 0.28-0.21 (m, 2H); MS (ES+) m/z 309.2 (M+1).

Example 13.4

Synthesis of ethyl 3-methyl-5-(2-oxo-3-phenethylimidazolidin-1-yl)thiophene-2-carboxylate

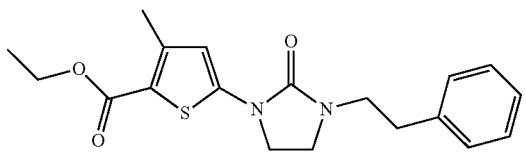

Following the procedure as described in Example 13, making variations as required to replace 4-(trifluoromethyl)benzyl bromide with phenethyl 4-methylbenzenesulfonate to react with ethyl 3-methyl-5-(2-oxoimidazolidin-1-yl)thiophene-2-carboxylate, the title compound was obtained as a colorless solid in 63% yield: $^1$H NMR (300 MHz, CDCl$_3$) δ 7.35-7.19 (m, 5H), 6.12 (s, 1H), 4.27 (q, J=7.1 Hz, 2H), 3.78-3.71 (m, 2H), 3.56 (t, J=7.4 Hz, 2H), 3.47-3.39 (m, 2H), 2.90 (t, J=7.4 Hz, 2H), 2.49 (s, 3H), 1.33 (t, J=7.1 Hz, 3H); MS (ES+) m/z 359.3 (M+1).

Example 13.5

Synthesis of ethyl 2-(3-((5-chlorobenzo[b]thiophen-3-yl)methyl)-2-oxoimidazolidin-1-yl)-4-methylthiazole-5-carboxylate

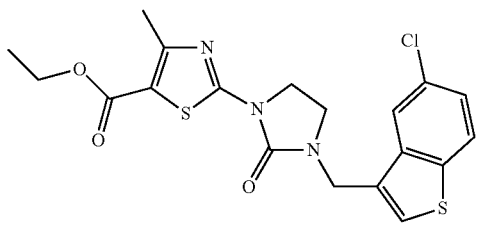

Following the procedure as described in Example 13, making variations as required to replace 4-(trifluoromethyl)benzyl bromide with 3-(bromomethyl)-5-chlorobenzo[b]thiophene to react with ethyl 4-methyl-2-(2-oxoimidazolidin-1-yl)thiazole-5-carboxylate, the title compound was obtained as a colorless solid in 65% yield: MS (ES+) m/z 436.1 (M+1).

Example 13.6

Synthesis of ethyl 2-(3-(isoquinolin-1-ylmethyl)-2-oxoimidazolidin-1-yl)-4-methylthiazole-5-carboxylate

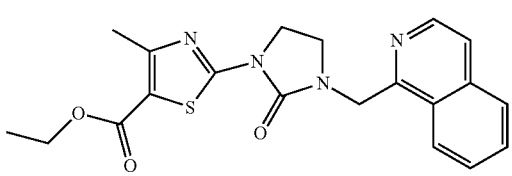

Following the procedure as described in Example 13, making variations as required to replace 4-(trifluoromethyl)benzyl bromide with 1-(bromomethyl)isoquinoline to react with ethyl 4-methyl-2-(2-oxoimidazolidin-1-yl)thiazole-5-carboxylate, the title compound was obtained as a colorless solid in 85% yield: MS (ES+) m/z 397.2 (M+1).

Example 13.7

Synthesis of ethyl 4-methyl-2-(2-oxo-3-(quinolin-8-ylmethyl)imidazolidin-1-yl)thiazole-5-carboxylate

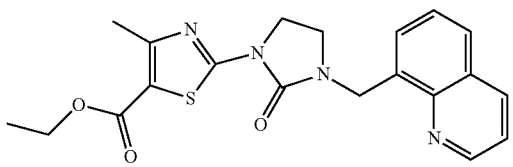

Following the procedure as described in Example 13, making variations as required to replace 4-(trifluoromethyl)benzyl bromide with 8-(bromomethyl)quinoline to react with ethyl 4-methyl-2-(2-oxoimidazolidin-1-yl)thiazole-5-carboxylate, the title compound was obtained as a colorless solid in 82% yield: MS (ES+) m/z 397.3 (M+1)

Example 13.8

Synthesis of ethyl 4-methyl-2-(3-((5-methylisoxazol-3-yl)methyl)-2-oxoimidazolidin-1-yl)thiazole-5-carboxylate

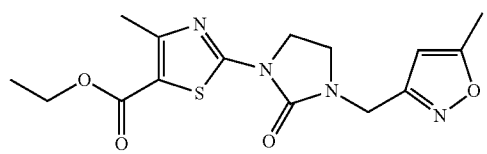

Following the procedure as described in Example 13, making variations as required to replace 4-(trifluoromethyl)benzyl bromide with 3-(bromomethyl)-5-methylisoxazole to react with ethyl 4-methyl-2-(2-oxoimidazolidin-1-yl)thiazole-5-carboxylate, the title compound was obtained as a colorless solid in 78% yield: MS (ES+) m/z 351.2 (M+1).

Example 13.9

Synthesis of ethyl 4-methyl-2-(3-((3-methyl-5-phenylisoxazol-4-yl)methyl)-2-oxoimidazolidin-1-yl)thiazole-5-carboxylate

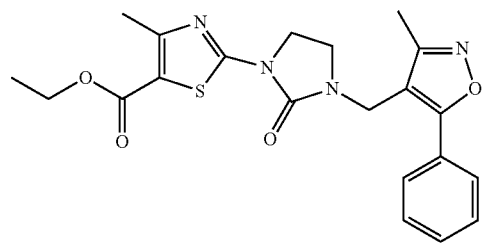

Following the procedure as described in Example 13, making variations as required to replace 4-(trifluoromethyl)benzyl bromide with 4-(bromomethyl)-3-methyl-5-phenylisoxazole to react with ethyl 4-methyl-2-(2-oxoimidazolidin-1-yl)thiazole-5-carboxylate, the title compound was obtained as a colorless solid in 87% yield: MS (ES+) m/z 427.2 (M+1).

Example 13.10

Synthesis of ethyl 4-methyl-2-(2-oxo-3-((5-phenyloxazol-4-yl)methyl)imidazolidin-1-yl)thiazole-5-carboxylate

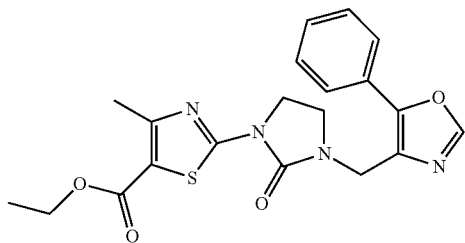

Following the procedure as described in Example 13, making variations as required to replace 4-(trifluoromethyl)benzyl bromide with 4-(bromomethyl)-5-phenyloxazole to react with ethyl 4-methyl-2-(2-oxoimidazolidin-1-yl)thiazole-5-carboxylate, the title compound was obtained as a colorless solid in 81% yield: MS (ES+) m/z 413.1 (M+1).

Example 13.11

Synthesis of ethyl 2-(3-(benzo[c][1,2,5]oxadiazol-5-ylmethyl)-2-oxoimidazolidin-1-yl)-4-methylthiazole-5-carboxylate

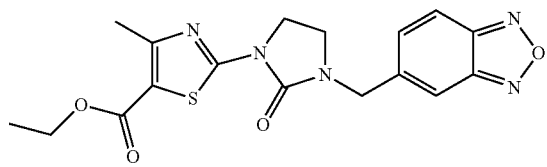

Following the procedure as described in Example 13, making variations as required to replace 4-(trifluoromethyl)benzyl bromide with 5-(bromomethyl)benzo[c]-[1,2,5]oxadiazole to react with ethyl 4-methyl-2-(2-oxoimidazolidin-1-yl)thiazole-5-carboxylate, the title compound was obtained as a colorless solid in 92% yield: MS (ES+) m/z 388.1 (M+1).

Example 13.12

Synthesis of ethyl 2-(3-(benzo[c][1,2,5]thiadiazol-5-ylmethyl)-2-oxoimidazolidin-1-yl)-4-methylthiazole-5-carboxylate

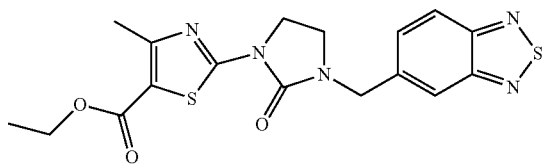

Following the procedure as described in Example 13, making variations as required to replace 4-(trifluoromethyl)benzyl bromide with 5-(bromomethyl)benzo[c][1,2,5]thiadiazole to react with ethyl 4-methyl-2-(2-oxoimidazolidin-1-yl)thiazole-5-carboxylate, the title compound was obtained as a colorless solid in 82% yield: MS (ES+) m/z 404.1 (M+1).

Example 13.13

Synthesis of ethyl 4-methyl-2-(2-oxo-3-(pyridin-2-ylmethyl)imidazolidin-1-yl)thiazole-5-carboxylate

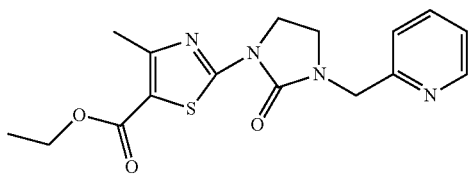

Following the procedure as described in Example 13, making variations as required to replace 4-(trifluoromethyl)benzyl bromide with 2-(bromomethyl)pyridine hydrochloride to react with ethyl 4-methyl-2-(2-oxoimidazolidin-1-yl)thiazole-5-carboxylate, the title compound was obtained as a colorless solid in 55% yield: MS (ES+) m/z 347.2 (M+1).

Example 13.14

Synthesis of ethyl 4-methyl-2-(2-oxo-3-(pyridin-4-ylmethyl)imidazolidin-1-yl)thiazole-5-carboxylate

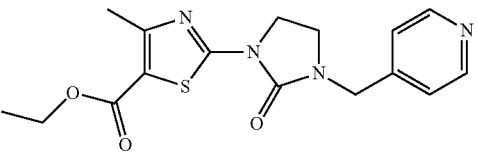

Following the procedure as described in Example 13, making variations as required to replace 4-(trifluoromethyl)benzyl bromide with 4-(bromomethyl)pyridine to react with ethyl 4-methyl-2-(2-oxoimidazolidin-1-yl)thiazole-5-carboxylate, the title compound was obtained as a colorless solid in quantitative yield: MS (ES+) m/z 347.1 (M+1).

Example 13.15

Synthesis of ethyl 4-methyl-2-(2-oxo-3-(pyridin-2-ylmethyl)imidazolidin-1-yl)thiazole-5-carboxylate

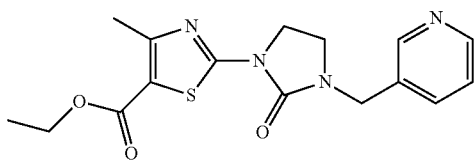

Following the procedure as described in Example 13, making variations as required to replace 4-(trifluoromethyl)benzyl bromide with 3-(bromomethyl)pyridine hydrochloride to react with ethyl 4-methyl-2-(2-oxoimidazolidin-1-yl)thiazole-5-carboxylate, the title compound was obtained as a colorless solid in 68% yield: MS (ES+) m/z 347.1 (M+1).

Example 13.16

Synthesis of ethyl 2-(3-(2-(1H-indol-3-yl)ethyl)-2-oxoimidazolidin-1-yl)-4-methylthiazole-5-carboxylate

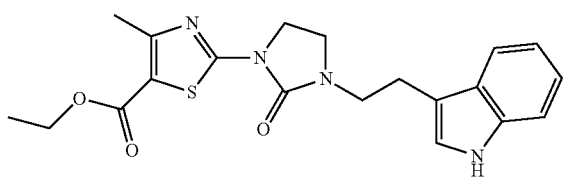

Following the procedure as described in Example 13, making variations as required to replace 4-(trifluoromethyl)benzyl bromide with 3-(2-bromoethyl)-1H-indole to react with ethyl 4-methyl-2-(2-oxoimidazolidin-1-yl)thiazole-5-carboxylate, the title compound was obtained as a colorless solid in 40% yield: $^1$H NMR (300 MHz, CDC$_3$) δ 8.09 (s, 1H), 7.63 (d, J=7.8 Hz, 1H), 7.39-7.36 (m, 1H), 7.24-7.09 (m, 3H), 4.29 (q, J=7.1 Hz, 2H), 4.04-3.99 (m, 2H), 3.69 (t, J=7.2 Hz, 2H), 3.52-3.46 (m, 2H), 3.08 (t, J=7.1 Hz, 2H), 2.62 (s, 3H), 1.34 (t, J=7.1 Hz, 3H); MS (ES+) m/z 399.3 (M+1).

Example 13.17

Synthesis of ethyl 2-(3-(4-fluorobenzyl)-2-oxoimidazolidin-1-yl)-4-methylthiazole-5-carboxylate

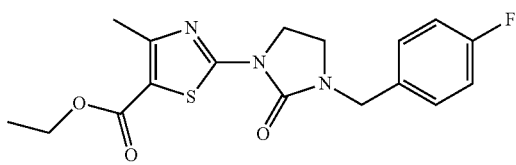

Following the procedure as described in Example 13, making variations as required to replace 4-(trifluoromethyl)benzyl bromide with 1-(bromomethyl)-4-fluorobenzene to react with ethyl 4-methyl-2-(2-oxoimidazolidin-1-yl)thiazole-5-carboxylate, the title compound was obtained as a colorless solid in 69% yield: $^1$H NMR (300 MHz, CDCl$_3$) δ 7.31-7.28 (m, 2H), 7.07-7.02 (m, 2H), 4.47 (s, 2H), 4.29 (q, J=6.0 Hz, 2H), 4.08 (t, J=9.0 Hz, 2H), 3.46 (t, J=9.0 Hz, 2H), 2.62 (s, 3H), 1.34 (t, J=6.0 Hz, 3H); MS (ES+) m/z 364.1.0 (M+1).

Example 13.18

Synthesis of ethyl 2-(3-(4-fluorobenzyl)-2-oxotetrahydropyrimidin-1(2H)-yl)-4-methylthiazole-5-carboxylate

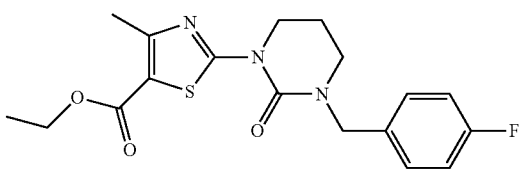

Following the procedure as described in Example 13, making variations as required to replace 4-(trifluoromethyl)benzyl bromide with 1-(bromomethyl)-4-fluorobenzene to react with ethyl 4-methyl-2-(2-oxotetrahydropyrimidin-1(2H)-yl)thiazole-5-carboxylate, the title compound was obtained as a colorless solid in quantitative yield: MS (ES+) m/z 378.2 (M+1).

Example 13.19

Synthesis of ethyl 2-(3-(cyclopropylmethyl)-2-oxotetrahydropyrimidin-1(2H)-yl)-4-methylthiazole-5-carboxylate

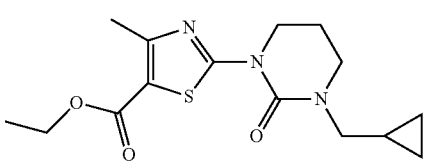

Following the procedure as described in Example 13, making variations as required to replace 4-(trifluoromethyl)benzyl bromide with (bromomethyl)cyclopropane to react with ethyl 4-methyl-2-(2-oxotetrahydropyrimidin-1(2H)-yl)thiazole-5-carboxylate, the title compound was obtained as a colorless solid in quantitative yield: MS (ES+) m/z 324.2 (M+1).

Example 14

Synthesis of 3-methyl-5-(2-oxo-3-(4-(trifluoromethyl)benzyl)imidazolidin-1-yl)thiophene-2-carboxylic acid

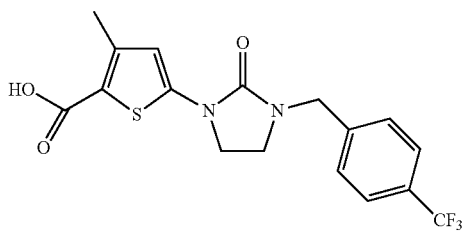

A mixture of ethyl 3-methyl-5-(2-oxo-3-(4-(trifluoromethyl)benzyl)imidazolidin-1-yl)thiophene-2-carboxylate (4.31 g, 10.5 mmol) and 1 N aqueous sodium hydroxide solution (60 mL, 60 mmol) in ethanol (120 mL) was stirred at reflux for 1.5 h, then cooled to 0° C. and acidified with 10% aqueous hydrochloric acid to pH ~2. The white precipitate was filtered, washed with water and ethanol, and then dried in vacuo to afford the title compound as a colorless solid in 91% yield (3.68 g): $^1$H NMR (300 MHz, DMSO-$d_6$) δ 12.37 (br s, 1H), 7.74 (d, J=8.1 Hz, 2H), 7.53 (d, J=8.1 Hz, 2H), 6.30 (s, 1H), 4.50 (s, 2H), 3.90-3.81 (m, 2H), 3.52-3.44 (m, 2H), 2.40 (s, 3H); MS (ES+) m/z 385.2 (M+1).

Example 14.1

Synthesis of 5-(3-benzyl-2-oxoimidazolidin-1-yl)-3-methylthiophene-2-carboxylic acid

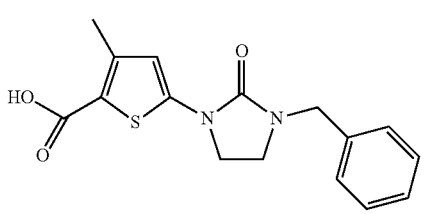

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 5-(3-benzyl-2-oxoimidazolidin-1-yl)-3-methylthiophene-2-carboxylate, the title compound was obtained as a colorless solid in 91% yield: $^1$H NMR (300 MHz, DMSO-$d_6$) δ 12.36 (br s, 1H), 7.41-7.26 (m, 5H), 6.29 (s, 1H), 4.40 (s, 2H), 3.87-3.80 (m, 2H), 3.48-3.41 (m, 2H), 2.40 (s, 3H); MS (ES+) m/z 317.2 (M+1).

Example 14.2

Synthesis of 5-(3-(4-fluorobenzyl)-2-oxoimidazolidin-1-yl)-3-methylthiophene-2-carboxylic acid

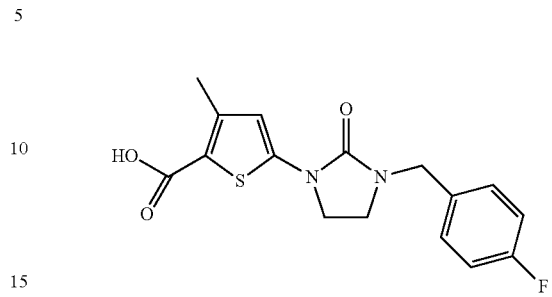

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 5-(3-(4-fluorobenzyl)-2-oxoimidazolidin-1-yl)-3-methylthiophene-2-carboxylate, the title compound was obtained as a colorless solid in 90% yield: $^1$H NMR (300 MHz, DMSO-$d_6$) δ 12.34 (br s, 1H), 7.35 (dd, J=8.6, 5.6 Hz, 2H), 7.19 (t, J=8.6 Hz, 2H), 6.29 (s, 1H), 4.39 (s, 2H), 3.87-3.78 (m, 2H), 3.48-3.40 (m, 2H), 2.40 (s, 3H); MS (ES+) m/z 335.2 (M+1).

Example 14.3

Synthesis of 5-(3-(cyclopropylmethyl)-2-oxoimidazolidin-1-yl)-3-methylthiophene-2-carboxylic acid

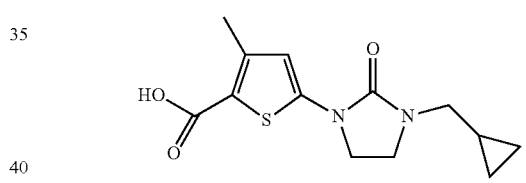

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 5-(3-(cyclopropylmethyl)-2-oxoimidazolidin-1-yl)-3-methylthiophene-2-carboxylate, the title compound was obtained as a colorless solid in 80% yield: $^1$H NMR (300 MHz, DMSO-$d_6$) δ 12.32 (br s, 1H), 6.27 (s, 1H), 3.89-3.78 (m, 2H), 3.69-3.58 (m, 2H), 3.06 (d, J=6.9 Hz, 2H), 2.39 (s, 3H), 1.00-0.86 (m, 1H), 0.53-0.44 (m, 2H), 0.25-0.18 (m, 2H); MS (ES+) m/z 281.2 (M+1).

Example 14.4

Synthesis of 3-methyl-5-(2-oxo-3-phenethylimidazolidin-1-yl)thiophene-2-carboxylic acid

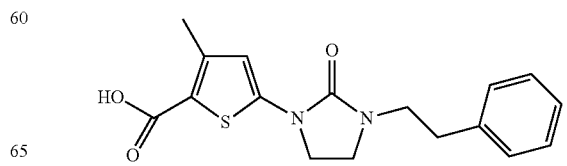

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 3-methyl-5-(2-oxo-3-phenethylimidazolidin-1-yl)thiophene-2-carboxylate, the title compound was obtained as a colorless solid in 78% yield: $^1$H NMR (300 MHz, DMSO-$d_6$) δ 7.47-7.17 (m, 5H), 6.25 (s, 1H), 3.83-3.74 (m, 2H), 3.56-3.40 (m, 4H), 2.82 (t, J=7.4 Hz, 2H), 2.38 (s, 3H); MS (ES+) m/z 331.3 (M+1).

Example 14.5

Synthesis of 2-(3-(isoquinolin-1-ylmethyl)-2-oxoimidazolidin-1-yl)-4-methylthiazole-5-carboxylic acid

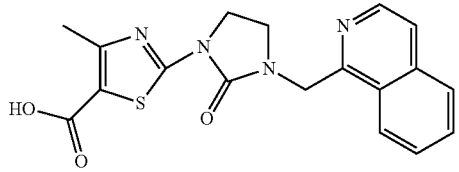

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 2-(3-(isoquinolin-1-ylmethyl)-2-oxoimidazolidin-1-yl)-4-methylthiazole-5-carboxylate, the title compound was obtained as a colorless solid in 75% yield: MS (ES+) m/z 369.1 (M+1).

Example 14.6

Synthesis of 4-methyl-2-(2-oxo-3-(quinolin-8-ylmethyl)imidazolidin-1-yl)thiazole-5-carboxylic acid

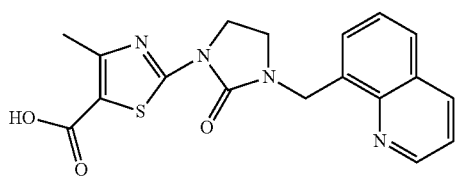

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 4-methyl-2-(2-oxo-3-(quinolin-8-ylmethyl) imidazolidin-1-yl)thiazole-5-carboxylate, the title compound was obtained as a colorless solid in 88% yield: MS (ES+) m/z 369.1 (M+1).

Example 14.7

Synthesis of 4-methyl-2-(3-((5-methylisoxazol-3-yl)methyl)-2-oxoimidazolidin-1-yl)thiazole-5-carboxylic acid

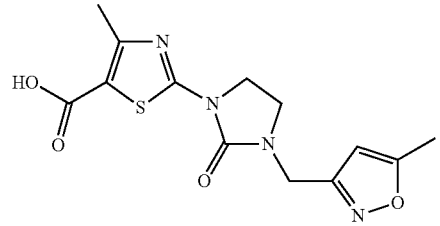

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 4-methyl-2-(3-((5-methylisoxazol-3-yl)methyl)-2-oxoimidazolidin-1-yl)thiazole-5-carboxylate, the title compound was obtained as a colorless solid in 85% yield: MS (ES+) m/z 323.1 (M+1).

Example 14.8

Synthesis of 4-methyl-2-((3-methyl-5-phenylisoxazol-4-yl)methyl)-2-oxoimidazolidin-1-yl)thiazole-5-carboxylic acid

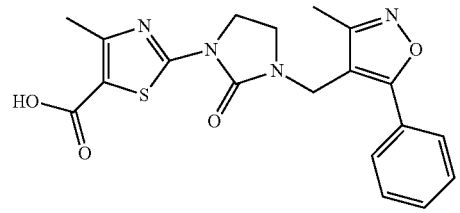

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 4-methyl-2-(3-((3-methyl-5-phenylisoxazol-4-yl)methyl)-2-oxoimidazolidin-1-yl) thiazole-5-carboxylate, the title compound was obtained as a colorless solid in 88% yield: $^1$H NMR (300 MHz, DMSO-$d_6$) δ 7.64-7.61 (m, 2H), 7.49-7.47 (m, 3H), 4.40 (s, 2H), 3.87-3.82 (m, 2H), 3.28-3.23 (m, 2H), 2.48 (s, 6H); MS (ES+) m/z 399.1 (M+1).

Example 14.9

Synthesis of 4-methyl-2-(2-oxo-3-((5-phenyloxazol-4-yl)methyl)imidazolidin-1-yl)thiazole-5-carboxylic acid

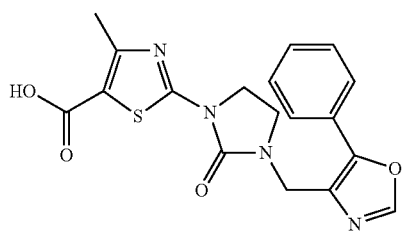

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 4-methyl-2-(2-oxo-3-((5-phenyloxazol-4-yl)methyl)imidazolidin-1-yl)thiazole-5-carboxylate, the title compound was obtained as a colorless solid in 20% yield: MS (ES+) m/z 385.1 (M+1).

Example 14.10

Synthesis of 2-(3-(benzo[c][1,2,5]oxadiazol-5-ylmethyl)-2-oxoimidazolidin-1-yl)-4-methylthiazole-5-carboxylic acid

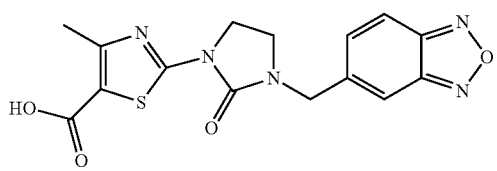

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 2-(3-(benzo[c][1,2,5]oxadiazol-5-ylmethyl)-2-oxoimidazolidin-1-yl)-4-methylthiazole-5-carboxylate, the title compound was obtained as a colorless solid in 89% yield: MS (ES+) m/z 360.1 (M+1).

Example 14.11

Synthesis of 2-(3-(benzo[c][1,2,5]thiadiazol-5-ylmethyl)-2-oxoimidazolidin-1-yl)-4-methylthiazole-5-carboxylic acid

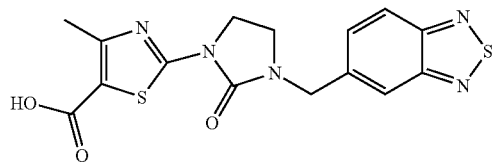

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 2-(3-(benzo[c][1,2,5]thiadiazol-5-ylmethyl)-2-oxoimidazolidin-1-yl)-4-methylthiazole-5-carboxylate, the title compound was obtained as a colorless solid in 85% yield: MS (ES+) m/z 376.1 (M+1).

Example 14.12

Synthesis of 4-methyl-2-(2-oxo-3-(pyridin-2-ylmethyl)imidazolidin-1-yl)thiazole-5-carboxylic acid

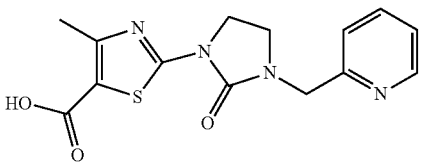

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 4-methyl-2-(2-oxo-3-(pyridin-2-ylmethyl) imidazolidin-1-yl)thiazole-5-carboxylate, the title compound was obtained as a colorless solid in 97% yield: MS (ES+) m/z 319.1 (M+1).

Example 14.13

Synthesis of 4-methyl-2-(2-oxo-3-(pyridin-4-ylmethyl)imidazolidin-1-yl)thiazole-5-carboxylic acid

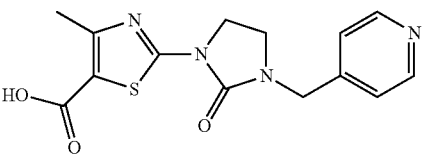

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 4-methyl-2-(2-oxo-3-(pyridin-4-ylmethyl)imidazolidin-1-yl)thiazole-5-carboxylate, the title compound was obtained as a colorless solid in quantitative yield: MS (ES+) m/z 319.2 (M+1).

Example 14.14

Synthesis of 4-methyl-2-(2-oxo-3-(pyridin-2-ylmethyl)imidazolidin-1-yl)thiazole-5-carboxylic acid

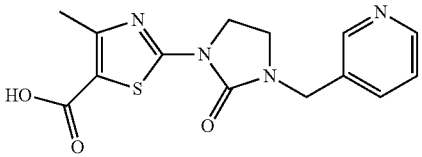

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 4-methyl-2-(2-oxo-3-(pyridin-3-ylmethyl)imidazolidin-1-yl)thiazole-5-carboxylate, the title compound was obtained as a colorless solid in quantitative yield: MS (ES+) m/z 319.1 (M+1).

Example 14.15

Synthesis of 2-(3-(4-fluorobenzyl)-2-oxoimidazolidin-1-yl)-4-methylthiazole-5-carboxylic acid

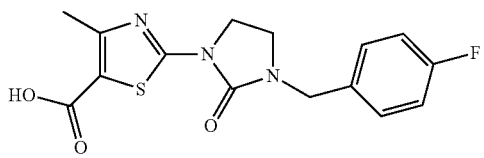

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 2-(3-(4-fluorobenzyl)-2-oxoimidazolidin-1-yl)-4-methylthiazole-5-carboxylate, the title compound was obtained as a colorless solid in 80% yield: $^1$H NMR (300 MHz, DMSO-$d_6$) δ 7.39-7.34 (m, 2H), 7.22-7.17 (m, 2H), 4.43 (s, 2H), 4.01-3.98 (m, 2H), 3.48-3.43 (m, 2H), 2.50 (s, 3H); MS (ES+) m/z 336.1 (M+1).

Example 14.16

Synthesis of 2-(3-(5-(benzylcarbamoyl)-4-methylthiazol-2-yl)-2-oxoimidazolidin-1-yl)acetic acid

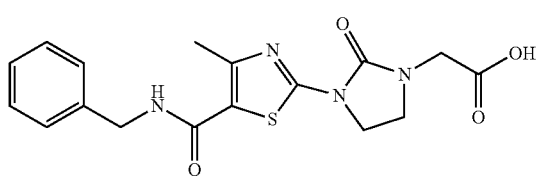

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 2-(3-(5-(benzylcarbamoyl)-4-methylthiazol-2-yl)-2-oxoimidazolidin-1-yl)acetate, the title compound was obtained as a colorless solid in 89% yield: $^1$H NMR (300 MHz, CDCl$_3$) δ 7.37-7.27 (m, 5H), 6.06 (t, J=5.4 Hz, 1H), 4.56 (d, J=5.4 Hz, 2H), 4.17-4.07 (m, 4H), 3.70 (t, J=8.1 Hz, 2H), 2.59 (s, 3H); MS (ES+) m/z 258.2 (M+1).

Example 14.17

Synthesis of 2-(3-(4-fluorobenzyl)-2-oxotetrahydropyrimidin-1(2H)-yl)-4-methylthiazole-5-carboxylic acid

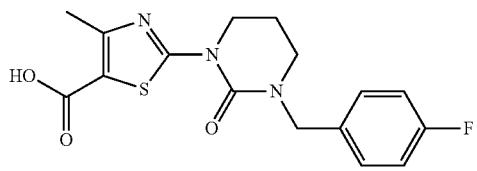

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 2-(3-(4-fluorobenzyl)-2-oxotetrahydropyrimidin-1(2H)-yl)-4-methylthiazole-5-carboxylate, the title compound was obtained as a colorless solid in 96% yield: MS (ES+) m/z 350.1 (M+1).

Example 14.18

Synthesis of 2-(3-(cyclopropylmethyl)-2-oxotetrahydropyrimidin-1(2H)-yl)-4-methylthiazole-5-carboxylic acid

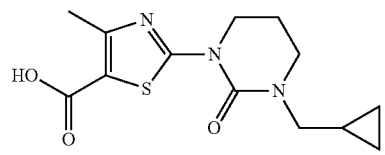

Following the procedure as described in Example 14, making variations as required to replace ethyl 3-methyl-5-(2-oxo-3-(4-(trifluoromethyl)benzyl)imidazolidin-1-yl)thiophene-2-carboxylate with ethyl 2-(3-(cyclopropylmethyl)-2-oxotetrahydropyrimidin-1(2H)-yl)-4-methylthiazole-5-carboxylate, the title compound was obtained as a colorless solid in 78% yield: MS (ES+) m/z 296.2 (M+1).

Example 15

Synthesis of 3-methyl-5-(2-oxo-3-(4-(trifluoromethyl)benzyl)imidazolidin-1-yl)-N-(pyridin-3-ylmethyl)thiophene-2-carboxamide

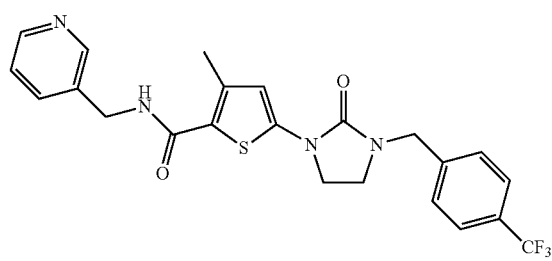

To a stirred mixture of 3-methyl-5-(2-oxo-3-(4-(trifluoromethyl)benzyl)-imidazolidin-1-yl)thiophene-2-carboxylic acid (3.68 g, 9.56 mmol), 1-hydroxybenzotriazole (1.94 g, 14.36 mmol) and 1-ethyl-3-(3-dimethylaminopropyl)-carbodiimide hydrochloride (2.75 g, 14.3 mmol) in N,N-dimethylformamide (40 mL) was added N,N-diisopropylethylamine (5.00 mL, 5.00 mmol), followed by the addition of 3-(aminomethyl)pyridine (0.97 mL, 9.57 mmol). The resulting reaction mixture was stirred for 16 h, then was diluted with ethyl acetate (300 mL). The organic layer was washed with saturated aqueous sodium bicarbonate solution (3×100 mL), water (100 mL) and brine (100 mL). The combined water/brine layer was extracted with dichloromethane (200 mL). The combined organic layer was dried over sodium sulfate, filtered and concentrated in vacuo. The residue was purified by recrystallization from 50% ethyl acetate in hexanes to afford the title compound as a colorless solid (2.48 g, 55%): mp 102-104° C. (hexanes/ethyl acetate); $^1$H NMR (300 MHz, CDCl$_3$) δ 8.59 (s, 1H), 8.52 (s, 1H), 7.69 (d, J=7.8 Hz, 1H), 7.60 (d, J=8.0 Hz, 2H), 7.40 (d, J=8.0 Hz, 2H), 7.29-7.22 (m, 1H), 6.20 (t, J=5.6 Hz, 1H), 6.10 (s, 1H), 4.58 (d, J=5.6 Hz, 2H), 4.50 (s, 2H), 3.85-3.77 (m, 2H), 3.50-3.42 (m, 2H), 2.48 (s, 3H); $^{13}$C NMR (75 MHz, CDCl$_3$) δ 163.5, 155.8, 149.1, 148.7, 142.3, 141.4, 140.1, 135.5, 134.2, 130.1 (d, $J_{C-F}$=32.6 Hz), 128.4, 125.7 (q, $J_{C-F}$=3.8 Hz), 123.5, 122.1, 119.2, 112.5, 47.7, 42.7, 41.6, 41.1, 16.0; MS (ES+) m/z 475.3 (M+1).

Example 15.1

Synthesis of 5-(3-benzyl-2-oxoimidazolidin-1-yl)-3-methyl-N-(pyridin-3-ylmethyl)thiophene-2-carboxamide

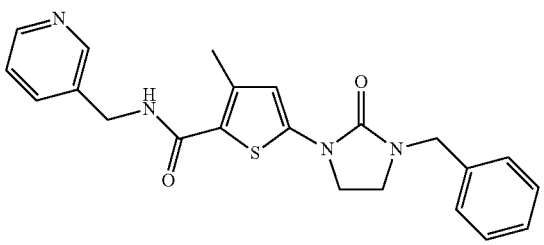

Following the procedure as described in Example 15, making variations as required to replace 3-methyl-5-(2-oxo-3-(4-(trifluoromethyl)benzyl)imidazolidin-1-yl)thiophene-2-carboxylic acid with 5-(3-benzyl-2-oxoimidazolidin-1-yl)-3-methylthiophene-2-carboxylic acid to react with 3-(aminomethyl)pyridine, the title compound was obtained as a colorless solid in 46% yield: mp 130-131° C.; $^1$H NMR (300 MHz, CDCl$_3$) δ 8.59 (s, 1H), 8.51 (s, 1H), 7.69 (d, J=7.8 Hz, 1H), 7.38-7.22 (m, 6H), 6.18 (t, J=5.6 Hz, 1H), 6.07 (s, 1H), 4.58 (d, J=5.6 Hz, 2H), 4.44 (s, 2H), 3.81-3.74 (m, 2H), 3.47-3.40 (m, 2H), 2.48 (s, 3H); $^{13}$C NMR (75 MHz, CDCl$_3$) δ 163.5, 155.9, 149.2, 148.8, 142.6, 141.8, 135.9, 135.5, 128.8, 128.2, 127.9, 123.6, 118.9, 112.3, 48.1, 42.7, 41.5, 41.2, 16.1; MS (ES+) m/z 407.3 (M+1).

Example 15.2

Synthesis of 5-(3-(4-fluorobenzyl)-2-oxoimidazolidin-1-yl)-3-methyl-N-(pyridin-3-ylmethyl)thiophene-2-carboxamide

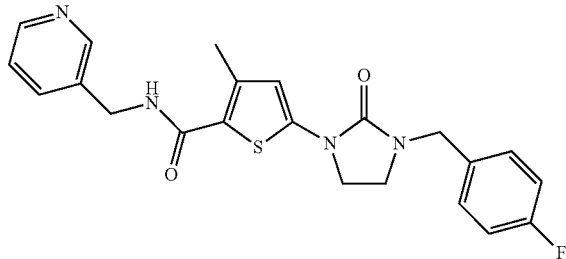

Following the procedure as described in Example 15, making variations as required to replace 3-methyl-5-(2-oxo-3-(4-(trifluoromethyl)benzyl)imidazolidin-1-yl)thiophene-2-carboxylic acid with 5-(3-(4-fluorobenzyl)-2-oxoimidazolidin-1-yl)-3-methylthiophene-2-carboxylic acid to react with 3-(aminomethyl)pyridine, the title compound was obtained as a colorless solid in 79% yield: mp 119-120° C.; $^1$H NMR (300 MHz, CDCl$_3$) δ 8.59 (s, 1H), 8.52 (d, J=4.7 Hz, 1H), 7.69 (d, J=7.8 Hz, 1H), 7.29-7.23 (m, 3H), 7.06-6.99 (m, 2H), 6.14 (t, J=5.7 Hz, 1H), 6.08 (s, 1H), 4.58 (d, J=5.7 Hz, 2H), 4.42 (s, 2H), 3.83-3.75 (m, 2H), 3.47-3.39 (m, 2H), 2.48 (s, 3H); $^{13}$C NMR (75 MHz, CDCl$_3$) δ 163.5, 162.4 (d, $J_{C-F}$=246.4 Hz), 155.8, 149.2, 148.8, 142.5, 141.7, 135.5, 134.1, 131.7, (d, $J_{C-F}$=3.1 Hz), 130.0 (d, $J_{C-F}$=8.2 Hz), 123.6, 119.0, 115.7 (d, $J_{C-F}$=21.5 Hz), 112.4, 47.4, 42.7, 41.4, 41.2, 16.1; MS (ES+) m/z 425.3 (M+1).

Example 15.3

Synthesis of 5-(3-(cyclopropylmethyl)-2-oxoimidazolidin-1-yl)-3-methyl-N-(pyridin-3-ylmethyl)thiophene-2-carboxamide

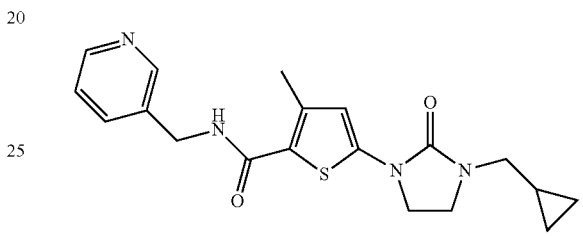

Following the procedure as described in Example 15, making variations as required to replace 3-methyl-5-(2-oxo-3-(4-(trifluoromethyl)benzyl)imidazolidin-1-yl)thiophene-2-carboxylic acid with 5-(3-(cyclopropylmethyl)-2-oxoimidazolidin-1-yl)-3-methylthiophene-2-carboxylic acid to react with 3-(aminomethyl)pyridine, the title compound was obtained as a colorless solid in 59% yield: mp 157-159° C.; $^1$H NMR (300 MHz, CDCl$_3$) δ 8.51 (s, 1H), 8.50 (d, J=4.1 Hz, 1H), 7.68 (d, J=7.8 Hz, 1H), 7.28-7.21 (m, 1H), 6.14 (t, J=5.6 Hz, 1H), 6.06 (s, 1H), 4.57 (d, J=5.6 Hz, 2H), 3.85-3.77 (m, 2H), 3.70-3.63 (m, 2H), 3.14 (d, J=7.1 Hz, 2H), 2.48 (s, 3H), 0.99-0.84 (m, 1H), 0.58-0.50 (m, 2H), 0.25-0.19 (m, 2H); $^{13}$C NMR (75 MHz, CDCl$_3$) δ 163.6, 155.8, 149.2, 148.8, 142.8, 141.8, 135.5, 134.2, 123.5, 118.6, 112.1, 48.8, 42.9, 42.1, 41.2, 16.1, 9.0, 3.4; MS (ES+) m/z 371.3 (M+1).

Example 15.4

Synthesis of 3-methyl-5-(2-oxo-3-phenethylimidazolidin-1-yl)-N-(pyridin-3-ylmethyl)thiophene-2-carboxamide

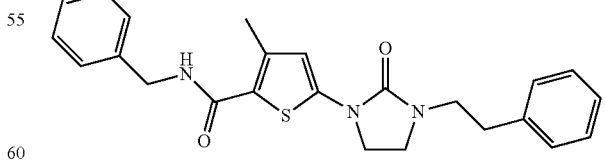

Following the procedure as described in Example 15, making variations as required to replace 3-methyl-5-(2-oxo-3-(4-(trifluoromethyl)benzyl)imidazolidin-1-yl)thiophene-2-carboxylic acid with 3-methyl-5-(2-oxo-3-phenethylimidazolidin-1-yl)thiophene-2-carboxylic acid to react with 3-(aminomethyl)pyridine, the title compound was obtained as a colorless solid in 74% yield: mp 95-97° C.; $^1$H NMR (300 MHz, CDCl$_3$) δ 8.59 (s, 1H), 8.52 (d, J=2.2 Hz, 1H), 7.69 (d, J=7.8 Hz, 1H), 7.35-7.18 (m, 6H), 6.12 (t, J=5.6 Hz, 1H), 6.05 (s, 1H), 4.57 (d, J=5.6 Hz, 2H), 3.77-3.70 (m, 2H), 3.54 (t, J=7.4 Hz, 2H), 3.46-3.39 (m, 2H), 2.88 (t, J=7.4 Hz, 2H), 2.48 (s, 3H); $^{13}$C NMR (75 MHz, CDCl$_3$) δ 163.6, 155.8, 149.2, 148.8, 142.6, 141.8, 138.4, 135.5, 134.1, 128.6, 126.6, 123.6, 118.7, 112.2, 45.5, 42.8, 42.6, 41.2, 34.1, 16.0; MS (ES+) m/z 421.3 (M+1).

Example 15.5

Synthesis of N-benzyl-2-(3-(2-(4-fluorobenzylamino)-2-oxoethyl)-2-oxoimidazolidin-1-yl)-4-methylthiazole-5-carboxamide

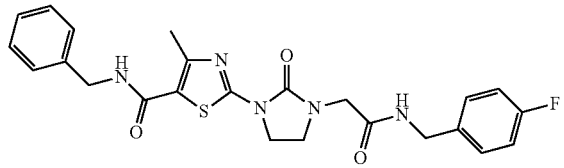

Following the procedure as described in Example 15, making variations as required to replace 3-methyl-5-(2-oxo-3-(4-(trifluoromethyl)benzyl)imidazolidin-1-yl)thiophene-2-carboxylic acid with 2-(3-(5-(benzylcarbamoyl)-4-methylthiazol-2-yl)-2-oxoimidazolidin-1-yl)acetic acid to react with 4-fluorobenzylamine, the title compound was obtained as a colorless solid in 75% yield: mp 232-234° C.; $^1$H NMR (300 MHz, DMSO-d$_6$) δ 8.64 (t, J=5.9 Hz, 1H), 8.52 (t, J=5.9 Hz, 1H), 7.37-7.12 (m, 9H), 4.38 (d, J=5.9 Hz, 2H), 4.29 (d, J=5.9 Hz, 2H), 4.05-3.98 (m, 2H), 3.93 (s, 2H), 3.65-3.57 (m, 2H), 2.48 (s, 3H); $^{13}$C NMR (75 MHz, DMSO-d$_6$) δ 167.4, 161.7, 161.1 (d, $J_{C-F}$=242.0 Hz), 157.3, 155.4, 150.8, 139.6, 135.3 (d, $J_{C-F}$=2.9 Hz), 129.1 (d, $J_{C-F}$=8.1 Hz), 128.2, 127.2, 126.6, 117.8, 115.0 (d, $J_{C-F}$=21.3 Hz), 46.2, 42.8, 42.5, 42.0, 41.3, 17.0; MS (ES+) m/z 482.1 (M+1).

Example 16

Synthesis of N-benzyl-2-(3-(4-fluorobenzyl)-5-hydroxy-2-oxoimidazolidin-1-yl)-4-methylthiazole-5-carboxamide

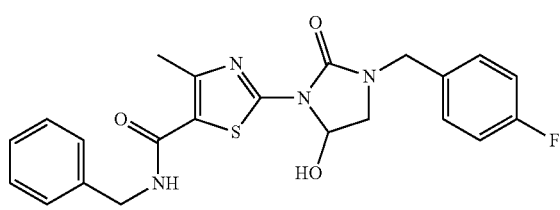

To a solution of N-benzyl-2-(3-(2,2-dimethoxyethyl)-3-(4-fluorobenzyl)ureido)-4-methylthiazole-5-carboxamide (0.47 g, 0.96 mmol) in tetrahydrofuran (10 mL) was added water (5 mL) and trifluoroacetic acid (5 mL) at ambient temperature. The resulting reaction mixture was heated to reflux for 5 hours. The solvent was removed in vacuo and the residue was purified by column chromatography to afford the title compound in 76% yield (0.32 g): mp 133-134° C.; $^1$H NMR (300 MHz, CDCl$_3$) δ 7.35-6.97 (m, 9H), 6.10 (t, J=5.7 Hz, 1H), 5.99 (d, J=5.9 Hz, 1H), 5.03 (s, 1H), 4.53 (d, J=5.7 Hz, 2H), 4.41 (s, 2H), 3.60-3.54 (m, 1H), 3.27-3.23 (m, 1H), 2.52 (s, 3H); $^{13}$C NMR (75 MHz, CDCl$_3$) δ 162.4, 162.1, 160.8, 157.0, 153.5, 152.4, 137.9, 131.1, 129.9, 128.7, 127.8, 117.9, 115.9, 115.7, 49.3, 46.6, 44.0, 17.0; MS (ES+) m/z 441.3 (M+1).

Example 16.1

Synthesis of 2-(3-(4-fluorophenethyl)-5-hydroxy-2-oxoimidazolidin-1-yl)-4-methyl-N-(pyridin-3-ylmethyl)thiazole-5-carboxamide

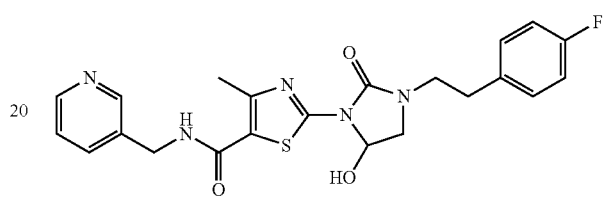

Following the procedure as described in Example 16, making variations as required to replace N-benzyl-2-(3-(2,2-dimethoxyethyl)-3-(4-fluorobenzyl)ureido)-4-methylthiazole-5-carboxamide with 2-(3-(2,2-dimethoxyethyl)-3-(4-fluorophenethyl)ureido)-4-methyl-N-(pyridin-3-ylmethyl)thiazole-5-carboxamide, the title compound was obtained as a colorless solid in 21% yield: mp 182-184° C. (ethyl acetate); $^1$H NMR (300 MHz, CDCl$_3$) δ 8.61-8.48 (m, 2H), 7.67 (d, J=7.2 Hz, 1H), 7.28 (br s, 1H), 7.18-7.03 (m, 2H), 6.97 (d, J=8.6 Hz, 2H), 6.12-5.93 (m, 2H), 4.72 (br s, 1H), 4.57 (d, J=5.7 Hz, 2H) 3.65-3.45 (m, 3H), 3.34-3.29 (m, 1H), 2.85 (t, J=7.2 Hz, 2H), 2.57 (s, 3H); $^{13}$C NMR (75 MHz, CDCl$_3$) δ 162.3, 160.1, 157.1, 153.4, 153.3, 149.2, 149.0, 135.6, 133.6, 130.1, 130.0, 117.2, 115.7, 115.4, 77.2, 50.2, 44.8, 41.4, 33.1, 17.2; MS (ES+) m/z 456.3 (M+1).

Example 16.2

Synthesis of 2-(3-(4-fluorobenzyl)-5-hydroxy-2-oxoimidazolidin-1-yl)-4-methyl-N-(pyridin-3-ylmethyl)thiazole-5-carboxamide

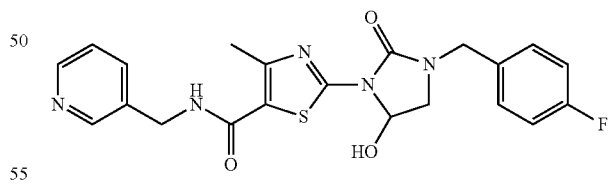

Following the procedure as described in Example 16, making variations as required to replace N-benzyl-2-(3-(2,2-dimethoxyethyl)-3-(4-fluorobenzyl)ureido)-4-methylthiazole-5-carboxamide with 2-(3-(2,2-dimethoxyethyl)-3-(4-fluorobenzyl)ureido)-4-methyl-N-(pyridin-3-ylmethyl)thiazole-5-carboxamide, the title compound was obtained as a colorless solid in 96% yield: mp 64-66° C. (ethyl acetate/hexanes); $^1$H NMR (300 MHz, CDCl$_3$) δ 8.64-8.45 (m, 2H), 7.68-7.63 (m, 1H), 7.30-7.10 (m, 3H), 7.05-6.97 (m, 2H), 6.57 (br s, 1H), 6.04-5.75 (m, 2H), 4.56 (d, J=6.0 Hz, 2H), 4.48 (s, 2H), 3.62-3.56 (m, 1H), 3.29-3.25 (m, 1H), 2.52 (s, 3H); $^{13}$C NMR (75 MHz, CDCl$_3$) δ 162.5, 162.4, 157.0, 153.7, 148.9, 135.7, 135.0, 133.9, 131.0, 129.9, 123.6, 117.4, 116.0, 115.7, 60.4, 49.5, 46.7, 41.4, 17.2; MS (ES+) m/z 442.3 (M+1).

Example 16.3

Synthesis of 2-(5-hydroxy-2-oxo-3-(4-(trifluoromethyl)benzyl)imidazolidin-1-yl)-4-methyl-N-(pyridin-3-ylmethyl)thiazole-5-carboxamide

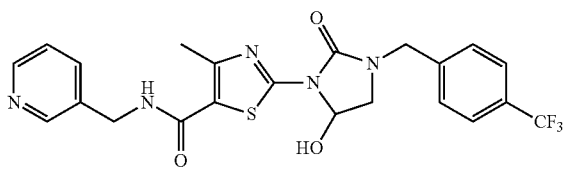

Following the procedure as described in Example 16, making variations as required to replace N-benzyl-2-(3-(2,2-dimethoxyethyl)-3-(4-fluorobenzyl)ureido)-4-methylthiazole-5-carboxamide with 2-(3-(2,2-dimethoxyethyl)-3-(4-(trifluoromethyl)-benzyl)ureido)-4-methyl-N-(pyridin-3-ylmethyl)thiazole-5-carboxamide, the title compound was obtained as a colorless solid in 98% yield: mp 171-172° C. (ethyl acetate/hexanes); $^1$H NMR (300 MHz, CDCl$_3$) δ 8.45-8.42 (m, 2H), 7.69-7.62 (m, 2H), 7.57 (d, J=8.1 Hz, 2H), 7.34 (d, J=8.1 Hz, 2H), 7.27-7.22 (m, 1H), 6.08-6.05 (m, 1H), 4.56-4.37 (m, 4H), 3.65-6.59 (m, 1H), 3.33-3.25 (m, 1H), 2.51 (s, 3H); $^{13}$C NMR (75 MHz, CDCl$_3$) δ 162.6, 157.1, 154.0, 153.1, 148.4, 139.4, 135.8, 135.0, 134.2, 130.1, 128.6, 125.9, 123.7, 121.8, 117.5, 50.2, 46.9, 41.4, 17.2; MS (ES+) m/z 492.2 (M+1).

Example 17

Synthesis of N-benzyl-2-(3-(4-fluorobenzyl)-2-oxo-2,3-dihydro-1H-imidazol-1-yl)-4-methylthiazole-5-carboxamide

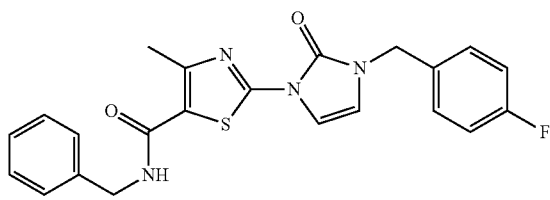

To a solution of N-benzyl-2-(3-(4-fluorobenzyl)-5-hydroxy-2-oxoimidazolidin-1-yl)-4-methylthiazole-5-carboxamide (0.22 g, 0.50 mmol) in chloroform (10 mL) was added trifluoroacetic acid (10 mL) at ambient temperature. The resulting reaction mixture was heated to reflux for 8 hours. The solvent was removed in vacuo and the residue was purified by column chromatography to afford the title compound in 64% yield (0.12 g): mp 167-168° C.; $^1$H NMR (300 MHz, CDCl$_3$) δ 7.34-6.96 (m, 10H), 6.30-6.29 (m, 1H), 6.12 (s, 1H), 4.76 (s, 2H), 4.55 (d, J=5.4 Hz, 2H), 2.59 (s, 3H); $^{13}$C NMR (75 MHz, CDCl$_3$) δ 162.6, 162.0, 153.4, 152.9, 150.5, 131.4, 129.8, 128.8, 127.8, 117.7, 120.0, 116.1, 115.8, 113.0, 107.6, 46.7, 44.1, 17.2; MS (ES+) m/z 423.2 (M+1).

Example 17.1

Synthesis of 2-(3-(4-fluorophenethyl)-2-oxo-2,3-dihydro-1H-imidazol-1-yl)-4-methyl-N-(pyridin-3-ylmethyl)thiazole-5-carboxamide

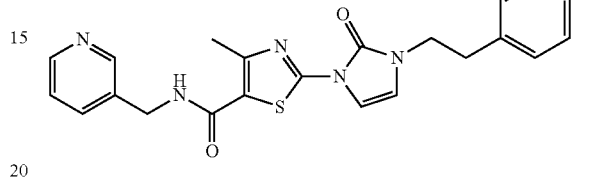

Following the procedure as described in Example 17, making variations as required to replace N-benzyl-2-(3-(4-fluorobenzyl)-5-hydroxy-2-oxoimidazolidin-1-yl)-4-methylthiazole-5-carboxamide with 2-(3-(4-fluorophenethyl)-5-hydroxy-2-oxoimidazolidin-1-yl)-4-methyl-N-(pyridin-3-ylmethyl)thiazole-5-carboxamide 2, the title compound was obtained as a colorless solid in 14% yield: mp 160-162° C. (ethyl acetate/hexanes); $^1$H NMR (300 MHz, DMSO-d$_6$) δ 8.72 (d, J=5.8 Hz, 1H), 8.50-8.49 (m, 1H), 8.42 (dd, J=4.7, 1.8 Hz, 1H), 7.68 (td, J=7.8, 1.8 Hz, 1H), 7.34-7.30 (m, 1H), 7.22-7.17 (m, 3H), 7.11-7.03 (m, 2H), 6.84 (d, J=3.2 Hz, 1H), 4.38 (d, J=5.8 Hz, 2H), 3.83 (t, J=7.1 Hz, 2H), 2.92 (t, J=7.1 Hz, 2H), 2.48 (s, 3H); $^{13}$C NMR (75 MHz, DMSO-d$_6$) δ 163.0, 161.9, 159.8, 153.8, 151.6, 150.3, 149.3, 148.5, 135.6, 135.3, 134.6, 131.0, 123.9, 120.7, 115.7, 106.7, 44.6, 40.9, 33.8, 17.4; MS (ES+) m/z 438.3 (M+1).

Example 17.2

2-(3-(4-fluorobenzyl)-2-oxo-2,3-dihydro-1H-imidazol-1-yl)-4-methyl-N-(pyridin-3-ylmethyl)thiazole-5-carboxamide

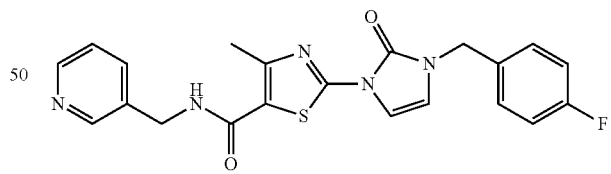

Following the procedure as described in Example 17, making variations as required to replace N-benzyl-2-(3-(4-fluorobenzyl)-5-hydroxy-2-oxoimidazolidin-1-yl)-4-methylthiazole-5-carboxamide with 2-(3-(4-fluorobenzyl)-5-hydroxy-2-oxoimidazolidin-1-yl)-4-methyl-N-(pyridin-3-ylmethyl)thiazole-5-carboxamide, the title compound was obtained as a colorless solid in 81% yield: mp 158-159° C. (ethyl acetate/hexanes); $^1$H NMR (300 MHz, CDCl$_3$) δ 8.58 (d, J=1.5 Hz, 1H), 8.49 (dd, J=4.5, 1.5 Hz, 1H), 7.69-7.65 (m, 1H), 7.26-7.16 (m, 4H), 7.04-6.97 (m, 2H), 6.47 (t, J=5.7 Hz, 1H), 6.29 (d, J=3.3 Hz, 1H), 4.78 (s, 2H), 4.58 (d, J=5.7 Hz, 2H), 2.62 (s, 3H); $^{13}$C NMR (75 MHz, CDCl$_3$) δ 162.6, 162.2, 153.5, 150.5, 149.2, 149.0, 135.6, 133.7, 131.3, 129.8, 123.6, 119.5, 116.1, 115.8, 113.1, 107.6, 46.7, 41.5, 17.2; MS (ES+) m/z 424.3 (M+1).

Example 17.3

Synthesis of 4-methyl-2-(2-oxo-3-(4-(trifluoromethyl)benzyl)-2,3-dihydro-1H-imidazol-1-yl)-N-(pyridin-3-ylmethyl)thiazole-5-carboxamide

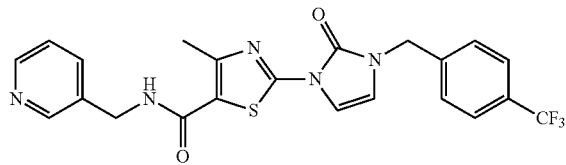

Following the procedure as described in Example 17, making variations as required to replace N-benzyl-2-(3-(4-fluorobenzyl)-5-hydroxy-2-oxoimidazolidin-1-yl)-4-methylthiazole-5-carboxamide with 2-(5-hydroxy-2-oxo-3-(4-(trifluoromethyl)benzyl)imidazolidin-1-yl)-4-methyl-N-(pyridin-3-ylmethyl)thiazole-5-carboxamide, the title compound was obtained as a colorless solid in 81% yield: mp 163-164° C. (ethyl acetate/hexanes); $^1$H NMR (300 MHz, CDCl$_3$) δ 8.58-8.48 (m, 2H), 7.71-7.67 (m, 1H), 7.59 (d, J=8.1 Hz, 2H), 7.37 (d, J=8.1 Hz, 2H), 7.29-7.21 (m, 3H), 6.29 (d, J=3.3 Hz, 1H), 4.82 (s, 2H), 4.53 (d, J=5.7 Hz, 2H), 2.63 (s, 3H); $^{13}$C NMR (75 MHz, CDCl$_3$) δ 162.2, 153.5, 153.4, 150.5, 149.2, 148.9, 139.5, 135.8, 133.7, 130.8, 128.4, 128.1, 126.0, 122.0, 119.6, 113.1, 107.9, 46.9, 41.5, 17.3; MS (ES+) m/z 474.3 (M+1).

Example 18

Synthesis of ethyl 4-methyl-2-(5-oxo-1H-1,2,4-triazol-4(5H)-yl)thiazole-5-carboxylate

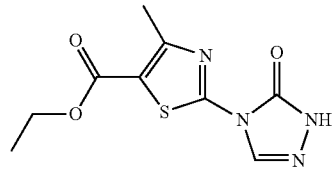

A solution of ethyl 2-(hydrazinecarboxamido)-4-methylthiazole-5-carboxylate (0.50 g, 2.05 mmol), trimethyl orthoformate (0.25 mL, 2.28 mmol) and p-toluenesulfonic acid monohydrate (10 mg) in methanol (10 mL) was subjected to microwave irradiation for 10 minutes at 90° C. (30 psi). The solvent was removed in vacuo and the residue was suspended in dichloromethane. The solid was collected by filtration, washed with saturated sodium bicarbonate and water, and dried to afford the title compound in 73% yield (0.38 g): $^1$H NMR (300 MHz, DMSO-d$_6$) δ 8.33 (s, 1H), 4.32 (q, J=6.9 Hz, 2H), 2.68 (s, 3H), 1.35 (t, J=6.9 Hz, 3H); MS (ES+) m/z 255.2 (M+1).

Example 19

Synthesis of ethyl 4-methyl-2-(5-oxo-1-(4-(trifluoromethyl)benzyl)-1H-1,2,4-triazol-4(5H)-yl)thiazole-5-carboxylate

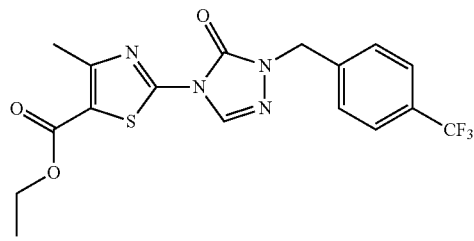

To a solution of ethyl 4-methyl-2-(5-oxo-1H-1,2,4-triazol-4(5H)-yl)thiazole-5-carboxylate (0.17 g, 0.68 mmol) and potassium carbonate (0.14 g, 1.03 mmol) in acetone (10 mL) was added 4-(trifluoromethyl)benzyl bromide (0.21 g, 0.89 mmol). The reaction mixture was heated to reflux for 3 hours. The solvent was removed in vacuo and the residue was washed with water and hexanes to afford the title compound in 60% yield (0.17 g): $^1$H NMR (300 MHz, CDCl$_3$) δ 8.29 (s, 1H), 7.61 (d, J=8.3 Hz, 2H), 7.50 (d, J=8.3 Hz, 2H), 5.07 (s, 2H), 4.32 (q, J=7.1 Hz, 2H), 2.67 (s, 3H), 1.35 (t, J=7.1 Hz, 3H); MS (ES+) m/z 413.2 (M+1).

Example 19.1

Synthesis of ethyl 4-methyl-2-(5-oxo-1-((5-(trifluoromethyl)furan-2-yl)methyl)-1H-1,2,4-triazol-4(5H)-yl)thiazole-5-carboxylate

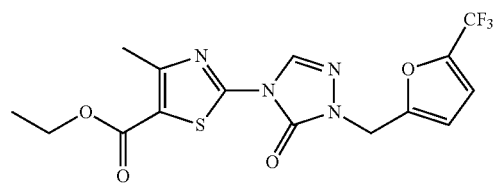

Following the procedure as described in Example 19, making variation as required to replace 4-(trifluoromethyl)benzyl bromide with 2-(bromomethyl)-5-(trifluoromethyl)furan to react with ethyl 4-methyl-2-(5-oxo-1H-1,2,4-triazol-4(5H)-yl)thiazole-5-carboxylate, the title compound was obtained as a white solid in 56% yield: $^1$H NMR (300 MHz, CDCl$_3$) δ 8.26 (s, 1H), 6.69-6.62 (m, 1H), 6.29-6.20 (m, 1H), 5.03 (s, 2H), 4.32 (q, J=7.0 Hz, 2H), 2.64 (s, 3H), 1.35 (t, J=7.0 Hz, 3H); MS (ES+) m/z 403.3 (M+1).

Example 19.2

Synthesis of ethyl 2-(1-(4-fluorobenzyl)-5-oxo-1H-1,2,4-triazol-4(5H)-yl)-4-methylthiazole-5-carboxylate

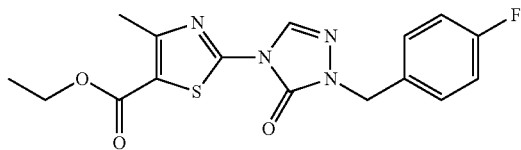

Following the procedure as described in Example 19, making variation as required to replace 4-(trifluoromethyl)benzyl bromide with 1-(bromomethyl)-4-fluorobenzene to react with ethyl 4-methyl-2-(5-oxo-1H-1,2,4-triazol-4(5H)-yl)thiazole-5-carboxylate, the title compound was obtained as a white solid in 84% yield: $^1$H NMR (300 MHz, CDCl$_3$) δ 8.27 (s, 1H), 7.47-7.30 (m, 2H), 7.11-6.97 (m, 2H), 4.98 (s, 2H), 4.32 (q, J=7.1 Hz, 2H), 2.65 (s, 3H), 1.34 (t, J=7.1 Hz, 3H); MS (ES+) m/z 363.1 (M+1).

Example 19.3

Synthesis of ethyl 2-(1-(cyclopropylmethyl)-5-oxo-1H-1,2,4-triazol-4(5H)-yl)-4-methylthiazole-5-carboxylate

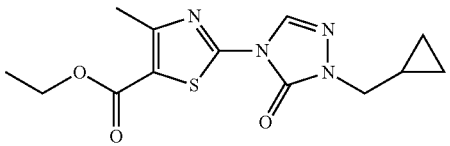

Following the procedure as described in Example 19, making variation as required to replace 4-(trifluoromethyl)benzyl bromide with (bromomethyl)cyclopropane to react with ethyl 4-methyl-2-(5-oxo-1H-1,2,4-triazol-4(5H)-yl)thiazole-5-carboxylate, the title compound was obtained as a white solid in 83% yield: $^1$H NMR (300 MHz, CDCl$_3$) δ 8.27 (s, 1H), 4.31 (q, J=7.1 Hz, 2H), 3.63 (d, J=7.1 Hz, 2H), 2.64 (s, 3H), 1.35 (t, J=7.1 Hz, 3H), 1.19-1.04 (m, 1H), 0.53-0.42 (m, 2H), 0.36-0.27 (m, 2H); MS (ES+) m/z 309.2 (M+1).

Example 19.4

Synthesis of ethyl 2-(1-(4-(difluoromethoxy)benzyl)-5-oxo-1H-1,2,4-triazol-4(5H)-yl)-4-methylthiazole-5-carboxylate

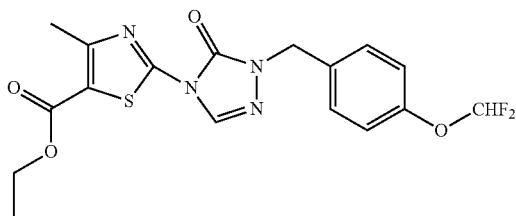

Following the procedure as described in Example 19, making variation as required to replace 4-(trifluoromethyl)benzyl bromide with 1-(bromomethyl)-4-(difluoromethoxy)benzene to react with ethyl 4-methyl-2-(5-oxo-1H-1,2,4-triazol-4(5H)-yl)thiazole-5-carboxylate, the title compound was obtained as a white solid in 79% yield: $^1$H NMR (300 MHz, CDCl$_3$) δ 8.27 (s, 1H), 7.44-7.36 (m, 2H), 7.14-7.06 (m, 2H), 6.47 (t, $J_{H-F}$=73.8 Hz, 1H), 4.99 (s, 2H), 4.32 (q, J=7.0 Hz, 2H), 2.66 (s, 3H), 1.35 (t, J=7.0 Hz, 3H); MS (ES+) m/z 411.2 (M+1).

Example 19.5

Synthesis of ethyl 4-methyl-2-(5-oxo-1-(4,4,4-trifluorobutyl)-1H-1,2,4-triazol-4(5H)-yl)thiazole-5-carboxylate

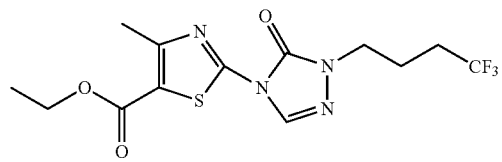

Following the procedure as described in Example 19, making variation as required to replace 4-(trifluoromethyl)benzyl bromide with 4-bromo-1,1,1-trifluorobutane to react with ethyl 4-methyl-2-(5-oxo-1H-1,2,4-triazol-4(5H)-yl)thiazole-5-carboxylate, the title compound was obtained as a white solid in 32% yield: $^1$H NMR (300 MHz, CDCl$_3$) δ 8.28 (s, 1H), 4.29 (q, J=7.1 Hz, 2H), 3.92 (t, J=6.6 Hz, 2H), 2.64 (s, 3H), 2.99-1.96 (m, 4H), 1.35 (t, J=7.1 Hz, 3H); MS (ES+) m/z 365.3 (M+1).

Example 19.6

Synthesis of ethyl 2-(1-(2-(4-fluorophenoxy)ethyl)-5-oxo-1H-1,2,4-triazol-4(5H)-yl)-4-methylthiazole-5-carboxylate

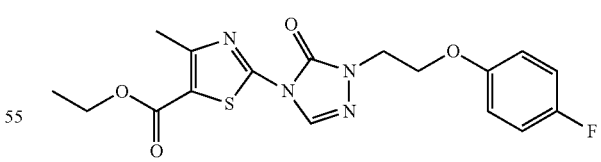

Following the procedure as described in Example 19, making variation as required to replace 4-(trifluoromethyl)benzyl bromide with 1-(2-bromoethoxy)-4-fluorobenzene to react with ethyl 4-methyl-2-(5-oxo-1H-1,2,4-triazol-4(5H)-yl)thiazole-5-carboxylate, the title compound was obtained as a white solid in 48% yield: $^1$H NMR (300 MHz, CDCl$_3$) δ 8.26 (s, 1H), 6.93-6.84 (m, 2H), 6.81-6.75 (m, 2H), 4.32-4.15 (m, 6H), 2.62 (s, 3H), 1.31 (t, J=7.1 Hz, 3H); MS (ES+) m/z 393.3 (M+1).

Example 19.7

Synthesis of 2-(1-((3,5-dimethylisoxazol-4-yl)methyl)-5-oxo-1H-1,2,4-triazol-4(5H)-yl)-4-methyl-N-(pyridin-3-ylmethyl)thiazole-5-carboxamide

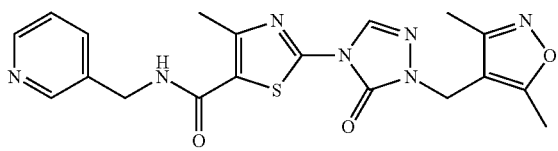

Following the procedure as described in Example 19, making variation as required to replace 4-(trifluoromethyl)benzyl bromide with 4-(chloromethyl)-3,5-dimethylisoxazole to react with 4-methyl-2-(5-oxo-1H-1,2,4-triazol-4(5H)-yl)-N-(pyridin-3-ylmethyl)thiazole-5-carboxamide, the title compound was obtained as a white solid in 45% yield: mp 233-234° C. (ethyl acetate/hexane); $^1$H NMR (300 MHz, CDCl$_3$) δ 8.74 (br s, 1H), 8.60 (br s, 1H), 8.22 (s, 1H), 7.87-7.80 (m, 1H), 7.52-7.31 (m, 1H), 6.51 (t, J=5.8 Hz, 1H), 4.74 (s, 2H), 4.64 (d, J=5.8 Hz, 2H), 2.64 (s, 3H), 2.48 (s, 3H), 2.32 (s, 3H); MS (ES+) m/z 426.1 (M+1).

Example 19.8

Synthesis of 4-methyl-2-(1-((2-methylthiazol-4-yl)methyl)-5-oxo-1H-1,2,4-triazol-4(5H)-yl)-N-(pyridin-3-ylmethyl)thiazole-5-carboxamide

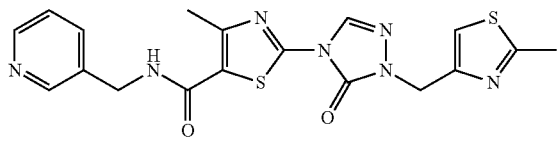

Following the procedure as described in Example 19, making variation as required to replace 4-(trifluoromethyl)benzyl bromide with 4-(chloromethyl)-2-methylthiazole hydrochloride to react with 4-methyl-2-(5-oxo-1H-1,2,4-triazol-4(5H)-yl)-N-(pyridin-3-ylmethyl)thiazole-5-carboxamide, the title compound was obtained as a white solid in 34% yield: $^1$H NMR (300 MHz, CDCl$_3$) δ 8.57 (br s, 1H), 8.46 (br s, 1H), 8.26 (s, 1H), 7.72-7.63 (m, 1H), 7.30-7.17 (m, 1H), 7.05 (s, 1H), 6.83 (t, J=5.8 Hz, 1H), 5.06 (s, 2H), 4.58 (d, J=5.8 Hz, 2H), 2.64 (s, 3H), 2.61 (s, 3H); MS (ES+) m/z 428.1 (M+1).

Example 19.9

Synthesis of 2-(1-(2-hydroxyethyl)-5-oxo-1H-1,2,4-triazol-4(5H)-yl)-4-methyl-N-(pyridin-3-ylmethyl)thiazole-5-carboxamide

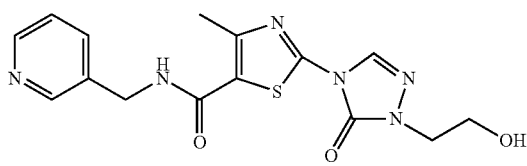

Following the procedure as described in Example 19, making variation as required to replace 4-(trifluoromethyl)benzyl bromide with 2-bromoethanol to react with 4-methyl-2-(5-oxo-1H-1,2,4-triazol-4(5H)-yl)-N-(pyridin-3-ylmethyl)thiazole-5-carboxamide, the title compound was obtained as a white solid in 76% yield: mp 201-202° C. (ethyl acetate/hexane); $^1$H NMR (300 MHz, DMSO-d$_6$) δ 8.87 (t, J=5.8 Hz, 1H), 8.71 (s, 1H), 8.51 (br s, 1H), 8.47-8.39 (m, 1H), 7.73-7.66 (m, 1H), 7.37-7.30 (m, 1H), 4.83 (t, J=5.8 Hz, 1H), 4.40 (d, J=5.8 Hz, 2H), 3.78 (t, J=5.5 Hz, 2H), 3.68-3.58 (m, 2H), 2.53 (s, 3H); MS (ES+) m/z 361.2 (M+1).

Example 19.10

Synthesis of 2-(1-(2-(4-chlorophenylamino)-2-oxoethyl)-5-oxo-1H-1,2,4-triazol-4(5H)-yl)-4-methyl-N-(pyridin-3-ylmethyl)thiazole-5-carboxamide

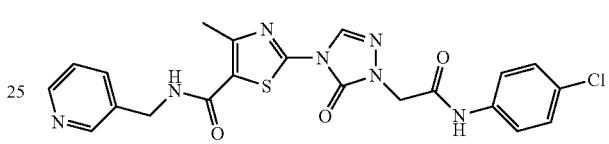

Following the procedure as described in Example 19, making variation as required to replace 4-(trifluoromethyl)benzyl bromide with 2-bromo-N-(4-chlorophenyl)acetamide to react with 4-methyl-2-(5-oxo-1H-1,2,4-triazol-4(5H)-yl)-N-(pyridin-3-ylmethyl)thiazole-5-carboxamide, the title compound was obtained as a white solid in 25% yield: mp 255-256° C. (ethyl acetate/hexane); $^1$H NMR (300 MHz, DMSO-d$_6$) δ 10.39 (s, 1H), 8.90 (t, J=5.8 Hz, 1H), 8.79 (s, 1H), 8.52 (br s, 1H), 8.44 (br s, 1H), 7.75-7.65 (m, 1H), 7.61-7.49 (m, 2H), 7.39-7.28 (m, 3H), 4.67 (s, 2H), 4.40 (d, J=5.8 Hz, 2H), 2.54 (s, 3H); MS (ES+) m/z 484.2 (M+1).

Example 20

Synthesis of 4-methyl-2-(5-oxo-1-(4-(trifluoromethyl)benzyl)-1H-1,2,4-triazol-4(5H)-yl)thiazole-5-carboxylic acid

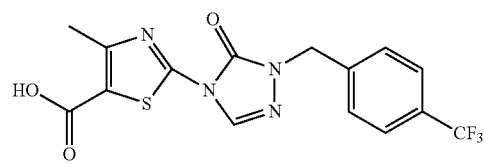

To a solution of ethyl 4-methyl-2-(5-oxo-1-(4-(trifluoromethyl)benzyl)-1H-1,2,4-triazol-4(5H)-yl)thiazole-5-carboxylate (0.16 g, 0.39 mmol) in tetrahydrofuran (8 mL), and water (2 mL) was added lithium hydroxide monohydrate (0.08 g, 1.99 mmol) at ambient temperature. The resulting reaction mixture was heated to reflux for 17 hours. The organic solvent was removed in vacuo and the residue was neutralized to pH 4~5 with 10% hydrochloric acid. The resulting precipitate was filtered and dried to afford the title compound in 99% yield (0.15 g): MS (ES+) m/z 385.2 (M+1).

Example 20.1

Synthesis of 2-(1-(4-(difluoromethoxy)benzyl)-5-oxo-1H-1,2,4-triazol-4(5H)-yl)-4-methylthiazole-5-carboxylic acid

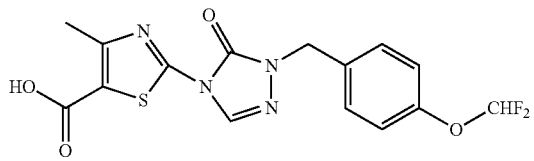

Following the procedure as described in Example 20, making variation as required to replace ethyl 4-methyl-2-(5-oxo-1-(4-(trifluoromethyl)benzyl)-1H-1,2,4-triazol-4(5H)-yl)thiazole-5-carboxylate with ethyl 2-(1-(4-(difluoromethoxy)benzyl)-5-oxo-1H-1,2,4-triazol-4(5H)-yl)-4-methylthiazole-5-carboxylate, the title compound was obtained as a white solid in 91% yield: MS (ES−) m/z 381.1 (M−1).

Example 20.2

Synthesis of 4-methyl-2-(5-oxo-1H-1,2,4-triazol-4(5H)-yl)thiazole-5-carboxylic acid

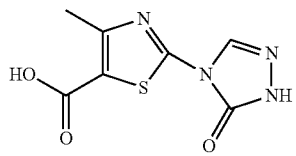

Following the procedure as described in Example 20, making variation as required to replace ethyl 4-methyl-2-(5-oxo-1-(4-(trifluoromethyl)benzyl)-1H-1,2,4-triazol-4(5H)-yl)thiazole-5-carboxylate with ethyl 4-methyl-2-(5-oxo-1H-1,2,4-triazol-4(5H)-yl)thiazole-5-carboxylate, the title compound was obtained as a white solid in 94% yield: MS (ES−) m/z: 225.0 (M−1).

Example 20.3

Synthesis of 2-(1-(2-(4-fluorophenoxy)ethyl)-5-oxo-1H-1,2,4-triazol-4(5H)-yl)-4-methylthiazole-5-carboxylic acid

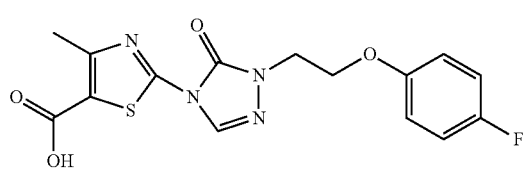

Following the procedure as described in Example 20, making variation as required to replace ethyl 4-methyl-2-(5-oxo-1-(4-(trifluoromethyl)benzyl)-1H-1,2,4-triazol-4(5H)-yl)thiazole-5-carboxylate with ethyl 2-(1-(2-(4-fluorophenoxy)ethyl)-5-oxo-1H-1,2,4-triazol-4(5H)-yl)-4-methylthiazole-5-carboxylate, the title compound was obtained as a white solid in 90% yield: MS (ES−) m/z 363.1 (M−1).

Example 20.4

Synthesis of 2-(1-(4-fluorobenzyl)-5-oxo-1H-1,2,4-triazol-4(5H)-yl)-4-methylthiazole-5-carboxylic acid

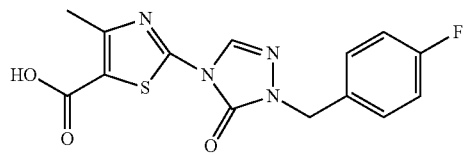

Following the procedure as described in Example 20, making variation as required to replace ethyl 4-methyl-2-(5-oxo-1-(4-(trifluoromethyl)benzyl)-1H-1,2,4-triazol-4(5H)-yl)thiazole-5-carboxylate with ethyl 2-(1-(4-fluorobenzyl)-5-oxo-1H-1,2,4-triazol-4(5H)-yl)-4-methylthiazole-5-carboxylate, the title compound was obtained as a white solid in 99% yield: $^1$H NMR (300 MHz, DMSO-$d_6$) δ 13.40 (br s, 1H), 8.74 (s, 1H), 7.37-7.31 (m, 2H), 7.19-7.11 (m, 2H), 4.96 (s, 2H), 2.57 (s, 3H); MS (ES−) m/z 333.0 (M−1).

Example 20.5

Synthesis of 2-(1-(cyclopropylmethyl)-5-oxo-1H-1,2,4-triazol-4(5H)-yl)-4-methylthiazole-5-carboxylic acid

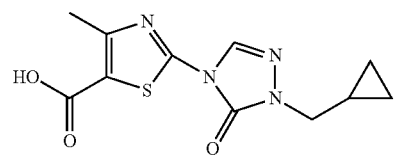

Following the procedure as described in Example 20, making variation as required to replace ethyl 4-methyl-2-(5-oxo-1-(4-(trifluoromethyl)benzyl)-1H-1,2,4-triazol-4(5H)-yl)thiazole-5-carboxylate with ethyl 2-(1-(cyclopropylmethyl)-5-oxo-1H-1,2,4-triazol-4(5H)-yl)-4-methylthiazole-5-carboxylate, the title compound was obtained as a white solid in 92% yield: $^1$H NMR (300 MHz, DMSO-$d_6$) δ 13.39 (br s, 1H), 8.72 (s, 1H), 3.63 (d, J=7.1 Hz, 2H), 2.57 (s, 3H), 1.19-1.04 (m, 1H), 0.53-0.42 (m, 2H), 0.36-0.27 (m, 2H); MS (ES−) m/z 279.0 (M−1).

Example 20.6

Synthesis of 4-methyl-2-(5-oxo-1-(4,4,4-trifluorobutyl)-1H-1,2,4-triazol-4(5H)-yl)thiazole-5-carboxylic acid

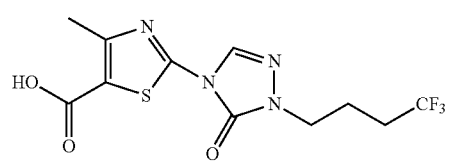

Following the procedure as described in Example 20, making variation as required to replace ethyl 4-methyl-2-(5-oxo-1-(4-(trifluoromethyl)benzyl)-1H-1,2,4-triazol-4(5H)-yl)thiazole-5-carboxylate with ethyl 4-methyl-2-(5-oxo-1-(4,4,4-trifluorobutyl)-1H-1,2,4-triazol-4(5H)-yl)thiazole-5-carboxylate, the title compound was obtained as a white solid in 84% yield: MS (ES−) m/z 335.2 (M−1).

Example 20.7

Synthesis of 4-methyl-2-(5-oxo-1-((5-(trifluoromethyl)furan-2-yl)methyl)-1H-1,2,4-triazol-4(5H)-yl)thiazole-5-carboxylic acid

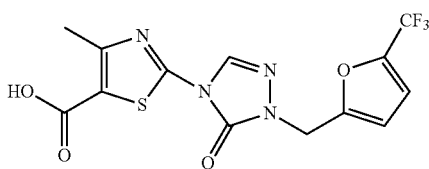

Following the procedure as described in Example 20, making variation as required to replace ethyl 4-methyl-2-(5-oxo-1-(4-(trifluoromethyl)benzyl)-1H-1,2,4-triazol-4(5H)-yl)thiazole-5-carboxylate with ethyl 4-methyl-2-(5-oxo-1-((5-(trifluoromethyl)furan-2-yl)methyl)-1H-1,2,4-triazol-4(5H)-yl)thiazole-5-carboxylate, the title compound was obtained as a white solid in 84% yield: MS (ES−) m/z 373.0 (M−1).

Example 21

Synthesis 4-methyl-2-(5-oxo-1-(4-(trifluoromethyl)benzyl)-1H-1,2,4-triazol-4(5H)-yl)-N-(pyridin-3-ylmethyl)thiazole-5-carboxamide

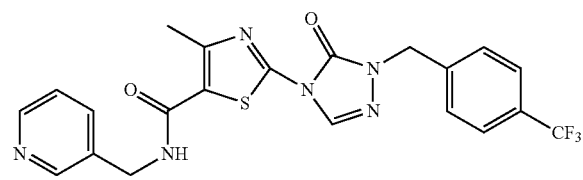

To a solution of 4-methyl-2-(5-oxo-1-(4-(trifluoromethyl)benzyl)-1H-1,2,4-triazol-4(5H)-yl)thiazole-5-carboxylic acid (0.15 g, 0.39 mmol), 1-(3-dimethylaminopropyl)-3-ethylcarbodiimide hydrochloride (0.97 g, 0.51 mmol) and N,N-diisopropylethylamine (0.09 mL, 0.51 mmol) in N,N-dimethylformamide (3 mL) was added 1-hydroxybenzotriazole (0.07 g, 0.51 mmol). The resulting mixture was stirred at ambient temperature for 15 minutes and followed by the addition of 3-(aminomethyl)pyridine (0.05 mL, 0.05 mmol). The reaction mixture was stirred for 17 hours at ambient temperature, diluted with ethyl acetate (30 mL) and washed with water and brine. The organic solution was dried over anhydrous sodium sulfate and filtered. The filtrate was concentrated in vacuo and the residue was purified by column chromatography to afford the title compound as a white powder in 59% yield (0.11 g): mp 156-158° C.; $^1$H NMR (300 MHz, CDCl$_3$) δ 8.58 (s, 1H), 8.51 (s, 1H), 8.27 (s, 1H), 7.68 (d, J=7.8 Hz, 1H), 7.59 (d, J=8.1 Hz, 2H), 7.46 (d, J=8.1 Hz, 2H), 7.31-7.19 (m, 1H), 6.46 (t, J=5.8 Hz, 1H), 5.04 (s, 2H), 4.59 (d, J=5.8 Hz, 2H), 2.63 (s, 3H); $^{13}$C NMR (75 MHz, CDCl$_3$) δ 161.4, 153.4, 150.9, 149.9, 149.3, 149.2, 138.9, 135.7, 131.2, 128.7, 125.8, 123.7, 121.8, 49.1, 41.6, 17.2; MS (ES+) m/z 475.3 (M+1).

Example 21.1

Synthesis of 2-(1-(4-(difluoromethoxy)benzyl)-5-oxo-1H-1,2,4-triazol-4(5H)-yl)-4-methyl-N-(pyridin-3-ylmethyl)thiazole-5-carboxamide

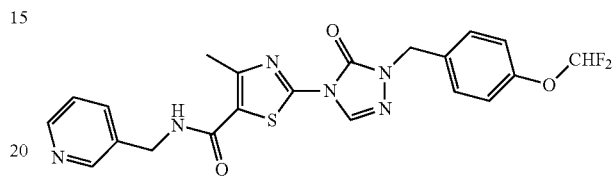

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-(difluoromethoxy)benzyl)-5-oxo-1H-1,2,4-triazol-4(5H)-yl)-4-methylthiazole-5-carboxylic acid to react with pyridin-3-ylmethanamine, the title compound was obtained as a white solid in 49% yield: mp 151-152° C. (ethyl acetate/hexane); $^1$H NMR (300 MHz, CDCl$_3$) δ 8.55 (br s, 2H), 8.23 (s, 1H), 7.72-7.63 (m, 1H), 7.43-7.30 (m, 2H), 7.29-7.20 (m, 1H), 7.12-7.00 (m, 2H), 6.78 (t, J=5.6 Hz, 1H), 6.46 (t, J$_{H-F}$=73.8 Hz, 1H), 4.94 (s, 2H), 4.57 (d, J=5.6 Hz, 2H), 2.61 (s, 3H); $^{13}$C NMR (75 MHz, CDCl$_3$) δ 161.7, 153.4, 151.1, 150.9, 149.9, 149.2, 148.9, 135.8, 132.2, 130.0, 129.9, 121.7, 119.9, 119.2, 115.7, 112.3, 48.9, 41.6, 17.2; MS (ES+) m/z 473.3 (M+1).

Example 21.2

Synthesis of 2-(1-(2-(4-fluorophenoxy)ethyl)-5-oxo-1H-1,2,4-triazol-4(5H)-yl)-4-methyl-N-(pyridin-3-ylmethyl)thiazole-5-carboxamide

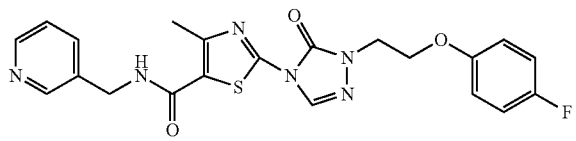

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(2-(4-fluorophenoxy)ethyl)-5-oxo-1H-1,2,4-triazol-4(5H)-yl)-4-methylthiazole-5-carboxylic acid to react with pyridin-3-ylmethanamine, the title compound was obtained as a white solid in 45% yield: mp 154-155° C. (ethyl acetate/hexane); $^1$H NMR (300 MHz, CDCl$_3$) δ 8.58 (br s, 1H), 8.53-8.45 (m, 1H), 8.26 (s, 1H), 7.72-7.65 (m, 1H), 7.30-7.21 (m, 1H), 6.98-6.86 (m, 2H), 6.85-6.75 (m, 2H), 6.61 (t, J=5.8 Hz, 1H), 4.59 (d, J=5.8 Hz, 2H), 4.28-4.15 (m, 4H), 2.63 (s, 3H); $^{13}$C NMR (75 MHz, CDCl$_3$) δ 161.7, 157.6, 154.2, 153.4, 151.0, 149.3, 149.1, 135.8, 133.6, 131.0, 123.7, 121.6, 116.0, 115.9, 115.8, 65.5, 45.3, 41.6, 17.2; MS (ES+) m/z 455.3 (M+1).

Example 21.3

Synthesis of 2-(1-(4-fluorobenzyl)-5-oxo-1H-1,2,4-triazol-4(5H)-yl)-4-methyl-N-(pyridin-3-ylmethyl)thiazole-5-carboxamide

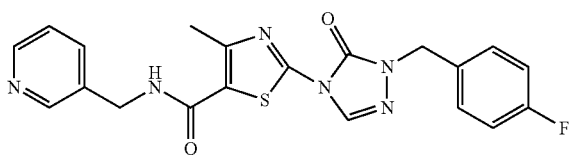

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with pyridin-3-ylmethanamine, the title compound was obtained as a white solid in 68% yield: mp 178-179° C. (ethyl acetate/hexane); $^1$H NMR (300 MHz, CDCl$_3$) δ 8.58 (br s, 1H), 8.51 (br s, 1H), 8.27 (s, 1H), 7.72-7.64 (m, 1H), 7.63-7.54 (m, 2H), 7.51-7.42 (m, 2H), 7.33-7.21 (m, 1H), 6.46 (t, J=5.8 Hz, 1H), 5.04 (s, 2H), 4.59 (d, J=5.8 Hz, 2H), 2.63 (s, 3H); $^{13}$C NMR (75 MHz, CDCl$_3$) δ 164.3, 161.7, 161.0, 153.4, 150.9, 149.9, 149.3, 149.1, 135.7, 130.9, 130.3, 130.2, 121.6, 115.9, 115.7, 48.9, 41.6, 17.2; MS (ES+) m/z 425.3 (M+1).

Example 21.4

Synthesis of 2-(1-(cyclopropylmethyl)-5-oxo-1H-1,2,4-triazol-4(5H)-yl)-4-methyl-N-(pyridin-3-ylmethyl)thiazole-5-carboxamide

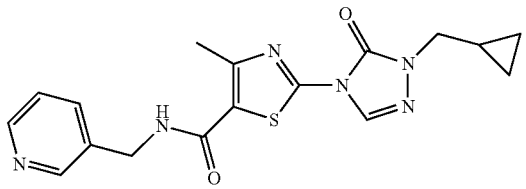

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(cyclopropylmethyl)-5-oxo-1H-1,2,4-triazol-4(5H)-yl)-4-methylthiazole-5-carboxylic acid to react with pyridin-3-ylmethanamine, the title compound was obtained as a white solid in 49% yield: mp 116-117° C. (ethyl acetate/hexane); $^1$H NMR (300 MHz, CDCl$_3$) δ 8.57 (br s, 1H), 8.47 (br s, 1H), 8.24 (s, 1H), 7.79-7.71 (m, 1H), 7.44-7.27 (m, 1H), 6.38 (t, J=5.8 Hz, 1H), 4.62 (d, J=5.8 Hz, 2H), 3.70 (d, J=7.2 Hz, 2H), 2.65 (s, 3H), 1.34-1.14 (m, 1H), 0.63-0.52 (m, 2H), 0.46-0.31 (m, 2H); $^{13}$C NMR (75 MHz, CDCl$_3$) δ 161.8, 153.4, 151.2, 149.9, 149.2, 148.9, 135.8, 130.5, 123.8, 121.4, 117.9, 50.6, 41.6, 17.2, 10.2, 3.7; MS (ES+) m/z 371.3 (M+1).

Example 21.5

Synthesis of 4-methyl-2-(5-oxo-1-(4,4,4-trifluorobutyl)-1H-1,2,4-triazol-4(5H)-yl)-N-(pyridin-3-ylmethyl)thiazole-5-carboxamide

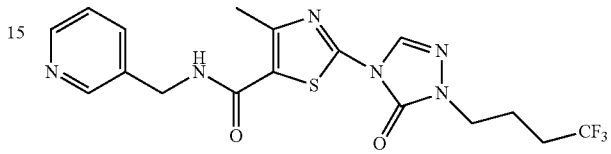

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 4-methyl-2-(5-oxo-1-(4,4,4-trifluorobutyl)-1H-1,2,4-triazol-4(5H)-yl)thiazole-5-carboxylic acid to react with pyridin-3-ylmethanamine, the title compound was obtained as a white solid in 35% yield: mp 184-185° C. (ethyl acetate/hexane); $^1$H NMR (300 MHz, CDCl$_3$) δ 8.57 (br s, 1H), 8.49 (br s, 1H), 8.27 (s, 1H), 7.75-7.63 (m, 1H), 7.32-7.20 (m, 1H), 6.62 (t, J=5.6 Hz, 1H), 4.59 (d, J=5.6 Hz, 2H), 3.91 (t, J=6.5 Hz, 2H), 2.63 (s, 3H), 2.28-1.96 (m, 4H); $^{13}$C NMR (75 MHz, CDCl$_3$) δ 161.7, 153.4, 150.9, 150.0, 149.2, 149.1, 135.8, 131.0, 128.5, 124.8, 121.2, 44.5, 41.2, 31.3, 30.9, 21.3, 17.2; MS (ES+) m/z 427.3 (M+1).

Example 21.6

Synthesis of 4-methyl-2-(5-oxo-1-((5-(trifluoromethyl)furan-2-yl)methyl)-1H-1,2,4-triazol-4(5H)-yl)-N-(pyridin-3-ylmethyl)thiazole-5-carboxamide

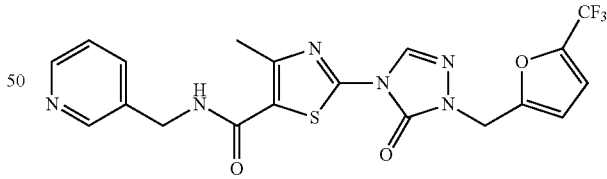

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 4-methyl-2-(5-oxo-1-((5-(trifluoromethyl)furan-2-yl)methyl)-1H-1,2,4-triazol-4(5H)-yl)thiazole-5-carboxylic acid to react with pyridin-3-ylmethanamine, the title compound was obtained as a white solid in 57% yield: mp 124-125° C. (ethyl acetate/hexane); $^1$H NMR (300 MHz, CDCl$_3$) δ 8.63 (s, 2H), 8.28 (s, 1H), 7.82-7.75 (m, 1H), 7.36 (m, 1H), 6.77-6.72 (m, 1H), 6.52 (t, J=5.5 Hz, 1H), 6.47-6.42 (m, 1H), 5.04 (s, 2H), 4.66-4.60 (m, 2H), 2.64 (s, 3H); $^{13}$C NMR (75 MHz, CDCl$_3$) δ 161.6, 115.4, 150.9, 150.8, 149.7, 149.3, 149.2, 135.7, 131.4, 123.7, 121.8, 120.5, 116.9, 112.6, 112.5, 110.4, 42.1, 41.6, 17.2; MS (ES+) m/z 465.3 (M+1).

Example 21.7

Synthesis of 4-methyl-2-(5-oxo-1H-1,2,4-triazol-4(5H)-yl)-N-(pyridin-3-ylmethyl)thiazole-5-carboxamide

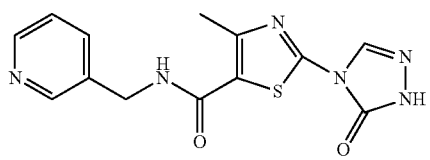

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 4-methyl-2-(5-oxo-1H-1,2,4-triazol-4(5H)-yl)thiazole-5-carboxylic acid to react with pyridin-3-ylmethanamine, the title compound was obtained as a white solid in 65% yield: mp 278-279° C. (ethyl acetate/hexane); $^1$H NMR (300 MHz, DMSO-$d_6$) δ 8.87 (t, J=5.8 Hz, 1H), 8.61 (s, 1H), 8.53-8.48 (m, 1H), 8.45-8.39 (m, 1H), 7.72-7.65 (m, 1H), 7.37-7.29 (m, 1H), 4.39 (d, J=5.8 Hz, 2H), 2.53 (s, 3H); $^{13}$C NMR (75 MHz, DMSO-$d_6$) δ 161.6, 151.9, 151.8, 149.4, 148.6, 135.7, 135.2, 133.4, 123.9, 122.3, 41.0, 17.4; MS (ES+) m/z 317.2 (M+1).

Example 21.8

Synthesis of 2-(1-(4-fluorobenzyl)-5-oxo-1H-1,2,4-triazol-4(5H)-yl)-4-methyl-N-(oxazol-2-ylmethyl)thiazole-5-carboxamide

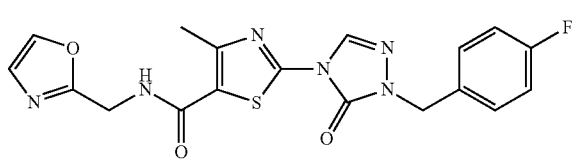

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with oxazol-2-ylmethanamine hydrochloride, the title compound was obtained as a white solid in 57% yield: mp 152-153° C. (ethyl acetate/hexane); $^1$H NMR (300 MHz, CDCl$_3$) δ 8.26 (s, 1H), 7.65 (s, 1H), 7.41-7.32 (m, 2H), 7.09 (s, 1H), 7.07-6.98 (m, 2H), 6.54 (t, J=5.2 Hz, 1H), 4.98 (s, 2H), 4.73 (d, J=5.2 Hz, 2H), 2.67 (s, 3H); MS (ES+) m/z 415.1 (M+1).

Example 21.9

Synthesis of N-((1H-pyrazol-3-yl)methyl)-2-(1-(4-fluorobenzyl)-5-oxo-1H-1,2,4-triazol-4(5H)-yl)-4-methylthiazole-5-carboxamide

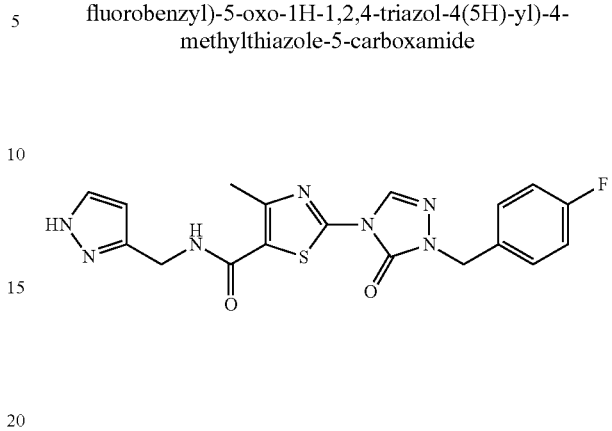

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with (1H-pyrazol-3-yl)methanamine, the title compound was obtained as a white solid in 49% yield: mp 178-179° C. (ethyl acetate/hexane); $^1$H NMR (300 MHz, CDCl$_3$) δ 8.23 (s, 1H), 7.59 (br s, 1H), 7.39-7.30 (m, 2H), 7.06-6.96 (m, 2H), 6.88 (t, J=4.7 Hz, 1H), 6.33 (br s, 1H), 6.05 (br s, 1H), 4.95 (s, 2H), 4.64 (d, J=4.7 Hz, 2H), 2.63 (s, 3H); MS (ES+) m/z 414.2 (M+1).

Example 21.10

Synthesis of 2-(1-(4-fluorobenzyl)-5-oxo-1H-1,2,4-triazol-4(5H)-yl)-4-methyl-N-((1-methyl-1H-pyrazol-4-yl)methyl)thiazole-5-carboxamide

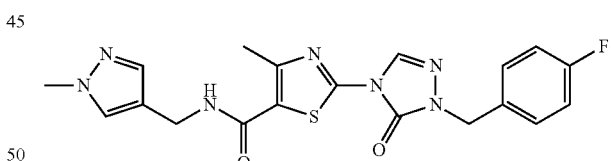

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with (1-methyl-1H-pyrazol-4-yl)methanamine, the title compound was obtained as a white solid in 63% yield: mp 205-206° C. (ethyl acetate/hexane); $^1$H NMR (300 MHz, CDCl$_3$) δ 8.24 (s, 1H), 7.45 (s, 1H), 7.41-7.32 (m, 3H), 7.07-6.98 (m, 2H), 5.88 (t, J=5.3 Hz, 1H), 4.97 (s, 2H), 4.42 (d, J=5.3 Hz, 2H), 3.88 (s, 3H), 2.62 (s, 3H); MS (ES+) m/z 428.2 (M+1).

Example 21.11

Synthesis of 2-(1-(4-fluorobenzyl)-5-oxo-1H-1,2,4-triazol-4(5H)-yl)-4-methyl-N-((2-methylthiazol-5-yl)methyl)thiazole-5-carboxamide

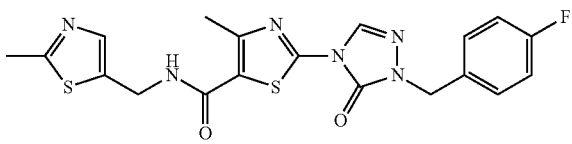

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with (2-methylthiazol-5-yl)methanamine hydrochloride, the title compound was obtained as a white solid in 68% yield: mp 176-177° C. (ethyl acetate/hexane); $^1$H NMR (300 MHz, CDCl$_3$) δ 8.25 (s, 1H), 7.41-7.31 (m, 2H), 7.07-6.97 (m, 3H), 6.49 (t, J=5.3 Hz, 1H), 4.97 (s, 2H), 4.62 (d, J=5.3 Hz, 2H), 2.70 (s, 3H), 2.64 (s, 3H); MS (ES+) m/z 445.1 (M+1).

Example 21.12

Synthesis of 2-(1-(4-fluorobenzyl)-5-oxo-1H-1,2,4-triazol-4(5H)-yl)-4-methyl-N-(thiazol-2-ylmethyl)thiazole-5-carboxamide

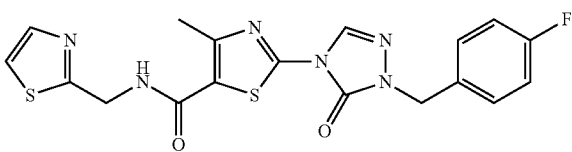

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with thiazol-2-ylmethanamine hydrochloride, the title compound was obtained as a white solid in 66% yield: mp 189-190° C. (ethyl acetate/hexane); $^1$H NMR (300 MHz, CDCl$_3$) δ 8.25 (s, 1H), 7.74 (br s, 1H), 7.40-7.31 (m, 3H), 7.06-6.97 (m, 2H), 6.78 (t, J=5.4 Hz, 1H), 4.97 (s, 2H), 4.92 (d, J=5.4 Hz, 2H), 2.67 (s, 3H); MS (ES+) m/z 431.1 (M+1).

Example 21.13

Synthesis of 2-(1-(4-fluorobenzyl)-5-oxo-1H-1,2,4-triazol-4(5H)-yl)-4-methyl-N-(oxazol-4-ylmethyl)thiazole-5-carboxamide

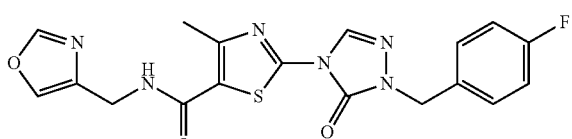

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with oxazol-4-ylmethanamine hydrochloride, the title compound was obtained as a white solid in 51% yield: mp 183-184° C. (ethyl acetate/hexane); $^1$H NMR (300 MHz, CDCl$_3$) δ 8.25 (s, 1H), 7.88 (s, 1H), 7.67 (s, 1H), 7.41-7.32 (m, 2H), 7.08-6.97 (m, 2H), 6.31 (t, J=5.3 Hz, 1H), 4.97 (s, 2H), 4.52 (d, J=5.3 Hz, 2H), 2.63 (s, 3H); MS (ES+) m/z 415.2 (M+1).

Example 21.14

Synthesis of 2-(1-(4-fluorobenzyl)-5-oxo-1H-1,2,4-triazol-4(5H)-yl)-4-methyl-N-((1-methyl-1H-imidazol-4-yl)methyl)thiazole-5-carboxamide

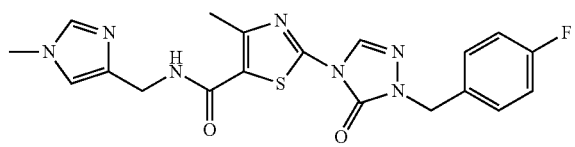

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with (1-methyl-1H-imidazol-4-yl)methanamine, the title compound was obtained as a white solid in 71% yield: mp 225-226° C. (ethyl acetate/hexane); $^1$H NMR (300 MHz, CDCl$_3$) δ 8.24 (s, 1H), 7.55 (s, 1H), 7.41-7.32 (m, 2H), 7.08-6.97 (m, 2H), 6.91 (s, 1H), 6.78 (t, J=5.3 Hz, 1H), 4.96 (s, 2H), 4.53 (d, J=5.3 Hz, 2H), 3.70 (s, 3H), 2.64 (s, 3H); MS (ES+) m/z 428.2 (M+1).

Example 21.15

Synthesis of 2-(1-(4-fluorobenzyl)-5-oxo-1H-1,2,4-triazol-4(5H)-yl)-4-methyl-N-((5-methylpyrazin-2-yl)methyl)thiazole-5-carboxamide

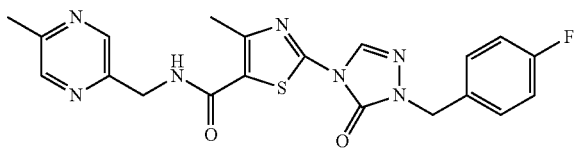

Following the procedure as described in Example 21, making variations as required to replace 4-methyl-2-(5-oxo-1-(4-(trifluoromethyl)benzyl)-1H-1,2,4-triazol-4(5H)-yl)thiazole-5-carboxylic acid with 2-(1-(4-fluorobenzyl)-5-oxo-1H-1,2,4-triazol-4(5H)-yl)-4-methylthiazole-5-carboxylic acid to react with (5-methylpyrazin-2-yl)methanamine, the title compound was obtained as a white solid in 64% yield: mp 188-189° C. (ethyl acetate/hexane); $^1$H NMR (300 MHz, CDCl$_3$) δ 8.53 (s, 1H), 8.40 (s, 1H), 8.26 (s, 1H), 7.43-7.33 (m, 2H), 7.10-6.99 (m, 2H), 6.97 (t, J=4.8 Hz, 1H), 4.98 (s, 2H), 4.72 (d, J=4.8 Hz, 2H), 2.66 (s, 3H), 2.58 (s, 3H); MS (ES+) m/z 440.2 (M+1).

Example 22

Synthesis of N-benzyl-4-methyl-2-(2-oxoimidazolidin-1-yl)thiazole-5-carboxamide

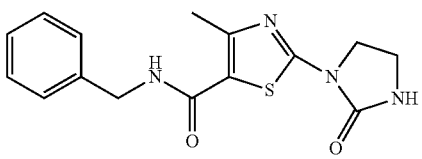

To a solution of 2-amino-N-benzyl-4-methylthiazole-5-carboxamide (3.00 g, 12.1 mmol) in tetrahydrofuran (70 mL) was added N,N-diisopropylethylamine (3.13 g, 24.3 mmol), followed by the addition of 2-chloroethyl isocyanate (1.66 g, 15.76 mmol) at ambient temperature. The resulting reaction mixture was stirred at ambient temperature for 2 days. The solvent was removed in vacuo and the residue was washed with water (100 mL) and t-butyl methyl ether (200 mL). The resulting white solid was added to a suspension of potassium carbonate (2.01 g, 14.55 mmol) and tetrabutylammonium iodide (0.16 g, 0.44 mmol) in dioxane (50 mL). The reaction mixture was refluxed for 24 hours. The solvent was removed in vacuo, and the residue was washed with water (200 mL) and ethyl acetate (50 mL). The residue was recrystallized in methanol to afford the title compound as a colorless solid in 60% yield (2.3 g): mp 226-228° C. (methanol); $^1$H NMR (300 MHz, DMSO-d$_6$) δ 8.45 (t, J=5.8 Hz, 1H), 7.71 (s, 1H), 7.31-7.16 (m, 5H), 4.33 (d, J=5.8 Hz, 2H), 3.99 (m, 2H), 3.46 (m, 2H), 2.43 (s, 3H); $^{13}$C NMR (75 MHz, DMSO-d$_6$) δ 162.2, 157.6, 157.1, 151.4, 140.1, 128.6, 127.6, 127.1, 118.1, 44.5, 43.0, 37.7, 17.5; MS (ES+) m/z 317.2 (M+1).

Example 23

Synthesis of N-benzyl-2-(3-(4-cyanobenzyl)-2-oxoimidazolidin-1-yl)-4-methylthiazole-5-carboxamide

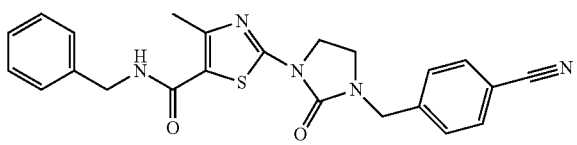

To a solution of N-benzyl-4-methyl-2-(2-oxoimidazolidin-1-yl)thiazole-5-carboxamide (0.20 g, 0.63 mmol) in anhydrous N,N-dimethylformamide (8 mL) was added potassium carbonate (0.10 g, 0.69 mmol), followed by the addition of 4-(chloromethyl)benzonitrile (0.11 g, 0.69 mmol). The reaction mixture was stirred at 80° C. for 4 hours. The solvent was concentrated in vacuo to one-fourth, then diluted with ethyl acetate (150 mL) and washed with water (150 mL). The organic layer was dried over anhydrous sodium sulfate, filtered and concentrated in vacuo. The residue was purified by column chromatography eluted with ethyl acetate/hexane to afford the title compound as a colorless solid in 40% yield (0.11 g): mp 176-178° C. (ethyl acetate/hexanes); $^1$H NMR (300 MHz, CDCl$_3$) δ 7.65-7.63 (m, 2H), 7.40-7.24 (m, 7H), 5.88 (t, J=5.6 Hz, 1H), 4.56 (d, J=5.6 Hz, 2H), 4.51 (s, 2H), 4.13-4.07 (m, 2H), 3.50-3.44 (m, 2H), 2.60 (s, 3H); $^{13}$C NMR (75 MHz, CDCl$_3$) δ 162.2, 157.0, 155.5, 152.8, 141.1, 137.8, 132.7, 129.0, 128.8, 128.7, 127.8, 118.3, 117.6, 112.1, 47.7, 44.1, 42.0, 17.2; MS (ES+) m/z 432.3 (M+1).

Example 23.1

Synthesis of N-benzyl-4-methyl-2-(2-oxo-3-(2-(trifluoromethyl)benzyl)imidazolidin-1-yl)thiazole-5-carboxamide

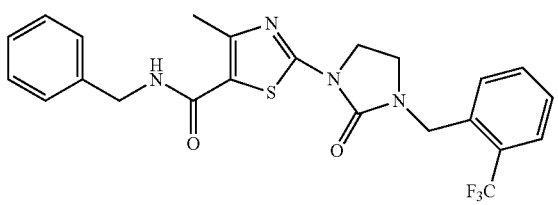

Following the procedure as described in Example 23, making variations as required to replace 4-(chloromethyl)benzonitrile with 1-(bromomethyl)-2-(trifluoromethyl)benzene to react with N-benzyl-4-methyl-2-(2-oxoimidazolidin-1-yl)thiazole-5-carboxamide, the title compound was obtained as a colorless solid in 34% yield: mp 138-140° C. (ethyl acetate/hexanes); $^1$H NMR (300 MHz, CDCl$_3$) δ 7.67-7.65 (m, 1H), 7.59-7.46 (m, 2H), 7.42-7.27 (m, 6H), 5.89 (t, J=5.5 Hz, 1H), 4.68 (s, 2H), 4.56 (d, J=5.5 Hz, 2H), 4.11-4.05 (m, 2H), 3.49-3.43 (m, 2H), 2.61 (s, 3H); $^{13}$C NMR (75 MHz, CDCl$_3$); 162.3, 157.2, 155.7, 153.2, 137.9, 134.7, 132.5, 130.0, 128.8, 127.8, 126.1, 125.9, 122.3, 117.4, 44.0, 43.9, 42.0, 41.9, 17.2; MS (ES+) m/z 475.3 (M+1).

Example 23.2

Synthesis of ethyl 3-((3-(5-(benzylcarbamoyl)-4-methylthiazol-2-yl)-2-oxoimidazolidin-1-yl)methyl)benzoate

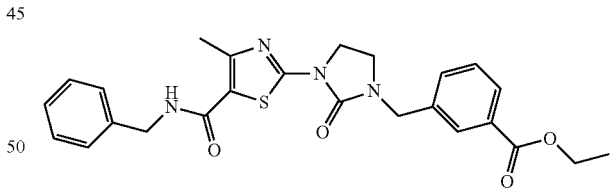

Following the procedure as described in Example 23, making variations as required to replace 4-(chloromethyl)benzonitrile with ethyl 4-(bromomethyl)benzoate to react with N-benzyl-4-methyl-2-(2-oxoimidazolidin-1-yl)thiazole-5-carboxamide, the title compound was obtained as a colorless solid in 20% yield: mp 118-120° C. (ethyl acetate/hexanes); $^1$H NMR (300 MHz, CDCl$_3$) δ 8.01 (d, J=8.3 Hz, 2H), 7.35-7.27 (m, 7H), 5.88 (t, J=5.5 Hz, 1H), 4.56 (d, J=5.5 Hz, 2H), 4.51 (s, 2H), 4.36 (q, J=7.1 Hz, 2H), 4.10-4.05 (m, 2H), 3.47-3.42 (m, 2H), 2.60 (s, 3H), 1.37 (t, J=7.1 Hz, 3H); $^{13}$C NMR (75 MHz, CDCl$_3$) δ 166.1, 162.3, 157.1, 155.4, 153.1, 140.5, 137.9, 130.3, 130.1, 128.8, 128.1, 127.8, 127.6, 117.3, 61.1, 47.7, 44.0, 42.0, 41.8, 17.2, 14.3; MS (ES+) m/z 479.4 (M+1).

Example 23.3

Synthesis of N-benzyl-2-(3-(3-fluorobenzyl)-2-ox-oimidazolidin-1-yl)-4-methylthiazole-5-carboxamide

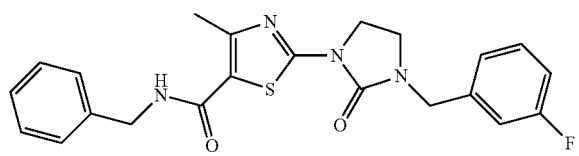

Following the procedure as described in Example 23, making variations as required to replace 4-(chloromethyl)benzonitrile with 1-(bromomethyl)-3-fluorobenzene to react with N-benzyl-4-methyl-2-(2-oxoimidazolidin-1-yl)thiazole-5-carboxamide, the title compound was obtained as a colorless solid in 8% yield: mp 155-156° C. (ethyl acetate); $^1$H NMR (300 MHz, CDCl$_3$) δ 7.40-7.27 (m, 6H), 7.06-6.96 (m, 3H), 5.87 (t, J=5.7 Hz, 1H), 4.56 (d, J=5.7 Hz, 2H), 4.45 (s, 2H), 4.10-4.05 (m, 2H), 3.49-3.43 (m, 2H), 2.60 (s, 3H); $^{13}$C NMR (75 MHz, CDCl$_3$) δ 162.2, 157.8, 155.5, 151.4, 140.1, 136.7, 129.1, 128.7, 128.2, 127.9, 127.6, 127.1, 118.2, 47.3, 43.0, 42.4, 42.0, 17.5; MS (ES+) m/z 425.3 (M+1).

Example 23.4

Synthesis of N-benzyl-4-methyl-2-(2-oxo-3-((5-(trifluoromethyl)furan-2-yl)methyl)imidazolidin-1-yl) thiazole-5-carboxamide

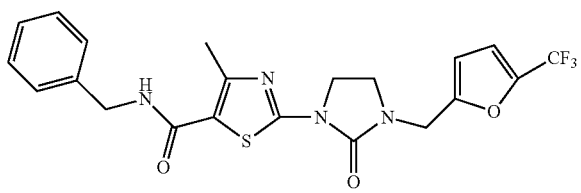

Following the procedure as described in Example 23, making variations as required to replace 4-(chloromethyl)benzonitrile with 2-(bromomethyl)-5-(trifluoromethyl)furan to react with N-benzyl-4-methyl-2-(2-oxoimidazolidin-1-yl) thiazole-5-carboxamide, the title compound was obtained as a colorless solid in 27% yield: mp 143-145° C. (dichloromethane/hexanes); $^1$H NMR (300 MHz, CDCl$_3$) δ 7.35-7.28 (m, 5H), 6.76-6.75 (m, 1H), 6.39 (d, J=3.0 Hz, 1H), 5.90 (t, J=6.0 Hz, 1H), 4.57 (d, J=6.0 Hz, 2H), 4.51 (s, 2H), 4.11 (t, J=9.0 Hz, 2H), 3.64 (t, J=9.0 Hz, 2H), 2.62 (s, 3H); MS (ES+) m/z 465.3 (M+1).

Example 23.5

Synthesis of N-benzyl-4-methyl-2-(3-((5-methyl-1-phenyl-1H-1,2,4-triazol-3-yl)methyl)-2-oxoimidazolidin-1-yl)thiazole-5-carboxamide

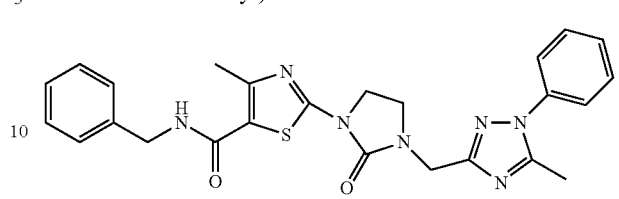

Following the procedure as described in Example 23, making variations as required to replace 4-(chloromethyl)benzonitrile with 3-(bromomethyl)-5-methyl-1-phenyl-1H-1,2,4-triazole to react with N-benzyl-4-methyl-2-(2-oxoimidazolidin-1-yl)thiazole-5-carboxamide, the title compound was obtained as a colorless solid in 17% yield: mp 139-141° C. (dichloromethane/hexanes); $^1$H NMR (300 MHz, CDCl$_3$) δ 7.98 (d, J=8.3 Hz, 2H), 7.49-7.29 (m, 8H), 5.88 (s, 1H), 4.62 (s, 2H), 4.57 (d, J=5.6 Hz, 2H), 4.13-4.08 (m, 2H), 3.68-3.62 (m, 2H), 2.63 (s, 3H), 2.41 (s, 3H); MS (ES+) m/z: 488.3 (M+1).

Example 23.6

Synthesis of N-benzyl-4-methyl-2-(2-oxo-3-((tetrahydro-2H-pyran-2-yl)methyl) imidazolidin-1-yl) thiazole-5-carboxamide

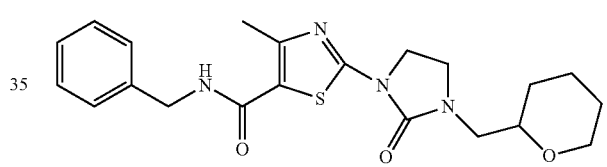

Following the procedure as described in Example 23, making variations as required to replace 4-(chloromethyl)benzonitrile with 2-(bromomethyl)tetrahydro-2H-pyran to react with N-benzyl-4-methyl-2-(2-oxoimidazolidin-1-yl)thiazole-5-carboxamide, the title compound was obtained as a colorless solid in 27% yield: $^1$H NMR (300 MHz, CDCl$_3$) δ 7.34-7.30 (m, 5H), 5.86 (s, 1H), 4.56 (d, J=3.0 Hz, 2H), 4.08 (t, J=9.0 Hz, 2H), 3.98-3.94 (m, 1H), 3.84-3.3.63 (m, 2H), 3.55-3.35 (m, 3H), 3.18-3.16 (m, 1H), 2.62 (s, 3H), 1.86-1.83 (m, 1H), 1.60-1.22 (m, 5H); MS (ES+) m/z 415.3 (M+1).

Example 23.7

Synthesis of 2-(3-(2-(1H-indol-3-yl)ethyl)-2-oxoimidazolidin-1-yl)-N-benzyl-4-methylthiazole-5-carboxamide

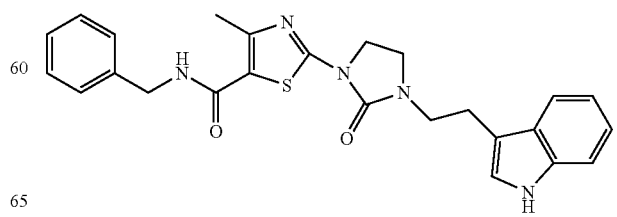

Following the procedure as described in Example 23, making variations as required to replace 4-(chloromethyl)benzonitrile with 3-(2-bromoethyl)-1H-indole to react with N-benzyl-4-methyl-2-(2-oxoimidazolidin-1-yl)thiazole-5-carboxamide, the title compound was obtained as a colorless solid in 22% yield: mp 215-217° C. (dichloromethane/hexanes); $^1$H NMR (300 MHz, DMSO-d$_6$) δ 10.86 (s, 1H), 8.50 (t, J=6.0 Hz, 1H), 7.57 (d, J=6.0 Hz, 1H), 7.36-7.20 (m, 7H), 7.10-6.96 (m, 2H), 4.38 (d, J=6.0 Hz, 2H), 3.96 (t, J=9.0 Hz, 2H), 3.61-3.51 (m, 4H), 2.95 (t, J=9.0 Hz, 2H), 2.47 (s, 3H); MS (ES+) m/z 460.2 (M+1).

Example 23.8

Synthesis of N-benzyl-2-(3-((2,3-dihydrobenzo[b][1,4]dioxin-2-yl)methyl)-2-oxoimidazolidin-1-yl)-4-methylthiazole-5-carboxamide

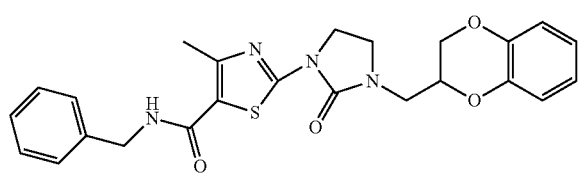

Following the procedure as described in Example 23, making variations as required to replace 4-(chloromethyl)benzonitrile with 2-(bromomethyl)-2,3-dihydrobenzo[b][1,4]dioxine to react with N-benzyl-4-methyl-2-(2-oxoimidazolidin-1-yl)thiazole-5-carboxamide, the title compound was obtained as an oil in 3% yield: $^1$H NMR (300 MHz, CDCl$_3$) δ 7.35-7.31 (m, 5H), 6.88-6.87 (m, 4H), 5.89 (br s, 1H), 4.57 (d, J=6.0 Hz, 2H), 4.43-4.39 (m, 1H), 4.33-4.28 (m, 1H), 4.17-3.97 (m, 3H), 3.86-3.53 (m, 4H), 2.63 (s, 3H); MS (ES+) m/z 465.2 (M+1).

Example 23.9

Synthesis of methyl 3-((3-(5-(benzylcarbamoyl)-4-methylthiazol-2-yl)-2-oxoimidazolidin-1-yl)methyl)benzoate

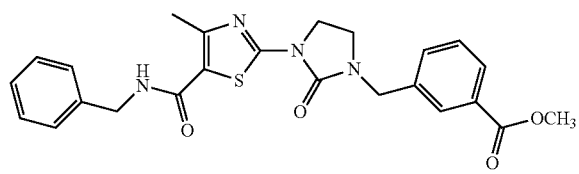

Following the procedure as described in Example 23, making variations as required to replace 4-(chloromethyl)benzonitrile with methyl 3-(bromomethyl)benzoate to react with N-benzyl-4-methyl-2-(2-oxoimidazolidin-1-yl)thiazole-5-carboxamide, the title compound was obtained as a colorless solid in 43% yield: mp 49-51° C. (dichloromethane/hexanes); $^1$H NMR (300 MHz, CDCl$_3$) δ 8.01-7.94 (m, 2H), 7.53-7.31 (m, 7H), 5.91 (br s, 1H), 4.58 (d, J=6.0 Hz, 2H), 4.53 (s, 2H), 4.12-4.06 (m, 2H), 3.92 (s, 3H), 3.50-3.44 (m, 2H), 2.62 (s, 3H); MS (ES+) m/z 465.2 (M+1).

Example 23.10

Synthesis of methyl 2-((3-(5-(benzylcarbamoyl)-4-methylthiazol-2-yl)-2-oxoimidazolidin-1-yl)methyl)benzoate

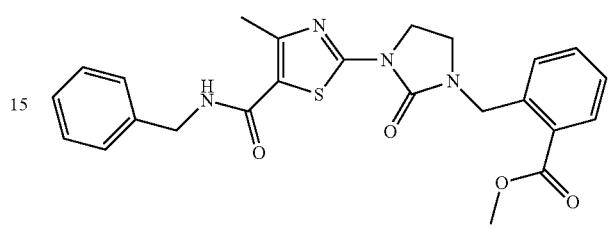

Following the procedure as described in Example 23, making variations as required to replace 4-(chloromethyl)benzonitrile with methyl 2-(bromomethyl)benzoate (prepared according to Dvornikovs, V., and Smithrud, D. B., J. Org. Chem., (2002), 67, 2160-2167) to react with N-benzyl-4-methyl-2-(2-oxoimidazolidin-1-yl)thiazole-5-carboxamide, the title compound was obtained as a colorless solid in 52% yield: mp 130-133° C. (dichloromethane/hexanes); $^1$H NMR (300 MHz, CDCl$_3$) δ 7.97-7.94 (m, 1H), 7.51-7.27 (m, 8H), 5.95 (br s, 1H), 4.90 (s, 2H), 4.56 (d, J=5.6 Hz, 2H), 4.10-4.05 (m, 2H), 3.90 (s, 3H), 3.56-3.51 (m, 2H), 2.62 (s, 3H); MS (ES+) m/z 465.2 (M+1).

Example 24

Synthesis of methyl 2-(3-(cyclopropylmethyl)-2-oxoimidazolidin-1-yl)thiazole-5-carboxylate

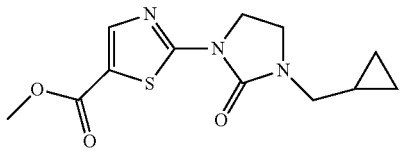

To a solution of methyl 2-(2-oxoimidazolidin-1-yl)thiazole-5-carboxylate (0.50 g, 2.20 mmol) in N,N-dimethylformamide (15 mL) was added sodium hydride (0.084 g, 3.52 mmol, 60% in mineral oil) at 0° C. The reaction mixture was stirred at 0° C. for 0.5 hours, followed by the addition of (bromomethyl)cyclopropane (0.36 g, 2.64 mmol) and catalytic amount of tetra-n-butylammonium iodide. The reaction mixture was stirred at ambient temperature for 20 hours. The solvent was concentrated in vacuo, then diluted with ethyl acetate (200 mL) and washed with water (150 mL). The organic layer was dried over anhydrous sodium sulfate, filtered and concentrated in vacuo. The residue was purified by column chromatography eluted with ethyl acetate/hexane (2/3) to afford the title compound as a colorless solid in 24% yield (0.15 g): mp 124-126° C. (ethyl acetate/hexanes); $^1$H NMR (300 MHz, CDCl$_3$) δ 8.01 (s, 1H), 4.15-4.10 (m, 2H), 3.83 (s, 3H), 3.73-3.68 (m, 2H) 3.20 (d, J=7.1 Hz, 2H), 0.97-0.92 (m, 1H), 0.61-0.53 (m, 2H), 0.30-0.20 (m, 2H); $^{13}$C NMR (75 MHz, CDCl$_3$) δ 163.4, 162.6, 155.0, 145.2, 121.6, 52.0, 48.6, 42.2, 42.1, 8.9, 3.4; MS (ES+) m/z 282.2 (M+1).

Example 24.1

Synthesis of ethyl 2-(3-(4-fluorobenzyl)-2-oxoimidazolidin-1-yl)-4-(trifluoromethyl)thiazole-5-carboxylate

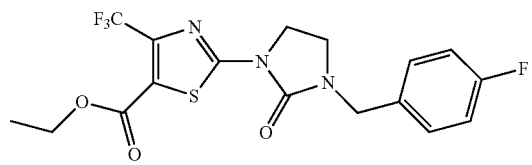

Following the procedure as described in Example 24, making variations as required to replace 2-(2-oxoimidazolidin-1-yl)thiazole-5-carboxylate with ethyl 2-(2-oxoimidazolidin-1-yl)-4-(trifluoromethyl)thiazole-5-carboxylate to react with 1-(bromomethyl)-4-fluorobenzene, the title compound was obtained as a colorless solid in 94% yield: $^1$H NMR (300 MHz, CDCl$_3$) δ 7.28-7.25 (m, 2H), 7.06-7.01 (m, 2H), 4.46 (s, 2H), 4.33 (q, J=7.1 Hz, 2H), 4.13-4.07 (m, 2H), 3.50-3.44 (m, 2H), 1.34 (t, J=7.1 Hz, 3H); MS (ES+) m/z 418.1 (M+1).

Example 25

Synthesis of 3-((3-(5-(benzylcarbamoyl)-4-methylthiazol-2-yl)-2-oxoimidazolidin-1-yl)methyl)benzoic acid

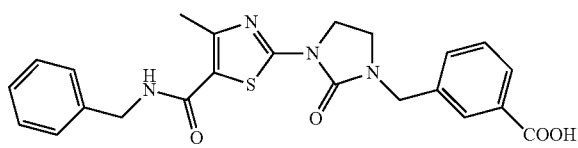

To a solution of ethyl 3-((3-(5-(benzylcarbamoyl)-4-methylthiazol-2-yl)-2-oxoimidazolidin-1-yl)methyl)benzoate (0.093 g, 0.19 mmol) in tetrahydrofuran (5 mL) and water (2.5 mL) was added lithium hydroxide monohydrate (0.032 g, 0.77 mmol) at ambient temperature. The resulting reaction mixture was heated to reflux for 14 hours. The solvent was removed in vacuo, and the residue was neutralized to pH 3-4 with 10% hydrochloric acid solution. The resulting precipitate was filtered, washed with water (30 mL), hexane (30 mL) and dried to afford the title compound as a colorless solid in 97% yield (0.083 g): mp 120-123° C. (water); $^1$H NMR (300 MHz, DMSO-d$_6$) δ 13.10 (br s, 1H), 8.49 (t, J=6.0 Hz, 1H), 7.91-7.88 (m, 2H), 7.40-7.38 (m, 2H), 7.32-7.16 (m, 5H), 4.48 (s, 2H), 4.35-4.33 (m, 2H), 4.01-3.96 (m, 2H), 3.48-3.42 (m, 2H), 2.44 (s, 3H); $^{13}$C NMR (75 MHz, DMSO-d$_6$) δ 167.5, 162.2, 157.8, 155.6, 151.3, 142.0, 140.1, 130.4, 130.1, 128.7, 128.2, 127.6, 127.1, 118.3, 47.1, 43.0, 42.4, 42.2, 17.5; MS (ES+) m/z 451.2 (M+1).

Example 25.1

Synthesis of 2-(3-(cyclopropylmethyl)-2-oxoimidazolidin-1-yl)thiazole-5-carboxylic acid

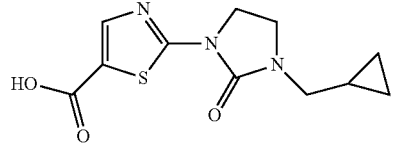

Following the procedure as described in Example 25, making variations as required to replace ethyl 3-((3-(5-(benzylcarbamoyl)-4-methylthiazol-2-yl)-2-oxoimidazolidin-1-yl)methyl)benzoate with methyl 2-(3-(cyclopropylmethyl)-2-oxoimidazolidin-1-yl)thiazole-5-carboxylate, the title compound was obtained as a colorless solid in 93% yield: mp 250-252° C. (water); $^1$H NMR (300 MHz, DMSO-d$_6$) δ 12.97 (s, 1H), 7.93 (s, 1H), 4.03-3.96 (m, 2H), 3.66-3.61 (m, 2H), 3.08 (d, J=7.1 Hz, 2H), 0.96-0.87 (m, 1H), 0.49-0.43 (m, 2H), 0.21-0.16 (m, 2H); $^{13}$C NMR (75 MHz, DMSO-d$_6$) δ 163.3, 162.8, 155.0, 145.2, 122.4, 48.2, 42.5, 42.4, 9.27, 3.62; MS (ES+) m/z 268.2 (M+1).

Example 25.2

Synthesis of 2-(3-(4-fluorobenzyl)-2-oxoimidazolidin-1-yl)-4-(trifluoromethyl)thiazole-5-carboxylic acid

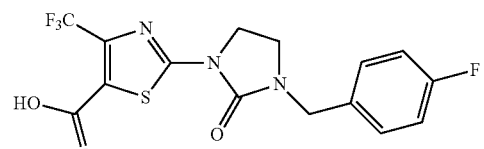

Following the procedure as described in Example 25, making variations as required to replace ethyl 3-((3-(5-(benzylcarbamoyl)-4-methylthiazol-2-yl)-2-oxoimidazolidin-1-yl)methyl)benzoate with ethyl 2-(3-(4-fluorobenzyl)-2-oxoimidazolidin-1-yl)-4-(trifluoromethyl)thiazole-5-carboxylate, the title compound was obtained as a colorless solid in 69% yield: $^1$H NMR (300 MHz, DMSO-d$_6$) δ 13.74 (br s, 1H), 7.36-7.30 (m, 2H), 7.19-7.13 (m, 2H), 4.41 (s, 2H), 4.02-3.97 (m, 2H), 3.47-3.41 (m, 2H); MS (ES+) m/z 390.1 (M+1).

Example 25.3

Synthesis of 3-((3-(5-(benzylcarbamoyl)-4-methylthiazol-2-yl)-2-oxoimidazolidin-1-yl)methyl)benzoic acid

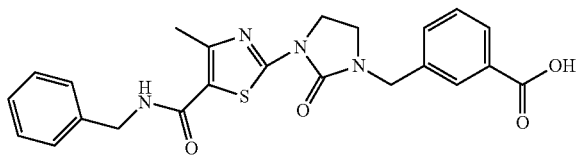

Following the procedure as described in Example 25, making variations as required to replace ethyl 3-((3-(5-(benzylcarbamoyl)-4-methylthiazol-2-yl)-2-oxoimidazolidin-1-yl)methyl)benzoate with methyl 3-((3-(5-(benzylcarbamoyl)-4-methylthiazol-2-yl)-2-oxoimidazolidin-1-yl)methyl) benzoate, the title compound was obtained as a colorless solid in 85% yield: mp 143-145° C. (methanol/hexanes); $^1$H NMR (300 MHz, DMSO-d$_6$) δ 8.55 (t, J=5.9 Hz, 1H), 7.89-7.87 (m, 2H), 7.58-7.46 (m, 2H), 7.37-7.20 (m, 5H), 4.51 (s, 2H), 4.38 (d, J=5.9 Hz, 2H), 4.04-3.98 (m, 2H), 3.50-3.3.45 (m, 2H), 2.47 (s, 3H); MS (ES+) m/z 451.2 (M+1).

Example 25.4

Synthesis of 2-((3-(5-(benzylcarbamoyl)-4-methylthiazol-2-yl)-2-oxoimidazolidin-1-yl)methyl)benzoic acid

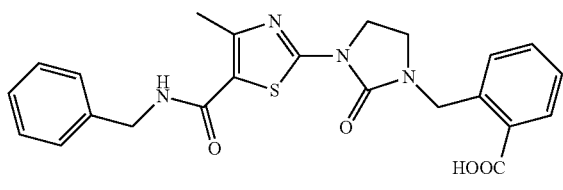

Following the procedure as described in Example 25, making variations as required to replace ethyl 3-((3-(5-(benzylcarbamoyl)-4-methylthiazol-2-yl)-2-oxoimidazolidin-1-yl)methyl)benzoate with methyl 2-((3-(5-(benzylcarbamoyl)-4-methylthiazol-2-yl)-2-oxoimidazolidin-1-yl)methyl) benzoate, the title compound was obtained as a colorless solid in 76% yield: mp 153-156° C. (methanol/hexanes); $^1$H NMR (300 MHz, DMSO-d$_6$) δ 8.49 (t, J=6.0 Hz, 1H), 7.86 (d, J=9.0 Hz, 1H), 7.57-7.51 (m, 1H), 7.40-7.19 (m, 7H), 4.78 (s, 2H), 4.34 (d, J=6.0 Hz, 2H), 4.01 (t, J=9.0 Hz, 2H), 3.50 (t, J=9.0 Hz, 2H), 2.46 (s, 3H); MS (ES+) m/z 451.2 (M+1).

Example 26

Synthesis of 2-(3-(cyclopropylmethyl)-2-oxoimidazolidin-1-yl)-N-(pyridin-3-ylmethyl)thiazole-5-carboxamide

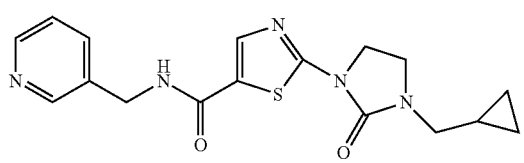

To a solution of 2-(3-(cyclopropylmethyl)-2-oxoimidazolidin-1-yl)thiazole-5-carboxylic acid (0.10 g, 0.37 mmol) in anhydrous N,N-dimethylformamide (10 mL) was added N,N-diisopropylethylamine (0.17 mL, 1.34 mmol), followed by the addition of 1-ethyl-3-(3-dimethylaminopropyl)carbodiimide hydrochloride (0.11 g, 0.59 mmol). The reaction was stirred at ambient temperature for 0.5 hours. 1-Hydroxybenzotriazole (0.07 g, 0.52 mmol) was added, followed by the addition of pyridin-3-ylmethanamine (0.06 g, 0.56 mmol). The reaction mixture was stirred at ambient temperature for 18 hours. The solvent was concentrated in vacuo. The residue was diluted with dichloromethane (150 mL), washed with water (100 mL) and brine (50 mL). The organic layer was dried over anhydrous sodium sulfate, filtered and concentrated in vacuo. The residue was crystallized in dichloromethane and hexane to yield the title compound as a colorless solid in 40% yield (0.065 g): mp 190-192° C. (dichloromethane/hexanes); $^1$H NMR (300 MHz, DMSO-d$_6$) δ 8.98 (t, J=5.8 Hz 1H), 8.49 (m, 1H), 8.43-8.39 (m, 1H), 7.98 (s, 1H), 7.68-7.65 (m, 1H), 7.34-7.30 (m, 1H), 4.40 (d, J=5.8 Hz, 2H), 4.01-3.95 (m, 2H), 3.65-3.59 (m, 2H), 3.07 (d, J=7.1 Hz, 2H), 1.01-0.85 (m, 1H), 0.53-0.39 (m, 2H), 0.21-0.16 (m, 2H); $^{13}$C NMR (75 MHz, DMSO-d$_6$) δ 161.5, 161.3, 155.1, 149.3, 148.6, 140.1, 135.7, 135.3, 127.1, 123.9, 48.2, 42.5, 42.3, 9.31, 3.63; MS (ES+) m/z 358.2 (M+1).

Example 26.1

Synthesis of 2-(3-(4-fluorobenzyl)-2-oxoimidazolidin-1-yl)-N-(pyridin-3-ylmethyl)-4-(trifluoromethyl)thiazole-5-carboxamide

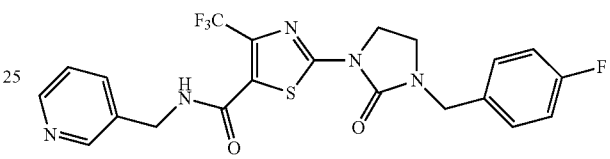

Following the procedure as described in Example 26, making variations as required to replace 2-(3-(cyclopropylmethyl)-2-oxoimidazolidin-1-yl)thiazole-5-carboxylic acid with 2-(3-(4-fluorobenzyl)-2-oxoimidazolidin-1-yl)-4-(trifluoromethyl)thiazole-5-carboxylic acid to react with pyridin-3-ylmethanamine, the title compound was obtained as a colorless solid in 37% yield: mp 161-162° C. (ethyl acetate/hexanes); $^1$H NMR (300 MHz, CDCl$_3$) δ 8.56-8.52 (m, 2H), 7.69-7.66 (m, 1H), 7.31-7.22 (m, 3H), 7.05-7.00 (m, 2H), 6.55-6.47 (m, 1H), 4.61 (d, J=5.8 Hz, 2H), 4.43 (s, 2H), 4.09-4.03 (m, 2H), 3.48-3.43 (m, 2H); $^{13}$C NMR (75 MHz, CDCl$_3$) δ 164.2, 160.9, 159.5, 159.0, 155.2, 149.2, 135.6, 132.9, 131.0, 130.1, 127.2, 123.7, 122.2, 118.6, 116.0, 47.3, 41.9, 41.6, 30.9; MS (ES+) m/z 480.5 (M+1).

Example 27

Synthesis of N-benzyl-2-(3-benzyl-2-(cyanoimino)imidazolidin-1-yl)-4-methylthiazole-5-carboxamide

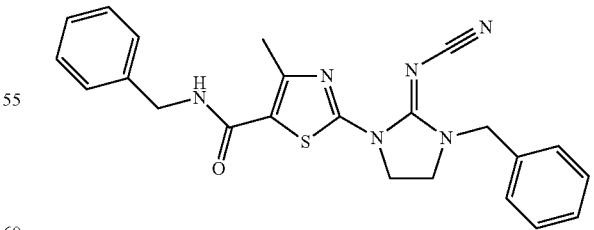

A mixture of N-benzyl-2-bromo-4-methylthiazole-5-carboxamide (0.25 g, 0.80 mmol), N-(1-benzylimidazolidin-2-ylidene)cyanamide (0.18 g, 0.88 mmol), copper(I) iodide (0.030 g, 0.16 mmol), cyclohexane-1,2-diamine (0.018 g, 0.16 mmol) and potassium carbonate (0.17 g, 1.20 mmol) in anhydrous N,N-dimethylformamide (15 mL) was heated at 100° C. under nitrogen atmosphere for 16 hours. The solvent was removed in vacuo, diluted with ethyl acetate (250 mL), washed with saturated sodium bicarbonate solution (50 mL) and brine (50 mL). The organic layer was dried over anhydrous sodium sulfate, filtered and concentrated in vacuo. The residue was recrystallized from ethyl acetate and hexane. The solid was collected by filtration and washed with methanol and hexane to afford the title compound as a colourless solid in 8% yield (0.030 g): mp 226-228° C. (ethyl acetate/hexanes); $^1$H NMR (300 MHz, DMSO-$d_6$) δ 8.59 (t, J=5.9 Hz, 1H), 7.49-7.17 (m, 10H), 4.99 (s, 2H), 4.35 (d, J=5.9 Hz, 2H), 4.14-4.08 (m, 2H), 3.66-3.60 (m, 2H), 2.44 (s, 3H); $^{13}$C NMR (75 MHz, DMSO-$d_6$) δ 161.9, 156.1, 153.3, 151.5, 140.0, 135.4, 129.3, 128.7, 128.4, 128.1, 127.7, 127.1, 119.8, 113.9, 49.0, 46.6, 44.72, 43.1, 17.5; MS (ES+) m/z 431.3 (M+1).

Example 27.1

Synthesis of N-benzyl-2-(5-benzyl-1,1-dioxido-1,2,5-thiadiazolidin-2-yl)-4-methyl-1,3-thiazole-5-carboxamide

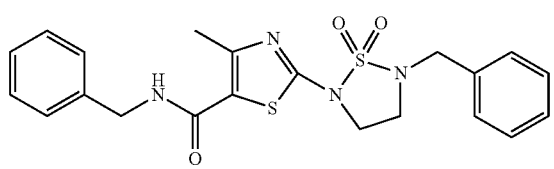

Following the procedure as described in Example 27, making variations as required to replace N-(1-benzylimidazolidin-2-ylidene)cyanamide with 2-benzyl-1,2,5-thiadiazolidine 1,1-dioxide to react with N-benzyl-2-bromo-4-methylthiazole-5-carboxamide, the title compound was obtained as a colorless solid in 78% yield: mp 135-137° C. (ethyl acetate/hexanes); $^1$H NMR (300 MHz, CDCl$_3$) δ 7.37-7.26 (m, 10H), 5.99 (t, J=5.6 Hz, 1H), 4.55 (d, J=5.6 Hz, 2H), 4.25 (s, 2H), 4.00 (t, J=6.6 Hz, 2H), 3.39 (t, J=6.6 Hz, 2H), 2.57 (s, 3H); $^{13}$C NMR (75 MHz, CDCl$_3$) δ 161.5, 156.6, 153.4, 137.7, 133.7, 128.9, 128.8, 128.6, 127.8, 127.7, 119.4, 51.4, 45.0, 44.1, 43.9, 17.3; MS (ES+) m/z 443.2 (M+1).

Example 27.2

Synthesis of 2-(5-benzyl-1,1-dioxido-1,2,5-thiadiazolidin-2-yl)-4-methyl-N-(pyridin-3-ylmethyl)-1,3-thiazole-5-carboxamide

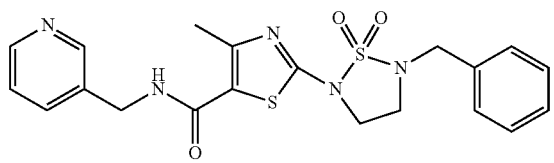

Following the procedure as described in Example 27, making variations as required to replace N-(1-benzylimidazolidin-2-ylidene)cyanamide with 2-benzyl-1,2,5-thiadiazolidine 1,1-dioxide to react with 2-bromo-4-methyl-N-(pyridin-3-ylmethyl)thiazole-5-carboxamide, the title compound was obtained as a colorless solid in 79% yield: mp 140-142° C. (ethyl acetate/hexanes); $^1$H NMR (300 MHz, DMSO-$d_6$) δ 8.68 (t, J=5.8 Hz, 1H), 8.49-8.43 (m, 2H), 7.67 (d, J=7.8 Hz, 1H), 7.39-7.28 (m, 6H), 4.37 (d, J=5.8 Hz, 2H), 4.26 (s, 2H), 3.46 (t, J=6.6 Hz, 2H), 3.99 (t, J=6.6 Hz, 2H), 2.46 (s, 3H); $^{13}$C NMR (75 MHz, DMSO-$d_6$) δ 161.3, 157.2, 152.9, 149.3, 148.5, 135.6, 135.2, 129.6, 129.0, 128.8, 128.5, 124.0, 119.6, 51.3, 46.0, 44.7, 40.9, 17.5; MS (ES+) m/z 444.3 (M+1).

Example 27.3

Synthesis of N-benzyl-2-(3-benzyl-2-iminoimidazolidin-1-yl)-4-methylthiazole-5-carboxamide

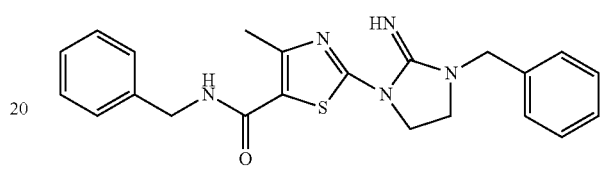

Following the procedure as described in Example 27, making variations as required to replace N-(1-benzylimidazolidin-2-ylidene)cyanamide with 1-benzylimidazolidin-2-imine to react with N-benzyl-2-bromo-4-methylthiazole-5-carboxamide, the title compound was obtained as a colorless solid in 4% yield: mp 125-126° C. (ethyl acetate/hexanes); $^1$H NMR (300 MHz, CDCl$_3$) δ 7.37-7.26 (m, 10H), 5.89 (t, J=5.5 Hz, 1H), 5.56 (br s, 1H), 4.54 (d, J=5.5 Hz, 2H), 4.33 (s, 2H), 4.15-4.01 (m, 2H), 3.44 (t, J=7.7 Hz, 2H), 2.62 (s, 3H); $^{13}$C NMR (75 MHz, CDCl$_3$) δ 159.4, 138.0, 128.9, 128.7, 128.0, 127.9, 127.6, 127.5, 105.6, 53.4, 49.3, 44.0, 43.8, 17.3; MS (ES+) m/z 406.4 (M+1).

Example 27.4

Synthesis of 2-(3-benzyl-2-iminoimidazolidin-1-yl)-N-(4-fluorobenzyl)-4-methylthiazole-5-carboxamide

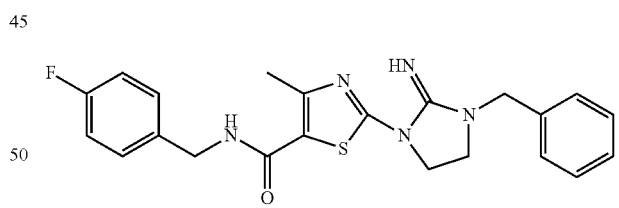

Following the procedure as described in Example 27, making variations as required to replace N-(1-benzylimidazolidin-2-ylidene)cyanamide with 1-benzylimidazolidin-2-imine to react with 2-bromo-N-(4-fluorobenzyl)-4-methylthiazole-5-carboxamide, the title compound was obtained as a colorless solid in 7% yield: mp 142-144° C. (ethyl acetate/hexanes); $^1$H NMR (300 MHz, DMSO-$d_6$) δ 8.35 (br s, 1H), 8.16 (t, J=5.9 Hz, 1H), 7.36-7.23 (m, 7H), 7.13-7.07 (m, 2H), 4.45 (s, 2H), 4.29 (d, J=5.9 Hz, 2H), 3.56-3.50 (m, 2H), 3.32-3.26 (m, 2H), 2.41 (s, 3H); $^{13}$C NMR (75 MHz, DMSO-$d_6$) δ 163.1, 162.4, 159.9, 159.0, 152.8, 137.4, 136.5, 129.6, 129.0, 128.1, 127.7, 115.5, 115.2, 47.6, 45.2, 42.3, 40.9, 17.8; MS (ES+) m/z 424.2 (M+1).

Example 27.5

Synthesis of 2-(3-benzyl-2-iminoimidazolidin-1-yl)-N-(3,4-difluorobenzyl)-4-methylthiazole-5-carboxamide

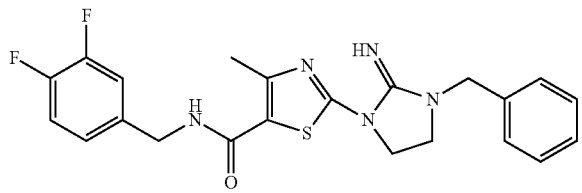

Following the procedure as described in Example 27, making variations as required to replace N-(1-benzylimidazolidin-2-ylidene)cyanamide with 1-benzylimidazolidin-2-imine to react with 2-bromo-N-(3,4-difluorobenzyl)-4-methylthiazole-5-carboxamide, the title compound was obtained as a colorless solid in 5% yield: mp 140-142° C. (ethyl acetate/hexanes); $^1$H NMR (300 MHz, DMSO-$d_6$) δ 8.41 (t, J=5.8 Hz, 1H), 7.39-7.23 (m, 7H), 7.12-7.08 (m, 1H), 6.68 (m, 1H), 4.43 (s, 2H), 4.30 (d, J=5.8 Hz, 2H) 3.94 (m, 2H), 3.35-3.27 (m, 2H), 2.42 (s, 3H); $^{13}$C NMR (75 MHz, DMSO-$d_6$) δ 162.8, 158.3, 153.5, 151.1, 150.4, 148.0, 147.9, 138.2, 137.2, 129.0, 128.2, 127.8, 124.4, 117.7, 116.5, 48.4, 44.4, 43.9, 42.1, 17.6; MS (ES+) m/z 442.2 (M+1).

Example 28

Synthesis of ethyl 3-methyl-5-(5-oxo-1H-1,2,4-triazol-4(5H)-yl)thiophene-2-carboxylate

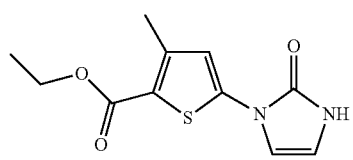

A mixture of ethyl 5-(hydrazinecarboxamido)-3-methylthiophene-2-carboxylate (12.80 g, 52.61 mmol), trimethyl orthoformate (6.33 mL, 57.86 mmol) and p-toluenesulfonic acid monohydrate (0.260 g, 1.367 mmol) in ethanol (130 mL) was stirred at reflux for 30 minutes. The reaction mixture was allowed to cool to ambient temperature, and kept at +5° C. for 16 h. The resulting solid was filtered and washed with ethyl acetate. The filtrate was concentrated, and the residue was triturated with ethanol. The combined material was dried to afford the title compound as a cream solid in 70% yield (9.37 g): $^1$H NMR (300 MHz, DMSO-$d_6$) δ 12.35 (s, 1H), 8.66 (s, 1H), 7.27 (s, 1H), 4.25 (q, J=7.1 Hz, 2H), 2.47 (s, 3H), 1.29 (t, J=7.1 Hz, 3H); MS (ES+) m/z 254.2 (M+1).

Example 29

Synthesis of ethyl 5-(1-(4-fluorobenzyl)-5-oxo-1H-1,2,4-triazol-4(5H)-yl)-3-methylthiophene-2-carboxylate

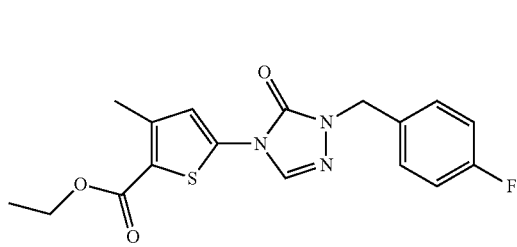

A mixture of ethyl 3-methyl-5-(5-oxo-1H-1,2,4-triazol-4(5H)-yl)thiophene-2-carboxylate (0.15 g, 0.59 mmol), potassium carbonate (0.16 g, 1.19 mmol) and 4-fluorobenzyl bromide (0.11 mL, 0.90 mmol) in N,N-dimethylformamide (3 mL) was stirred at 80° C. for 18 h. The reaction mixture was allowed to cool to ambient temperature, then partitioned between ethyl acetate (75 mL) and water (35 mL). The organic layer was washed with brine (35 mL), dried over sodium sulfate, filtered and concentrated in vacuo. The residue was purified by column chromatography eluted with 0-40% ethyl acetate in hexanes to afford the title compound as a cream solid in 81% yield (0.17 g): $^1$H NMR (300 MHz, CDCl$_3$) δ 7.72 (s, 1H), 7.42-7.36 (m, 2H), 7.08-7.01 (m, 2H), 6.93 (s, 1H), 4.98 (s, 2H), 4.32 (q, J=7.1 Hz, 2H), 2.54 (s, 3H), 1.36 (t, J=7.1 Hz, 3H); MS (ES+) m/z 362.2 (M+1).

Example 29.1

Synthesis of ethyl 5-(1-benzyl-5-oxo-1H-1,2,4-triazol-4(5H)-yl)-3-methylthiophene-2-carboxylate

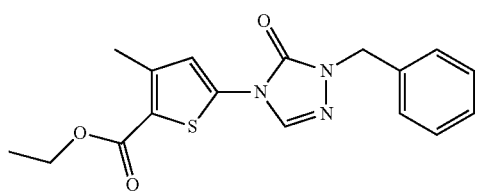

Following the procedure as described in Example 29, making variations as required to replace 4-fluorobenzyl bromide with benzyl bromide to react with ethyl 3-methyl-5-(5-oxo-1H-1,2,4-triazol-4(5H)-yl)thiophene-2-carboxylate, the title compound was obtained as a yellowish solid in 82% yield: $^1$H NMR (300 MHz, CDCl$_3$) δ 7.72 (s, 1H), 7.43-7.31 (m, 5H), 6.94 (s, 1H), 5.01 (s, 2H), 4.32 (q, J=7.1 Hz, 2H), 2.54 (s, 3H), 1.36 (t, J=7.1 Hz, 3H); MS (ES+) m/z 344.2 (M+1).

Example 29.2

Synthesis of ethyl 5-(1-(2-cyclopropylethyl)-5-oxo-1H-1,2,4-triazol-4(5H)-yl)-3-methylthiophene-2-carboxylate

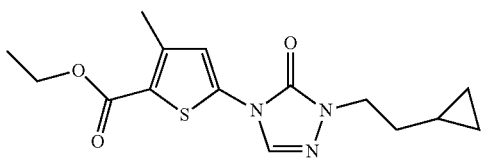

Following the procedure as described in Example 29, making variations as required to replace 4-fluorobenzyl bromide with 2-cyclopropylethyl 4-methylbenzenesulfonate to react with ethyl 3-methyl-5-(5-oxo-1H-1,2,4-triazol-4(5H)-yl)thiophene-2-carboxylate, the title compound was obtained as a yellowish solid in 80% yield: $^1$H NMR (300 MHz, CDCl$_3$) δ 7.74 (s, 1H), 6.94 (s, 1H), 4.32 (q, J=7.1 Hz, 2H), 2.54 (s, 3H), 3.94 (t, J=7.1 Hz, 2H), 1.72-1.63 (m, 2H), 1.36 (t, J=7.1 Hz, 3H), 0.77-0.63 (m, 1H), 0.49-0.41 (m, 2H), 0.08-0.01 (m, 2H); MS (ES+) m/z 322.3 (M+1).

Example 29.3

Synthesis of ethyl 3-methyl-5-(5-oxo-1-(4-(trifluoromethyl)benzyl)-1H-1,2,4-triazol-4(5H)-yl)thiophene-2-carboxylate

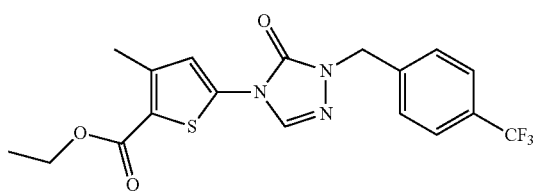

Following the procedure as described in Example 29, making variations as required to replace 4-fluorobenzyl bromide with 4-(trifluoromethyl)benzyl bromide to react with ethyl 3-methyl-5-(5-oxo-1H-1,2,4-triazol-4(5H)-yl)thiophene-2-carboxylate, the title compound was obtained as a yellowish solid in 94% yield: $^1$H NMR (300 MHz, CDCl$_3$) δ 7.75 (s, 1H), 7.62 (d, J=8.1 Hz, 2H), 7.51 (d, J=8.1 Hz, 2H), 6.95 (s, 1H), 5.07 (s, 2H), 4.32 (q, J=7.1 Hz, 2H), 2.55 (s, 3H), 1.36 (t, J=7.1 Hz, 3H); MS (ES+) m/z 412.2 (M+1).

Example 29.4

Synthesis of ethyl 3-methyl-5-(1-(4-(methylsulfonyl)benzyl)-5-oxo-1H-1,2,4-triazol-4(5H)-yl)thiophene-2-carboxylate

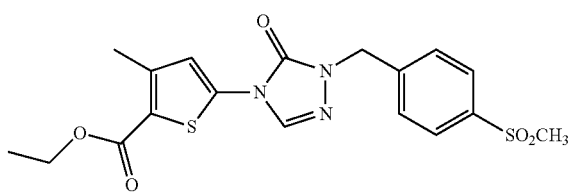

Following the procedure as described in Example 29, making variations as required to replace 4-fluorobenzyl bromide with 4-methylsulfonylbenzyl bromide to react with ethyl 3-methyl-5-(5-oxo-1H-1,2,4-triazol-4(5H)-yl)thiophene-2-carboxylate, the title compound was obtained as a yellowish solid in 81% yield: $^1$H NMR (300 MHz, CDCl$_3$) δ 7.94 (d, J=7.9 Hz, 2H), 7.76 (s, 1H), 7.59 (d, J=7.9 Hz, 2H), 6.95 (s, 1H), 5.10 (s, 2H), 4.32 (q, J=7.1 Hz, 2H), 3.04 (s, 3H), 2.55 (s, 3H), 1.36 (t, J=7.1 Hz, 3H); MS (ES+) m/z 444.3 (M+23).

Example 30

Synthesis of 5-(1-(4-fluorobenzyl)-5-oxo-1H-1,2,4-triazol-4(5H)-yl)-3-methylthiophene-2-carboxylic acid

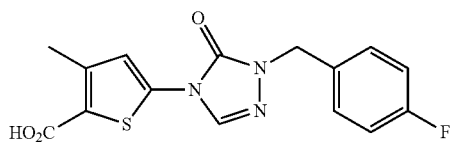

A mixture of ethyl 5-(1-(4-fluorobenzyl)-5-oxo-1H-1,2,4-triazol-4(5H)-yl)-3-methylthiophene-2-carboxylate (0.17 g, 0.47 mmol) and 1 N aqueous sodium hydroxide solution (3.0 mL, 3.0 mmol) in ethanol (6 mL) was stirred at reflux for 1 h, cooled to 0° C. and acidified with 10% aqueous hydrochloric acid to pH ~2. The resulting precipitate was filtered, washed with water and hexanes, and dried in vacuo to afford the title compound as a colorless solid in 82% yield (0.13 g): $^1$H NMR (300 MHz, DMSO-d$_6$) δ 12.94 (br s, 1H), 8.70 (s, 1H), 7.36-7.29 (m, 2H), 7.23 (s, 1H), 7.19-7.11 (m, 2H), 4.92 (s, 2H), 2.43 (s, 3H); MS (ES-) m/z 332.1 (M-1).

Example 30.1

Synthesis of 5-(1-benzyl-5-oxo-1H-1,2,4-triazol-4(5H)-yl)-3-methylthiophene-2-carboxylic acid

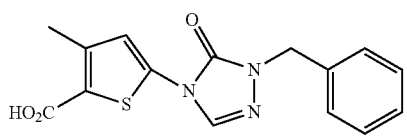

Following the procedure as described in Example 30, making variations as required to replace ethyl 5-(1-(4-fluorobenzyl)-5-oxo-1H-1,2,4-triazol-4(5H)-yl)-3-methylthiophene-2-carboxylate with ethyl 5-(1-benzyl-5-oxo-1H-1,2,4-triazol-4(5H)-yl)-3-methylthiophene-2-carboxylate, the title compound was obtained as a colorless solid in 86% yield: $^1$H NMR (300 MHz, DMSO-d$_6$) δ 12.99 (br s, 1H), 8.75 (s, 1H), 7.40-7.24 (m, 6H), 4.97 (s, 2H), 2.46 (s, 3H); MS (ES-) m/z 314.2 (M-1).

Example 30.2

Synthesis of 5-(1-(2-cyclopropylethyl)-5-oxo-1H-1,2,4-triazol-4(5H)-yl)-3-methylthiophene-2-carboxylic acid

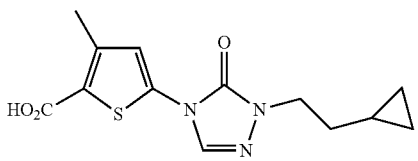

Following the procedure as described in Example 30, making variations as required to replace ethyl 5-(1-(4-fluorobenzyl)-5-oxo-1H-1,2,4-triazol-4(5H)-yl)-3-methylthiophene-2-carboxylate with ethyl 5-(1-(2-cyclopropylethyl)-5-oxo-1H-1,2,4-triazol-4(5H)-yl)-3-methylthiophene-2-carboxylate, the title compound was obtained as a colorless solid in 96% yield: $^1$H NMR (300 MHz, DMSO-d$_6$) δ 12.96 (br s, 1H), 8.72 (s, 1H), 7.26 (s, 1H), 3.81 (t, J=6.5 Hz, 2H), 2.46 (s, 3H), 1.62-1.52 (m, 2H), 0.75-0.60 (m, 1H), 0.40-0.32 (m, 2H), 0.05-0.05 (m, 2H); MS (ES-) m/z 292.3 (M-1).

Example 30.3

Synthesis of 3-methyl-5-(5-oxo-1-(4-(trifluoromethyl)benzyl)-1H-1,2,4-triazol-4(5H)-yl)thiophene-2-carboxylic acid

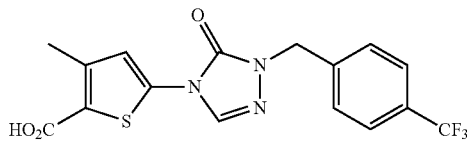

Following the procedure as described in Example 30, making variations as required to replace ethyl 5-(1-(4-fluorobenzyl)-5-oxo-1H-1,2,4-triazol-4(5H)-yl)-3-methylthiophene-2-carboxylate with ethyl 3-methyl-5-(5-oxo-1-(4-(trifluoromethyl)-benzyl)-1H-1,2,4-triazol-4(5H)-yl)thiophene-2-carboxylate, the title compound was obtained as a colorless solid in 78% yield: $^1$H NMR (300 MHz, DMSO-d$_6$) δ 12.98 (br s, 1H), 8.78 (s, 1H), 7.74 (d, J=8.1 Hz, 2H), 7.53 (d, J=8.1 Hz, 2H), 7.28 (s, 1H), 5.09 (s, 2H), 2.47 (s, 3H); MS (ES-) m/z 382.2 (M-1).

Example 30.4

Synthesis of 3-methyl-5-(1-(4-(methylsulfonyl)benzyl)-5-oxo-1H-1,2,4-triazol-4(5H)-yl)thiophene-2-carboxylic acid

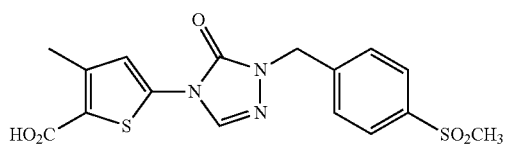

Following the procedure as described in Example 30, making variations as required to replace ethyl 5-(1-(4-fluorobenzyl)-5-oxo-1H-1,2,4-triazol-4(5H)-yl)-3-methylthiophene-2-carboxylate with ethyl 3-methyl-5-(1-(4-(methylsulfonyl)benzyl)-5-oxo-1H-1,2,4-triazol-4(5H)-yl)thiophene-2-carboxylate, the title compound was obtained as a beige solid in 74% yield: $^1$H NMR (300 MHz, DMSO-d$_6$) δ 13.02 (br s, 1H), 8.79 (s, 1H), 7.92 (d, J=7.1 Hz, 2H), 7.56 (d, J=7.1 Hz, 2H), 7.29 (s, 1H), 5.11 (s, 2H), 3.20 (s, 3H), 2.47 (s, 3H); MS (ES-) m/z 392.2 (M-1).

Example 31

Synthesis of 5-(1-(4-fluorobenzyl)-5-oxo-1H-1,2,4-triazol-4(5H)-yl)-3-methyl-N-(pyridin-3-ylmethyl)thiophene-2-carboxamide

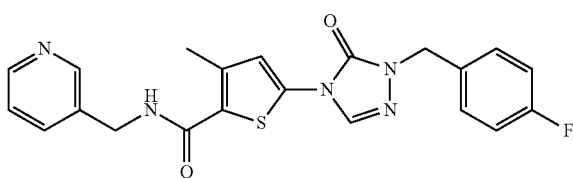

To a stirred mixture of 5-(1-(4-fluorobenzyl)-5-oxo-1H-1,2,4-triazol-4(5H)-yl)-3-methylthiophene-2-carboxylic acid (0.13 g, 0.38 mmol), 1-hydroxybenzotriazole (0.077 g, 0.57 mmol) and 1-ethyl-3-(3-dimethylaminopropyl)carbodiimide hydrochloride (0.11 g, 0.57 mmol) in N,N-dimethylformamide (2 mL) was added N,N-diisopropylethylamine (0.20 mL, 1.14 mmol) and 3-(aminomethyl)pyridine (0.04 mL, 0.39 mmol). The resulting reaction mixture was stirred for 18 h at ambient temperature, then diluted with ethyl acetate (75 mL). The organic layer was washed with saturated aqueous sodium bicarbonate solution (3×35 mL) and water (35 mL), dried over sodium sulfate, filtered and concentrated in vacuo. The residue was triturated with dichloromethane in hexanes to afford the title compound as a colorless solid in 87% yield (0.14 g): mp 180-182° C.; $^1$H NMR (300 MHz, CDCl$_3$) δ 8.59 (s, 1H), 8.52 (d, J=4.1 Hz, 1H), 7.72 (s, 1H), 7.69 (d, J=8.0 Hz, 1H), 7.39-7.33 (m, 2H), 7.30-7.24 (m, 1H), 7.06-6.98 (m, 2H), 6.87 (s, 1H), 643 (t, J=5.6 Hz, 1H), 4.95 (s, 2H), 4.59 (d, J=5.6 Hz, 2H), 2.50 (s, 3H); $^{13}$C NMR (75 MHz, CDCl$_3$) δ 162.64 (d, J$_{C-F}$=247.1 Hz), 162.6, 150.4, 149.3, 149.1, 140.8, 135.7, 134.5, 133.7, 132.3, 131.2 (d, J$_{C-F}$=3.2 Hz), 130.3 (d, J$_{C-F}$=8.3 Hz), 125.3, 123.7, 120.2, 115.8 (d, J$_{C-F}$=21.6 Hz), 49.0, 41.5, 16.0; MS (ES+) m/z 424.3 (M+1).

Example 31.1

Synthesis of 5-(1-benzyl-5-oxo-1H-1,2,4-triazol-4(5H)-yl)-3-methyl-N-(pyridin-3-ylmethyl)thiophene-2-carboxamide

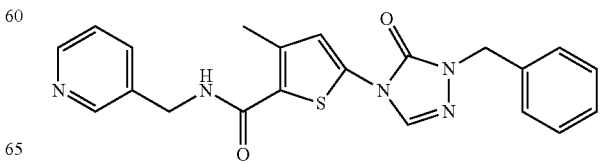

Following the procedure as described in Example 31, making variations as required to replace 5-(1-(4-fluorobenzyl)-5-oxo-1H-1,2,4-triazol-4(5H)-yl)-3-methylthiophene-2-carboxylic acid with 5-(1-benzyl-5-oxo-1H-1,2,4-triazol-4(5H)-yl)-3-methylthiophene-2-carboxylic acid to react with 3-(aminomethyl)pyridine, the title compound was obtained as a colorless solid in 89% yield: mp 180-181° C.; $^1$H NMR (300 MHz, CDCl$_3$) δ 8.61 (s, 1H), 8.54 (s, 1H), 7.73 (s, 1H), 7.71 (d, J=8.1 Hz, 1H), 7.43-7.25 (m, 6H), 6.88 (s, 1H), 6.48 (t, J=5.6 Hz, 1H), 5.00 (s, 2H), 4.61 (d, J=5.6 Hz, 2H), 2.52 (s, 3H); $^{13}$C NMR (75 MHz, CDCl$_3$) δ 162.6, 150.4, 149.2, 149.0, 140.8, 135.6, 135.3, 134.5, 132.2, 128.8, 128.4, 128.2, 125.1, 120.0, 49.8, 41.4, 16.0; MS (ES+) m/z 406.2 (M+1).

Example 31.2

Synthesis of 5-(1-(2-cyclopropylethyl)-5-oxo-1H-1,2,4-triazol-4(5H)-yl)-3-methyl-N-(pyridin-3-ylmethyl)thiophene-2-carboxamide

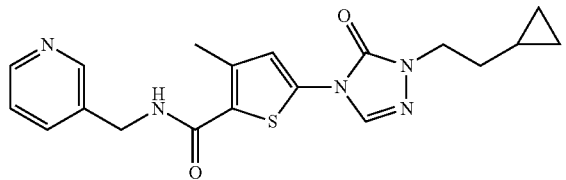

Following the procedure as described in Example 31, making variations as required to replace 5-(1-(4-fluorobenzyl)-5-oxo-1H-1,2,4-triazol-4(5H)-yl)-3-methylthiophene-2-carboxylic acid with 5-(1-(2-cyclopropylethyl)-5-oxo-1H-1,2,4-triazol-4(5H)-yl)-3-methylthiophene-2-carboxylic acid to react with 3-(aminomethyl)-pyridine, the title compound was obtained as a colorless solid in 87% yield: mp 148-150° C.; $^1$H NMR (300 MHz, CDCl$_3$) δ 8.58 (s, 1H), 8.52 (s, 1H), 7.74 (s, 1H), 7.69 (d, J=7.7 Hz, 1H), 7.27 (s, 1H), 6.87 (s, 1H), 6.44 (t, J=5.7 Hz, 1H), 4.60 (d, J=5.7 Hz, 2H), 3.91 (t, J=7.0 Hz, 2H), 2.50 (s, 3H), 1.70-1.61 (m, 2H), 0.75-0.60 (m, 1H), 0.47-0.39 (m, 2H), 0.06-0.02 (m, 2H); $^{13}$C NMR (75 MHz, CDCl$_3$) δ 162.6, 150.5, 149.2, 149.0, 140.8, 135.6, 134.7, 131.6, 125.0, 123.7, 119.9, 46.0, 41.4, 33.4, 16.0, 8.1, 4.0; MS (ES+) m/z 384.4 (M+1).

Example 31.3

Synthesis of 3-methyl-5-(5-oxo-1-(4-(trifluoromethyl)benzyl)-1H-1,2,4-triazol-4(5H)-yl)-N-(pyridin-3-ylmethyl)thiophene-2-carboxamide

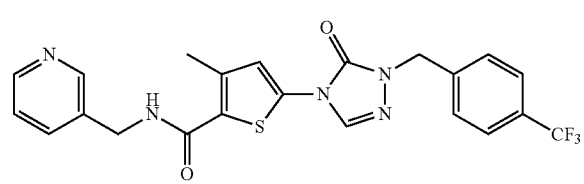

Following the procedure as described in Example 31, making variations as required to replace 5-(1-(4-fluorobenzyl)-5-oxo-1H-1,2,4-triazol-4(5H)-yl)-3-methylthiophene-2-carboxylic acid with 3-methyl-5-(5-oxo-1-(4-(trifluoromethyl)benzyl)-1H-1,2,4-triazol-4(5H)-yl)thiophene-2-carboxylic acid to react with 3-(aminomethyl)pyridine, the title compound was obtained as a colorless solid in 87% yield: mp 176-178° C.; $^1$H NMR (300 MHz, CDCl$_3$) δ 8.58 (s, 1H), 8.52 (d, J=3.2 Hz, 1H), 7.74 (s, 1H), 7.69 (d, J=7.9 Hz, 1H), 7.60 (d, J=8.1 Hz, 2H), 7.48 (d, J=8.1 Hz, 2H), 7.27 (dd, J=7.9, 3.2 Hz, 1H), 6.88 (s, 1H), 6.45 (t, J=5.5 Hz, 1H), 5.04 (s, 2H), 4.59 (d, J=5.5 Hz, 2H), 2.49 (s, 3H); $^{13}$C NMR (75 MHz, CDCl$_3$) δ 162.5, 150.5, 149.2, 149.0, 140.7, 139.2, 135.6, 134.4, 133.7, 132.6, 130.3, 128.6, 125.8 (q, J$_{C-F}$=3.8 Hz), 125.5, 123.6, 120.4, 49.1, 41.4, 16.0; MS (ES+) m/z 474.4 (M+1).

Example 31.4

Synthesis of 3-methyl-5-(1-(4-(methylsulfonyl)benzyl)-5-oxo-1H-1,2,4-triazol-4(5H)-yl)-N-(pyridin-3-ylmethyl)thiophene-2-carboxamide

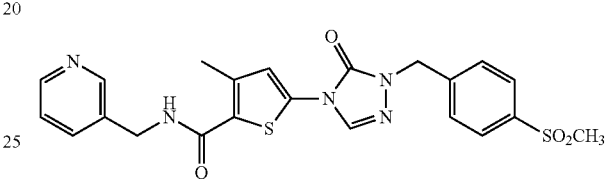

Following the procedure as described in Example 31, making variations as required to replace 5-(1-(4-fluorobenzyl)-5-oxo-1H-1,2,4-triazol-4(5H)-yl)-3-methylthiophene-2-carboxylic acid with 3-methyl-5-(1-(4-(methylsulfonyl)benzyl)-5-oxo-1H-1,2,4-triazol-4(5H)-yl)thiophene-2-carboxylic acid to react with 3-(aminomethyl)pyridine, the title compound was obtained as a colorless solid in 61% yield: mp 208-210° C.; $^1$H NMR (300 MHz, DMSO-d$_6$) δ 8.75 (s, 1H), 8.64 (t, J=5.6 Hz, 1H), 8.54 (s, 1H), 8.46 (d, J=4.4 Hz, 1H), 7.92 (d, J=8.1 Hz, 2H), 7.72 (d, J=7.7 Hz, 1H), 7.56 (d, J=8.1 Hz, 2H), 7.36 (dd, J=7.7, 4.4 Hz, 1H), 7.22 (s, 1H), 5.11 (s, 2H), 4.43 (d, J=5.6 Hz, 2H), 3.21 (s, 3H), 2.43 (s, 3H); $^{13}$C NMR (75 MHz, DMSO-d$_6$) δ 162.1, 150.0, 148.8, 148.0, 142.0, 140.1, 138.6, 135.0, 134.9, 134.3, 134.1, 128.4, 127.3, 125.6, 123.4, 119.4, 47.9, 43.4, 40.4, 15.6; MS (ES+) m/z 484.4 (M+1).

Example 31.5

Synthesis of 5-(1-(4-fluorobenzyl)-5-oxo-1H-1,2,4-triazol-4(5H)-yl)-3-methyl-N-((5-methylpyrazin-2-yl)methyl)thiophene-2-carboxamide

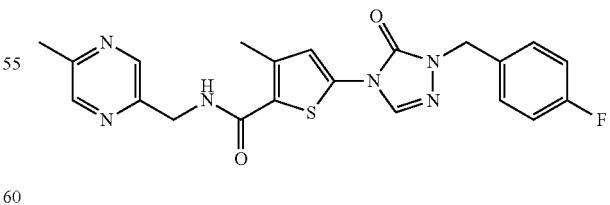

Following the procedure as described in Example 31, making variations as required to replace 3-(aminomethyl)pyridine with 2-(aminomethyl)-5-methylpyrazine to react with 5-(1-(4-fluorobenzyl)-5-oxo-1H-1,2,4-triazol-4(5H)-yl)-3-methylthiophene-2-carboxylic acid, the title compound was obtained as a colorless solid in 76% yield: mp 189-191° C.; $^1$H NMR (300 MHz, CDCl$_3$) δ 8.52 (s, 1H), 8.40 (s, 1H), 7.72

(s, 1H), 7.41-7.34 (m, 2H), 7.07-6.99 (m, 2H), 6.98 (t, J=4.7 Hz, 1H), 6.92 (s, 1H), 4.96 (s, 2H), 4.71 (d, J=4.7 Hz, 2H), 2.56 (s, 3H), 2.53 (s, 3H); $^{13}$C NMR (75 MHz, CDCl$_3$) δ 162.6 (d, J$_{C-F}$=246.9 Hz), 162.4, 152.7, 150.4, 148.4, 143.4, 142.8, 140.1, 134.8, 132.4, 131.2 (d, J$_{C-F}$=3.2 Hz), 130.3 (d, J$_{C-F}$=8.3 Hz), 126.1, 120.5, 115.7 (d, J$_{C-F}$=21.7 Hz), 49.0, 42.3, 21.2, 16.0; MS (ES+) m/z 439.2 (M+1).

Example 31.6

Synthesis of 5-(1-(4-fluorobenzyl)-5-oxo-1H-1,2,4-triazol-4(5H)-yl)-3-methyl-N-(oxazol-2-ylmethyl)thiophene-2-carboxamide

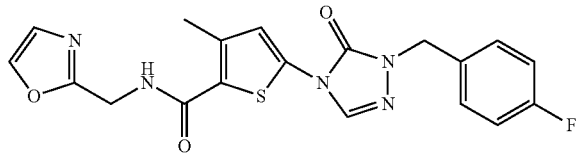

Following the procedure as described in Example 31, making variations as required to replace 3-(aminomethyl)pyridine with oxazol-2-yl-methylamine hydrochloride to react with 5-(1-(4-fluorobenzyl)-5-oxo-1H-1,2,4-triazol-4(5H)-yl)-3-methylthiophene-2-carboxylic acid, the title compound was obtained as a colorless solid in 50% yield: mp 163-165° C.; $^1$H NMR (300 MHz, CDCl$_3$) δ 7.72 (s, 1H), 7.64 (s, 1H), 7.40-7.34 (m, 2H), 7.08 (s, 1H), 7.06-6.99 (m, 2H), 6.91 (s, 1H), 6.64 (br s, 1H), 4.96 (s, 2H), 4.72 (d, J=5.2 Hz, 2H), 2.53 (s, 3H); $^{13}$C NMR (75 MHz, CDCl$_3$) δ 162.6 (d, J$_{C-F}$=247.0 Hz), 162.3, 150.4, 140.6, 139.3, 135.0, 132.3, 131.2 (d, J$_{C-F}$=3.3 Hz), 130.3 (d, J$_{C-F}$=8.3 Hz), 127.1, 125.4, 120.4, 115.7 (d, J$_{C-F}$=21.6 Hz), 48.9, 37.3, 16.0; MS (ES+) m/z 414.1 (M+1).

Example 31.7

Synthesis of 5-(1-(4-fluorobenzyl)-5-oxo-1H-1,2,4-triazol-4(5H)-yl)-3-methyl-N-((1-methyl-1H-pyrazol-4-yl)methyl)thiophene-2-carboxamide

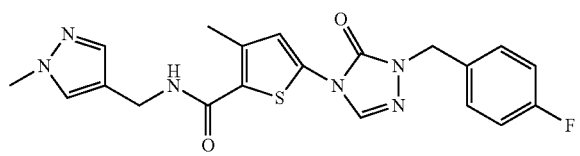

Following the procedure as described in Example 31, making variations as required to replace 3-(aminomethyl)pyridine with (1-methyl-1H-pyrazol-4-yl)methylamine to react with 5-(1-(4-fluorobenzyl)-5-oxo-1H-1,2,4-triazol-4(5H)-yl)-3-methylthiophene-2-carboxylic acid, the title compound was obtained as a colorless solid in 80% yield: mp 168-170° C.; $^1$H NMR (300 MHz, CDCl$_3$) δ 7.71 (s, 1H), 7.44 (s, 1H), 7.39 (s, 1H), 7.40-7.33 (m, 2H), 7.06-6.98 (m, 2H), 6.86 (s, 1H), 6.02 (t, J=5.0 Hz, 1H), 4.95 (s, 2H), 4.41 (d, J=5.0 Hz, 2H), 3.87 (s, 3H), 2.48 (s, 3H); $^{13}$C NMR (75 MHz, CDCl$_3$) δ 162.6 (d, J$_{C-F}$=247.1 Hz), 162.2, 150.4, 140.0, 138.7, 134.3, 132.3, 131.2 (d, J$_{C-F}$=3.3 Hz), 130.3 (d, J$_{C-F}$=8.3 Hz), 129.5, 125.9, 120.2, 118.1, 115.7 (d, J$_{C-F}$=21.7 Hz), 48.9, 38.9, 34.4, 15.9; MS (ES+) m/z 427.1 (M+1).

Example 31.8

Synthesis of 5-(1-(4-fluorobenzyl)-5-oxo-1H-1,2,4-triazol-4(5H)-yl)-3-methyl-N-((2-methylthiazol-4-yl)methyl)thiophene-2-carboxamide

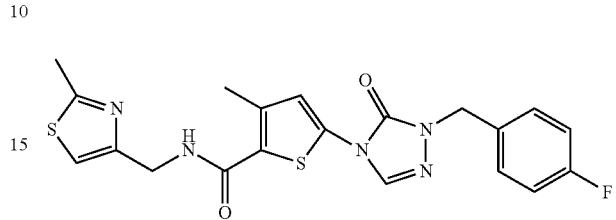

Following the procedure as described in Example 31, making variations as required to replace 3-(aminomethyl)pyridine with 1-(2-methyl-1,3-thiazol-4-yl)methylamine dihydrochloride to react with 5-(1-(4-fluorobenzyl)-5-oxo-1H-1,2,4-triazol-4(5H)-yl)-3-methylthiophene-2-carboxylic acid, the title compound was obtained as a colorless solid in 80% yield: mp 148-150° C.; $^1$H NMR (300 MHz, CDCl$_3$) δ 7.71 (s, 1H), 7.40-7.33 (m, 2H), 7.07-6.99 (m, 2H), 7.03 (s, 1H), 6.89 (s, 1H), 6.50 (t, J=4.9 Hz, 1H), 4.96 (s, 2H), 4.62 (d, J=4.9 Hz, 2H), 2.69 (s, 3H), 2.50 (s, 3H); $^{13}$C NMR (75 MHz, CDCl$_3$) δ 166.7, 162.6 (d, J$_{C-F}$=247.1 Hz), 162.2, 151.8, 150.4, 140.0, 134.5, 132.4, 131.2 (d, J$_{C-F}$=3.3 Hz), 130.3 (d, J$_{C-F}$=8.3 Hz), 126.1, 120.4, 115.7 (d, J$_{C-F}$=21.7 Hz), 115.0, 48.9, 40.0, 19.1, 16.0; MS (ES+) m/z 444.1 (M+1).

Example 32

Synthesis of 2-(3-((5-chlorobenzo[b]thiophen-3-yl)methyl)-2-oxoimidazolidin-1-yl)-4-methyl-N-(pyridin-3-ylmethyl)thiazole-5-carboxamide

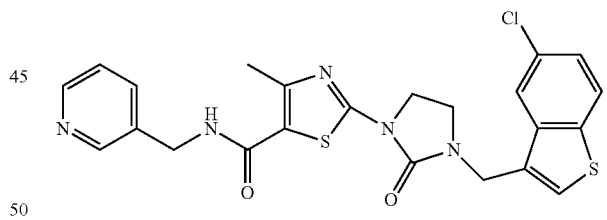

To a solution of 2-(3-((5-chlorobenzo[b]thiophen-3-yl)methyl)-2-oxoimidazolidin-1-yl)-4-methylthiazole-5-carboxylic acid (0.55 g, 1.35 mmol) in anhydrous N,N-dimethylformamide (10 mL) was added 1-hydroxy benzotriazole (0.22 g, 1.62 mmol), N-(3-dimethylaminopropyl)-N'-ethylcarbodiimide (0.31 g, 1.62 mmol), diisopropylethylamine (0.85 mL, 4.87 mmol) and 3-(aminomethyl)pyridine (0.17 mL, 1.62 mmol). The resulting solution was stirred at ambient temperature for 16 hours, then concentrated in vacuo. The residue was dissolved in dichloromethane (50 mL), washed with saturated aqueous sodium bicarbonate solution (15 mL) and brine (15 mL). The organic layer was dried over anhydrous sodium sulfate, filtered, and concentrated in vacuo. The residue was purified by column chromatography eluted with 55-75% ethyl acetate in hexanes to afford the title compound as a colorless solid in 45% yield (0.30 g): mp 185-187° C.

(dichloromethane/hexanes); $^1$H NMR (300 MHz, CDCl$_3$) δ 8.61 (s, 1H), 8.54 (d, J=6.0 Hz, 1H), 7.87 (s, 1H), 7.78 (d, J=6.0 Hz, 1H), 7.70 (d, J=9.0 Hz, 1H), 7.45 (s, 1H), 7.36-7.28 (m, 2H), 6.09 (br s, 1H), 4.70 (s, 2H), 4.60 (d, J=3.0 Hz, 2H), 4.06 (t, J=6.0 Hz, 2H), 3.47 (t, J=6.0 Hz, 2H), 2.61 (s, 3H); MS (ES+) m/z 498.1 (M+1).

Example 32.1

Synthesis of 2-(3-(isoquinolin-1-ylmethyl)-2-oxoimidazolidin-1-yl)-4-methyl-N-(pyridin-3-ylmethyl)thiazole-5-carboxamide

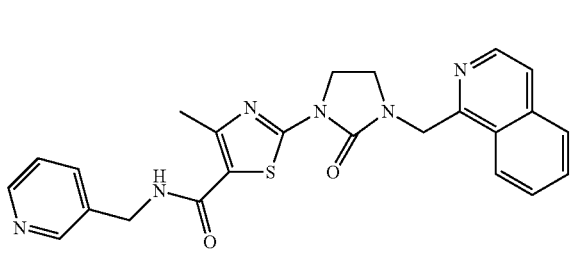

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(isoquinolin-1-ylmethyl)-2-oxoimidazolidin-1-yl)-4-methylthiazole-5-carboxylic acid to react with 3-(aminomethyl)-pyridine, the title compound was obtained as a colorless solid in 43% yield: mp 151-153° C. (dichloromethane/hexanes); $^1$H NMR (300 MHz, CDCl$_3$) δ 8.59 (s, 1H), 8.53 (d, J=3.0 Hz, 1H), 8.45 (d, J=6.0 Hz, 1H), 8.33 (d, J=9.0 Hz, 1H), 7.86 (d, J=6.0 Hz, 1H), 7.74-7.63 (m, 4H), 7.31-7.28 (m, 1H), 6.06 (br s, 1H), 5.12 (s, 2H), 4.59 (d, J=6.0 Hz, 2H), 4.08 (t, J=6.0 Hz, 2H), 3.61 (t, J=6.0 Hz, 2H), 2.61 (s, 3H); MS (ES+) m/z 459.3 (M+1).

Example 32.2

Synthesis of 4-methyl-2-(2-oxo-3-(quinolin-8-ylmethyl)imidazolidin-1-yl)-N-(pyridin-3-ylmethyl)thiazole-5-carboxamide

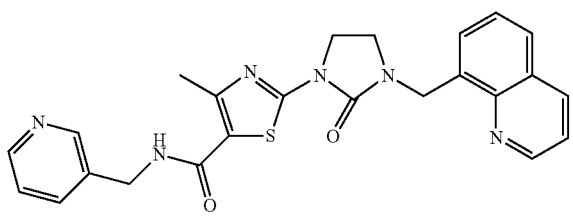

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 4-methyl-2-(2-oxo-3-(quinolin-8-ylmethyl)imidazolidin-1-yl)thiazole-5-carboxylic acid to react with 3-(aminomethyl)pyridine, the title compound was obtained as a colorless solid in 44% yield: mp 225-228° C. (methanol); $^1$H NMR (300 MHz, DMSO-d$_6$) δ 8.98-8.96 (m, 1H), 8.59-8.53 (m, 2H), 8.46-8.39 (m, 2H), 7.96-7.93 (m, 1H), 7.72-7.70 (m, 2H), 7.63-7.58 (m, 2H), 7.38-7.33 (m, 1H), 5.09 (s, 2H), 4.40 (d, J=5.8 Hz, 2H), 4.07-4.01 (m, 2H), 3.63-3.58 (m, 2H), 2.48 (s, 3H); MS (ES+) m/z 459.3 (M+1).

Example 32.3

Synthesis of 4-methyl-2-(3-((5-methylisoxazol-3-yl)methyl)-2-oxoimidazolidin-1-yl)-N-(pyridin-3-ylmethyl)thiazole-5-carboxamide

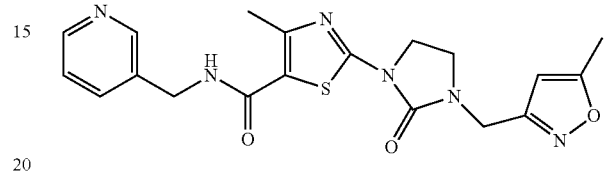

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 4-methyl-2-(3-((5-methylisoxazol-3-yl)methyl)-2-oxoimidazolidin-1-yl) thiazole-5-carboxylic acid to react with 3-(aminomethyl)pyridine, the title compound was obtained as a colorless solid in 57% yield: mp 185-188° C. (dichloromethane/hexanes); $^1$H NMR (300 MHz, CDCl$_3$) δ 8.59-8.58 (m, 1H), 8.51 (d, J=4.7 Hz, 1H), 7.69 (d, J=7.8 Hz, 1H), 7.29-7.25 (m, 1H), 6.22-6.19 (m, 1H), 5.98 (s, 1H), 4.58 (d, J=5.8 Hz, 2H), 4.49 (s, 2H), 4.12-4.06 (m, 2H), 3.61-3.55 (m, 2H), 2.60 (s, 3H), 2.40 (s, 3H); MS (ES+) m/z 413.2 (M+1).

Example 32.4

Synthesis of 4-methyl-2-(3-((3-methyl-5-phenylisoxazol-4-yl)methyl)-2-oxoimidazolidin-1-yl)-N-(pyridin-3-ylmethyl)thiazole-5-carboxamide

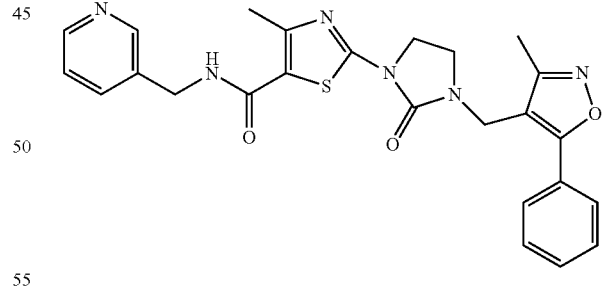

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 4-methyl-2-(3-((3-methyl-5-phenylisoxazol-4-yl)methyl)-2-oxoimidazolidin-1-yl) thiazole-5-carboxylic acid to react with 3-(aminomethyl) pyridine, the title compound was obtained as a colorless solid in 50% yield: mp 109-111° C. (dichloromethane/hexanes); $^1$H NMR (300 MHz, CDCl$_3$) δ 8.59 (s, 1H), 8.53-8.51 (m, 1H), 7.74-7.70 (m, 1H), 7.58-7.54 (m, 2H), 7.47-7.42 (m, 3H), 7.32-7.28 (m, 1H), 6.13 (br s, 1H), 4.58 (d, J=5.8 Hz, 2H), 4.45 (s, 2H), 3.91-3.85 (m, 2H), 3.19-3.14 (m, 2H), 2.58 (s, 3H), 2.51 (s, 3H); MS (ES+) m/z 489.3 (M+1).

Example 32.5

Synthesis of 4-methyl-2-(2-oxo-3-((5-phenyloxazol-4-yl)methyl)imidazolidin-1-yl)-N-(pyridin-3-ylmethyl)thiazole-5-carboxamide

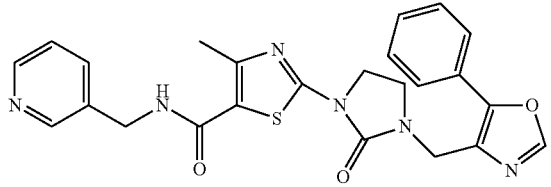

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 4-methyl-2-(2-oxo-3-((5-phenyloxazol-4-yl)methyl)imidazolidin-1-yl)thiazole-5-carboxylic acid to react with 3-(aminomethyl)-pyridine, the title compound was obtained as a colorless solid in 13% yield: mp 78-81° C. (dichloromethane/hexanes); $^1$H NMR (300 MHz, CDCl$_3$) δ 8.59 (s, 1H), 8.54 (d, J=4.8 Hz, 1H), 7.89 (s, 1H), 7.72-7.69 (m, 3H), 7.50-7.36 (m, 3H), 7.30-7.27 (m, 1H), 6.04-6.00 (m, 1H), 4.68 (s, 2H), 4.58 (d, J=5.8 Hz, 2H), 4.11-4.05 (m, 2H), 3.73-3.67 (m, 2H), 2.62 (s, 3H); MS (ES+) m/z 475.2 (M+1).

Example 32.6

Synthesis of 2-(3-(benzo[c][1,2,5]oxadiazol-5-ylmethyl)-2-oxoimidazolidin-1-yl)-4-methyl-N-(pyridin-3-ylmethyl)thiazole-5-carboxamide

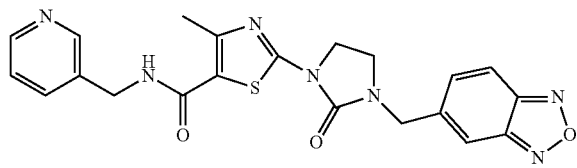

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(benzo[c][1,2,5]oxadiazol-5-ylmethyl)-2-oxoimidazolidin-1-yl)-4-methylthiazole-5-carboxylic acid to react with 3-(aminomethyl)pyridine, the title compound was obtained as a colorless solid in 34% yield: mp 110-112° C. (dichloromethane/hexanes); $^1$H NMR (300 MHz, CDCl$_3$) δ 8.60 (s, 1H), 8.54-8.52 (m, 1H), 7.85 (d, J=9.0 Hz, 1H), 7.72-7.69 (m, 2H), 7.39-7.35 (m, 1H), 7.30-7.28 (m, 1H), 6.14 (br s, 1H), 4.60 (d, J=6.0 Hz, 2H), 4.57 (s, 2H), 4.15 (t, J=6.0 Hz, 2H), 3.56 (t, J=6.0 Hz, 2H), 2.62 (s, 3H); MS (ES+) m/z 450.2 (M+1).

Example 32.7

Synthesis of 2-(3-(benzo[c][1,2,5]thiadiazol-5-ylmethyl)-2-oxoimidazolidin-1-yl)-4-methyl-N-(pyridin-3-ylmethyl)thiazole-5-carboxamide

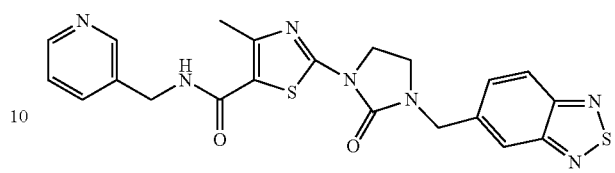

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(benzo[c][1,2,5]thiadiazol-5-ylmethyl)-2-oxoimidazolidin-1-yl)-4-methylthiazole-5-carboxylic acid to react with 3-(aminomethyl)pyridine, the title compound was obtained as a colorless solid in 44% yield: mp 105-107° C. (dichloromethane/hexanes); $^1$H NMR (300 MHz, CDCl$_3$) δ 8.57 (s, 1H), 8.50-8.48 (m, 1H), 7.96-7.93 (m, 1H), 7.71-7.68 (m, 1H), 7.57-7.55 (m, 2H), 7.29-7.24 (m, 1H), 6.18 (br s, 1H), 4.96 (s, 2H), 4.57 (d, J=5.8 Hz, 2H), 4.09-4.04 (m, 2H), 3.68-3.62 (m, 2H), 2.58 (s, 3H); MS (ES+) m/z 466.2 (M+1).

Example 32.8

Synthesis of 4-methyl-2-(2-oxo-3-(pyridin-2-ylmethyl)imidazolidin-1-yl)-N-(pyridin-3-ylmethyl)thiazole-5-carboxamide

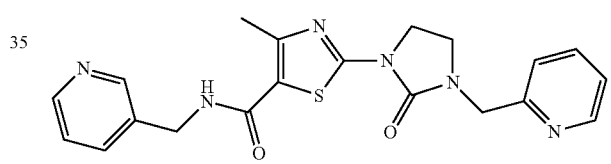

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 4-methyl-2-(2-oxo-3-(pyridin-2-ylmethyl)imidazolidin-1-yl)thiazole-5-carboxylic acid to react with 3-(aminomethyl)pyridine, the title compound was obtained as a colorless solid in 12% yield: mp 58-61° C. (dichloromethane/hexanes); $^1$H NMR (300 MHz, CDCl$_3$) δ 8.56-8.48 (m, 3H), 7.69-7.64 (m, 2H), 7.31-7.18 (m, 3H), 6.21 (br s, 1H), 4.58 (s, 2H), 4.56 (d, J=6.0 Hz, 2H), 4.09 (t, J=9.0 Hz, 2H), 3.62 (t, J=9.0 Hz, 2H), 2.59 (s, 3H); MS (ES+) m/z 409.2 (M+1).

Example 32.9

Synthesis of N-benzyl-4-methyl-2-(2-oxo-3-(pyridin-3-ylmethyl)imidazolidin-1-yl)thiazole-5-carboxamide

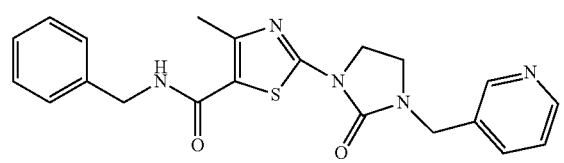

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 4-methyl-2-(2-oxo-3-(pyridin-3-ylmethyl)imidazolidin-1-yl)thiazole-5-carboxylic acid to react with benzylamine, the title compound was obtained as a colorless solid in 13% yield: mp 110-113° C. (dichloromethane/hexanes); $^1$H NMR (300 MHz, CDCl$_3$) δ 8.58-8.56 (m, 2H), 7.67 (d, J=7.8 Hz, 1H), 7.33-7.28 (m, 6H), 6.02 (br s, 1H), 4.57 (d, J=5.6 Hz, 2H), 4.49 (s, 2H), 4.11-4.06 (m, 2H), 3.51-3.45 (m, 2H), 2.61 (s, 3H); MS (ES+) m/z 408.2 (M+1).

Example 32.10

Synthesis of 2-(3-(4-fluorobenzyl)-2-oxoimidazolidin-1-yl)-4-methyl-N-((5-methylpyrazin-2-yl)methyl)thiazole-5-carboxamide

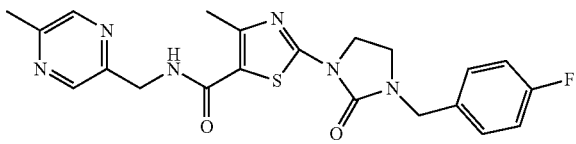

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with (5-methylpyrazin-2-yl)methanamine, the title compound was obtained as a colorless solid in 38% yield: mp 191-193° C.; $^1$H NMR (300 MHz, CDCl$_3$) δ 8.52 (s, 1H), 8.40 (s, 1H), 7.30-7.27 (m, 2H), 7.07-7.02 (m, 2H), 6.76 (br s, 1H), 4.70 (d, J=3.0 Hz, 2H), 4.47 (s, 2H), 4.09 (t, J=9.0 Hz, 2H), 3.46 (t, J=9.0 Hz, 2H), 2.63 (s, 3H), 2.57 (s, 3H); MS (ES+) m/z 441.2 (M+1).

Example 32.11

Synthesis of 2-(3-(4-fluorobenzyl)-2-oxoimidazolidin-1-yl)-4-methyl-N-(oxazol-2-ylmethyl)thiazole-5-carboxamide

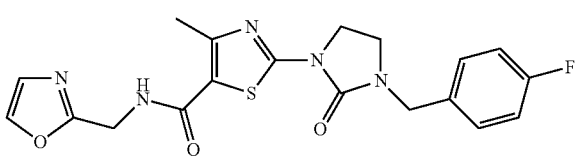

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with oxazol-2-ylmethanamine, the title compound was obtained as a colorless solid in 32% yield: mp 187-189° C.; $^1$H NMR (300 MHz, CDCl$_3$) δ 7.65 (s, 1H), 7.30-7.27 (m, 2H), 7.09-7.02 (m, 3H), 6.35 (br s, 1H), 4.70 (d, J=3.0 Hz, 2H), 4.47 (s, 2H), 4.10 (t, J=9.0 Hz, 2H), 3.46 (t, J=9.0 Hz, 2H), 2.64 (s, 3H); MS (ES+) m/z 416.2 (M+1).

Example 32.12

Synthesis of 2-(3-(4-fluorobenzyl)-2-oxoimidazolidin-1-yl)-4-methyl-N-((2-methylthiazol-5-yl)methyl)thiazole-5-carboxamide

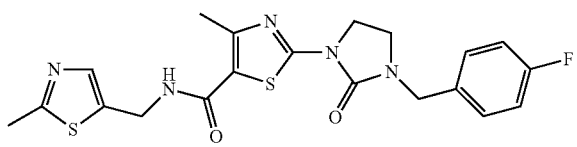

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with (2-methylthiazol-5-yl)methanamine, the title compound was obtained as a colorless solid in 45% yield: mp 213-215° C.; $^1$H NMR (300 MHz, CDCl$_3$) δ 7.30-7.25 (m, 2H), 7.07-7.01 (m, 3H), 6.29 (br s, 1H), 4.62 (d, J=5.3 Hz, 2H), 4.46 (s, 2H), 4.10-4.05 (m, 2H), 3.48-3.43 (m, 2H), 2.71 (s, 3H), 2.61 (s, 3H); MS (ES+) m/z 446.1 (M+1).

Example 32.13

Synthesis of 2-(3-(4-fluorobenzyl)-2-oxoimidazolidin-1-yl)-4-methyl-N-((1-methyl-1H-pyrazol-4-yl)methyl)thiazole-5-carboxamide

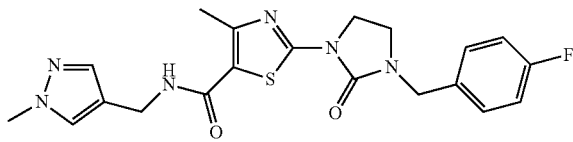

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with (1-methyl-1H-pyrazol-4-yl)methanamine, the title compound was obtained as a colorless solid in 44% yield: mp 173-175° C.; $^1$H NMR (300 MHz, DMSO-d$_6$) δ 8.29 (t, J=6.0 Hz, 1H), 7.57 (s, 1H), 7.38-7.32 (m, 3H), 7.23-7.17 (m, 2H), 4.42 (s, 2H), 4.18 (d, J=6.0 Hz, 2H), 3.99 (t, J=9.0 Hz, 2H), 3.78 (s, 3H), 3.45 (t, J=9.0 Hz, 2H), 2.45 (s, 3H); MS (ES+) m/z 429.2 (M+1).

Example 32.14

Synthesis of 2-(3-(4-fluorobenzyl)-2-oxoimidazolidin-1-yl)-4-methyl-N-(pyrimidin-4-ylmethyl)thiazole-5-carboxamide

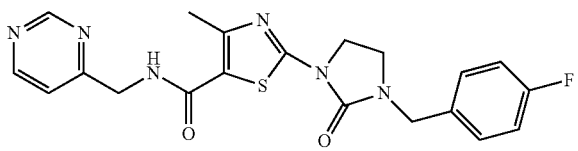

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with pyrimidin-4-ylmethanamine, the title compound was obtained as a colorless solid in 71% yield: mp 175-176° C.; $^1$H NMR (300 MHz, CDCl$_3$) δ 9.18 (s, 1H), 8.69 (d, J=6.0 Hz, 1H), 7.35-7.25 (m, 3H), 7.07-7.02 (m, 2H), 6.94 (br s, 1H), 4.70 (d, J=6.0 Hz, 2H), 4.47 (s, 2H), 4.10 (t, J=9.0 Hz, 2H), 3.47 (t, J=9.0 Hz, 2H), 2.64 (s, 3H); MS (ES+) m/z 427.2 (M+1).

Example 32.15

Synthesis of 2-(3-(4-fluorobenzyl)-2-oxoimidazolidin-1-yl)-4-methyl-N-(pyridazin-3-ylmethyl)thiazole-5-carboxamide

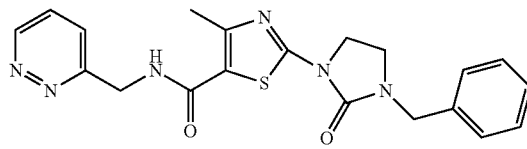

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with pyridazin-3-ylmethanamine, the title compound was obtained as a colorless solid in 52% yield: mp 222-225° C. (dichloromethane/hexanes); $^1$H NMR (300 MHz, DMSO-d$_6$) δ 9.15 (dd, J=4.8, 1.6 Hz, 1H), 8.67 (t, J=5.7 Hz, 1H), 7.71-7.66 (m, 1H), 7.62-7.59 (m, 1H), 7.40-7.35 (m, 2H), 7.24-7.18 (m, 2H), 4.69 (d, J=5.7 Hz, 2H), 4.44 (s, 2H), 4.05-4.00 (m, 2H), 3.50-3.45 (m, 2H), 2.50 (s, 3H); MS (ES+) m/z 427.2 (M+1).

Example 32.16

Synthesis of 2-(3-(4-fluorobenzyl)-2-oxoimidazolidin-1-yl)-4-methyl-N-(pyrimidin-2-ylmethyl)thiazole-5-carboxamide

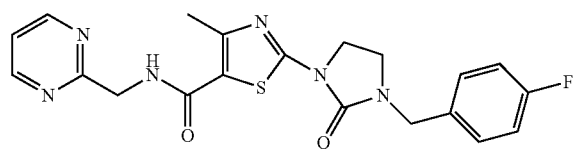

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with pyrimidin-2-ylmethanamine, the title compound was obtained as a colorless solid in 70% yield: mp 205-207° C. (dichloromethane/hexanes); $^1$H NMR (300 MHz, DMSO-d$_6$) δ 8.76 (d, J=4.8 Hz, 2H), 8.42-8.38 (m, 1H), 7.41-7.7.34 (m, 3H), 7.23-7.17 (m, 2H), 4.58 (d, J=5.7 Hz, 2H), 4.43 (s, 2H), 4.04-3.99 (m, 2H), 3.49-3.43 (m, 2H), 2.50 (s, 3H); MS (ES+) m/z 427.2 (M+1).

Example 32.17

Synthesis of 2-(3-(4-fluorobenzyl)-2-oxoimidazolidin-1-yl)-4-methyl-N-(pyrazin-2-ylmethyl)thiazole-5-carboxamide

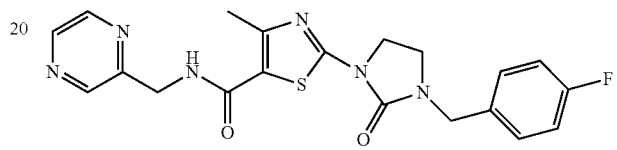

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with pyrazin-2-ylmethanamine, the title compound was obtained as a colorless solid in 42% yield: mp 185-187° C.; $^1$H NMR (300 MHz, CDCl$_3$) δ 8.65 (s, 1H), 8.53-8.51 (m, 2H), 7.30-7.25 (m, 2H), 7.07-7.01 (m, 2H), 6.83 (br s, 1H), 4.76 (d, J=6.0 Hz, 2H), 4.46 (s, 2H), 4.09 (t, J=9.0 Hz, 2H), 3.46 (t, J=9.0 Hz, 2H), 2.63 (s, 3H); MS (ES+) m/z 427.2 (M+1).

Example 32.18

Synthesis of 2-(3-(4-fluorobenzyl)-2-oxoimidazolidin-1-yl)-4-methylthiazole-5-carboxamide

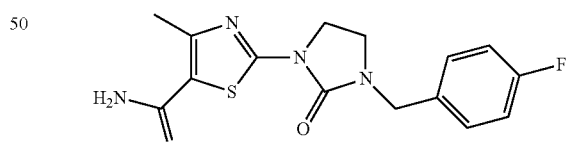

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with ammonium chloride, the title compound was obtained as a colorless solid in 43% yield: mp 201-203° C.; $^1$H NMR (300 MHz, DMSO-d$_6$) δ 7.38-7.31 (m, 4H), 7.23-7.17 (m, 2H), 4.42 (s, 2H), 3.99 (t, J=9.0 Hz, 2H), 3.45 (t, J=9.0 Hz, 2H), 2.46 (s, 3H); MS (ES+) m/z 335.1 (M+1).

Example 32.19

Synthesis of 2-(3-(4-fluorobenzyl)-2-oxoimidazolidin-1-yl)-N,4-dimethylthiazole-5-carboxamide

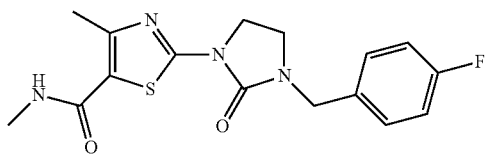

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with methylamine, the title compound was obtained as a colorless solid in 41% yield: mp 225-227° C.; $^1$H NMR (300 MHz, CDCl$_3$) δ 7.30-7.25 (m, 2H), 7.07-7.01 (m, 2H), 5.66 (br s, 1H), 4.46 (s, 2H), 4.08 (t, J=9.0 Hz, 2H), 3.45 (t, J=9.0 Hz, 2H), 2.94 (d, J=3.0 Hz, 3H), 2.60 (s, 3H); MS (ES+) m/z 349.2 (M+1).

Example 32.20

Synthesis of 2-(3-(2-(1H-indol-3-yl)ethyl)-2-oxoimidazolidin-1-yl)-4-methyl-N-(pyridin-3-ylmethyl)thiazole-5-carboxamide

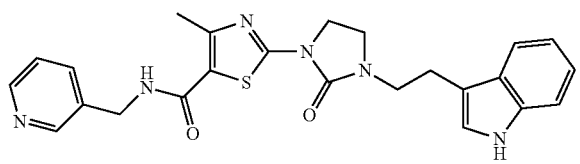

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(2-(1H-indol-3-yl)ethyl)-2-oxoimidazolidin-1-yl)-4-methylthiazole-5-carboxylic acid to react with pyridin-3-ylmethanamine, the title compound was obtained as a colorless solid in 36% yield: mp 198-201° C. (dichloromethane/hexanes); $^1$H NMR (300 MHz, CDCl$_3$) δ 8.60-8.52 (m, 2H), 8.27 (s, 1H), 7.71 (d, J=7.6 Hz, 1H), 7.60 (d, J=7.8 Hz, 1H), 7.31-7.06 (m, 5H), 6.26-6.23 (m, 1H), 4.56 (d, J=5.4 Hz, 2H), 3.99 (t, J=7.8 Hz, 2H), 3.67 (t, J=6.8 Hz, 2H), 3.48 (t, J=7.8 Hz, 2H), 3.05 (t, J=6.9 Hz, 2H), 2.60 (s, 3H); $^{13}$C NMR (75 MHz, CDCl$_3$) δ 162.7, 155.4, 153.7, 149.0, 148.9, 148.6, 136.3, 135.9, 127.2, 122.2, 121.9, 119.5, 118.4, 116.6, 112.3, 111.3, 44.2, 42.5, 42.1, 41.3, 23.5, 17.3; MS (ES+) m/z 341.2 (M+1); MS (ES+) m/z 461.3 (M+1).

Example 32.21

Synthesis of 2-(3-(4-fluorobenzyl)-2-oxoimidazolidin-1-yl)-4-methyl-N-(pyridin-2-ylmethyl)thiazole-5-carboxamide

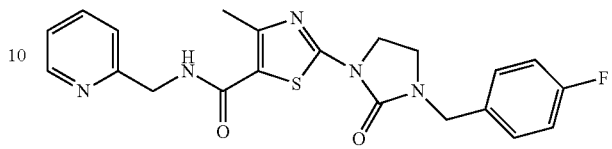

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with pyridin-2-ylmethanamine, the title compound was obtained as a colorless solid in 54% yield: mp 183-185° C.; $^1$H NMR (300 MHz, DMSO-d$_6$) δ 8.60-8.56 (m, 2H), 7.85-7.80 (m, 1H), 7.45-7.23 (m, 6H), 4.55 (d, J=6.0 Hz, 2H), 4.49 (s, 2H), 4.07 (t, J=9.0 Hz, 2H), 3.52 (t, J=9.0 Hz, 2H) 2.55 (s, 3H); MS (ES+) m/z 426.2 (M+1).

Example 32.22

Synthesis of 2-(3-(4-fluorobenzyl)-2-oxoimidazolidin-1-yl)-N,N,4-trimethylthiazole-5-carboxamide

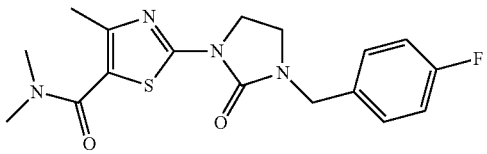

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with dimethylamine hydrochloride, the title compound was obtained as a colorless solid in 34% yield: mp 162-164° C.; $^1$H NMR (300 MHz, CDCl$_3$) δ 7.29-7.25 (m, 2H), 7.06-7.01 (m, 2H), 4.45 (s, 2H), 4.06 (t, J=9.0 Hz, 2H), 3.45 (t, J=9.0 Hz, 2H), 3.07 (s, 6H), 2.34 (s, 3H); MS (ES+) m/z 363.3 (M+1).

Example 32.23

Synthesis of 2-(3-(4-fluorobenzyl)-2-oxoimidazolidin-1-yl)-4-methyl-N-(pyridin-4-ylmethyl)thiazole-5-carboxamide

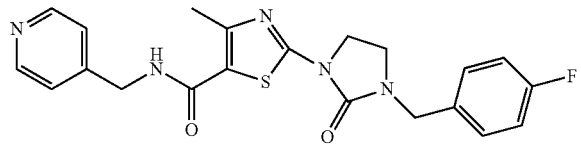

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxoimidazolidin-1-yl)-4-methylthiazole-5-carboxylic acid to react with pyridin-4-ylmethanamine, the title compound was obtained as a colorless solid in 60% yield: mp 146-149° C.; $^1$H NMR (300 MHz, CDCl$_3$) δ 8.51 (d, J=6.0 Hz, 2H), 7.29-7.24 (m, 4H), 7.07-7.01 (m, 2H), 6.21 (br s, 1H), 4.59 (d, J=6.0 Hz, 2H), 4.45 (s, 2H), 4.08 (t, J=9.0 Hz, 2H), 3.46 (t, J=9.0 Hz, 2H), 2.61 (s, 3H); MS (ES+) m/z 426.3 (M+1).

Example 32.24

Synthesis of 2-(3-(cyclopropylmethyl)-2-oxoimidazolidin-1-yl)-4-methyl-N-(pyridin-2-ylmethyl)thiazole-5-carboxamide

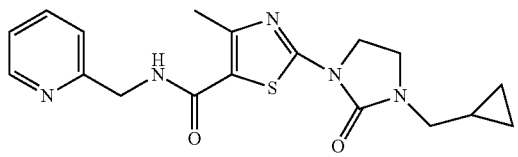

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(cyclopropylmethyl)-2-oxoimidazolidin-1-yl)-4-methylthiazole-5-carboxylic acid to react with pyridin-3-ylmethanamine, the title compound was obtained as a colorless solid in 64% yield: mp 148-151° C. (dichloromethane/hexanes); $^1$H NMR (300 MHz, CDCl$_3$) δ 8.54 (d, J=4.9 Hz, 1H), 7.70-7.64 (m, 1H), 7.31-7.23 (m, 1H), 7.21-7.18 (m, 1H), 7.11-7.09 (m, 1H), 4.69 (d, J=4.9 Hz, 2H), 4.15-4.09 (m, 2H), 3.73-3.67 (m, 2H), 3.19 (d, J=7.1 Hz, 2H), 2.64 (s, 3H), 1.00-0.91 (m, 1H), 0.60-0.54 (m, 2H), 0.27-0.22 (m, 2H); $^{13}$C NMR (75 MHz, CDCl$_3$) δ 162.6, 157.8, 155.9, 155.2, 152.4, 148.8, 136.8, 122.4, 122.0, 117.8, 48.6, 44.6, 42.3, 42.1, 17.2, 8.9, 3.4; MS (ES+) m/z 372.3 (M+1).

Example 32.25

Synthesis of 2-(3-(4-fluorobenzyl)-2-oxotetrahydropyrimidin-1(2H)-yl)-4-methyl-N-(pyridin-3-ylmethyl)thiazole-5-carboxamide

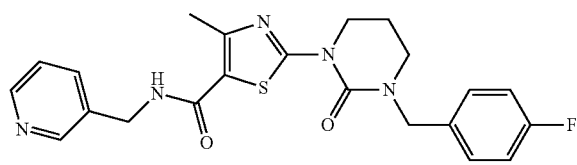

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(4-fluorobenzyl)-2-oxotetrahydropyrimidin-1(2H)-yl)-4-methylthiazole-5-carboxylic acid to react with pyridin-3-ylmethanamine, the title compound was obtained as a colorless solid in 15% yield: mp 48-50° C. (dichloromethane/hexanes); $^1$H NMR (300 MHz, CDCl$_3$) δ 8.60-8.54 (m, 2H), 7.70 (d, J=7.6 Hz, 1H), 7.31-7.25 (m, 3H), 7.04-6.99 (m, 2H), 6.05-6.01 (m, 1H), 4.59-4.57 (m, 4H), 4.17 (t, J=5.8 Hz, 2H), 3.32 (t, J=5.8 Hz, 2H), 2.62 (s, 3H), 2.11-2.04 (m, 2H); MS (ES+) m/z 440.2 (M+1).

Example 32.26

Synthesis of 2-(3-(cyclopropylmethyl)-2-oxotetrahydropyrimidin-1(2H)-yl)-4-methyl-N-(pyridin-3-ylmethyl)thiazole-5-carboxamide

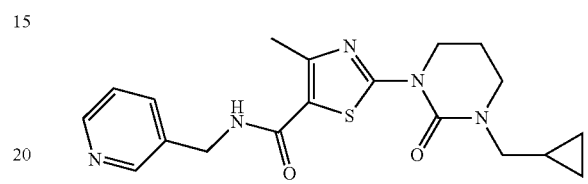

Following the procedure as described in Example 32, making variations as required to replace 2-(3-((5-chlorobenzo[b]thiophen-3-yl)methyl)-2-oxoimidazolidin-1-yl)-4-methylthiazole-5-carboxylic acid with 2-(3-(cyclopropylmethyl)-2-oxotetrahydropyrimidin-1(2H)-yl)-4-methylthiazole-5-carboxylic acid to react with pyridin-3-ylmethanamine, the title compound was obtained as a colorless solid in 22% yield: mp 142-145° C. (dichloromethane/hexanes); $^1$H NMR (300 MHz, CDCl$_3$) δ 8.57 (s, 1H), 8.52-8.51 (m, 1H), 7.68-7.65 (m, 1H), 7.28-7.23 (m, 1H), 6.07 (m, 1H), 4.56 (d, J=5.8 Hz, 2H), 4.15 (t, J=5.9 Hz, 2H), 3.48 (t, J=5.9 Hz, 2H), 3.31 (d, J=7.0 Hz, 2H), 2.61 (s, 3H), 2.16-2.09 (m, 2H), 1.05-0.98 (m, 1H), 0.55-0.49 (m, 2H), 0.28-0.23 (m, 2H); $^{13}$C NMR (75 MHz, CDCl$_3$) δ 163.0, 159.2, 152.9, 152.7, 149.0, 148.6, 135.6, 133.9, 123.6, 117.6, 52.8, 45.6, 45.5, 41.2, 21.3, 17.3, 9.3, 3.4; MS (ES+) m/z 386.2 (M+1).

Example 33

Synthesis of 4-methyl-2-(2-oxo-3-(pyridin-4-ylmethyl)imidazolidin-1-yl)-N-(pyridin-3-ylmethyl)thiazole-5-carboxamide

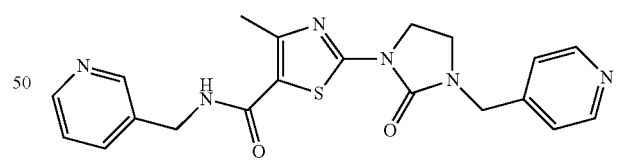

To a solution of 4-methyl-2-(2-oxo-3-(pyridin-4-ylmethyl)imidazolidin-1-yl)thiazole-5-carboxylic acid (0.67 g, 2.12 mmol) in anhydrous N,N-dimethyl formamide (10 mL) was added benzotriazol-1-yloxy-tris(dimethylamino)phosphonium hexafluorophosphate (0.94 g, 2.12 mmol), diisopropylethylamine (1.12 mL, 6.35 mmol) and 3-(aminomethyl)pyridine (0.22 mL, 2.12 mmol). The resulting solution was stirred at ambient temperature for 24 hours. The reaction mixture was concentrated in vacuo. The residue was dissolved in dichloromethane (50 mL), washed with saturated aqueous sodium bicarbonate solution (15 mL) and brine (15 mL). The separated organic layer was dried over anhydrous sodium sulfate, filtered and concentrated in vacuo. The residue was purified by column chromatography eluted with 10-20% methanol in ethyl acetate as an eluent to afford the title compound as a colorless solid (10%, 0.092 g): mp 233-235° C. (dichloromethane/hexanes); $^1$H NMR (300 MHz, CDCl$_3$) δ 8.57-8.49 (m, 4H), 7.67 (d, J=7.7 Hz, 1H), 7.26-7.17 (m, 3H), 6.36 (br s, 1H), 4.56 (d, J=5.8 Hz, 2H), 4.45 (s, 2H), 4.12-4.07 (m, 2H), 3.50-3.45 (m, 2H), 2.58 (s, 3H); MS (ES+) m/z 409.2 (M+1).

Example 34

Synthesis of N-benzyl-2-(3-(4-fluorobenzoyl)-2-oxoimidazolidin-1-yl)-4-methylthiazole-5-carboxamide

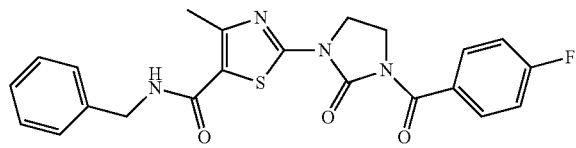

To a solution of N-benzyl-4-methyl-2-(2-oxoimidazolidin-1-yl)thiazole-5-carboxamide (0.30 g, 0.95 mmol) in N,N-dimethylformamide (15 mL) was added sodium hydride (60% in mineral oil, 0.38 g, 0.95 mmol). The reaction mixture was stirred at ambient temperature for 30 minutes. To the resulting solution was added 4-fluorobenzoyl chloride (0.11 mL, 0.95 mmol). The reaction mixture was stirred at ambient temperature for 16 hours and concentrated in vacuo. The residue was dissolved in dichloromethane (50 mL) and washed with water. The organic layer was dried over anhydrous sodium sulphate, filtered, and concentrated in vacuo. The residue was purified by column chromatography eluted with 60-80% ethyl acetate in hexanes to afford the title compound in 23% yield (0.10 g, 23%): mp 130-132° C.; $^1$H NMR (300 MHz, CDCl$_3$) δ 7.66-7.61 (m, 2H), 7.29-7.23 (m, 5H), 7.10-7.04 (m, 2H), 5.86 (br s, 1H), 4.49 (d, J=5.5 Hz, 2H), 4.21-4.15 (m, 4H), 2.60 (s, 3H), MS (ES+) m/z 439.2 (M+1).

Example 35

Synthesis of 1-(5-acetyl-4-methylthiazol-2-yl)imidazolidin-2-one

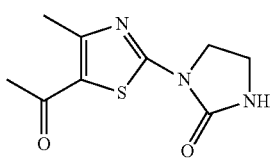

To a solution of 5-acetyl-2-amino-4-methylthiazole (5.50 g, 35.20 mmol) in tetrahydrofuran (200 mL) was added triethylamine (15.0 mL, 107.6 mmol) and 2-chloroethyl isocyanate (3.90 mL, 45.70 mmol). The reaction mixture was stirred at ambient temperature for 18 hours, and then heated to reflux for 27 hours. The solvent was removed in vacuo, and the residue was washed with water (200 mL) and ethyl acetate/hexanes (1/1, 50 mL) to afford the title compound in 99% yield (7.9 g): MS (ES+) m/z 226.1 (M+1).

Example 36

Synthesis of (E)-1-(5-(3-(dimethylamino)acryloyl)-4-methylthiazol-2-yl)-3-(4-(trifluoromethyl)benzyl)imidazolidin-2-one

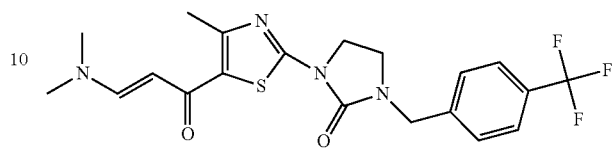

To a solution of 1-(5-acetyl-4-methylthiazol-2-yl)-3-(4-(trifluoromethyl)benzyl)-imidazolidin-2-one (1.00 g, 2.60 mmol) in N,N-dimethylformamide (20 mL) was added N,N-dimethylformamide dimethyl acetal (0.45 mL, 3.17 mmol). The reaction mixture was heated at 110° C. for 18 hours. The solvent was removed in vacuo, and the residue was washed with water to afford the title compound in 98% yield (1.12 g): $^1$H NMR (300 MHz, DMSO-d$_6$) δ 7.70 (d, J=8.1 Hz, 2H), 7.60 (d, J=8.1 Hz, 2H), 7.58 (d, J=12.0 Hz, 1H), 5.28 (d, J=12.0 Hz, 1H), 4.50 (s, 2H), 4.01-3.95 (m, 2H), 3.48-3.43 (m, 2H), 3.08 (s, 3H), 2.81 (s, 3H), 2.48 (s, 3H); MS (ES+) m/z 439.1 (M+1).

Example 37

Synthesis of (E)-1-(5-(3-(dimethylamino)but-2-enoyl)-4-methylthiazol-2-yl)-3-(4-(trifluoromethyl)benzyl)imidazolidin-2-one

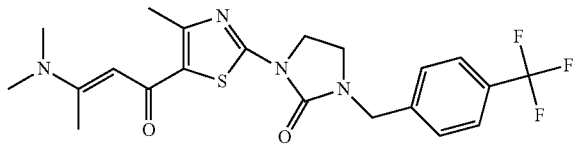

To a solution of 1-(5-acetyl-4-methylthiazol-2-yl)-3-(4-(trifluoromethyl)benzyl)-imidazolidin-2-one (1.00 g, 2.60 mmol) in N,N-dimethylacetamide (10 mL) was added N,N-dimethylacetamide dimethyl acetal (1.0 mL, 6.15 mmol). The reaction mixture was heated for 20 hours at 110° C. The solvent was removed in vacuo, and the residue was washed with water to afford the title compound as a colorless solid in 90% yield (1.07 g): $^1$H NMR (300 MHz, DMSO-d$_6$) δ 7.70 (d, J=8.1 Hz, 2H), 7.60 (d, J=8.1 Hz, 2H), 5.23 (s, 1H), 4.49 (s, 2H), 3.99-3.91 (m, 2H), 3.48-3.40 (m, 2H), 2.98 (s, 6H), 2.49-2.43 (m, 6H); MS (ES+) m/z 453.1 (M+1).

Example 38

Synthesis of 1-(4-methyl-5-(1H-pyrazol-3-yl)thiazol-2-yl)-3-(4-(trifluoromethyl)-benzyl)imidazolidin-2-one

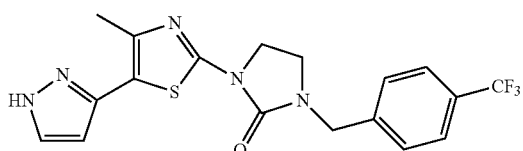

To a solution of (E)-1-(5-(3-(dimethylamino)acryloyl)-4-methylthiazol-2-yl)-3-(4-(trifluoromethyl)benzyl)imidazolidin-2-one (0.44 g, 1.00 mmol) in ethanol (10 mL) was added hydrazine monohydrate (0.12 mL, 1.58 mmol). The reaction mixture was heated to reflux for 3 hours. The solvent was removed in vacuo, and the residue was purified by column chromatography to afford the title compound as a colorless solid in 72% yield (0.30 g): mp 212-213° C. (ethyl acetate); $^1$H NMR (300 MHz, CDCl$_3$ & CD$_3$OD) δ 7.54-7.20 (m, 5H), 6.24 (s, 1H), 4.39 (s, 2H), 3.98-3.89 (m, 2H), 3.35-3.30 (m, 2H), 2.27 (s, 3H); $^{13}$C NMR (75 MHz, CDCl$_3$ & CD$_3$OD) δ 156.9, 155.8, 139.8, 130.2, 129.8, 129.3, 128.2, 125.6, 125.5, 122.0, 103.8, 47.2, 41.9, 41.8, 15.7; MS (ES+) m/z 408.1 (M+1).

Example 38.1

Synthesis of 1-(5-(isoxazol-5-yl)-4-methylthiazol-2-yl)-3-(4-(trifluoromethyl)benzyl)-imidazolidin-2-one

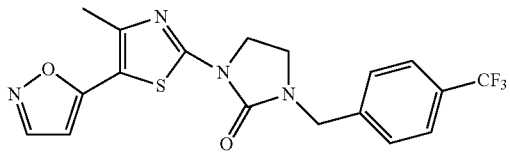

Following the procedure as described in Example 38, making variations as required to replace hydrazine monohydrate with hydroxylamine hydrochloride to react with (E)-1-(5-(3-(dimethylamino)acryloyl)-4-methylthiazol-2-yl)-3-(4-(trifluoromethyl)benzyl)imidazolidin-2-one, the title compound was obtained as a colorless solid in 76% yield: mp 153-154° C. (ethyl acetate/hexanes); $^1$H NMR (300 MHz, CDCl$_3$) δ 8.23 (d, J=1.8 Hz, 1H), 7.67 (d, J=8.1 Hz, 2H), 7.43 (d, J=8.1 Hz, 2H), 6.23 (d, J=1.8 Hz, 1H), 4.53 (s, 2H), 4.17-4.04 (m, 2H), 3.54-3.41 (m, 2H), 2.53 (s, 3H); $^{13}$C NMR (75 MHz, CDCl$_3$) δ 163.2, 158.4, 155.5, 150.5, 148.1, 139.7, 128.5, 125.9, 125.8, 122.1, 111.8, 99.4, 47.6, 42.1, 41.9, 17.1; MS (ES+) m/z 409.1 (M+1).

Example 38.2

Synthesis of 1-(4-methyl-5-(5-methyl-1H-pyrazol-3-yl)thiazol-2-yl)-3-(4-(trifluoromethyl)benzyl)imidazolidin-2-one

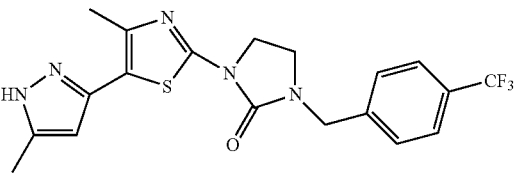

Following the procedure as described in Example 38, making variations as required to replace (E)-1-(5-(3-(dimethylamino)acryloyl)-4-methylthiazol-2-yl)-3-(4-(trifluoromethyl)benzyl)imidazolidin-2-one with (E)-1-(5-(3-(dimethylamino)but-2-enoyl)-4-methylthiazol-2-yl)-3-(4-(trifluoromethyl)benzyl)imidazolidin-2-one to react with hydrazine monohydrate, the title compound was obtained as a colorless solid in 67% yield: mp 238-239° C. (ethyl acetate); $^1$H NMR (300 MHz, CDCl$_3$) δ 7.53 (d, J=7.8 Hz, 2H), 7.34 (d, J=7.8 Hz, 2H), 6.08 (s 1H), 4.52 (s, 2H), 4.04-3.99 (m, 2H), 3.42-3.36 (m, 2H), 2.36 (s, 3H), 2.24 (s, 3H); $^{13}$C NMR (75 MHz, CDCl$_3$) δ 156.8, 155.8, 143.1, 139.9, 130.3, 129.9, 128.3, 125.8, 125.7, 122.1, 103.6, 47.5, 41.9, 41.8, 16.0, 10.8; MS (ES+) m/z 422.1 (M+1).

Example 38.3

Synthesis of 1-(4-methyl-5-(3-methylisoxazol-5-yl)thiazol-2-yl)-3-(4-(trifluoromethyl)benzyl)imidazolidin-2-one

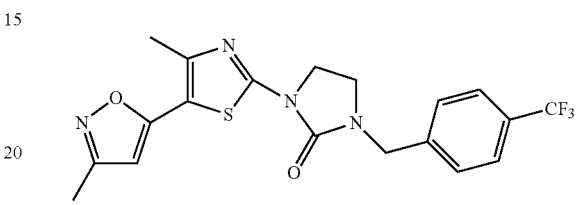

Following the procedure as described in Example 38, making variations as required to replace (E)-1-(5-(3-(dimethylamino)acryloyl)-4-methylthiazol-2-yl)-3-(4-(trifluoromethyl)benzyl)imidazolidin-2-one with (E)-1-(5-(3-(dimethylamino)but-2-enoyl)-4-methylthiazol-2-yl)-3-(4-(trifluoromethyl)benzyl)imidazolidin-2-one to react with hydroxylamine hydrochloride, the title compound was obtained as a colorless solid in 53% yield: mp 201-203° C. (ethyl acetate/hexanes); $^1$H NMR (300 MHz, CDCl$_3$) δ 7.59 (d, J=8.1 Hz, 2H), 7.41 (d, J=8.1 Hz, 2H), 6.07 (s, 1H), 4.54 (s, 2H), 4.12-4.06 (m, 2H), 3.50-3.44 (m, 2H), 2.51 (s, 3H), 2.24 (s, 3H); $^{13}$C NMR (75 MHz, CDCl$_3$) δ 163.4, 160.8, 158.2, 155.5, 147.8, 139.8, 130.5, 128.5, 125.9, 122.1, 112.0, 101.0, 47.6, 42.0, 41.9, 17.0, 11.4; MS (ES+) m/z 423.1 (M+1).

Example 39

Synthesis of 1-(4-methyl-5-(1H-pyrazol-5-yl)thiazol-2-yl)-3-(4-(piperidine-1-carbonyl)benzyl)imidazolidin-2-one

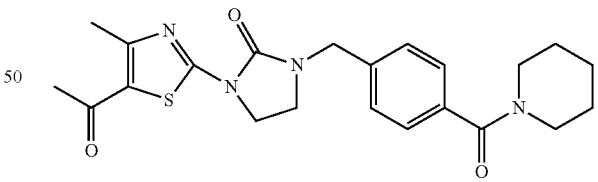

To a solution of 1-(5-acetyl-4-methylthiazol-2-yl)-3-(4-(piperidine-1-carbonyl)benzyl)imidazolidin-2-one (0.43 g, 1.00 mmol) in N,N-dimethylformamide (10 mL) was added N,N-dimethylformamide dimethyl acetal (0.20 mL, 1.50 mmol). The reaction mixture was heated for 20 hours at 110° C., and hydrazine monohydrate (0.25 mL, 5.14 mmol) was added. The reaction mixture was heated for another 10 minutes at 110° C., then cooled to ambient temperature, diluted with ethyl acetate and washed with water. The organic phase was dried over anhydrous sodium sulfate, filtered and concentrated in vacuo. The residue was purified by column chromatography to afford the title compound as a colorless solid in 54% yield (0.26 g): mp 156-157° C. (ethyl acetate); $^1$H NMR (300 MHz, CDCl$_3$) δ 7.45-7.22 (m, 4H), 4.50 (s, 2H), 4.15-4.01 (m, 2H), 3.69-3.32 (m, 6H), 2.60 (s, 3H), 2.40 (s, 3H), 1.71-1.20 (m, 6H); MS (ES+) m/z 427.1 (M+1).

Example 40

Synthesis of 1-(4-methyl-5-(3-methyl-1H-pyrazol-5-yl)thiazol-2-yl)-3-(4-(piperidine-1-carbonyl)benzyl)imidazolidin-2-one

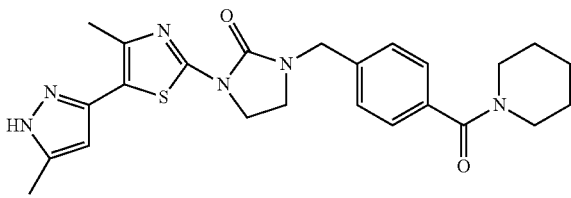

To a solution of 1-(5-acetyl-4-methylthiazol-2-yl)-3-(4-(piperidine-1-carbonyl)benzyl)imidazolidin-2-one (0.43 g, 1.00 mmol) in N,N-dimethylacetamide (5 mL) was added N,N-dimethylacetamide dimethyl acetal (0.5 mL, 3.40 mmol). The reaction mixture was heated for 24 hours at 110° C., and hydrazine monohydrate (0.30 mL, 6.18 mmol) was added. The reaction mixture was heated for another 10 minutes at 110° C., then cooled to ambient temperature, diluted with ethyl acetate and washed with water. The organic phase was dried over anhydrous sodium sulfate, filtered and concentrated in vacuo. The residue was purified by column chromatography to afford the title compound as a colorless solid in 46% yield (0.25 g): mp 182-183° C. (ethyl acetate); $^1$H NMR (300 MHz, CDCl$_3$) δ 7.38-7.30 (m, 4H), 6.16 (s, 1H), 4.49 (s, 2H), 4.10-4.04 (m, 2H), 3.68 (br s, 2H), 3.46-3.31 (m, 4H), 2.46 (s, 3H), 2.32 (s, 3H), 1.56-1.49 (m, 6H); $^{13}$C NMR (75 MHz, CDCl$_3$) δ 169.9, 156.6, 155.8, 143.6, 137.3, 136.1, 128.2, 127.4, 104.2, 48.7, 47.7, 41.8, 26.5, 25.6, 24.5, 21.1, 16.5; MS (ES+) m/z 465.2 (M+1).

Example 40.1

Synthesis of 1-(4-fluorobenzyl)-3-(4-methyl-5-(5-methyl-1H-pyrazol-3-yl)thiazol-2-yl)imidazolidin-2-one

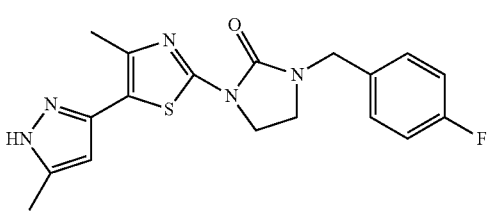

Following the procedure as described in Example 40, making variations as required to replace 1-(5-acetyl-4-methylthiazol-2-yl)-3-(4-(piperidine-1-carbonyl)benzyl)imidazolidin-2-one with 1-(5-acetyl-4-methylthiazol-2-yl)-3-(4-fluorobenzyl)imidazolidin-2-one to react with N,N-dimethylacetamide dimethyl acetal and further with hydrazine monohydrate, the title compound was obtained as a colorless solid in 46% yield: mp 218-221° C. (ethyl acetate); $^1$H NMR (300 MHz, CDCl$_3$) δ 7.28-7.23 (m, 2H), 7.05-6.97 (m, 2H), 6.15 (s, 1H), 4.44 (s, 2H), 4.09-4.02 (m, 2H), 3.43-3.38 (m, 2H), 2.52 (s, 3H), 2.24 (s, 3H); $^{13}$C NMR (75 MHz, CDCl$_3$) δ 164.1, 160.8, 156.5, 155.7, 143.4, 131.7, 130.1, 129.9, 115.8, 115.6, 103.7, 47.3, 42.0, 41.7, 16.5, 11.4; MS (ES+) m/z 372.2 (M+1).

Example 40.2

Synthesis of N-methyl-4-((3-(4-methyl-5-(3-methyl-1H-pyrazol-5-yl)thiazol-2-yl)-2-oxoimidazolidin-1-yl)methyl)benzamide

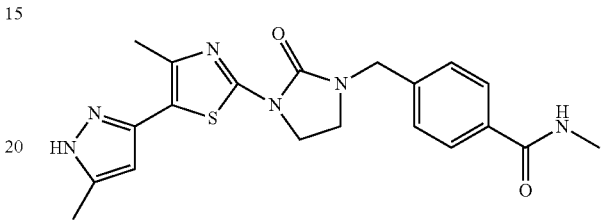

Following the procedure as described in Example 40, making variations as required to replace 1-(5-acetyl-4-methylthiazol-2-yl)-3-(4-(piperidine-1-carbonyl)benzyl)imidazolidin-2-one with 4-((3-(5-acetyl-4-methylthiazol-2-yl)-2-oxoimidazolidin-1-yl)methyl)-N-methylbenzamide to react with N,N-dimethylacetamide dimethyl acetal and further with hydrazine monohydrate, the title compound was obtained as a colorless solid in 80% yield: mp 236-238° C. (ethyl acetate); $^1$H NMR (300 MHz, DMSO-d$_6$) δ 8.40 (d, J=4.2 Hz, 1H), 7.79 (d, J=8.1 Hz, 2H), 7.35 (d, J=8.1 Hz, 2H), 6.16 (s, 1H), 4.44 (s, 2H), 4.03-3.93 (m, 2H), 3.45-3.40 (m, 2H), 2.67 (d, J=4.2 Hz, 3H), 2.34 (s, 3H), 2.22 (s, 3H); $^{13}$C NMR (75 MHz, DMSO-d$_6$) δ 166.7, 155.8, 144.0, 142.3, 140.1, 134.1, 128.0, 127.8, 102.7, 102.6, 47.1, 42.4, 42.3, 42.2, 26.7, 16.9; MS (ES+) m/z 411.1 (M+1).

Example 40.3

Synthesis of N-methyl-3-((3-(4-methyl-5-(3-methyl-1H-pyrazol-5-yl)thiazol-2-yl)-2-oxoimidazolidin-1-yl)methyl)benzamide

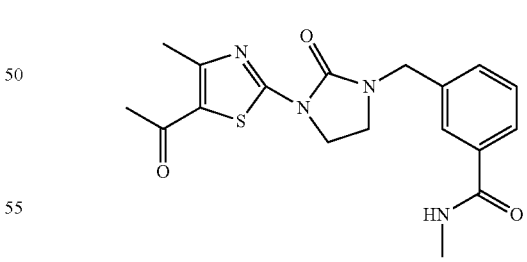

Following the procedure as described in Example 40, making variations as required to replace 1-(5-acetyl-4-methylthiazol-2-yl)-3-(4-(piperidine-1-carbonyl)benzyl)imidazolidin-2-one with 3-((3-(5-acetyl-4-methylthiazol-2-yl)-2-oxoimidazolidin-1-yl)methyl)-N-methylbenzamide to react with N,N-dimethylacetamide dimethyl acetal and further with hydrazine monohydrate, the title compound was obtained as a colorless solid in 54% yield: mp 259-261° C. (ethyl acetate); $^1$H NMR (300 MHz, DMSO-d$_6$) δ 7.73-7.62

(m, 2H), 7.42-7.34 (m, 2H), 6.32 (br s, 1H), 4.51 (s, 2H), 4.13-4.04 (m, 2H), 3.49-3.41 (m, 2H), 2.97 (d, J=4.8 Hz, 3H), 2.60 (s, 3H), 2.45 (s, 3H); MS (ES+) m/z 373.1 (M+1).

Example 41

Synthesis of 1-(5-(hydroxymethyl)-4-methylthiazol-2-yl)-3-(4-(trifluoromethyl)benzyl)imidazolidin-2-one

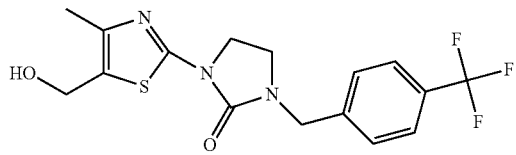

To a solution of ethyl 4-methyl-2-(2-oxo-3-(4-(trifluoromethyl)benzyl)-imidazolidin-1-yl)thiazole-5-carboxylate (1.00 g, 2.41 mmol) in tetrahedrofuran (50 mL) was added lithium borohydride (2.7 mL of 2.0 M solution in tetrahedrofuran, 5.4 mmol) and methanol (0.10 mL, 2.47 mmol). The reaction mixture was stirred for 22 hours at ambient temperature and quenched with water. The resulting solution was extracted with chloroform and washed with water. The organic solution was dried over anhydrous sodium sulfate, filtered and concentrated in vacuo, and the residue was purified by column chromatography to afford the title compound in 56% yield (0.51 g): mp 153-154° C. (ethyl acetate/hexanes); $^1$H NMR (300 MHz, DMSO-d$_6$) δ 7.59 (d, J=8.1 Hz, 2H), 7.40 (d, J=8.1 Hz, 2H), 4.69 (d, J=5.1 Hz, 2H), 4.52 (s, 2H), 4.13-4.02 (m, 2H), 3.45-3.40 (m, 2H), 2.26 (s, 3H); MS (ES+) m/z 372.1 (M+1).

Example 42

Synthesis of 4-methyl-2-(2-oxo-3-(4-(trifluoromethyl)benzyl)imidazolidin-1-yl)thiazole-5-carbaldehyde

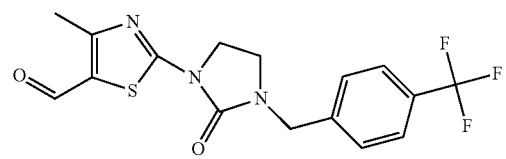

To a solution of 1-(5-(hydroxymethyl)-4-methylthiazol-2-yl)-3-(4-(trifluoromethyl)benzyl)imidazolidin-2-one (0.40 g, 1.07 mmol) in dichloromethane (50 mL) was added Dess-Mertin periodinane (0.60 g, 1.40 mmol). The reaction mixture was stirred for 6 hours at ambient temperature, and then diluted with ethyl acetate, washed with 10% sodium thiosulfate solution, saturated sodium bicarbonate solution and brine. The organic solution was dried over anhydrous sodium sulfate and filtered. The filtrate was concentrated in vacuo to afford the title compound in 80% yield (0.32 g): MS (ES+) m/z 370.1 (M+1).

Example 43

Synthesis of 1-(4-methyl-5-(oxazol-5-yl)thiazol-2-yl)-3-(4-(trifluoromethyl)benzyl)-imidazolidin-2-one

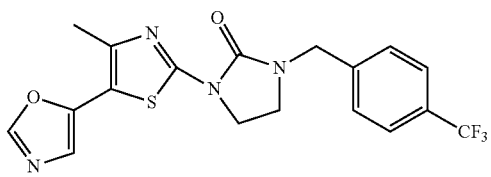

To a solution of 4-methyl-2-(2-oxo-3-(4-(trifluoromethyl)benzyl)imidazolidin-1-yl)thiazole-5-carbaldehyde (0.32 g, 0.86 mmol) in methanol (20 mL) was added potassium carbonate (0.30 g, 2.17 mmol) and tosylmethyl isocyanide (0.23 g, 1.17 mmol). The reaction mixture was stirred at ambient temperature for 1 h, heated to reflux for 1 h, and then cooled to ambient temperature. The mixture was diluted with ethyl acetate, washed with water and brine. The organic solution was dried over anhydrous sodium sulfate, filtered and concentrated in vacuo. The residue was purified by column chromatography to afford the title compound as a colorless solid in 47% yield (0.32 g): mp 160-162° C. (ethyl acetate/hexanes); $^1$H NMR (300 MHz, CDCl$_3$) δ 7.85 (s, 1H), 7.59 (d, J=8.1 Hz, 2H), 7.40 (d, J=8.1 Hz, 2H), 7.07 (s, 1H), 4.53 (s, 2H), 4.12-4.06 (m, 2H), 3.49-3.44 (m, 2H), 2.43 (s, 3H); $^1$H NMR (75 MHz, CDCl$_3$) δ 157.5, 155.6, 149.8, 145.4, 145.1, 139.8, 130.5, 128.5, 125.9, 122.4, 122.1, 111.7, 47.6, 42.1, 42.0, 16.7; MS (ES+) m/z 409.1 (M+1).

Example 44

Synthesis of 1-(4-methyl-5-(3-methyl-1,2,4-oxadiazol-5-yl)thiazol-2-yl)-3-(4-(trifluoromethyl)benzyl)imidazolidin-2-one

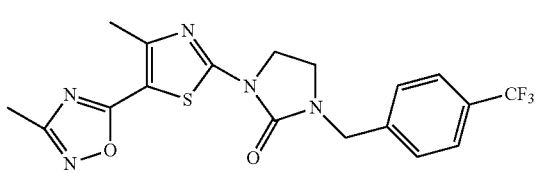

To a solution of 4-methyl-2-(2-oxo-3-(4-(trifluoromethyl)benzyl)imidazolidin-1-yl)thiazole-5-carboxylic acid (0.39 g, 1.00 mmol) in N,N-dimethylformamide (10 mL) was added 1,1'-carbonyldiimidazole (0.24 g, 1.50 mmol). The reaction mixture was stirred at ambient temperature for 10 minutes, and N-hydroxyacetamidine (0.08 g, 1.1 mmol) was added. The stirring was continued at ambient temperature for 6 hours, and another portion of N-hydroxyacetamidine (0.08 g, 1.1 mmol) was added. The reaction mixture was heated for 23 hours at 110° C. and cooled to ambient temperature, diluted with ethyl acetate and washed with water and brine. The organic solution was dried over anhydrous sodium sulfate, and filtered and concentrated in vacuo. The residue was purified by column chromatography to afford the title compound in 15% yield (0.06 g): mp 163-164° C. (ethyl acetate); $^1$H NMR (300 MHz, CDCl$_3$) δ 7.60 (d, J=8.1 Hz, 2H), 7.41 (d, J=8.1 Hz, 2H), 4.55 (s, 2H), 4.15-4.09 (m, 2H), 3.51-3.45 (m, 2H), 2.68 (s, 3H), 2.41 (s, 3H); $^{13}$C NMR (75 MHz, CDCl$_3$)

δ 170.8, 167.3, 160.5, 155.3, 154.5, 139.6, 128.5, 125.9, 125.8, 122.1, 109.0, 47.6, 42.1, 41.9, 17.5, 11.6; MS (ES+) m/z 424.1 (M+1).

Example 45

Synthesis of 1-(5-bromo-4-methylthiazol-2-yl)-3-(4-(trifluoromethyl)-benzyl)imidazolidin-2-one

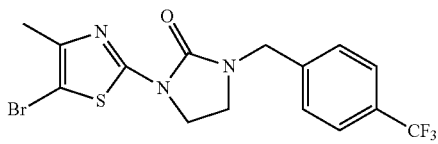

To a solution of 1-(4-methylthiazol-2-yl)-3-(4-(trifluoromethyl)benzyl)-imidazolidin-2-one (1.40 g, 4.10 mmol) in acetonitrile (40 mL) was added N-bromosuccinimide (0.73 g, 4.10 mmol). The reaction mixture was stirred at 0° C. for 1 h, quenched with 10% sodium thiosulfate solution (10 mL), diluted with ethyl acetate (200 mL), washed with water and brine. The organic solution was dried over anhydrous sodium sulfate, filtered and concentrated in vacuo. The residue was purified by column chromatography to afford the title compound as a colorless solid in 69% yield (1.20 g): mp 107-108° C. (ethyl acetate/hexanes); $^1$H NMR (300 MHz, CDCl$_3$) δ 7.59 (d, J=7.8 Hz, 2H), 7.39 (d, J=7.8 Hz, 2H), 4.51 (s, 2H), 4.08-3.99 (m, 2H), 3.47-3.41 (m, 2H), 2.25 (s, 3H); MS (ES+) m/z 420.1 (M+1), 422.1 (M+1).

Example 46

Synthesis of 2-(4-(4-methyl-5-(pyridin-3-ylmethyl-carbamoyl)thiazol-2-yl)-5-oxo-4,5-dihydro-1H-1,2,4-triazol-1-yl)ethyl methanesulfonate

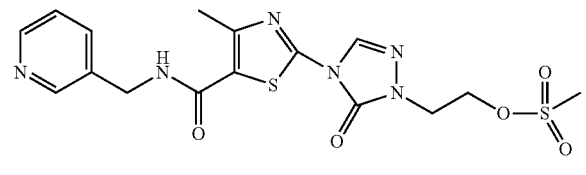

To the solution of 2-(1-(2-hydroxyethyl)-5-oxo-1H-1,2,4-triazol-4(5H)-yl)-4-methyl-N-(pyridin-3-ylmethyl)thiazole-5-carboxamide (0.20 g, 0.56 mmol) and triethylamine (0.15 mL, 1.11 mmol) in anhydrous tetrahydrofuran (10 mL) was added dropwise methanesulfonyl chloride (0.08 g, 0.67 mmol) at 0° C. The reaction mixture was stirred at ambient temperature for 3 hours, diluted with ethyl acetate (15 mL) and washed with water and brine. The organic solution was dried over anhydrous sodium sulphate, filtered and concentrated in vacuo to afford the title compound as a yellow solid in 70% yield (0.17 g); $^1$H NMR (300 MHz, CDCl$_3$) δ 8.60 (s, 1H), 8.55-8.51 (m, 1H), 8.31 (s, 1H), 7.72-7.66 (m, 1H), 7.31-7.25 (m, 1H), 6.26 (t, J=5.8 Hz, 1H), 4.60 (d, J=5.8 Hz, 2H), 4.54 (t, J=5.1 Hz, 2H), 4.19 (t, J=5.1 Hz, 2H), 3.02 (s, 3H), 2.65 (s, 3H); MS (ES+) m/z 439.2 (M+1).

Example 47

Synthesis of 2-(1-(2-(4-fluorobenzylamino)ethyl)-5-oxo-1H-1,2,4-triazol-4(5H)-yl)-4-methyl-N-(pyridin-3-ylmethyl)thiazole-5-carboxamide

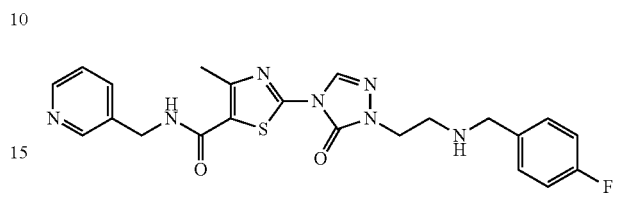

A solution of 2-(4-(4-methyl-5-(pyridin-3-ylmethylcarbamoyl)thiazol-2-yl)-5-oxo-4,5-dihydro-1H-1,2,4-triazol-1-yl)ethyl methanesulfonate (0.10 g, 0.23 mmol) and (4-fluorophenyl)methanamine (0.09 g, 0.69 mmol) in anhydrous methanol (5 mL) was heated at reflux for 6 hours. The solvent was removed in vacuo and the residue was purified by column chromatography eluted with ethyl acetate to afford the title compound as a white solid in 66% yield (0.07 g): mp 106-107° C. (ethyl acetate/hexane); $^1$H NMR (300 MHz, CDCl$_3$) δ 8.59 (br s, 1H), 8.56-8.47 (m, 1H), 8.25 (s, 1H), 7.73-7.65 (m, 1H), 7.32-7.18 (m, 3H), 7.00-6.89 (m, 2H), 6.44 (t, J=5.8 Hz, 1H), 4.59 (d, J=5.8 Hz, 2H), 3.98 (t, J=5.8 Hz, 2H), 3.77 (s, 2H), 3.00 (t, J=5.8 Hz, 2H), 2.64 (s, 3H); MS (ES+) m/z 468.2 (M+1).

Example 47.1

Synthesis of 2-(1-(2-(4-fluorophenylamino)ethyl)-5-oxo-1H-1,2,4-triazol-4(5H)-yl)-4-methyl-N-(pyridin-3-ylmethyl)thiazole-5-carboxamide

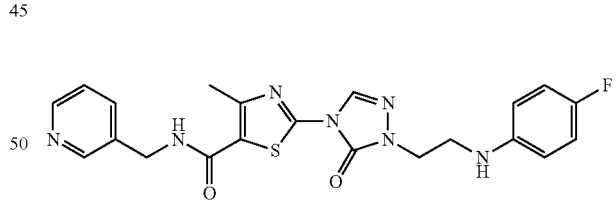

Following the procedure as described in Example 47, making variations as required to replace (4-fluorophenyl)methanamine with 4-fluoroaniline to react with 2-(4-(4-methyl-5-(pyridin-3-ylmethylcarbamoyl)thiazol-2-yl)-5-oxo-4,5-dihydro-1H-1,2,4-triazol-1-yl)ethyl methanesulfonate, the title compound was obtained as a colorless solid in 66% yield: mp 163-164° C. (ethyl acetate/hexane); $^1$H NMR (300 MHz, CDCl$_3$) δ 8.56 (br s, 1H), 8.51-8.41 (m, 1H), 8.22 (s, 1H), 7.71-7.62 (m, 1H), 7.23-7.19 (m, 1H), 691-6.75 (m, 3H), 6.54-6.47 (m, 2H), 4.57 (d, J=5.8 Hz, 2H), 4.09-3.92 (m, 3H), 3.53-3.39 (m, 2H), 2.61 (s, 3H); MS (ES+) m/z 454.1 (M+1).

Example 48

Synthesis of 2-(4-(4-methyl-5-(pyridin-3-ylmethylcarbamoyl)thiazol-2-yl)-5-oxo-4,5-dihydro-1H-1,2,4-triazol-1-yl)ethyl 4-fluorobenzylcarbamate

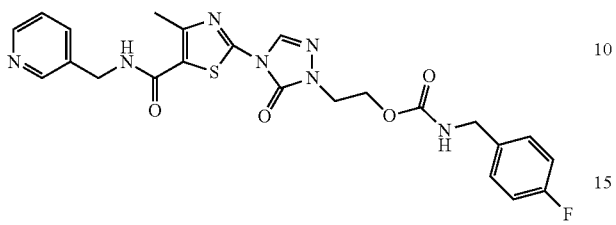

To the solution of 2-(4-(4-methyl-5-(pyridin-3-ylmethylcarbamoyl)thiazol-2-yl)-5-oxo-4,5-dihydro-1H-1,2,4-triazol-1-yl)ethyl methanesulfonate (0.40 g, 0.91 mmol) in anhydrous tetrahydrofuran (10 mL) was added potassium carbonate (0.32 g, 2.28 mmol). The reaction mixture was stirred at ambient temperature for 1 minute, followed by the addition of (4-fluorophenyl)methanamine (0.10 mL, 0.91 mmol). The reaction mixture was stirred at ambient temperature for 17 hours, and then partitioned between ethyl acetate and brine. The organic layer was separated, washed with brine, dried over anhydrous sodium sulphate, filtered and concentrated in vacuo. The residue was purified by column chromatography eluted with ethyl acetate to afford the title compound as a white solid in 77% yield (0.36 g): mp 149-150° C. (ethyl acetate); $^1$H NMR (300 MHz, CDCl$_3$) δ 8.58 (br s, 1H), 8.49 (br s, 1H), 8.22 (s, 1H), 7.72-7.64 (m, 1H), 7.31-7.14 (m, 3H), 7.00-6.89 (m, 2H), 6.54 (t, J=5.8 Hz, 1H), 5.33 (t, J=5.9 Hz, 1H), 4.59 (d, J=5.8 Hz, 2H), 4.38 (t, J=5.1 Hz, 2H), 4.25 (d, J=5.9 Hz, 2H), 4.06 (t, J=5.1 Hz, 2H), 2.62 (s, 3H); MS (ES+) m/z 512.4 (M+1).

Example 49

Synthesis of 2-(1-(2-(4-fluorobenzyloxy)ethyl)-5-oxo-1H-1,2,4-triazol-4(5H)-yl)-4-methyl-N-(pyridin-3-ylmethyl)thiazole-5-carboxamide

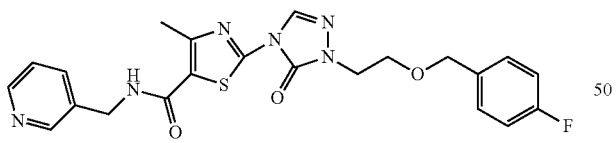

To the solution of 2-(1-(2-hydroxyethyl)-5-oxo-1H-1,2,4-triazol-4(5H)-yl)-4-methyl-N-(pyridin-3-ylmethyl)thiazole-5-carboxamide (0.11 g, 0.31 mmol) in anhydrous tetrahydrofuran was added sodium hydride (60% in mineral oil, 0.015 g, 0.35 mmol) at 0° C. The reaction mixture was stirred for 30 minutes, followed by the addition of 1-(bromomethyl)-4-fluorobenzene (0.04 mL, 0.31 mmol). The resulting mixture was stirred at ambient temperature for 17 hours, diluted with ethyl acetate and washed with water and brine. The organic solution was dried over anhydrous sodium sulphate, filtered and concentrated in vacuo. The residue was purified by column chromatography eluted with ethyl acetate to afford the title compound as a white solid in 46% yield (0.06 g): mp 235-236° C. (ethyl acetate); $^1$H NMR (300 MHz, DMSO-d$_6$) δ 9.14 (br s, 1H), 9.11-9.06 (m, 1H), 8.95 (t, J=5.5 Hz, 1H), 8.73 (s, 1H), 8.56-8.48 (m, 1H), 8.15-8.08 (m, 1H), 7.65-7.56 (m, 2H), 7.32-7.22 (m, 2H), 5.81 (s, 2H), 4.57 (d, J=5.5 Hz, 2H), 3.79 (t, J=5.4 Hz, 2H), 3.64 (t, J=5.4 Hz, 2H), 2.54 (s, 3H); $^{13}$C NMR (75 MHz, DMSO-d$_6$) δ 162.0, 161.4, 152.6, 152.1, 150.6, 145.1, 143.8, 14-3.7, 141.1, 131.9, 131.9, 131.0, 128.7, 121.9, 116.6, 62.9, 58.6, 48.3, 40.7, 17.5; MS (ES+) m/z 469.2 (M+1).

Example 50

Synthesis of ethyl 5-(3-(2-(tert-butyldimethylsilyloxy)ethyl)-2-oxoimidazolidin-1-yl)-3-methylthiophene-2-carboxylate

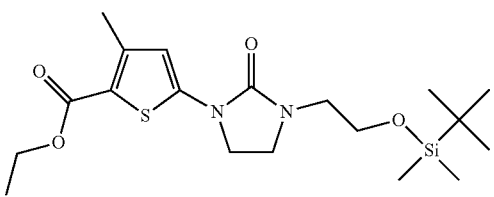

To a stirred suspension of ethyl 3-methyl-5-(2-oxoimidazolidin-1-yl)thiophene-2-carboxylate (0.85 g, 3.33 mmol) in anhydrous N,N-dimethylformamide (8 mL) under nitrogen atmosphere was added in one portion sodium hydride (60% in mineral oil, 0.16 g, 4.00 mmol). The resulting reaction mixture was stirred at ambient temperature for 1 h, and then (2-bromoethoxy)(tert-butyl)dimethylsilane (0.86 mL, 4.01 mmol) was added. The resulting reaction mixture was stirred at ambient temperature for 16 h, and then partitioned between ethyl acetate (100 mL), water (35 mL) and brine (35 mL). The aqueous layer was extracted with ethyl acetate (100 mL), and the combined organic layer was dried over sodium sulfate, filtered and concentrated in vacuo. The residue was purified by column chromatography eluted with 0-30% ethyl acetate in hexanes to afford the title compound as a colorless solid in 79% yield (1.09 g): $^1$H NMR (300 MHz, CDCl$_3$) δ 6.13 (s, 1H), 4.26 (q, J=7.1 Hz, 2H), 3.85-3.69 (m, 6H), 3.41 (t, J=5.2 Hz, 2H), 2.49 (s, 3H), 1.33 (t, J=7.1 Hz, 3H), 0.89 (s, 9H), 0.06 (s, 6H); MS (ES+) m/z 413.4 (M+1).

Example 50.1

Synthesis of ethyl 3-methyl-5-(2-oxo-3-(2-oxo-2-phenylethyl)imidazolidin-1-yl)thiophene-2-carboxylate

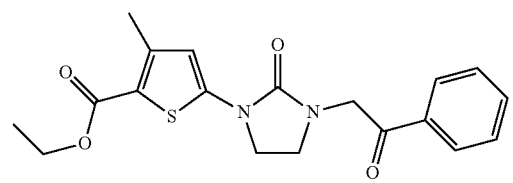

Following the procedure as described in Example 50, making variations as required to replace (2-bromoethoxy)(tert-butyl)dimethylsilane with 2-bromoacetophenone to react with ethyl 3-methyl-5-(2-oxoimidazolidin-1-yl)thiophene-2-carboxylate, the title compound was obtained as a colorless solid in 39% yield: $^1$H NMR (300 MHz, CDCl$_3$) δ 7.95 (d, J=8.3 Hz, 2H), 7.60-7.56 (m, 1H), 7.52-7.44 (m, 2H), 6.18 (s, 1H), 4.73 (s, 2H), 4.24 (q, J=7.1 Hz, 2H), 3.94-3.86 (m, 2H), 3.76-3.68 (m, 2H), 2.48 (s, 3H), 1.30 (t, J=7.1 Hz, 3H); MS (ES+) m/z 373.2 (M+1).

Example 50.2

Synthesis of ethyl 5-(3-(4-cyanobenzyl)-2-oxoimidazolidin-1-yl)-3-methylthiophene-2-carboxylate

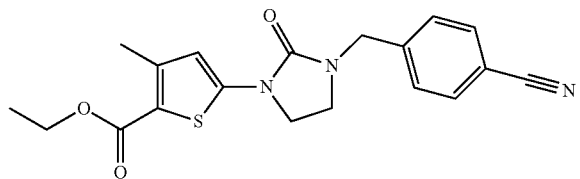

Following the procedure as described in Example 50, making variations as required to replace (2-bromoethoxy)(tert-butyl)dimethylsilane with 4-(chloromethyl)benzonitrile to react with ethyl 3-methyl-5-(2-oxoimidazolidin-1-yl)thiophene-2-carboxylate, the title compound was obtained as a cream solid in 86% yield: $^1$H NMR (300 MHz, CDCl$_3$) δ 7.66 (d, J=8.1 Hz, 2H), 7.43 (d, J=8.1 Hz, 2H), 6.18 (s, 1H), 4.53 (s, 2H), 4.28 (q, J=7.1 Hz, 2H), 3.89-3.81 (m, 2H), 3.52-3.43 (m, 2H), 2.50 (s, 3H), 1.34 (t, J=7.1 Hz, 3H); MS (ES+) m/z 370.2 (M+1).

Example 50.3

Synthesis of ethyl 5-(3-(4-(tert-butoxycarbonylamino)benzyl)-2-oxoimidazolidin-1-yl)-3-methylthiophene-2-carboxylate

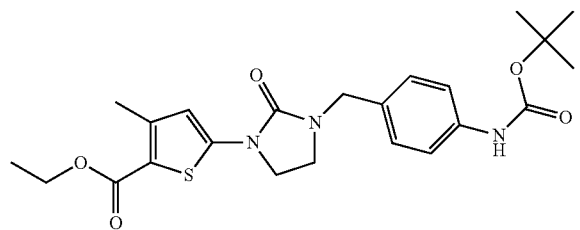

Following the procedure as described in Example 50, making variations as required to replace (2-bromoethoxy)(tert-butyl)dimethylsilane with tert-butyl 4-(chloromethyl)phenylcarbamate to react with ethyl 3-methyl-5-(2-oxoimidazolidin-1-yl)thiophene-2-carboxylate, the title compound was obtained as an off-white solid in 80% yield: $^1$H NMR (300 MHz, CDCl$_3$) δ 7.34 (d, J=8.2 Hz, 2H), 7.22 (d, J=8.2 Hz, 2H), 6.49 (br s, 1H), 6.14 (s, 1H), 4.41 (s, 2H), 4.27 (q, J=7.1 Hz, 2H), 3.81-3.73 (m, 2H), 3.45-3.37 (m, 2H), 2.49 (s, 3H), 1.51 (s, 9H), 1.34 (t, J=7.1 Hz, 3H); MS (ES+) m/z 482.5 (M+23).

Example 51

Synthesis of ethyl 5-(3-(2-hydroxyethyl)-2-oxoimidazolidin-1-yl)-3-methylthiophene-2-carboxylate

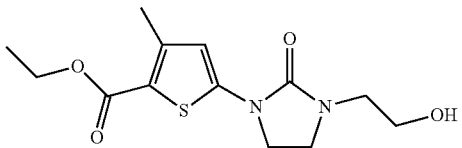

Ethyl 5-(3-(2-(tert-butyldimethylsilyloxy)ethyl)-2-oxoimidazolidin-1-yl)-3-methylthiophene-2-carboxylate (1.09 g 2.63 mmol) in acetic acid (10 mL) was stirred at 40° C. for 64 h. The reaction mixture was allowed to cool to ambient temperature and concentrated in vacuo. The residue was purified by column chromatography eluted with ethyl acetate and then with 5% methanol in dichloromethane to afford the title compound as a colorless solid in 78% yield (0.62 g): $^1$H NMR (300 MHz, CDCl$_3$) δ 6.15 (s, 1H), 4.27 (q, J=7.1 Hz, 2H), 3.89-3.82 (m, 4H), 3.74-3.67 (m, 2H), 3.49-3.44 (m, 2H), 2.49 (s, 3H), 2.34 (t, J=5.3 Hz, 1H), 1.33 (t, J=7.1 Hz, 3H); MS (ES+) m/z 299.2 (M+1).

Example 52

Synthesis of ethyl 3-methyl-5-(2-oxo-3-(2-(tosyloxy)ethyl)imidazolidin-1-yl)thiophene-2-carboxylate

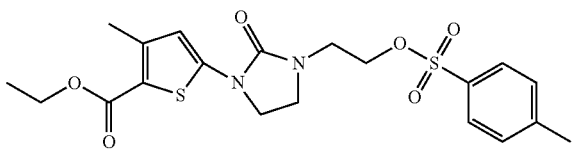

To a stirred solution of ethyl 5-(3-(2-hydroxyethyl)-2-oxoimidazolidin-1-yl)-3-methylthiophene-2-carboxylate (0.61 g, 2.04 mmol) in dichloromethane (6 mL) and pyridine (0.25 mL) at 0° C. was added toluenesulfonyl chloride in dichloromethane (1 mL). The resulting mixture was allowed to warm to ambient temperature, stirred for 18 h and diluted with dichloromethane (100 mL). The organic layer was washed sequentially with 10% aqueous hydrochloric acid (2×50 mL) and saturated aqueous sodium bicarbonate solution (50 mL), dried over sodium sulfate, filtered and concentrated in vacuo. The residue was purified by column chromatography eluted with 0-10% ethyl acetate in dichloromethane to afford the title compound as a colorless solid in 56% yield (0.52 g): $^1$H NMR (300 MHz, CDCl$_3$) δ 7.77 (d, J=8.1 Hz, 2H), 7.31 (d, J=8.1 Hz, 2H), 6.11 (s, 1H), 4.31-4.20 (m, 4H), 3.77-3.61 (m, 4H), 3.54 (t, J=4.8 Hz, 2H), 2.49 (s, 3H), 2.36 (s, 3H), 1.33 (t, J=7.1 Hz, 3H); MS (ES+) m/z 453.3 (M+1).

Example 53

Synthesis of ethyl 3-methyl-5-(2-oxo-3-(2-phenoxy-ethyl)imidazolidin-1-yl)thiophene-2-carboxylate

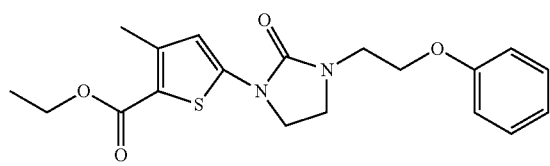

A mixture of ethyl 3-methyl-5-(2-oxo-3-(2-(tosyloxy)ethyl)imidazolidin-1-yl)thiophene-2-carboxylate (0.16 g, 0.35 mmol), phenol (0.03 g, 0.36 mmol) and potassium carbonate (0.05 g, 0.35 mmol) in N,N-dimethylformamide (3 mL) was stirred at 70° C. for 16 h, cooled to ambient temperature, and partitioned between ethyl acetate (75 mL) and water (35 mL). The organic layer was washed with brine (35 mL), dried over sodium sulfate, filtered and concentrated in vacuo. The residue was purified by column chromatography eluted with 0-40% ethyl acetate in hexanes to afford the title compound as a colorless solid 72% yield (0.10 g): $^1$H NMR (300 MHz, CDCl$_3$) δ 7.32-7.26 (m, 2H), 7.00-6.94 (m, 1H), 6.89 (d, J=7.6 Hz, 2H), 6.14 (s, 1H), 4.27 (q, J=7.1 Hz, 2H), 4.17 (t, J=4.9 Hz, 2H), 3.81 (br s, 4H), 3.72 (t, J=4.9 Hz, 2H), 2.49 (s, 3H), 1.33 (t, J=7.1 Hz, 3H); MS (ES+) m/z 375.2 (M+1).

Example 54

Synthesis of 3-methyl-5-(2-oxo-3-(2-phenoxyethyl)imidazolidin-1-yl)thiophene-2-carboxylic acid

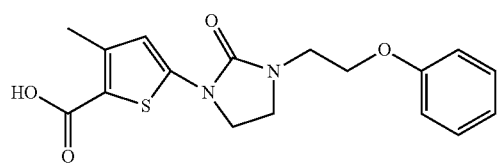

A mixture of ethyl 3-methyl-5-(2-oxo-3-(2-phenoxyethyl)imidazolidin-1-yl)thiophene-2-carboxylate (0.09 g, 0.24 mmol) and 1 N aqueous sodium hydroxide solution (1.5 mL, 1.5 mmol) in ethanol (3 mL) was stirred at reflux for 1 h, and then cooled to 0° C. and acidified with 10% aqueous hydrochloric acid to pH ~2. The aqueous layer was extracted with dichloromethane (2×50 mL), and the combined organic layer was dried over sodium sulfate, filtered and concentrated in vacuo to afford the title compound as a colorless solid in 99% yield (0.08 g): $^1$H NMR (300 MHz, DMSO-d$_6$) δ 12.33 (br s, 1H), 7.29 (dd, J=8.8, 7.2 Hz, 2H), 6.99-6.93 (m, 3H), 6.28 (s, 1H), 4.13 (t, J=5.3 Hz, 2H), 3.87-3.79 (m, 2H), 3.72-3.64 (m, 2H), 3.58 (t, J=5.3 Hz, 2H), 2.39 (s, 3H); MS (ES+) m/z 347.3 (M+1).

Example 54.1

Synthesis of 3-methyl-5-(2-oxo-3-(2-oxo-2-phenyl-ethyl)imidazolidin-1-yl)thiophene-2-carboxylic acid

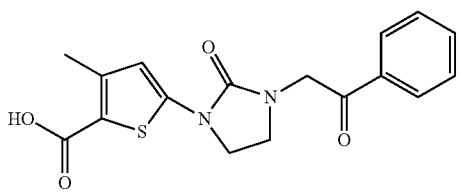

Following the procedure as described in Example 54, making variations as required to replace ethyl 3-methyl-5-(2-oxo-3-(2-phenoxyethyl)imidazolidin-1-yl)-thiophene-2-carboxylate with ethyl 3-methyl-5-(2-oxo-3-(2-oxo-2-phenylethyl)-imidazolidin-1-yl)thiophene-2-carboxylate, the title compound was obtained as a yellow solid in 58% yield: $^1$H NMR (300 MHz, DMSO-d$_6$) δ 12.36 (br s, 1H), 8.02 (d, J=7.3 Hz, 2H), 7.74-7.67 (m, 1H), 7.61-7.54 (m, 2H), 6.34 (s, 1H), 4.85 (s, 2H), 3.97-3.88 (m, 2H), 3.67-3.58 (m, 2H), 2.41 (s, 3H); MS (ES+) m/z 345.3 (M+1).

Example 54.2

Synthesis of 5-(3-(4-carbamoylbenzyl)-2-oxoimidazolidin-1-yl)-3-methylthiophene-2-carboxylic acid

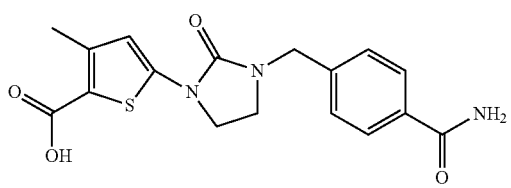

Following the procedure as described in Example 54, making variations as required to replace ethyl 3-methyl-5-(2-oxo-3-(2-phenoxyethyl)imidazolidin-1-yl)-thiophene-2-carboxylate with ethyl 5-(3-(4-cyanobenzyl)-2-oxoimidazolidin-1-yl)-3-methylthiophene-2-carboxylate, the title compound was obtained as a colorless solid in 77% yield: $^1$H NMR (300 MHz, DMSO-d$_6$) δ 7.97 (br s, 1H), 7.87 (d, J=7.9 Hz, 2H), 7.36 (d, J=7.9 Hz, 2H), 6.30 (s, 1H), 4.45 (s, 2H), 3.90-3.80 (m, 2H), 3.54-3.42 (m, 4H), 2.40 (s, 3H); MS (ES+) m/z 382.3 (M+23).

Example 54.3

Synthesis of 5-(3-(4-(tert-butoxycarbonylamino)benzyl)-2-oxoimidazolidin-1-yl)-3-methylthiophene-2-carboxylic acid

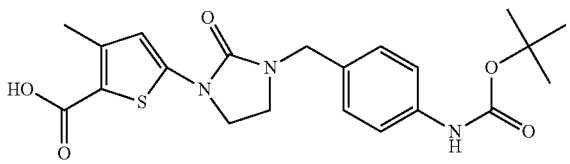

Following the procedure as described in Example 54, making variations as required to replace ethyl 3-methyl-5-(2-oxo-3-(2-phenoxyethyl)imidazolidin-1-yl)-thiophene-2-carboxylate with ethyl 5-(3-(4-(tert-butoxycarbonylamino)benzyl)-2-oxoimidazolidin-1-yl)-3-methylthiophene-2-carboxylate, the title compound was obtained as a pinkish solid in 64% yield: $^1$H NMR (300 MHz, DMSO-d$_6$) δ 9.35 (br s, 1H), 7.43 (d, J=8.4 Hz, 2H), 7.17 (d, J=8.4 Hz, 2H), 6.27 (s, 1H), 4.31 (s, 2H), 3.85-3.76 (m, 2H), 3.45-3.36 (m, 2H), 2.39 (s, 3H), 1.46 (s, 9H); MS (ES−) m/z 430.4 (M−1).

Example 55

Synthesis of 3-methyl-5-(2-oxo-3-(2-phenoxyethyl)imidazolidin-1-yl)-N-(pyridin-3-ylmethyl)thiophene-2-carboxamide

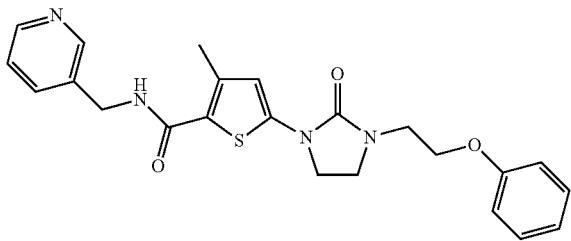

To a 3-methyl-5-(2-oxo-3-(2-phenoxyethyl)imidazolidin-1-yl)thiophene-2-carboxylic acid (0.08 g, 0.23 mmol), 1-hydroxybenzotriazole (0.05 g, 0.35 mmol) and 1-ethyl-3-(3-dimethylaminopropyl)carbodiimide hydrochloride (0.07 g, 0.35 mmol) in N,N-dimethylformamide (2 mL) was added N,N-diisopropylethylamine (0.12 mL, 0.70 mmol), followed by the addition of 3-(aminomethyl)pyridine (0.02 mL, 0.24 mmol). The resulting reaction mixture was stirred at ambient temperature for 18 h, and then diluted with ethyl acetate (75 mL). The organic layer was washed with saturated aqueous sodium bicarbonate solution (3×35 mL) and water (35 mL), dried over sodium sulfate, filtered and concentrated in vacuo. The residue was triturated with ethyl acetate in hexanes to afford the title compound as a colorless solid in 79% yield (0.08 g): mp 78-80° C.; $^1$H NMR (300 MHz, CDCl$_3$) δ 8.59 (s, 1H), 8.52 (s, 1H), 7.69 (d, J=7.8 Hz, 1H), 7.32-7.23 (m, 3H), 6.96 (t, J=7.6 Hz, 1H), 6.88 (d, J=7.6 Hz, 2H), 6.15 (t, J=5.7 Hz, 1H), 6.08 (s, 1H), 4.57 (d, J=5.7 Hz, 2H), 4.15 (t, J=4.9 Hz, 2H), 3.80 (br s, 4H), 3.69 (t, J=4.9 Hz, 2H), 2.48 (s, 3H); $^{13}$C NMR (75 MHz, CDCl$_3$) δ 163.5, 158.2, 156.0, 149.2, 148.8, 142.5, 141.7, 135.5, 129.6, 123.6, 121.2, 118.9, 114.3, 112.4, 66.9, 43.8, 43.0, 41.2, 16.1; MS (ES+) m/z 437.4 (M+1).

Example 55.1

Synthesis of 3-methyl-5-(2-oxo-3-(2-oxo-2-phenylethyl)imidazolidin-1-yl)-N-(pyridin-3-ylmethyl)thiophene-2-carboxamide

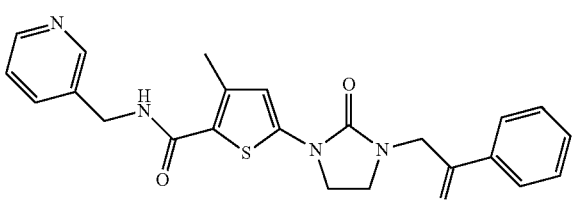

Following the procedures as described in Example 55, making variations as required to replace 3-methyl-5-(2-oxo-3-(2-phenoxyethyl)imidazolidin-1-yl)thiophene-2-carboxylic acid with 3-methyl-5-(2-oxo-3-(2-oxo-2-phenylethyl)imidazolidin-1-yl)thiophene-2-carboxylic acid to react with 3-(aminomethyl)pyridine, the title compound was obtained as a cream solid in 61% yield: mp 174-176° C.; $^1$H NMR (300 MHz, CDCl$_3$) δ 8.58 (s, 1H), 8.48 (d, J=4.4 Hz, 1H), 7.97-7.92 (m, 2H), 7.67 (d, J=7.8 Hz, 1H), 7.64-7.57 (m, 1H), 7.51-7.44 (m, 2H), 7.23 (dd, J=7.8, 4.4 Hz, 1H), 6.24 (t, J=5.7 Hz, 1H), 6.11 (s, 1H), 4.72 (s, 2H), 4.56 (d, J=5.7 Hz, 2H), 3.93-3.85 (m, 2H), 3.75-3.67 (m, 2H), 2.48 (s, 3H); $^{13}$C NMR (75 MHz, CDCl$_3$) δ 193.8, 163.5, 156.2, 149.2, 148.7, 142.4, 141.6, 135.5, 134.6, 134.2, 134.0, 128.9, 127.9, 123.5, 112.6, 50.0, 43.0, 42.7, 41.1, 16.1; MS (ES+) m/z 435.4 (M+1).

Example 55.2

Synthesis of 5-(3-(4-carbamoylbenzyl)-2-oxoimidazolidin-1-yl)-3-methyl-N-(pyridin-3-ylmethyl)thiophene-2-carboxamide

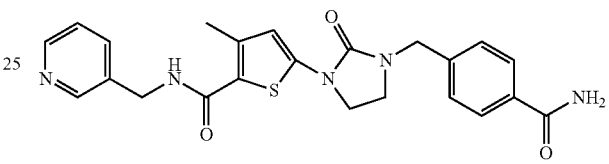

Following the procedures as described in Example 55, making variations as required to replace 3-methyl-5-(2-oxo-3-(2-phenoxyethyl)imidazolidin-1-yl)thiophene-2-carboxylic acid with 5-(3-(4-carbamoylbenzyl)-2-oxoimidazolidin-1-yl)-3-methylthiophene-2-carboxylic acid to react with 3-(aminomethyl)pyridine, the title compound was obtained as a cream solid in 71% yield: mp 188° C. (dec.); $^1$H NMR (300 MHz, DMSO-d$_6$) δ 8.53 (s, 1H), 8.45 (d, J=4.0 Hz, 1H), 8.31, (t, J=5.8 Hz, 1H), 7.97 (s, 1H), 7.86 (d, J=8.0 Hz, 2H), 7.71 (d, J=7.8 Hz, 1H), 7.42-7.32 (m, 4H), 6.24 (s, 1H), 4.44 (s, 2H), 4.39 (d, J=5.8 Hz, 2H), 3.84 (t, J=7.8 Hz, 2H), 3.45 (t, J=7.8 Hz, 2H), 2.37 (s, 3H); $^{13}$C NMR (75 MHz, DMSO-d$_6$) δ 167.5, 162.9, 155.5, 148.8, 147.8, 140.0, 139.0, 135.4, 135.0, 133.4, 127.7, 127.4, 123.3, 119.9, 112.0, 46.8, 42.5, 41.5, 15.7; MS (ES+) m/z 450.4 (M+1).

Example 55.3

Synthesis of tert-butyl 4-((3-(4-methyl-5-(pyridin-3-ylmethylcarbamoyl)thiophen-2-yl)-2-oxoimidazolidin-1-yl)methyl)phenylcarbamate

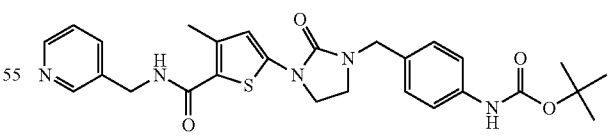

Following the procedures as described in Example 55, making variations as required to replace 3-methyl-5-(2-oxo-3-(2-phenoxyethyl)imidazolidin-1-yl)thiophene-2-carboxylic acid with 5-(3-(4-(tert-butoxycarbonylamino)benzyl)-2-oxoimidazolidin-1-yl)-3-methylthiophene-2-carboxylic acid to react with 3-(aminomethyl)pyridine, the title compound was obtained as a beige solid in 75% yield: $^1$H NMR (300 MHz, CDCl$_3$) δ 8.60 (s, 1H), 8.53 (d, J=4.5 Hz, 1H), 7.70 (d, J=7.8 Hz, 1H), 7.33 (d, J=8.3 Hz, 2H), 7.27 (dd, J=7.8, 4.5 Hz, 1H), 7.21 (d, J=8.3 Hz, 2H), 6.51 (br s, 1H), 6.08 (br s, 2H), 4.58 (d, J=5.8 Hz, 2H), 4.40 (s, 2H), 3.82-3.73 (m, 2H), 3.45-3.37 (m, 2H), 2.50 (s, 3H), 1.51 (s, 9H); MS (ES+) m/z 522.5 (M+1).

Example 55.4

Synthesis of N-((1H-benzo[d]imidazol-2-yl)methyl)-5-(3-(4-fluorobenzyl)-2-oxoimidazolidin-1-yl)-3-methylthiophene-2-carboxamide

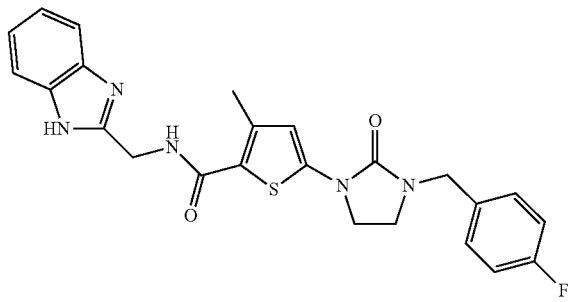

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1H-benzo[d]imidazol-2-yl)methanamine dihydrochloride, the title compound was obtained as a colorless solid in 80% yield: mp 265-267° C.; $^1$H NMR (300 MHz, DMSO-$d_6$) δ 12.19 (br s, 1H), 8.23 (t, J=5.5 Hz, 1H), 7.54-7.46 (m, 2H), 7.38-7.31 (m, 2H), 7.24-7.10 (m, 4H), 6.25 (s, 1H), 4.60 (d, J=5.5 Hz, 2H), 4.39 (s, 2H), 3.87-3.78 (m, 2H), 3.48-3.39 (m, 2H), 2.42 (s, 3H); $^{13}$C NMR (75 MHz, DMSO-$d_6$) δ 163.1, 159.9, 155.5, 152.5, 142.9, 139.2, 132.9 (d, $J_{C-F}$=3.0 Hz), 129.9 (d, $J_{C-F}$=8.2 Hz), 121.3, 120.0, 115.3 (d, $J_{C-F}$=21.2 Hz), 112.1, 46.3, 42.5, 41.3, 37.7, 15.8; MS (ES+) m/z 464.4 (M+1).

Example 55.5

Synthesis of 5-(3-(4-fluorobenzyl)-2-oxoimidazolidin-1-yl)-3-methyl-N-(thiophen-2-ylmethyl)thiophene-2-carboxamide

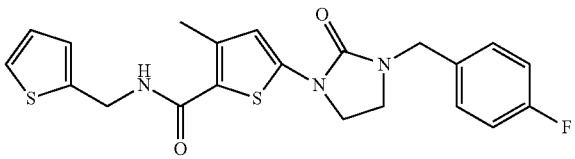

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with thiophen-2-ylmethanamine, the title compound was obtained as a colorless solid in 82% yield: mp 128-131° C.; $^1$H NMR (300 MHz, CDCl$_3$) δ 7.30-7.20 (m, 3H), 7.06-6.93 (m, 4H), 6.08 (s, 1H), 6.01 (t, J=5.4 Hz, 1H), 4.73 (d, J=5.4 Hz, 2H), 4.42 (s, 2H), 3.82-3.74 (m, 2H), 3.47-3.39 (m, 2H), 2.49 (s, 3H); $^{13}$C NMR (75 MHz, DMSO-$d_6$) δ 163.1, 162.4 (d, $J_{C-F}$=246.4 Hz), 155.8, 142.5, 141.4, 140.9, 131.8 ($J_{C-F}$=3.1 Hz), 130.0 ($J_{C-F}$=8.2 Hz), 126.9, 126.1, 125.2, 119.3, 115.7 ($J_{C-F}$=21.5 Hz), 112.4, 47.4, 42.7, 41.4, 38.5, 16.1; MS (ES+) m/z 452.3 (M+23).

Example 55.6

Synthesis of 5-(3-(4-fluorobenzyl)-2-oxoimidazolidin-1-yl)-3-methyl-N-((6-(trifluoromethyl)pyridin-3-yl)methyl)thiophene-2-carboxamide

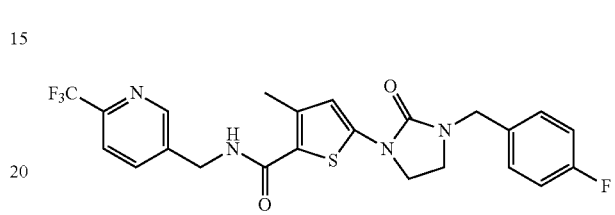

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (6-(trifluoromethyl)pyridin-3-yl)methanamine, the title compound was obtained as a colorless solid in 63% yield: $^1$H NMR (300 MHz, CDCl$_3$) δ 8.70 (s, 1H), 7.89 (d, J=8.0 Hz, 1H), 7.65 (d, J=8.0 Hz, 1H), 7.30-7.23 (m, 2H), 7.08-6.99 (m, 2H), 6.20 (t, J=5.8 Hz, 1H), 6.09 (s, 1H), 4.65 (d, J=5.8 Hz, 2H), 4.43 (s, 2H), 3.85-3.77 (m, 2H), 3.49-3.40 (m, 2H), 2.49 (s, 3H); MS (ES+) m/z 493.2 (M+1).

Example 55.7

Synthesis of 5-(3-(4-fluorobenzyl)-2-oxoimidazolidin-1-yl)-3-methyl-N-((3-methylthiophen-2-yl)methyl)thiophene-2-carboxamide

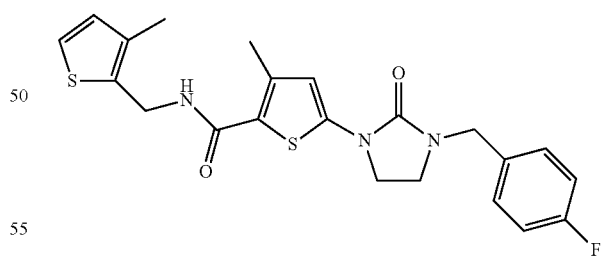

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (3-methylthiophen-2-yl)methanamine, the title compound was obtained as a colorless solid in 73% yield: $^1$H NMR (300 MHz, CDCl$_3$) δ 7.30-7.23 (m, 2H), 7.13 (d, J=5.0 Hz, 1H), 7.08-6.99 (m, 2H), 6.82 (d, J=5.0 Hz, 1H), 6.08 (s, 1H), 5.83

(br s, 1H), 4.65 (d, J=5.0 Hz, 2H), 4.42 (s, 2H), 3.83-3.74 (m, 2H), 3.47-3.39 (m, 2H), 2.49 (s, 3H), 2.24 (s, 3H); MS (ES+) m/z 444.2 (M+1).

Example 55.8

Synthesis of N-(2,3-dihydro-1H-inden-2-yl)-5-(3-(4-fluorobenzyl)-2-oxoimidazolidin-1-yl)-3-methylthiophene-2-carboxamide

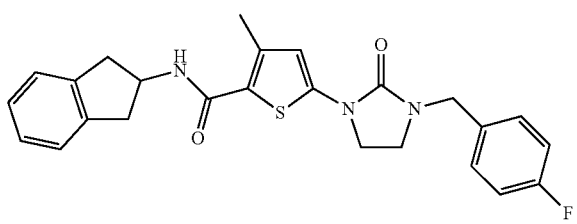

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with 2,3-dihydro-1H-inden-2-amine, the title compound was obtained as an off-white solid in 84% yield: $^1$H NMR (300 MHz, CDCl$_3$) δ 7.30-7.15 (m, 6H), 7.07-6.98 (m, 2H), 6.06 (s, 1H), 5.90 (d, J=7.2 Hz, 1H), 4.92-4.80 (m, 1H), 4.42 (s, 2H), 3.84-3.74 (m, 2H), 3.47-3.32 (m, 4H), 2.90 (d, J=4.7 Hz, 1H), 2.85 (d, J=4.7 Hz, 1H), 2.47 (s, 3H); MS (ES+) m/z 450.2 (M+1).

Example 55.9

Synthesis of N-(benzo[b]thiophen-2-ylmethyl)-5-(3-(4-fluorobenzyl)-2-oxoimidazolidin-1-yl)-3-methylthiophene-2-carboxamide

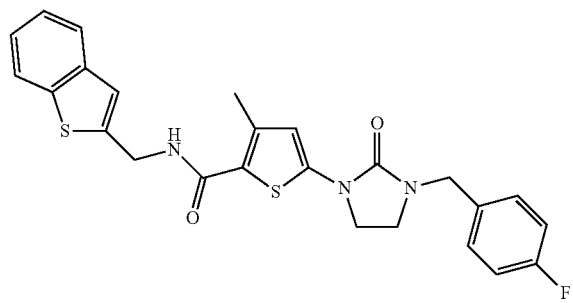

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with benzo[b]thiophen-2-ylmethanamine, the title compound was obtained as a colorless solid in 78% yield: $^1$H NMR (300 MHz, CDCl$_3$) δ 7.78 (d, J=7.6 Hz, 1H), 7.70 (d, J=7.6 Hz, 1H), 7.36-7.22 (m, 5H), 7.08-6.99 (m, 2H), 6.14 (t, J=5.4 Hz, 1H), 6.10 (s, 1H), 4.82 (d, J=5.4 Hz, 2H), 4.42 (s, 2H), 3.83-3.74 (m, 2H), 3.47-3.38 (m, 2H), 2.51 (s, 3H); MS (ES+) m/z 480.2 (M+1).

Example 55.10

Synthesis of N-(benzo[d]thiazol-2-ylmethyl)-5-(3-(4-fluorobenzyl)-2-oxoimidazolidin-1-yl)-3-methylthiophene-2-carboxamide

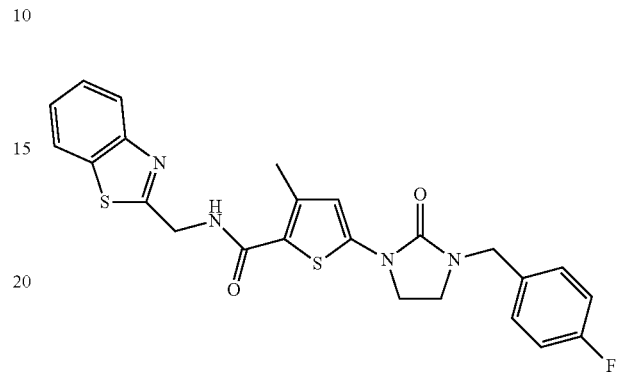

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with benzo[d]thiazol-2-ylmethanamine, the title compound was obtained as a colorless solid in 81% yield: $^1$H NMR (300 MHz, CDCl$_3$) δ 8.00 (d, J=8.0 Hz, 1H), 7.85 (d, J=8.0 Hz, 1H), 7.51-7.44 (m, 1H), 7.41-7.34 (m, 1H), 7.31-7.24 (m, 2H), 7.07-6.98 (m, 2H), 6.63 (t, J=5.5 Hz, 1H), 6.13 (s, 1H), 5.01 (d, J=5.5 Hz, 2H), 4.44 (s, 2H), 3.84-3.76 (m, 2H), 3.48-3.40 (m, 2H), 2.53 (s, 3H); MS (ES+) m/z 481.2 (M+1).

Example 55.11

Synthesis of N-(benzo[d][1,3]dioxol-5-ylmethyl)-5-(3-(4-fluorobenzyl)-2-oxoimidazolidin-1-yl)-3-methylthiophene-2-carboxamide

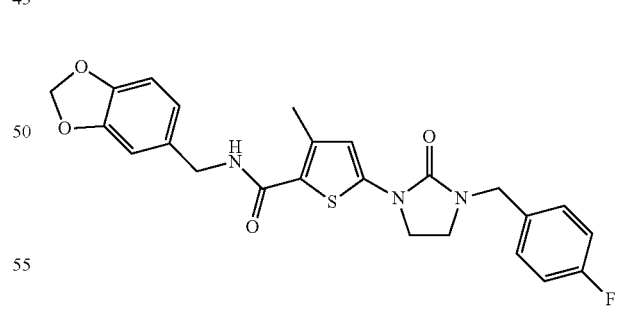

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with benzo[d][1,3]dioxol-5-ylmethanamine, the title compound was obtained as a colorless solid in 82% yield: $^1$H NMR (300 MHz, CDCl$_3$) δ 7.30-7.23 (m, 2H), 7.07-6.98 (m, 2H), 6.85-6.73 (m, 3H), 6.09 (s, 1H), 5.95 (s, 2H), 5.92 (t, J=5.5 Hz, 1H), 4.46 (d, J=5.5 Hz, 2H), 4.42 (s, 2H), 3.84-3.76 (m, 2H), 3.48-3.40 (m, 2H), 2.49 (s, 3H); MS (ES+) m/z 468.2 (M+1).

Example 55.12

Synthesis of N-(benzooxazol-2-ylmethyl)-5-(3-(4-fluorobenzyl)-2-oxoimidazolidin-1-yl)-3-methylthiophene-2-carboxamide

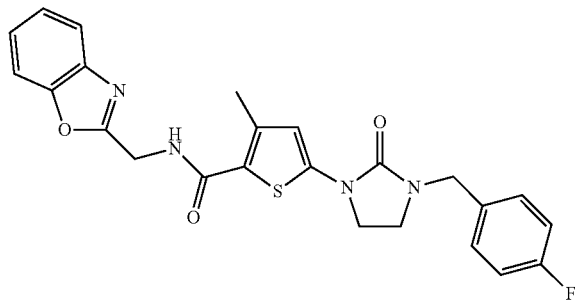

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with benzo[d]oxazol-2-ylmethanamine hydrochloride, the title compound was obtained as an off-white solid in 85% yield: $^1$H NMR (300 MHz, CDCl$_3$) δ 7.74-7.68 (m, 1H), 7.56-7.49 (m, 1H), 7.40-7.24 (m, 4H), 7.09-6.99 (m, 2H), 6.50 (t, J=4.6 Hz, 1H), 6.14 (s, 1H), 4.88 (d, J=4.6 Hz, 2H), 4.44 (s, 2H), 3.85-3.76 (m, 2H), 3.49-3.39 (m, 2H), 2.53 (s, 3H); MS (ES+) m/z 465.2 (M+1), 487.2 (M+23).

Example 55.13

Synthesis of N-((1H-indol-2-yl)methyl)-5-(3-(4-fluorobenzyl)-2-oxoimidazolidin-1-yl)-3-methylthiophene-2-carboxamide

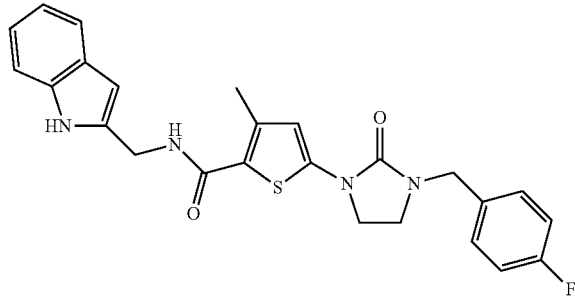

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1H-indol-2-yl)methanamine methanesulfonate, the title compound was obtained as an off-white solid in 75% yield: $^1$H NMR (300 MHz, CDCl$_3$) δ 9.18 (br s, 1H), 7.55 (d, J=7.8 Hz, 1H), 7.35 (d, J=7.8 Hz, 1H), 7.30-7.22 (m, 2H), 7.19-6.98 (m, 4H), 6.36 (s, 1H), 6.28 (t, J=5.9 Hz, 1H), 6.10 (s, 1H), 4.62 (d, J=5.9 Hz, 2H), 4.42 (s, 2H), 3.81-3.73 (m, 2H), 3.45-3.38 (m, 2H), 2.50 (s, 3H); MS (ES+) m/z 463.2 (M+1), 485.2 (M+23).

Example 55.14

Synthesis of 5-(3-(4-fluorobenzyl)-2-oxoimidazolidin-1-yl)-3-methyl-N-((1-methyl-1H-pyrrol-2-yl)methyl)thiophene-2-carboxamide

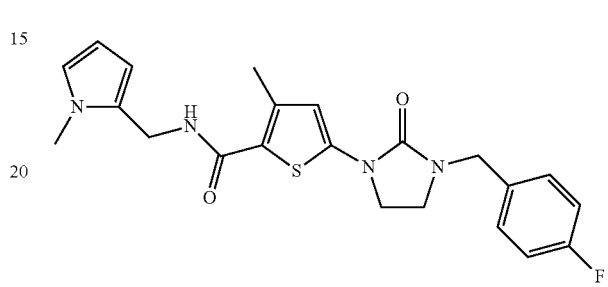

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1-methyl-1H-pyrrol-2-yl)methanamine, the title compound was obtained as a colorless solid in 26% yield: $^1$H NMR (300 MHz, CDCl$_3$) δ 7.30-7.23 (m, 2H), 7.07-6.99 (m, 2H), 6.61 (s, 1H), 6.13-6.03 (m, 3H), 5.71 (t, J=4.6 Hz, 1H), 4.55 (d, J=4.6 Hz, 2H), 4.42 (s, 2H), 3.83-3.75 (m, 2H), 3.61 (s, 3H), 3.47-3.39 (m, 2H), 2.48 (s, 3H); MS (ES+) m/z 427.2 (M+1).

Example 55.15

Synthesis of 5-(3-(4-fluorobenzyl)-2-oxoimidazolidin-1-yl)-3-methyl-N-((5-phenyl-1,3,4-oxadiazol-2-yl)methyl)thiophene-2-carboxamide

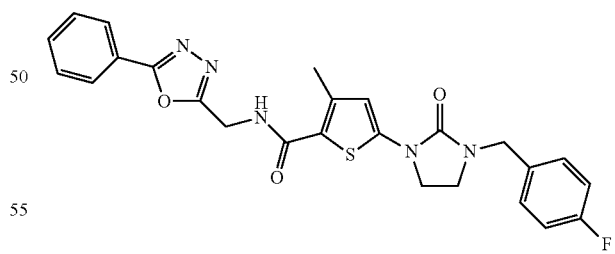

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (5-phenyl-1,3,4-oxadiazol-2-yl)methanamine oxalate, the title compound was obtained as a colorless solid in 67% yield: $^1$H NMR (300 MHz, CDCl$_3$) δ 8.06-8.01 (m, 2H), 7.55-7.45 (m, 3H), 7.30-7.24 (m, 2H), 7.07-6.98 (m, 2H), 6.45 (t, J=5.4

Hz, 1H), 6.11 (s, 1H), 4.90 (d, J=5.4 Hz, 2H), 4.43 (s, 2H), 3.84-3.76 (m, 2H), 3.48-3.40 (m, 2H), 2.50 (s, 3H); MS (ES+) m/z 514.1 (M+23).

Example 55.16

Synthesis of ethyl 5-((5-(3-(4-fluorobenzyl)-2-oxoimidazolidin-1-yl)-3-methylthiophene-2-carboxamido)methyl)furan-2-carboxylate

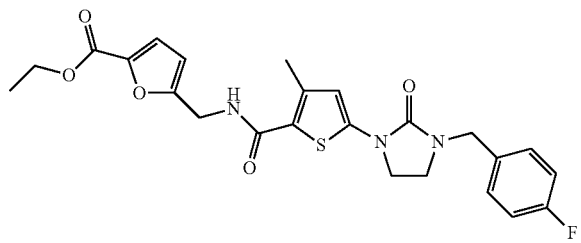

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with ethyl 5-(aminomethyl)furan-2-carboxylate hydrochloride, the title compound was obtained as a colorless solid in 59% yield: $^1$H NMR (300 MHz, CDCl$_3$) δ 7.30-7.23 (m, 2H), 7.11 (d, J=3.4 Hz, 1H), 7.07-6.99 (m, 2H), 6.41 (d, J=3.4 Hz, 1H), 6.10 (br s, 2H), 4.62 (d, J=5.7 Hz, 2H), 4.43 (s, 2H), 4.36 (q, J=7.1 Hz, 2H), 3.83-3.75 (m, 2H), 3.47-3.40 (m, 2H), 2.48 (s, 3H), 1.38 (t, J=7.1 Hz, 3H); MS (ES+) m/z 508.15 (M+23).

Example 55.17

Synthesis of N-((6-chloropyridin-3-yl)methyl)-5-(3-(4-fluorobenzyl)-2-oxoimidazolidin-1-yl)-3-methylthiophene-2-carboxamide

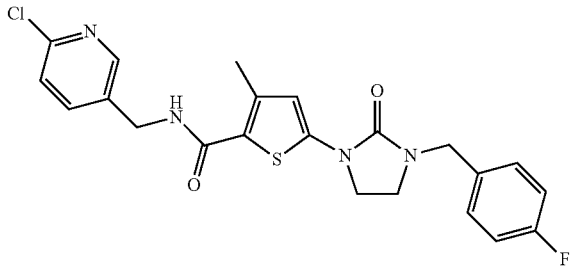

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (6-chloropyridin-3-yl)methanamine, the title compound was obtained as a colorless solid in 80% yield: $^1$H NMR (300 MHz, CDCl$_3$) δ 8.36 (d, J=1.5 Hz, 1H), 7.68 (dd, J=8.2, 2.4 Hz, 1H), 7.30-7.23 (m, 3H), 7.08-6.99 (m, 2H), 6.13 (t, J=5.8 Hz, 1H), 6.09 (s, 1H), 4.55 (d, J=5.8 Hz, 2H), 4.43 (s, 2H), 3.84-3.76 (m, 2H), 3.48-3.40 (m, 2H), 2.48 (s, 3H); MS (ES+) m/z 459.1 (M+1).

Example 55.18

Synthesis of N-((1H-pyrazol-3-yl)methyl)-5-(3-(4-fluorobenzyl)-2-oxoimidazolidin-1-yl)-3-methylthiophene-2-carboxamide

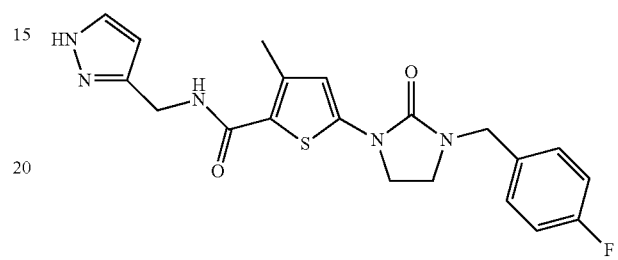

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1H-pyrazol-3-yl)methanamine, the title compound was obtained as a colorless solid in 72% yield: $^1$H NMR (300 MHz, CDCl$_3$) δ 7.54 (s, 1H), 7.30-7.23 (m, 2H), 7.07-6.98 (m, 2H), 6.46 (t, J=5.0 Hz, 1H), 6.28 (s, 1H), 6.09 (s, 1H), 5.70 (br s, 1H), 4.60 (d, J=5.0 Hz, 2H), 4.43 (s, 2H), 3.83-3.74 (m, 2H), 3.47-3.39 (m, 2H), 2.48 (s, 3H); MS (ES+) m/z 436.2 (M+23).

Example 55.19

Synthesis of 5-(3-(4-fluorobenzyl)-2-oxoimidazolidin-1-yl)-3-methyl-N-((5-methylfuran-2-yl)methyl)thiophene-2-carboxamide

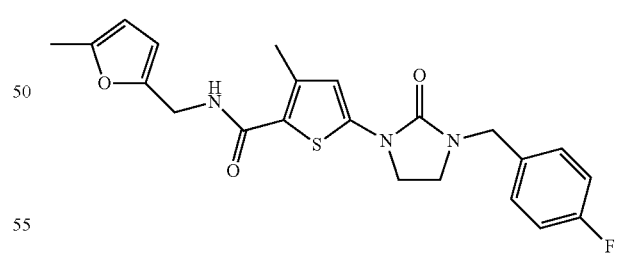

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (5-methylfuran-2-yl)methanamine, the title compound was obtained as a yellowish solid in 78% yield: $^1$H NMR (300 MHz, CDCl$_3$) δ 7.30-7.23 (m, 2H), 7.08-6.98 (m, 2H), 6.12 (d, J=2.4 Hz, 1H), 6.07 (s, 1H), 5.93 (t, J=4.8 Hz, 1H), 5.89 (d, J=2.4 Hz, 1H), 4.49 (d, J=4.8 Hz, 2H), 4.42 (s, 2H), 3.83-3.74 (m, 2H), 3.49-3.39 (m, 2H), 2.48 (s, 3H), 2.27 (s, 3H); MS (ES+) m/z 450.1 (M+23).

Example 55.20

Synthesis of 5-(3-(4-fluorobenzyl)-2-oxoimidazolidin-1-yl)-3-methyl-N-((4-methylthiophen-2-yl)methyl)thiophene-2-carboxamide

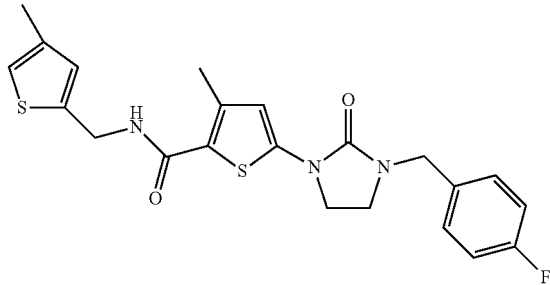

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (4-methylthiophen-2-yl)methanamine, the title compound was obtained as a colorless solid in 80% yield: $^1$H NMR (300 MHz, CDCl$_3$) δ 7.30-7.24 (m, 2H), 7.08-6.98 (m, 2H), 6.82 (s, 1H), 6.78 (s, 1H), 6.09 (s, 1H), 5.96 (t, J=5.2 Hz, 1H), 4.66 (d, J=5.2 Hz, 2H), 4.42 (s, 2H), 3.83-3.75 (m, 2H), 3.47-3.39 (m, 2H), 2.49 (s, 3H), 2.22 (s, 3H); MS (ES+) m/z 444.1 (M+1).

Example 55.21

Synthesis of 5-(3-(4-fluorobenzyl)-2-oxoimidazolidin-1-yl)-3-methyl-N-(thiazol-2-ylmethyl)thiophene-2-carboxamide

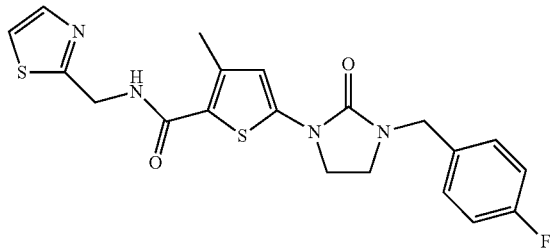

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with thiazol-2-ylmethanamine, the title compound was obtained as a colorless solid in 48% yield: $^1$H NMR (300 MHz, CDCl$_3$) δ 7.72 (d, J=3.3 Hz, 1H), 7.31-7.23 (m, 3H), 7.07-6.99 (m, 2H), 6.50 (t, J=5.4 Hz, 1H), 6.12 (s, 1H), 4.90 (d, J=5.4 Hz, 2H), 4.43 (s, 2H), 3.84-3.75 (m, 2H), 3.47-3.39 (m, 2H), 2.50 (s, 3H); MS (ES+) m/z 453.1 (M+23).

Example 55.22

Synthesis of N-((1,5-dimethyl-1H-pyrrol-2-yl)methyl)-5-(3-(4-fluorobenzyl)-2-oxoimidazolidin-1-yl)-3-methylthiophene-2-carboxamide

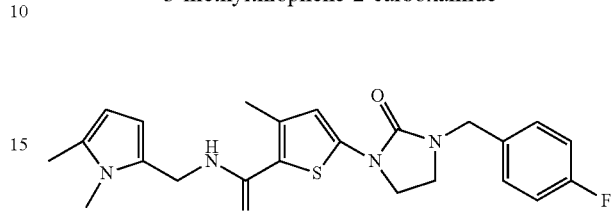

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1,5-dimethyl-1H-pyrrol-2-yl)methanamine, the title compound was obtained as a beige solid in 57% yield: $^1$H NMR (300 MHz, CDCl$_3$) δ 7.30-7.23 (m, 2H), 7.07-6.98 (m, 2H), 6.08 (s, 1H), 6.00 (d, J=3.2 Hz, 1H), 5.81 (d, J=3.2 Hz, 1H), 5.67 (t, J=4.4 Hz, 1H), 4.53 (d, J=4.4 Hz, 2H), 4.42 (s, 2H), 3.83-3.74 (m, 2H), 3.49-3.39 (m, 5H), 2.48 (s, 3H), 2.21 (s, 3H); MS (ES+) m/z 463.1 (M+23).

Example 55.23

Synthesis of 5-(3-(4-fluorobenzyl)-2-oxoimidazolidin-1-yl)-3-methyl-N-((5-methylthiophen-2-yl)methyl)thiophene-2-carboxamide

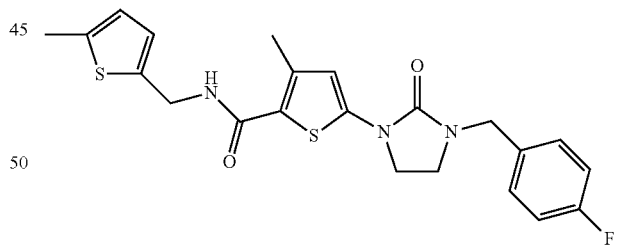

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (5-methylthiophen-2-yl)methanamine, the title compound was obtained as a colorless solid in 41% yield: $^1$H NMR (300 MHz, CDCl$_3$) δ 7.30-7.23 (m, 2H), 7.07-6.98 (m, 2H), 6.78 (d, J=3.2 Hz, 1H), 6.58 (d, J=3.2 Hz, 1H), 6.09 (s, 1H), 5.94 (t, J=5.1 Hz, 1H), 4.64 (d, J=5.1 Hz, 2H), 4.42 (s, 2H), 3.83-3.74 (m, 2H), 3.47-3.39 (m, 2H), 2.49 (s, 3H), 2.44 (s, 3H); MS (ES+) m/z 466.2 (M+23).

Example 55.24

Synthesis of 5-(3-(4-fluorobenzyl)-2-oxoimidazolidin-1-yl)-3-methyl-N-((1-methyl-1H-imidazol-5-yl)methyl)thiophene-2-carboxamide

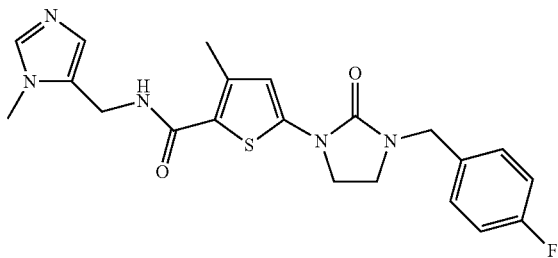

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1-methyl-1H-imidazol-5-yl)methanamine, the title compound was obtained as a colorless solid in 75% yield: $^1$H NMR (300 MHz, CDCl$_3$) δ 7.48 (s, 1H), 7.30-7.22 (m, 2H), 7.08-6.98 (m, 3H), 6.08 (s, 1H), 5.86 (t, J=5.0 Hz, 1H), 4.59 (d, J=5.0 Hz, 2H), 4.42 (s, 2H), 3.84-3.75 (m, 2H), 3.65 (s, 3H), 3.49-3.40 (m, 2H), 2.48 (s, 3H); MS (ES+) m/z 428.2 (M+1).

Example 55.25

Synthesis of 5-(3-(4-fluorobenzyl)-2-oxoimidazolidin-1-yl)-3-methyl-N-((1-methyl-1H-imidazol-4-yl)methyl)thiophene-2-carboxamide

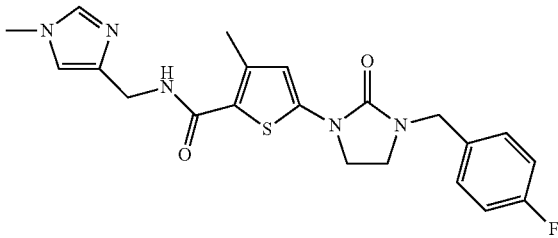

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1-methyl-1H-imidazol-4-yl)methanamine, the title compound was obtained as a yellowish solid in 74% yield: $^1$H NMR (300 MHz, CDCl$_3$) δ 7.39 (s, 1H), 7.30-7.23 (m, 2H), 7.07-6.98 (m, 2H), 6.87 (s, 1H), 6.28 (t, J=5.0 Hz, 1H), 6.11 (s, 1H), 4.49 (d, J=5.0 Hz, 2H), 4.42 (s, 2H), 3.82-3.74 (m, 2H), 3.66 (s, 3H), 3.46-3.38 (m, 2H), 2.47 (s, 3H); MS (ES+) m/z 428.2 (M+1).

Example 55.26

Synthesis of 5-(3-(4-fluorobenzyl)-2-oxoimidazolidin-1-yl)-3-methyl-N-((5-methylpyrazin-2-yl)methyl)thiophene-2-carboxamide

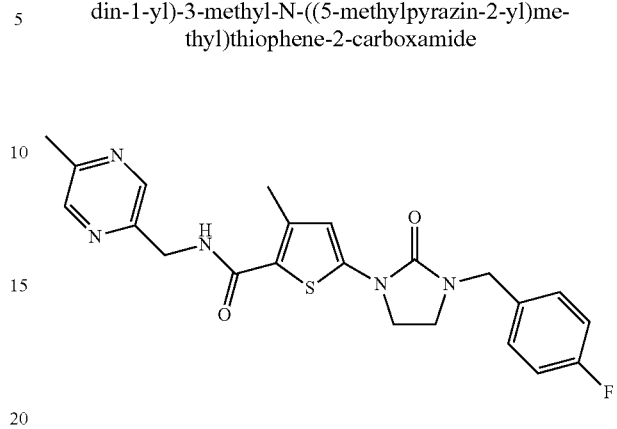

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (5-methylpyrazin-2-yl)methanamine, the title compound was obtained as a colorless solid in 78% yield: $^1$H NMR (300 MHz, CDCl$_3$) δ 7.52 (s, 1H), 8.40 (s, 1H), 7.31-7.23 (m, 2H), 7.08-6.99 (m, 2H), 6.72 (t, J=4.6 Hz, 1H), 6.12 (s, 1H), 4.70 (d, J=4.6 Hz, 2H), 4.44 (s, 2H), 3.84-3.76 (m, 2H), 3.48-3.39 (m, 2H), 2.57 (s, 3H), 2.50 (s, 3H); MS (ES+) m/z 440.2 (M+1).

Example 55.27

Synthesis of 5-(3-(4-fluorobenzyl)-2-oxoimidazolidin-1-yl)-3-methyl-N-((2-methylthiazol-4-yl)methyl)thiophene-2-carboxamide

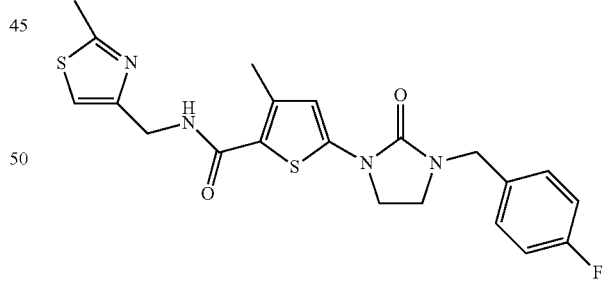

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (2-methylthiazol-4-yl)methanamine dihydrochloride, the title compound was obtained as a colorless solid in 71% yield: $^1$H NMR (300 MHz, CDCl$_3$) δ 7.30-7.23 (m, 2H), 7.07-6.99 (m, 3H), 6.28 (t, J=5.2 Hz, 1H), 6.10 (s, 1H), 4.63 (d, J=5.2 Hz, 2H), 4.43 (s, 2H), 3.83-3.75 (m, 2H), 3.47-3.39 (m, 2H), 2.71 (s, 3H), 2.49 (s, 3H); MS (ES+) m/z 445.2 (M+1).

Example 55.28

5-(3-(4-fluorobenzyl)-2-oxoimidazolidin-1-yl)-3-methyl-N-((1-methyl-1H-pyrazol-4-yl)methyl)thiophene-2-carboxamide

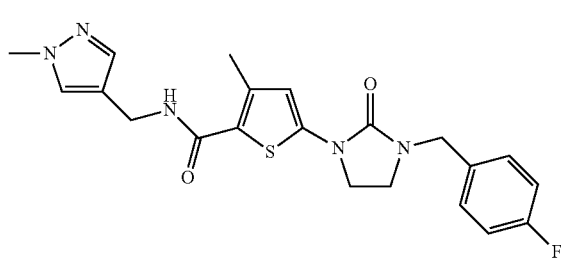

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (1-methyl-1H-pyrazol-4-yl)methanamine, the title compound was obtained as a colorless solid in 76% yield: $^1$H NMR (300 MHz, CDCl$_3$) δ 7.45 (s, 1H), 7.39 (s, 1H), 7.30-7.23 (m, 2H), 7.07-6.98 (m, 2H), 6.08 (s, 1H), 5.84 (t, J=4.0 Hz, 1H), 4.44-4.39 (m, 4H), 3.88 (s, 3H), 3.83-3.75 (m, 2H), 3.47-3.39 (m, 2H), 2.48 (s, 3H); MS (ES+) m/z 428.2 (M+1).

Example 55.29

Synthesis of 5-(3-(4-fluorobenzyl)-2-oxoimidazolidin-1-yl)-3-methyl-N-(oxazol-2-ylmethyl)thiophene-2-carboxamide

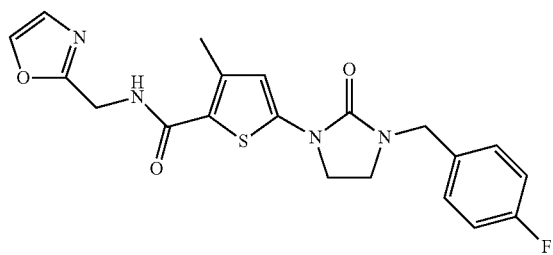

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with oxazol-2-ylmethanamine, the title compound was obtained as a colorless solid in 35% yield: $^1$H NMR (300 MHz, CDCl$_3$) δ 7.63 (s, 1H), 7.31-7.24 (m, 2H), 7.09-7.00 (m, 3H), 6.34 (t, J=5.0 Hz, 1H), 6.12 (s, 1H), 4.71 (d, J=5.0 Hz, 2H), 4.44 (s, 2H), 3.84-3.76 (m, 2H), 3.47-3.40 (m, 2H), 2.50 (s, 3H); MS (ES+) m/z 437.1 (M+23).

Example 55.30

Synthesis of N-((3,5-dimethyl-1H-pyrazol-4-yl)methyl)-5-(3-(4-fluorobenzyl)-2-oxoimidazolidin-1-yl)-3-methylthiophene-2-carboxamide

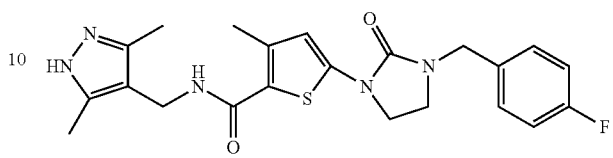

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (3,5-dimethyl-1H-pyrazol-4-yl)methanamine dioxalate monohydrate, the title compound was obtained as a colorless solid in 24% yield: $^1$H NMR (300 MHz, CDCl$_3$) δ 7.30-7.23 (m, 2H), 7.07-6.99 (m, 2H), 6.08 (s, 1H), 5.61 (t, J=4.6 Hz, 1H), 4.42 (s, 2H), 4.35 (d, J=4.6 Hz, 2H), 3.83-3.75 (m, 2H), 3.47-3.39 (m, 2H), 2.48 (s, 3H), 2.28 (s, 6H); MS (ES+) m/z 442.2 (M+1).

Example 55.31

Synthesis of N-((5-tert-butyl-1H-pyrazol-3-yl)methyl)-5-(3-(4-fluorobenzyl)-2-oxoimidazolidin-1-yl)-3-methylthiophene-2-carboxamide

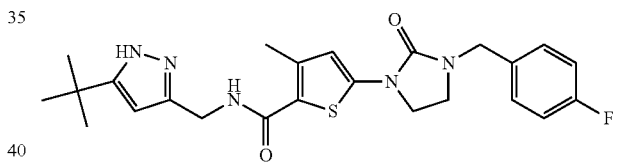

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with (5-tert-butyl-1H-pyrazol-3-yl)methanamine, the title compound was obtained as a colorless solid in 41% yield: $^1$H NMR (300 MHz, CDCl$_3$) δ 7.30-7.23 (m, 2H), 7.07-6.99 (m, 2H), 6.42 (t, J=5.4 Hz, 1H), 6.10 (s, 1H), 6.05 (s, 1H), 4.55 (d, J=5.4 Hz, 2H), 4.42 (s, 2H), 3.83-3.75 (m, 2H), 3.47-3.39 (m, 2H), 2.49 (s, 3H), 1.32 (s, 9H); MS (ES+) m/z 470.2 (M+1).

Example 55.32

Synthesis of 5-(3-(4-fluorobenzyl)-2-oxoimidazolidin-1-yl)-3-methyl-N-(quinolin-3-ylmethyl)thiophene-2-carboxamide

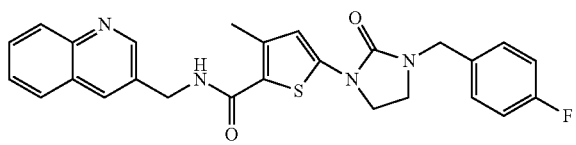

Following the procedures as described in Example 55, making variations as required to replace 3-methyl-5-(2-oxo-3-(2-phenoxyethyl)imidazolidin-1-yl)thiophene-2-carboxylic acid with 5-(3-(4-fluorobenzyl)-2-oxoimidazolidin-1-yl)-3-methylthiophene-2-carboxylic acid to react with quinolin-3-ylmethanaminium chloride, the title compound was obtained as a colorless solid in 50% yield: $^1$H NMR (300 MHz, CDCl$_3$) δ 8.91 (s, 1H), 8.15-8.08 (m, 2H), 7.81 (d, J=8.2 Hz, 1H), 7.74-7.66 (m, 1H), 7.58-7.51 (m, 1H), 7.30-7.22 (m, 2H), 7.07-6.98 (m, 2H), 6.22 (t, J=5.6 Hz, 1H), 6.09 (s, 1H), 4.74 (d, J=5.6 Hz, 2H), 4.42 (s, 2H), 3.83-3.74 (m, 2H), 3.47-3.38 (m, 2H), 2.50 (s, 3H); MS (ES+) m/z 475.2 (M+1).

Example 56

Synthesis of 4-((3-(4-methyl-5-(pyridin-3-ylmethylcarbamoyl)thiophen-2-yl)-2-oxoimidazolidin-1-yl)methyl)benzoic acid

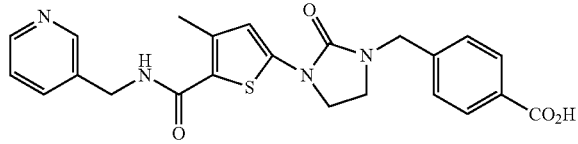

A mixture of 5-(3-(4-carbamoylbenzyl)-2-oxoimidazolidin-1-yl)-3-methyl-N-(pyridin-3-ylmethyl)thiophene-2-carboxamide (0.16 g, 0.36 mmol) and 5 N aqueous potassium hydroxide solution (5.0 mL, 25.0 mmol) in ethanol (5 mL) was stirred at reflux for 2 h, cooled to 0° C. and acidified with glacial acetic acid to pH~6. The mixture was diluted with water (25 mL) and extracted with dichloromethane (2×50 mL). The combined organic layer was dried over sodium sulfate, filtered and concentrated in vacuo. The residue was triturated with ether in hexanes to afford the title compound as a colorless solid in 50% yield (0.08 g): mp 120° C. (dec.); $^1$H NMR (300 MHz, DMSO-d$_6$) δ 8.53 (s, 1H), 8.46 (s, 1H), 8.30 (t, J=5.8 Hz, 1H), 7.93 (d, J=8.1 Hz, 2H), 7.71 (d, J=7.8 Hz, 1H), 7.44-7.32 (m, 2H), 6.24 (s, 1H), 4.47 (s, 2H), 4.39 (d, J=5.8 Hz, 2H), 3.88-3.79 (m, 2H), 3.51-3.43 (m, 2H), 2.37 (s, 3H); $^{13}$C NMR (75 MHz, DMSO-d$_6$) δ 167.0, 162.9, 155.5, 148.8, 147.8, 142.5, 141.7, 139.0, 135.0, 130.0, 129.6, 127.7, 123.4, 119.9, 113.8, 112.1, 46.8, 42.5, 41.5, 15.7; MS (ES+) m/z 450.4 (M+1).

Example 57

Synthesis of 5-(3-(2-hydroxy-2-phenylethyl)-2-oxoimidazolidin-1-yl)-3-methyl-N-(pyridin-3-ylmethyl)thiophene-2-carboxamide

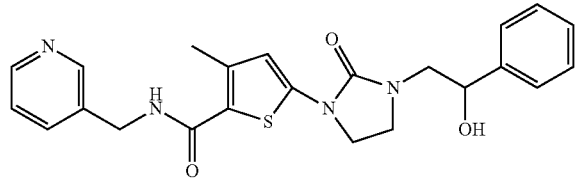

To a stirred solution of 3-methyl-5-(2-oxo-3-(2-oxo-2-phenylethyl)imidazolidin-1-yl)-N-(pyridin-3-ylmethyl)thiophene-2-carboxamide (0.09 g, 0.20 mmol) in methanol (3 mL) and chloroform (1.5 mL) at 0° C. was added sodium borohydride (0.01 g, 0.29 mmol) under nitrogen atmosphere. The resulting mixture was stirred at 0° C. for 1 h, and then quenched with water (25 mL). The aqueous layer was extracted with dichloromethane (2×50 mL), and the combined organic layer was dried over sodium sulfate, filtered and concentrated in vacuo. The residue was triturated with dichloromethane in hexanes to afford the title compound as a brownish solid in 92% yield (0.08 g): mp 75° C. (dec.); $^1$H NMR (300 MHz, CDCl$_3$) δ 8.52 (s, 1H), 8.43 (s, 1H), 7.65 (d, J=7.8 Hz, 1H), 7.39-7.17 (m, 6H), 6.37 (t, J=5.5 Hz, 1H), 5.98 (s, 1H), 4.94 (dd, J=7.7, 3.3 Hz, 1H), 4.52 (d, J=5.5 Hz, 2H), 3.87 (br s, 1H), 3.75-3.35 (m, 6H), 2.43 (s, 3H); $^{13}$C NMR (75 MHz, CDCl$_3$) δ 163.6, 156.6, 149.0, 148.5, 142.4, 141.7, 141.6, 135.6, 134.3, 128.5, 127.9, 125.8, 123.6, 119.0, 112.4, 72.8, 52.3, 43.8, 43.1, 41.1, 16.1; MS (ES+) m/z 437.4 (M+1).

Example 58

Synthesis of 5-(3-(4-aminobenzyl)-2-oxoimidazolidin-1-yl)-3-methyl-N-(pyridin-3-ylmethyl)thiophene-2-carboxamide

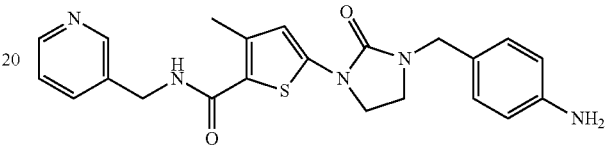

A mixture of tert-butyl 4-((3-(4-methyl-5-(pyridin-3-ylmethylcarbamoyl)-thiophen-2-yl)-2-oxoimidazolidin-1-yl)methyl)phenylcarbamate (0.18 g, 0.34 mmol) and trifluoroacetic acid (2 mL) in dichloromethane (2 mL) was stirred at ambient temperature for 2 h and concentrated. The residue was taken up in saturated aqueous sodium bicarbonate solution (25 mL) and extracted with dichloromethane (2×50 mL). The combined organic layer was dried over sodium sulfate, filtered and concentrated in vacuo. The residue was purified by column chromatography eluted with 0-10% methanol in dichloromethane to afford the title compound as a cream solid in 46% yield (0.07 g): mp 118-120° C.; $^1$H NMR (300 MHz, DMSO-d$_6$) δ 8.52 (s, 1H), 8.44 (s, 1H), 8.30 (t, J=5.9 Hz, 1H), 7.70 (d, J=7.9 Hz, 1H), 7.53 (dd, J=7.9, 4.8 Hz, 1H), 6.93 (d, J=8.4 Hz, 2H), 6.52 (d, J=8.4 Hz, 2H), 6.18 (s, 1H), 5.09 (br s, 2H), 4.38 (d, J=5.9 Hz, 2H), 4.18 (s, 2H), 3.80-3.72 (m, 2H), 3.40-3.32 (m, 2H), 2.36 (s, 3H); $^{13}$C NMR (75 MHz, DMSO-d$_6$) δ 162.9, 155.3, 148.8, 148.0, 147.8, 142.7, 139.1, 135.4, 135.0, 128.9, 123.4, 123.0, 119.7, 113.8, 111.8, 46.8, 42.4, 40.9, 15.7; MS (ES+) m/z 422.2 (M+1).

Example 59

Synthesis of 1-(5-(4-benzyl-4,5-dihydro-1H-imidazol-2-yl)-4-methylthiophen-2-yl)-3-(4-fluorobenzyl)imidazolidin-2-one

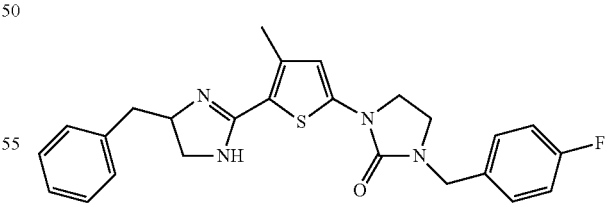

To a stirred solution of (S)-3-phenylpropane-1,2-diamine (0.37 g, 2.48 mmol) in toluene (20 mL) at 0° C. under nitrogen atmosphere was added dropwise trimethylaluminum (1.24 mL of 2.0 M solution in toluene, 2.48 mmol). When the fuming ceased, ethyl 5-(3-(4-fluorobenzyl)-2-oxoimidazolidin-1-yl)-3-methylthiophene-2-carboxylate (0.60 g, 1.66 mmol) in toluene (5 mL) was added slowly. The resulting mixture was stirred at reflux for 18 h, cooled to ambient temperature and partitioned between ethyl acetate (75 mL)

and water (50 mL). The aqueous layer was extracted with ethyl acetate (3×75 mL), and the combined organic layer was dried over sodium sulfate, filtered and concentrated in vacuo. The residue was purified by column chromatography eluted with dichloromethane/methanol/triethyl amine (9/1/0.1) to afford the title compound as brown viscous oil in 29% yield (0.06 g): MS (ES+) m/z 449.2 (M+1).

Example 60

Synthesis of 1-(5-(4-benzyl-1H-imidazol-2-yl)-4-methylthiophen-2-yl)-3-(4-fluorobenzyl)imidazolidin-2-one

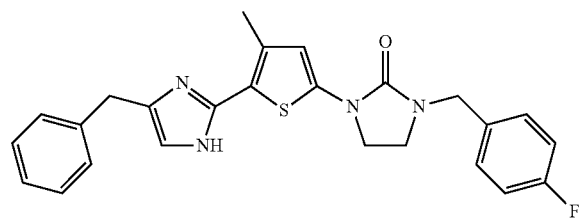

To a stirred solution of oxalyl chloride (0.05 mL, 0.62 mmol) in dichloromethane (1 mL) at −78° C. under nitrogen atmosphere was added dropwise N,N-dimethylsulfoxide (0.06 mL, 0.83 mmol). After 10 minutes, 1-(5-(4-benzyl-4,5-dihydro-1H-imidazol-2-yl)-4-methylthiophen-2-yl)-3-(4-fluorobenzyl)imidazolidin-2-one (0.06 g, 0.14 mmol) in dichloromethane (0.5 mL) was added dropwise. The resulting mixture was stirred at −78° C. for 40 minutes, then triethylamine (0.23 mL, 1.66 mmol) was added, and the cooling bath was removed. After stirred for 1 h, the reaction mixture was partitioned between water (25 mL) and dichloromethane (50 mL). The aqueous layer was extracted with dichloromethane (50 mL), and the combined organic layer was dried over sodium sulfate, filtered and concentrated in vacuo. The residue was purified by ion exchange chromatography eluted sequentially with methanol, 2.0 M ammonia in methanol solution, and further purified by preparative thin layer chromatography eluted with dichloromethane/methanol/triethylamine (95/5/0.5) to afford the title compound as a light yellow solid in 9% yield (0.01 g): $^1$H NMR (300 MHz, CDCl$_3$) δ 7.34-7.21 (m, 8H), 7.06-6.99 (m, 2H), 6.72 (s, 1H), 6.13 (s, 1H), 4.41 (s, 2H), 3.98 (s, 2H), 3.81-3.73 (m, 2H), 3.44-3.37 (m, 2H), 2.42 (s, 3H); MS (ES+) m/z 447.2 (M+1).

Example 61

Synthesis of ethyl 2-(3-((5-(difluoromethyl)furan-2-yl)methyl)-2-oxoimidazolidin-1-yl)-4-methylthiazole-5-carboxylate

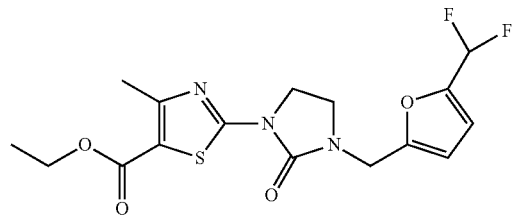

To the solution of ethyl 4-methyl-2-(2-oxoimidazolidin-1-yl)thiazole-5-carboxylate (0.35 g, 1.37 mmol) and (5-(difluoromethyl)furan-2-yl)methanol (0.20 g, 1.37 mmol) in anhydrous tetrahydrofuran (10 mL) was added dropwise tributylphosphine (0.51 mL, 2.06 mmol) at 0° C. The reaction mixture was stirred at 0° C. for 10 minutes and followed by the addition of 1,1'-azobis(N,N-dimethylformamide) (0.35 g, 2.06 mmol). The reaction mixture was stirred at ambient temperature for 18 hours, quenched with saturated aqueous ammonium chloride solution and extracted with ethyl acetate (4×20 mL). The organic solutions were combined, dried over anhydrous sodium sulphate, filtered and concentrated in vacuo. The residue was purified by column chromatography eluted with ethyl acetate/hexane (1/4) to afford the title compound as a white solid in 53% yield (0.25 g): $^1$H NMR (300 MHz, CDCl$_3$) δ 6.60-6.50 (m, 1H), 6.52 (t, J$_{H-F}$=54.2 Hz, 1H), 6.37-6.29 (m, 1H), 4.45 (s, 2H), 4.21 (q, J=7.1 Hz, 2H), 4.09-3.98 (m, 2H), 3.60-3.49 (m, 2H), 2.54 (s, 3H), 1.27 (t, J=7.1 Hz, 3H); MS (ES+) m/z 386.3 (M+1).

Example 62

Synthesis of 2-(1-(2-(4-fluorophenylamino)ethyl)-5-oxo-1H-1,2,4-triazol-4(5H)-yl)-N,4-dimethyl-N-(pyridin-3-ylmethyl)thiazole-5-carboxamide

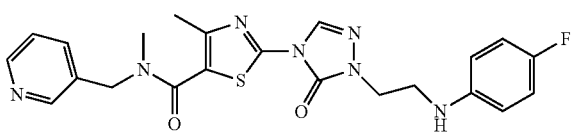

A solution of 2-(1-(2-(4-fluorophenylamino)ethyl)-5-oxo-1H-1,2,4-triazol-4(5H)-yl)-4-methyl-N-(pyridin-3-ylmethyl)thiazole-5-carboxamide (0.10 g, 0.40 mmol) in anhydrous tetrahydrofuran (10 mL) was treated with sodium hydride (60% suspension in mineral oil, 0.02 g, 0.47 mmol) at ambient temperature for 30 minutes, followed by the addition of iodomethane (0.015 mL, 0.24 mmol). The reaction mixture was stirred at ambient temperature for 1 hour, quenched with water and extracted with ethyl acetate. The organic layer was dried over anhydrous sodium sulphate, filtered and concentrated in vacuo. The residue was purified by column chromatography eluted with ethyl acetate to afford the title compound as a white solid in 25% yield (0.03 g): $^1$H NMR (300 MHz, CDCl$_3$) δ 8.60-8.49 (m, 2H), 8.24 (s, 1H), 7.69-7.59 (m, 1H), 7.35-7.27 (m, 1H), 6.91-6.77 (m, 2H), 6.59-6.49 (m, 2H), 4.69 (s, 2H), 4.15-4.04 (m, 2H), 3.99-3.87 (m, 1H), 3.54-3.44 (m, 2H), 2.98 (s, 3H), 2.39 (s, 3H); MS (ES+) m/z 468.18 (M+1).

Example 63

Measuring Stearoyl-CoA Desaturase Inhibition Activity of a Test Compound Using Mouse Liver Microsomes The identification of compounds of the invention as SCD inhibitors was readily accomplished using the SCD microsomal assay procedure described in Shanklin J. and Summerville C., *Proc. Natl. Acad. Sci. USA* (1991), Vol. 88, pp. 2510-2514.

Preparation of Mouse Liver Microsomes:

Male ICR outbread mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1/3 w/v) containing 0.25 M sucrose, 62 mM potassium phosphate buffer (pH 7.0), 0.15 M KCl, 15 mM N-acetylcysteine, 5 mM MgCl$_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Desaturase activity is measured as the release of $^3H_2O$ from [9,10-$^3$H]stearoyl-CoA. Reactions per assay point conditions are as follows: 2 µL 1.5 mM stearoyl-CoA, 0.25 µL 1 mCi/mL $^3$H stearoyl CoA, 10 µL 20 mM NADH, 36.75 µL 0.1 M PK buffer ($K_2HPO_4$/$NaH_2PO_4$, pH 7.2). The test compound or control solution is added in a 1 µL volume. Reactions are started by adding 50 µL of microsomes (1.25 mg/mL). The plates are mixed and after 15 min incubation on a heating block (25° C.), the reactions are stopped by the addition of 10 µL 60% PCA. An aliquot of 100 µL is then transferred to a filter plate pretreated with charcoal and the plate centrifuged at 4000 rpm for 1 minute. The flow through containing the $^3H_2O$ released by the SCD1 desaturation reaction is added to scintillation fluid and the radioactivity measured in a Packard TopCount. The data is analysed to identify the $IC_{50}$ for test compounds and reference compounds. Representative compounds of the invention showed activity as inhibitors of SCD when tested in this assay. The activity was defined in terms of % SCD enzyme activity remaining at the desired concentration of the test compound or as the $IC_{50}$ concentration. The $IC_{50}$ (affinity) of the example compounds toward the stearoyl-CoA desaturase is comprised between around 20 mM and 0.0001 µM or between around 5 µM and 0.0001 µM or between around 1 µM and 0.0001 µM.

The following Table provides data that exemplifies representative compounds and their Microsomal $IC_{50}$ (µM) data.

| Example | Compound name | Microsomal IC50 (µM) |
|---|---|---|
| 9.39 | 2-(3-ethyl-2-oxoimidazolidin-1-yl)-4-methyl-N-(pyridin-3-ylmethyl)thiazole-5-carboxamide | 0.124 |
| 26.1 | 2-(3-(4-fluorobenzyl)-2-oxoimidazolidin-1-yl)-N-(pyridin-3-ylmethyl)-4-(trifluoromethyl)thiazole-5-carboxamide | 0.039 |
| 55.8 | N-(2,3-dihydro-1H-inden-2-yl)-5-(3-(4-fluorobenzyl)-2-oxoimidazolidin-1-yl)-3-methylthiophene-2-carboxamide | 0.027 |
| 32.8 | 4-methyl-2-(2-oxo-3-(pyridin-2-ylmethyl)imidazolidin-1-yl)-N-(pyridin-3-ylmethyl)thiazole-5-carboxamide | 0.267 |
| 60 | 1-(5-(4-benzyl-1H-imidazol-2-yl)-4-methylthiophen-2-yl)-3-(4-fluorobenzyl)imidazolidin-2-one | 0.428 |
| 38.1 | 1-(5-(isoxazol-5-yl)-4-methylthiazol-2-yl)-3-(4-(trifluoromethyl)benzyl)imidazolidin-2-one | 1.243 |
| 44 | 1-(4-methyl-5-(3-methyl-1,2,4-oxadiazol-5-yl)thiazol-2-yl)-3-(4-(trifluoromethyl)benzyl)imidazolidin-2-one | 0.152 |
| 23.6 | N-benzyl-4-methyl-2-(2-oxo-3-((tetrahydro-2H-pyran-2-yl)methyl)imidazolidin-1-yl)thiazole-5-carboxamide | 0.495 |
| 19.10 | 2-(1-(2-(4-chlorophenylamino)-2-oxoethyl)-5-oxo-1H-1,2,4-triazol-4(5H)-yl)-4-methyl-N-(pyridin-3-ylmethyl)thiazole-5-carboxamide | 0.577 |
| 27.3 | N-benzyl-2-(3-benzyl-2-iminoimidazolidin-1-yl)-4-methylthiazole-5-carboxamide | 0.025 |
| 17.3 | 4-methyl-2-(2-oxo-3-(4-(trifluoromethyl)benzyl)-2,3-dihydro-1H-imidazol-1-yl)-N-(pyridin-3-ylmethyl)thiazole-5-carboxamide | 0.012 |
| 23.2 | ethyl 4-((3-(5-(benzylcarbamoyl)-4-methylthiazol-2-yl)-2-oxoimidazolidin-1-yl)methyl)benzoate | 0.061 |
| 45 | 1-(5-bromo-4-methylthiazol-2-yl)-3-(4-(trifluoromethyl)benzyl)imidazolidin-2-one | 0.459 |

Those skilled in the art are aware of a variety of modifications to this assay that can be useful for measuring inhibition of stearoyl-CoA desaturase activity in microsomes or in cells by test compounds.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. 2-(3-Benzyl-2-oxoimidazolidin-1-yl)-4-methyl-N-(pyridin-2-ylmethyl)thiazole-5-carboxamide, or a pharmaceutically acceptable salt thereof.

2. A pharmaceutical composition, comprising:
a therapeutically effective amount of 2-(3-benzyl-2-oxoimidazolidin-1-yl)-4-methyl-N-(pyridin-2-ylmethyl)thiazole-5-carboxamide, or a pharmaceutically acceptable salt thereof, in combination with a therapeutically effective amount of insulin, an insulin derivative or mimetic, an insulin secretagogue, an insulinotropic sulfonylurea receptor ligand, a PPAR ligand, an insulin sensitizer, a biguanide, an alpha-glucosidase inhibitor, GLP-1, a GLP-1 analog or mimetic, a DPPIV inhibitor, a HMG-CoA reductase inhibitor, a squalene synthase inhibitor, a FXR or LXR ligand, cholestyramine, a fibrate, nicotinic acid, or aspirin.

* * * * *